(12) United States Patent
Chowdhury et al.

(10) Patent No.: US 10,801,065 B2
(45) Date of Patent: Oct. 13, 2020

(54) METHODS OF DETERMINING LEVELS OF EXPOSURE TO RADIATION AND USES THEREOF

(71) Applicants: Dana-Farber Cancer Institute, Inc., Boston, MA (US); Albert Einstein College of Medicine, Inc., Bronx, NY (US)

(72) Inventors: Dipanjan Chowdhury, Brookline, MA (US); Chandan Guha, Bronx, NY (US)

(73) Assignees: Dana-Farber Cancer Institute, Inc., Boston, MA (US); Albert Einstein College of Medicine, Inc., Bronx, NY (US)

( * ) Notice: Subject to any disclaimer, the term of this patent is extended or adjusted under 35 U.S.C. 154(b) by 188 days.

(21) Appl. No.: 15/546,337

(22) PCT Filed: Feb. 9, 2016

(86) PCT No.: PCT/US2016/017187
§ 371 (c)(1),
(2) Date: Jul. 26, 2017

(87) PCT Pub. No.: WO2016/130572
PCT Pub. Date: Aug. 18, 2016

(65) Prior Publication Data
US 2018/0148782 A1    May 31, 2018

Related U.S. Application Data

(60) Provisional application No. 62/114,456, filed on Feb. 10, 2015.

(51) Int. Cl.
*C12Q 1/6876* (2018.01)
*C12Q 1/6883* (2018.01)
*G01N 33/50* (2006.01)

(52) U.S. Cl.
CPC ........ *C12Q 1/6876* (2013.01); *C12Q 1/6883* (2013.01); *G01N 33/5088* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 5,137,765 A | 8/1992 | Farnsworth |
| 5,143,854 A | 9/1992 | Pirrung |
| 5,242,974 A | 9/1993 | Holmes |
| 5,252,743 A | 10/1993 | Barrett |
| 5,266,222 A | 11/1993 | Willis |
| 5,324,633 A | 6/1994 | Fodor |
| 5,384,261 A | 1/1995 | Winkler |
| 5,405,783 A | 4/1995 | Pirrung |
| 5,424,186 A | 6/1995 | Fodor |
| 5,451,683 A | 9/1995 | Barrett |
| 5,482,867 A | 1/1996 | Barrett |
| 5,491,074 A | 2/1996 | Aldwin |
| 5,527,681 A | 6/1996 | Holmes |
| 5,550,215 A | 8/1996 | Holmes |
| 5,571,639 A | 11/1996 | Hubbell |
| 5,578,832 A | 11/1996 | Trulson |
| 5,593,839 A | 1/1997 | Hubbell |
| 5,599,695 A | 2/1997 | Pease |
| 5,624,711 A | 4/1997 | Sundberg |
| 5,631,734 A | 5/1997 | Stern |
| 5,795,716 A | 8/1998 | Chee |
| 5,831,070 A | 11/1998 | Pease |
| 5,837,832 A | 11/1998 | Chee et al. |
| 5,856,101 A | 1/1999 | Hubbell |
| 5,858,659 A | 1/1999 | Sapolsky et al. |
| 5,889,165 A | 3/1999 | Fodor |
| 5,936,324 A | 8/1999 | Montagu |
| 5,959,098 A | 9/1999 | Goldberg |
| 5,968,740 A | 10/1999 | Fodor |
| 5,974,164 A | 10/1999 | Chee |
| 5,981,185 A | 11/1999 | Matson |
| 5,981,956 A | 11/1999 | Stern |

(Continued)

FOREIGN PATENT DOCUMENTS

| | | |
|---|---|---|
| WO | WO 1999/36760 | 7/1999 |
| WO | WO 2000/58516 | 10/2000 |
| WO | WO 2001/58593 | 8/2001 |

OTHER PUBLICATIONS

Shah (PloS One 11(4):e0153691 pp. 1-8 Apr. 28, 2016).*

(Continued)

*Primary Examiner* — Amanda Haney
(74) *Attorney, Agent, or Firm* — Fish & Richardson P.C.

(57) ABSTRACT

Provided herein are methods of determining a subject's level of exposure to radiation and methods of determining a subject's risk of subsequent development of radiation disease or risk of poor prognosis from radiation exposure that include determining a level of one or more miRNAs selected from the group consisting of mouse and human homologues of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p, in a sample including a biological fluid from the subject.

19 Claims, 42 Drawing Sheets
Specification includes a Sequence Listing.

(56) References Cited

U.S. PATENT DOCUMENTS

| | | | |
|---|---|---|---|
| 6,025,601 | A | 2/2000 | Trulson |
| 6,033,860 | A | 3/2000 | Lockhart |
| 6,040,193 | A | 3/2000 | Winkler |
| 6,090,555 | A | 7/2000 | Fiekowsky |
| 6,147,205 | A | 11/2000 | McGall |
| 6,262,216 | B1 | 7/2001 | McGall |
| 6,269,846 | B1 | 8/2001 | Overbeck |
| 6,310,189 | B1 | 10/2001 | Fodor |
| 6,428,752 | B1 | 8/2002 | Montagu |
| 6,649,348 | B2 | 11/2003 | Bass |
| 2014/0206852 | A1 | 7/2014 | Hoge et al. |
| 2014/0341841 | A1* | 11/2014 | Jacob ............. C12Q 1/6883 424/85.1 |

OTHER PUBLICATIONS

Cui (Plasma miRNA as Biomarkers for Assessment of Total-Body Radiation Exposure Dosimetry, PloS One Aug. 2011 vol. 6 Issue 8 e22988).*
Leung, CM et al., "Comprehensive MicroRNA Profiling of Prostate Cancer Cells After Ionizing Radiation Treatment," Oncology Reports 31(3):1067-1078 (Jan. 21, 2014).
Cui, W., et al., "Plasma miRNA as Biomarkers for Assessment of Total Body Radiation Exposure Dosimetry," PLoS One 6(8)1-12 (Aug. 17, 2011).
International Search Report and Written Opinion issued by ISA/US for PCT/US2016/017187 (Jul. 26, 2016), 36 pages.
International Preliminary Report on Patentability in International Application No. PCT/US2016/017187, dated Aug. 15, 2017, 28 pages.
Bloomston et al., *MicroRNA expression patterns to differentiate pancreatic adenocarcinoma from normal pancreas and chronic pancreatitis*, JAMA 297(17):1901-1908, (May 2007).
Calin et al.,*MicroRNA profiling reveals distinct signatures in B cell chronic lymphocytic leukemias*, Proc. Natl. Acad. Sci. U.S.A. 101(32):11755-11760, (Aug. 2004).
Chen et al., *Real-time quantification of microRNAs by stem-loop RT-PCR*, Nucleic Acids Res. 33(20):e179, (Nov. 2005) (9 pages).
Coleman et al., Medicine. *Modulation of radiation injury*, Science 304(5671):693-694, (Apr. 2004).

Guo, et al., *Direct fluorescence analysis of genetic polymorphisms by hybridization with oligonucleotide arrays on glass supports*, Nucleic Acids Res. 22(24):5456-5465, (Dec. 1994).
Landgraf et al., *A mammalian microRNA expression atlas based on small RNA library sequencing*, Cell 129(7):1401-1414, (Jun. 2007).
Li et al., *Method for microRNA isolation from clinical serum sample*, Anal. Biochem. 431(1):69-75, (Dec. 2012).
Liang et al., *Characterization of microRNA expression profiles in normal human tissues*, BMC Genomics 8:166, (Jun. 2007) (20 pages).
Maskos et al., *Oligonucleotide hybridizations on glass supports: a novel linker for oligonucleotide synthesis and hybridization properties of oligonucleotides synthesised in situ*, Nucleic Acids Res. 20(7):1679-1684, (Apr. 1992).
Mattie et al., *Optimized high-throughput microRNA expression profiling provides novel biomarker assessment of clinical prostate and breast cancer biopsies*, Mol. Cancer 5:24, (Jun. 2006) (14 pages).
Mauch et al., *Hematopoietic stem cell compartment: acute and late effects of radiation therapy and chemotherapy*, Int. J. Radiat. Oncol. Biol. Phys. 31(5):1319-1339, (Mar. 1995).
Parmar et al. *Hematopoietic stem cell defects in mice with deficiency of Fancd2 or Uspl*, Stem Cells 28(7):1186-1195, (Jul. 2010).
Porkka et al., *MicroRNA expression profiling in prostate cancer*, Cancer Res. 67(13):6130-6135, (Jul. 2007).
Raymond et al., *Simple, quantitative primer-extension Pcr assay for direct monitoring of microRNAs and short-interfering RNAs*, RNA 11(11):1737-1744, (Nov. 2005).
Seo et al., *An interactive power analysis tool for microarray hypothesis testing and generation*, Bioinformatics 22(7):808-814, (Apr. 2006).
Southern, et al., *Arrays of complementary oligonucleotides for analysing the hybridisation behaviour of nucleic acids*, Nucleic Acids Res. 22(8):1368-1373, (Apr. 1994.
Volinia et al., *A microRNA expression signature of human solid tumors defines cancer gene targets*, Proc. Natl. Acad. Sci. U.S.A. 103(7):2257-2261, (Feb. 2006).
Wang et al., *Direct and sensitive miRNA profiling from low-input total RNA*, RNA 13(1):151-159, (Jan. 2007).
Waselenko et al., *Medical management of the acute radiation syndrome: recommendations of the Strategic National Stockpile Radiation Working Group*, Ann. Intern. Med. 140(12):1037-1051, (Jun. 2004).

* cited by examiner

METHODS OF DETERMINING LEVELS OF EXPOSURE TO RADIATION AND USES THEREOF

CROSS-REFERENCE TO RELATED APPLICATIONS

This application is a U.S. National Stage application of International Application No. PCT/US2016/017187, filed Feb. 9, 2016, which claims the benefit of priority of U.S. Provisional Application No. 62/114,456, filed Feb. 10, 2015. The contents of all of the prior applications are incorporated herein by reference in their entirety.

STATEMENT OF FEDERALLY SPONSORED RESEARCH

This invention was made with government support under grant numbers AI101897, CA142698, and AI091175 awarded by The National Institutes of Health. The government has certain rights in the invention.

TECHNICAL FIELD

This invention relates generally to the fields of medicine and radiation biology.

BACKGROUND

Radiation disease, also known as acute radiation syndrome (ARS), is caused by exposure to a large dose of radiation often over a short period of time. The symptoms of radiation disease include, but are not limited to, nausea, vomiting, diarrhea, headache, fever, skin damage, loss of bone marrow stem cells, internal bleeding, and possibly death. The severity and onset of symptoms depend upon the amount of radiation absorbed by the body. In general, greater doses of radiation result in a more rapid onset of severe radiation disease in a subject.

MicroRNAs (miRNAs) are small non-coding RNAs, typically about 19-22 nucleotides in size, that play important roles in the regulation of gene expression and various biological processes, such as cell cycle control. MiRNAs have been implicated in a number of diseases and are detected in biological fluids, such as serum.

SUMMARY

The present disclosure is based, at least in part, on the discovery that specific changes in the serum levels of specific miRNAs occur in subjects that have been exposed to total body irradiation, and that the changes in the levels of these specific miRNAs are radiation dose-dependent and correlate with a subject's risk of subsequent development of radiation disease, a subject's risk of poor prognosis from radiation exposure, and the efficacy of a treatment for reducing radiation-induced damage in a subject exposed to a significant dose of radiation (e.g., when the treatment for reducing radiation-induced damage in a subject is administered before or after total body irradiation). These specific miRNAs can include, e.g., one or more (e.g., two or more, three or more, four or more, five or more, six or more, seven or more, eight or more, nine or more, ten or more, eleven or more, twelve or more, thirteen or more, fifteen or more, sixteen or more, seventeen or more, eighteen or more, nineteen or more, or twenty or more) of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p, and human homologues of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In view of these discoveries, provided herein are methods of determining a subject's level of exposure to radiation, methods of determining whether a subject has been exposed to a radiation dose of 2 Gy or more, methods of determining a subject's risk of poor prognosis from radiation exposure, methods of determining a subject's risk of subsequent development of radiation disease, methods of selecting a treatment for reducing radiation-induced damage for a subject, methods of selecting a subject for treatment of radiation disease, methods of triaging a plurality of subjects exposed to or suspected of having been exposed to radiation, and methods of determining the efficacy of a treatment administered to a subject exposed to a significant dose of radiation, that include, e.g., determining a level of one or more (e.g., two or more, three or more, four or more, five or more, six or more, seven or more, eight or more, nine or more, ten or more, eleven or more, twelve or more, thirteen or more, fifteen or more, sixteen or more, seventeen or more, eighteen or more, nineteen or more, or twenty or more) of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p, and human homologues of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p in a sample including a biological fluid from a subject. Also provided are kits that comprise, consist, or consist essentially of at least one nucleic acid that comprises, consists, or consists essentially of a sequence (e.g., a sequence to between 5 to 20 nucleotides or between 5 to 15 nucleotides) that is complementary to one or more of the human homologues of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, and miR-126-3p.

Provided herein are methods for determining a subject's level of exposure to radiation that include: (a) determining a level of three or more miRNAs selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p and human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p in a sample including a biological fluid from the subject; (b) comparing the level(s) of the one or more miRNAs in the sample to reference levels of the three or more miRNAs; and (c) determining the subject's level of exposure to radiation based on the comparison of the levels of the three or more miRNAs in the sample to the reference levels of the three or more miRNAs. In some embodiments of any of the methods described herein, the subject is a mouse, and the three or more miRNAs are selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In some embodiments of any of the methods described herein, (i) three or more of: an elevated level of one or more of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of mouse miR-150-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to the reference levels, indicates that the subject's exposure to radiation is equal to or less than 2 Gy; (ii) three or more of an elevated level of one or more of miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference levels, indicates that the subject's exposure to radiation is between greater than 2 Gy and about 6.5 Gy; or (iii) three or more of: an elevated level of one or more of mouse miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference levels, indicates that the subject's exposure to radiation is greater than about 6.5 Gy. In some embodiments of any of the methods described herein, in (i) the reference levels are the level(s) of mouse miR-130a-3p, miR-150-5p, miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in a sample including a biological fluid from a subject not exposed to a significant dose of radiation; in (ii) the reference levels are the levels of mouse miR-17-3p, miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in a sample including a biological fluid from a subject not exposed to a significant dose of radiation or a subject exposed to about 2 Gy of radiation; and in (iii) the reference levels are the levels of mouse miR-30a-3p, miR-30c-5p, miR-187-3p, miR-194-5p, miR-27a-3p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in a sample including a biological fluid from a subject not exposed to a significant dose of radiation, a subject exposed to about 2 Gy of radiation, or a subject exposed to about 6.5 Gy of radiation.

In some embodiments of any of the methods described herein, the subject is a human, and the three or more miRNAs are selected from the group of human homologues of mouse miRNAs miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In some embodiments of any of the methods described herein, (i) three or more of: an elevated level of one or more of the human homologue of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of the human homologue of mouse miR-150-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to the reference levels, indicates that the subject's exposure to radiation is equal to or less than 2 Gy; (ii) three or more of: an elevated level of one or more of the human homologue of mouse miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of the human homologue of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference levels, indicates that the subject's exposure to radiation is between greater than 2 Gy and about 6.5 Gy; or (iii) three or more of: an elevated level of one or more of the human homologue of mouse miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR- 486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologue of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference levels, indicates that the subject's exposure to radiation is greater than about 6.5 Gy. In some embodiments of any of the methods described herein, in (i) the reference levels are the levels of the human homologues of mouse miR-130a-3p, miR-150-5p, miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in a sample including a biological fluid from a subject not exposed to a significant dose of radiation; in (ii) the reference levels are the levels of the human homologues of mouse miR-17-3p, miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in a sample including a biological fluid from a subject not exposed to a significant dose of radiation or a subject exposed to about 2 Gy of radiation; and in (iii) the reference levels are the levels of the human homologues of mouse miR-30a-3p, miR-30c-5p, miR-187-3p, miR-194-5p, miR-27a-3p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in a sample including a biological fluid from a subject not exposed to a significant dose of radiation, a subject exposed to about 2 Gy of radiation, or a subject exposed to about 6.5 Gy of radiation.

Some embodiments of any of the methods described herein further include administering a treatment to the subject based on the subject's determined level of exposure to radiation.

Also provided are methods of determining whether a subject has been exposed to a radiation dose of 2 Gy or more that include: (a) determining a level of one or more miRNAs selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p, and human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p in a sample including a biological fluid from the subject; (b) comparing the level(s) of the one or more miRNAs in the sample with a reference level(s) of the one or more miRNAs; and (c) determining whether the subject has been exposed to a radiation dose of 2 Gy or more based on the comparison of the level(s) of the one or more miRNAs in the sample with the reference level(s) of the one or more miRNAs. In some embodiments of any of the methods described herein, the subject is a mouse and the one or more miRNAs are selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR- 486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p. In some embodiments of any of the methods described herein, one or more of: an elevated level of one or more of mouse miR-130a-3p, miR-30a-3p, miR-30c-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p, and/or a decreased level of one or more of mouse miR-150-5p, miR-17-3p, miR-187-3p, miR-194-5p, miR-27a-3p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, and miR-204-5p in the sample, as compared to the reference level(s), indicates that the subject has been exposed to 2 Gy or more radiation. In some embodiments of any of the methods described herein, (i) the reference level(s) for mouse miR-130a-3p, miR-150-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, miR-1966-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, and miR-204-5p are the level(s) of mouse miR-130a-3p, miR-150-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, miR-1966-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, and miR-204-5p in a sample including a biological fluid from a subject not exposed to a significant dose of radiation; (ii) the reference level for mouse miR-17-3p is the level of mouse miR-17-3p in a sample including a biological fluid from a subject not exposed to a significant dose of radiation or a subject exposed to about 2 Gy of radiation; and (iii) the reference level(s) for mouse miR-187-3p, miR-194-5p, miR-27a-3p, miR-30a-3p, and miR-30c-5p are the level(s) of mouse miR-187-3p, miR-194-5p, miR-27a-3p, miR-30a-3p, and miR-30c-5p in a sample including a biological fluid from a subject not exposed to a significant dose of radiation or a subject exposed to about 2 Gy of radiation, or a subject exposed to about 6.5 Gy radiation.

In some embodiments of any of the methods described herein, the subject is a human and the one or more miRNAs are selected from the group of human homologues of miR-130a-3p, miR-150-5p, miR-17-3p, miR-187-3p, miR-194-5p, miR-27a-3p, miR-30a-3p, miR-30c-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p. In some embodiments of any of the methods described herein, one or more of: an elevated level of one or more of the human homologues of mouse miR-130a-3p, miR-30a-3p, miR-30c-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p, and/or a decreased level of one or more of the human homologues of mouse miR-150-5p, miR-17-3p, miR-187-3p, miR-194-5p, miR-27a-3p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to reference level(s), indicates that the subject has been exposed to 2 Gy or more radiation. In some embodiments of any of the methods described herein, (i) the reference level(s) for the human homologues of mouse miR-130a-3p, miR-150-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, miR-1966-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, and miR-204-5p are the level(s) of the human homologues of mouse miR-130a-3p, miR-150-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, miR-1966-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-

3p, miR-34b-3p, miR-139-5p, miR-149-5p, miR-1a-3p, miR-23b-3p, miR-215-5p, and miR-204-5p in a sample including a biological fluid from a subject not exposed to a significant dose of radiation; (ii) the reference level for the human homologues of mouse miR-17-3p is the level of the human homologues of mouse miR-17-3p in a sample including a biological fluid from a subject not exposed to a significant dose of radiation or a subject exposed to about 2 Gy of radiation; and (iii) the reference level(s) for the human homologues of mouse miR-187-3p, miR-194-5p, miR-27a-3p, miR-30a-3p, and miR-30c-5p are the level(s) of the human homologues of mouse miR-187-3p, miR-194-5p, miR-27a-3p, miR-30a-3p, and miR-30c-5p in a sample including a biological fluid from a subject not exposed to a significant dose of radiation or a subject exposed to about 2 Gy of radiation, or a subject exposed to about 6.5 Gy radiation.

Some embodiments of any of the methods described herein further include administering a treatment for reducing radiation-induced damage to the subject determined to have been exposed to 2 Gy or more radiation.

Also provided are methods of determining a subject's risk of poor prognosis from radiation exposure that include: (a) determining a level of three or more miRNAs in a sample including a biological fluid from the subject; (b) comparing the levels of the three or more miRNAs in the sample to reference levels of the three or more miRNAs; and (c) determining the subject's risk of poor prognosis from radiation exposure based on the comparison of the levels of the three or more miRNAs in the sample to the reference levels of the three or more miRNAs. Also provided are methods of assessing a subject's risk of subsequent development of radiation disease, where the subject has been exposed or is suspected of being exposed, to a significant dose of radiation that include: (a) determining a level of three or more miRNAs in a sample including a biological fluid from the subject; (b) comparing the levels of the three or more miRNAs in the sample to reference levels of the three or more miRNAs; and (c) determining the subject's risk of subsequent radiation disease based on the comparison of the levels of the three or more miRNAs in the sample to the reference levels of the three or more miRNAs.

In some embodiments of any of the methods described herein, the subject is a mouse, and the three or more miRNAs are selected from the group of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, miR-30c-5p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In some embodiments of any of the methods described herein, (i) three or more of: an elevated level of one or more of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-17-3p, miR-29a-3p, miR-200b-5p, miR-25-3p, miR-338-3p, and miR-196b-5p, and/or a decreased level of one or more of mouse miR-142-5p, miR-150-5p, miR-342-3p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in the sample, as compared to the reference levels, indicates that the subject's risk of poor prognosis is moderate; (ii) three or more of: an elevated level of one or more of mouse miR-34b-3p, miR-126-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference levels, indicates that the subject's risk of poor prognosis is high; or (iii) three or more of: an elevated level of one or more of mouse miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s), indicates that the subject's risk of poor prognosis is very high.

In some embodiments of any of the methods described herein, the subject is a mouse, and the three or more miRNAs are selected from the group of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, miR-30c-5p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-

5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In some embodiments of any of the methods described herein, (i) three or more of: an elevated level of one or more of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of mouse miR-142-5p, miR-150-5p, miR-342-3p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in the sample, as compared to the reference levels, indicates that the subject's risk of subsequent development of radiation disease is moderate; (ii) three or more of: an elevated level of one or more of mouse miR-34b-3p, miR-126-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-5p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference levels, indicates that the subject's risk of subsequent development of radiation disease is high; or (iii) three or more of: an elevated level of one or more of mouse miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference levels, indicates that the subject's risk of subsequent development of radiation disease is very high.

In some embodiments of any of the methods described herein, in (i) the reference levels are the levels of mouse miR-130a-3p, miR-142-5p, miR-150-5p, miR-342-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, miR-196b-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in a sample including a biological fluid from a subject not exposed to a significant dose of radiation; in (ii) the reference levels are the levels of mouse miR-34b-3p, miR-126-3p, miR-17-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in a sample including a biological fluid from a subject not exposed to a significant dose of radiation or a subject exposed to about 2 Gy of radiation; and in (iii) the reference levels are the levels of mouse miR-30a-3p, miR-30c-5p, miR-187-3p, miR-194-5p, miR-27a-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in a sample including a biological fluid from a subject not exposed to a significant dose of radiation, a subject exposed to about 2 Gy of radiation, or a subject exposed to about 6.5 Gy of radiation.

In some embodiments of any of the methods described herein, the subject is a human, and the three or more miRNAs are selected from the group of human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, miR-30c-5p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR- 486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In some embodiments of any of the methods described herein, (i) three or more of: an elevated level of one or more of the human homologue of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or and a decreased level of one or more of the human homologues of mouse miR-142-5p, miR-150-5p, miR-342-3p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in the sample, as compared to the reference levels, indicates that the subject's risk of poor prognosis is moderate; (ii) three or more of: an elevated level of one or more of the human homologues of mouse miR-34b-3p, miR-126-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of the human homologue of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference levels, indicates that the subject's risk of poor prognosis is high; or (iii) three or more of: an elevated level of one or more of the human homologues of mouse miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologues of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference levels, indicates that the subject's risk of poor prognosis is very high.

In some embodiments of any of the methods described herein, the subject is a human, and the three or more miRNAs are selected from the group of human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, miR-30c-5p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In some embodiments of any of the methods described herein, (i) three or more of: an elevated level of one or more of the human homologue of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of the human homologues of mouse miR-142-5p, miR-150-5p, miR-342-3p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in the sample, as compared to the reference levels, indicates that the subject's risk of subsequent development of radiation disease is moderate; (ii) three or more of: an elevated level of one or more of the human homologues of mouse miR-34b-3p, miR-126-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one of more of the human homologue of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference levels, indicates that the subject's risk of subsequent development of radiation disease is high; or (iii) three or more of: an elevated level of one or more of the human homologues of mouse miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR- 1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologues of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s), indicates that the subject's risk of subsequent development of radiation disease is very high.

In some embodiments of any of the methods described herein, in (i) the reference levels are the levels of the human homologues of mouse miR-130a-3p, miR-142-5p, miR-150-5p, miR-342-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7d-5p, miR-15a-3p, miR-17-3p, miR-29a-3p, miR-200b-5p, miR-25-3p, miR-338-3p, miR-196b-5p, miR-320-3p, miR-142a-3p, miR-126-3p, miR-706, miR-29a-5p, miR-30a-3p, miR-194-5p, miR-let-7d-5p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in a sample including a biological fluid from a subject not exposed to a significant dose of radiation; in (ii) the reference levels are the levels of the human homologues of mouse miR-34b-3p, miR-126-3p, miR-17-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in a sample including a biological fluid from a subject not exposed to a significant dose of radiation or a subject exposed to about 2 Gy of radiation; and in (iii) the reference levels are the levels of the human homologues of mouse miR-30a-3p, miR-30c-5p, miR-187-3p, miR-194-5p, miR-27a-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in a sample including a biological fluid from a subject not exposed to a significant dose of radiation, a subject exposed to about 2 Gy of radiation, or a subject exposed to about 6.5 Gy of radiation.

Some embodiments of any of the methods described herein further include (d) hospitalizing a subject identified as having a very high risk or a high risk of poor prognosis from radiation exposure, or treating a subject identified as having a moderate risk of poor prognosis from radiation exposure on an outpatient basis. Some embodiments of any of the methods described herein further include (d) hospitalizing a subject identified as having a very high risk or high risk of subsequent development of radiation disease, or treating a subject identified as having a moderate risk of subsequent development of radiation disease on an outpatient basis.

Also provided are methods of selecting a treatment for a subject that include (a) determining a level of one or more miRNAs selected from the group of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p and human homologues of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in a sample including a biological fluid from the subject; (b) comparing the level(s) of the one or more miRNAs in the sample to reference level(s) of the one or more miRNAs; and (c) selecting a treatment for reducing radiation-induced damage for a subject based on the comparison of the level(s) of the one or more miRNAs in the sample to the reference level(s) of the one or more miRNAs.

Also provided are methods of selecting a subject for treatment of radiation disease that include: (a) determining a level of one or more miRNAs selected from the group of mouse miR-130a-3p, miR-150-5p, miR-17-3p, miR-187-3p, miR-194-5p, miR-27a-3p, miR-30a-3p, miR-30c-5p, miR- 320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p and human homologues of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in a sample including a biological fluid from the subject; (b) comparing the level(s) of the one or more miRNAs in the sample to reference level(s) of the one or more miRNAs; and (c) selecting a subject for treatment of radiation disease based on the comparison of the level(s) of the one or more miRNAs in the sample to the reference level(s) of the one or more miRNAs.

In some embodiments of any of the methods described herein, the subject is a mouse and the one or more miRNAs are selected from the group of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p. In some embodiments of any of the methods described herein, a treatment for reducing radiation-induced damage is selected for a subject having one or more of: an elevated level of one or more of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s).

In some embodiments of any of the methods described herein, the subject is a mouse and the one or more miRNAs are selected from the group of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p. In some embodiments of any of the methods described herein, a subject having one or more of: an elevated level of one or more of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s), is selected for treatment of radiation disease, or a subject not having one or more of: an elevated level of one or more of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s), is not selected for treatment of radiation disease.

In some embodiments of any of the methods described herein, (i) the reference level(s) for mouse miR-130a-3p, miR-150-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p are the level(s) of mouse miR-130a-3p and miR-150-5p in a sample including a biological fluid from a subject not exposed to a significant dose of radiation; (ii) the reference level for mouse miR-17-3p is the level of mouse miR-17-3p in a sample including a biological fluid from a subject not exposed to a significant dose of radiation or a subject exposed to about 2 Gy of radiation; and (iii) the reference level(s) for mouse miR-187-3p, miR-194-5p, miR-27a-3p, miR-30a-3p, and miR-30c-5p are the level(s) or mouse miR-187-3p, miR-194-5p, miR-27a-3p, miR-30a-3p, and miR-30c-5p in a sample including a biological fluid from a subject not exposed to a significant dose of radiation, a subject exposed to about 2G of radiation, or exposed to about 6.5 Gy of radiation.

In some embodiments of any of the methods described herein, the subject is a human and the one or more miRNAs are selected from the group of human homologues of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p. In some embodiments of any of the methods described herein, a treatment for reducing radiation-induced damage is selected for a subject having one or more of: an elevated level of one or more of the human homologues of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologues of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s).

In some embodiments of any of the methods described herein, the subject is a human and the one or more miRNAs are selected from the group of human homologues of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p. In some embodiments of any of the methods described herein, a subject having one or more of: an elevated level of one or more of the human homologues of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologues of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s), is selected for treatment of radiation disease, or a subject not having one or more of: an elevated level of one or more of the human homologues of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologues of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s), is not selected for treatment of radiation disease.

In some embodiments of any of the methods described herein, (i) the reference level(s) for the human homologues of mouse miR-130a-3p, miR-150-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p are the level(s) of the human homologues of mouse miR-130a-3p, miR-150-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in a sample including a biological fluid from a subject not exposed to a significant dose of radiation; (ii) the reference level for the human homologues of mouse miR-17-3p is the level of the human homologues of mouse miR-17-3p in a sample including a biological fluid from a subject not exposed to a significant dose of radiation or a subject exposed to about 2 Gy of radiation; and (iii) the reference level(s) for the human homologues of mouse miR-187-3p, miR-194-5p, miR-27a-3p, miR-30a-3p, and miR-30c-5p are the level(s) of the human homologues of mouse miR-187-3p, miR-194-5p, miR-27a-3p, miR-30a-3p, and miR-30c-5p in a sample including a biological fluid from a subject not exposed to a significant dose of radiation, a subject exposed to about 2 Gy of radiation, or exposed to about 6.5 Gy of radiation.

In some embodiments of any of the methods described herein, the treatment for reducing radiation-induced damage is selected from the group of: administration of one or more of a cytokine, potassium iodide, Prussian blue, and diethylenetriamine pentaacetic acid, bone marrow transplantation, blood transfusion, and surgery to remove damaged tissues. In some embodiments of any of the methods described herein, the cytokine is selected from the group of granulocyte colony-stimulating factor, filgrastim, and pegfilgrastim. In some embodiments of any of the methods described herein, the selected treatment includes inpatient treatment. Some embodiments of any of the methods described herein further include administering the selected treatment to the subject.

In some embodiments of any of the methods described herein, the subject has been identified as being exposed to radiation or is suspected of having been exposed to radiation. In some embodiments of any of the methods described herein, the subject is or was previously at a location having or suspected of having had a significant level of radiation. In some embodiments of any of the methods described herein, the location is the site of a nuclear attack, the site of radiation release from a nuclear weapon, a nuclear energy facility, a nuclear waste facility, or a nuclear medicine facility. In some embodiments of any of the methods described herein, the sample is obtained from the subject within 30 minutes to 96 hours after the subject's possible exposure to radiation.

Also provided herein are methods of triaging a plurality of subjects exposed or suspected of being exposed to radiation that include, for each subject in the plurality: (a) determining a level of three or more miRNAs selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p and human homologues of one or more of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p in a sample including a biological fluid from the subject; (b) comparing the levels of the three or more miRNAs in the sample to reference levels of the three or more miRNAs; and (c) triaging the subject based on the comparison of the levels of the three or more miRNAs in the sample to the reference levels of the three or more miRNAs.

In some embodiments of any of the methods described herein, the subject is a mouse and the three or more miRNAs are selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In some embodiments of any of the methods described herein, (i) a subject having three or more of: an elevated level of one or more of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR- 30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more mouse miR-150-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to the reference levels, is given low priority in triaging; (ii) a subject having three or more of: an elevated level of one or more of mouse miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference levels, is given medium priority in triaging; or (iii) a subject having three or more of: an elevated level of one or more of mouse miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference levels, is given high priority in triaging. In some embodiments of any of the methods described herein, (i) the reference levels for mouse miR-130a-3p, miR-150-5p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, miR-196b-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p are the levels of mouse miR-130a-3p, miR-150-5p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, miR-196b-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in a sample including a biological fluid from a subject not exposed to a significant dose of radiation; (ii) the reference levels for mouse miR-17-3p, miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p are the levels of mouse miR-17-3p, miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in a sample including a biological fluid from a subject not exposed to a significant dose of radiation or a subject exposed to about 2 Gy of radiation; and (iii) the reference levels for mouse miR-187-3p, miR-194-5p, miR-27a-3p, miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-

3p, miR-215-5p, miR-338-3p, and miR-196b-5p are the levels of mouse miR-187-3p, miR-194-5p, miR-27a-3p, miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in a sample including a biological fluid from a subject not exposed to a significant dose of radiation, a subject exposed to about 2G of radiation, or exposed to about 6.5 Gy of radiation.

In some embodiments of any of the methods described herein, the subject is a human and the three or more miRNAs are selected from the group of human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In some embodiments of any of the methods described herein, (i) a subject having three or more of: an elevated level of one or more of the human homologue of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of the human homologue of mouse miR-150-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to the reference levels, is given low priority in triaging; (ii) a subject having three or more of: an elevated level of one or more of the human homologue of mouse miR-320-3p, miR-30c-5p, miR-126-3p, miR-375-3p, miR-99b-5p, miR-30a-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologue of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference levels, is given medium priority in triaging; or (iii) a subject having three or more of: an elevated level of one or more of the human homologues of mouse miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologues of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference levels, is given high priority in triaging. In some embodiments of any of the methods described herein, (i) the reference levels for the human homologues of mouse miR-130a-3p, miR-150-5p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, miR-196b-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p are the levels of the human homologues of mouse miR-130a-3p, miR-150-5p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, miR-196b-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in a sample including a biological fluid from a subject not exposed to a significant dose of radiation; (ii) the reference levels for the human homologues of mouse miR-17-3p, miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p are the levels of the human homologues of mouse miR-17-3p, miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-196b-5p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in a sample including a biological fluid from a subject not exposed to a significant dose of radiation or a subject exposed to about 2 Gy of radiation; and (iii) the reference levels for the human homologues of mouse miR-187-3p, miR-194-5p, miR-27a-3p, miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p are the levels of the human homologues of mouse miR-187-3p, miR-194-5p, miR-27a-3p, miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in a sample including a biological fluid from a subject not exposed to a significant dose of radiation, a subject exposed to about 2G of radiation, or a subject exposed to about 6.5 Gy of radiation.

In some embodiments of any of the methods described herein, at least two of the plurality of subjects are or were previously at a location having or suspected of having had a significant level of radiation. In some embodiments of any of the methods described herein, the location is the site of a nuclear attack, the site of radiation release from a nuclear weapon, a nuclear energy facility, a nuclear waste facility, or a nuclear medicine facility.

Also provided herein are methods of determining the efficacy of a treatment administered to a subject exposed to a significant dose of radiation that include: (a) determining a first level of one or more miRNAs in a sample including a biological fluid obtained from the subject exposed to a significant dose radiation a first time point; (b) after the first time point and before a second time point, administering a treatment for reducing radiation-induced damage to the subject; (c) determining a second level of the one or more miRNAs in a sample comprising a biological fluid obtained from the subject at the second time point; and (d) determining the efficacy of the treatment administered to the subject based on a comparison of the second level(s) of the one or more miRNAs to the first level(s) of the one or more miRNAs.

In some embodiments of any of the methods described herein, the subject is a mouse, and the one or more miRNAs are selected from the group of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p. In some embodiments of any of the methods described herein, one or more of: an elevation in the second level of one or more of mouse miR-142-5p, miR-150-5p, miR-342-3p, miR-17-3p, miR-187-3p, miR-194-5p, and miR-27a-3p, and/or a decrease in the second level of one or more of mouse miR-130a-3p, miR-126-3p, miR-346-3p, miR-30a-3p, and miR-30c-5p, as compared to the first level(s) of one or more of mouse miR-142-5p, miR-150-5p, miR-342-3p, miR-17-3p, miR-187-3p, miR-194-5p, miR-27a-3p, miR-130a-3p, miR-126-3p, miR-346-3p, miR-30a-3p, and miR-30c-5p, indicates that the treatment administered to the subject was effective.

In some embodiments of any of the methods described herein, the subject is a human, and the one or more miRNAs are selected from the group of human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p. In some embodiments of any of the methods described herein, one or more of: an elevation in the second level of one or more of the human homologues of mouse miR-142-5p, miR-150-5p, miR-342-3p, miR-17-3p, miR-187-3p, miR-194-5p, and miR-27a-3p, and/or a decrease in the second level of one or more of the human homologues of mouse miR-130a-3p, miR-126-3p, miR-346-3p, miR-30a-3p, and miR-30c-5p, as compared to the first level(s) of one or more of the human homologues of mouse miR-142-5p, miR-150-5p, miR-342-3p, miR-17-3p, miR-187-3p, miR-194-5p, miR-27a-3p, miR-130a-3p, miR-126-3p, miR-346-3p, miR-30a-3p, and miR-30c-5p, indicates that the treatment administered to the subject was effective.

In some embodiments of any of the methods described herein, the treatment for reducing radiation-induced damage is selected from the group of: cytokines, potassium iodide, Prussian blue, diethylenetriamine pentaacetic acid, bone marrow transplantation, blood transfusion, and surgery to remove damaged tissues. In some embodiments of any of the methods described herein, the cytokines are selected from the group of granulocyte colony-stimulating factor, filgrastim, and pegfilgrastim.

In some embodiments of any of the methods described herein, the first and second level(s) of the one or more miRNAs in the samples are determined in steps (a) and (c) by amplifying the miRNAs present in the sample(s) to generate amplification products, contacting the amplified products to a substrate, and detecting the amplified products bound to the substrate.

Also provided are methods for determining the efficacy of a treatment for reducing radiation-induced damage in a subject exposed to a significant level of radiation that include: (a) determining a level of one or more miRNAs in a sample including a biological fluid from a subject previously exposed to a significant level of radiation and thereafter administered a treatment for reducing radiation-induced damage; (b) comparing the level(s) of the one or more miRNAs in the sample to reference level(s) of the one or more miRNAs; and (c) determining efficacy of the treatment for reducing radiation-induced damage in the subject based on the comparison of the level(s) of the one or more miRNAs in the sample to the reference level(s) of the one or more miRNAs.

In some embodiments of any of the methods described herein, the subject is a mouse and the one or more miRNAs are selected from the group of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p. In some embodiments of any of the methods described herein, one or more of: an elevated level of one or more of mouse miR-130a-3p, miR-34-3p, miR-126-3p, miR-30a-3p, and miR-30c-5p, and/or a decreased level of one or more of mouse miR-142-5p, miR-150-5p, miR-342-3p, miR-17-3p, miR-187-3p, miR-194-5p, and miR-27a-3p, in the sample, as compared to the reference level(s), indicates that treatment was not effective, or a non-elevated level of mouse miR-130a-3p, miR-34-3p, miR-126-3p, miR-30a-3p, and miR-30c-5p, and a non-decreased level of mouse miR-142-5p, miR-150-5p, miR-342-3p, miR-17-3p, miR-187-3p, miR-194-5p, and miR-27a-3p, in the sample, as compared to the reference level(s), indicates that treatment was effective. In some embodiments of any of the methods described herein, the reference level(s) for mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p are the level(s) of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p in a sample including a biological fluid from a subject not exposed to a significant dose of radiation, a subject exposed to a significant level of radiation and not administered a treatment or not administered an effective treatment, or a control subject that was exposed to a significant level of radiation and administered an effective treatment.

In some embodiments of any of the methods described herein, the subject is a human and the one or more miRNAs are selected from the group of human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p. In some embodiments of any of the methods described herein, one or more of: an elevated level of one or more of the human homologues of mouse miR-130a-3p, miR-34-3p, miR-126-3p, miR-30a-3p, and miR-30c-5p, and/or a decreased level of one or more of the human homologues of mouse miR-142-5p, miR-150-5p, miR-342-3p, miR-17-3p, miR-187-3p, miR-194-5p, and miR-27a-3p, in the sample, as compared to the reference level(s), indicates that treatment was not effective, or a non-elevated level of the human homologues of mouse miR-130a-3p, miR-34-3p, miR-126-3p, miR-30a-3p, and miR-30c-5p, and a non-decreased level of the human homologues of mouse miR-142-5p, miR-150-5p, miR-342-3p, miR-17-3p, miR-187-3p, miR-194-5p, and miR-27a-3p, in the sample, as compared to the reference level(s), indicates that treatment was effective. In some embodiments of any of the methods described herein, the reference level(s) for the human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p, are the level(s) of the reference level(s) of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p in a sample including a biological fluid from a subject not exposed to a significant dose of radiation, a subject exposed to a significant level of radiation and not administered a treatment or not administered an effective treatment, or a control subject that was exposed to a significant level of radiation and administered an effective treatment.

In some embodiments of any of the methods described herein, the biological fluid is selected from the group of: blood, plasma, serum, saliva, or urine. In some embodiments of any of the methods described herein, the level(s) of the one or more miRNAs in the sample is determined in step (a) by amplifying the miRNAs present in the sample to generate amplification products, contacting the amplified products to a substrate, and detecting the amplified products bound to the substrate.

Also provided are kits consisting or consisting essentially of one or more of: (i) at least one nucleic acid including a sequence that is complementary to all or a part of the sequence of the human homolog of mouse miR-130a-3p; (ii) at least one nucleic acid including a sequence that is complementary to all or a part of the sequence of the human homolog of mouse miR-150-5p; (iii) at least one nucleic acid including a sequence that is complementary to all or a part of the sequence of the human homolog of mouse miR-17-3p; (iv) at least one nucleic acid including a sequence that is complementary to all or a part of the sequence of the human homolog of mouse miR-187-3p; (v) at least one nucleic acid including a sequence that is complementary to all or a part of the sequence of the human homolog of mouse miR-194-5p; (vi) at least one nucleic acid including a sequence that is complementary to all or a part of the sequence of the human homolog of mouse miR-27a-3p; (vii) at least one nucleic acid including a sequence that is complementary to all or a part of the sequence of the human homolog of mouse miR-30a-3p; and (viii) at least one nucleic acid including a sequence that is complementary to all or a part of the sequence of the human homolog of mouse miR-30c-5p.

Some embodiments of any of the kits described herein further include one or more of: (ix) at least one nucleic acid including a sequence that is complementary to all or a part of the sequence of the human homolog of mouse miR-142-5p; (x) at least one nucleic acid including a sequence that is complementary to all or a part of the sequence of the human homolog of mouse miR-342-3p; (xi) at least one nucleic acid including a sequence that is complementary to all or a part of the sequence of the human homolog of mouse miR-34b-3p; (xii) at least one nucleic acid including a sequence that is complementary to all or a part of the sequence of the human homolog of mouse miR-126-3p; (xiii) at least one nucleic acid including a sequence that is complementary to all or a part of the sequence of the human homolog of mouse miR-320-3p; (xiv) at least one nucleic acid including a sequence that is complementary to all or a part of the sequence of the human homolog of mouse miR-136-5p; (xv) at least one nucleic acid including a sequence that is complementary to all or a part of the sequence of the human homolog of mouse miR-33-5p; (xvi) at least one nucleic acid including a sequence that is complementary to all or a part of the sequence of the human homolog of mouse miR-142a-3p; (xvii) at least one nucleic acid including a sequence that is complementary to all or a part of the sequence of the human homolog of mouse miR-706; (xviii) at least one nucleic acid including a sequence that is complementary to all or a part of the sequence of the human homolog of mouse miR-375-3p; (xix) at least one nucleic acid including a sequence that is complementary to all or a part of the sequence of the human homolog of mouse miR-29a-5p; (xx) at least one nucleic acid including a sequence that is complementary to all or a part of the sequence of the human homolog of mouse miR-193a-3p; (xxi) at least one nucleic acid including a sequence that is complementary to all or a part of the sequence of the human homolog of mouse miR-99b-5p; (xxii) at least one nucleic acid including a sequence that is complementary to all or a part of the sequence of the human homolog of mouse miR-151-3p; (xxiii) at least one nucleic acid including a sequence that is complementary to all or a part of the sequence of the human homolog of mouse miR-let-7d-3p; (xxiv) at least one nucleic acid including a sequence that is complementary to all or a part of the sequence of the human homolog of mouse miR-486-5p; (xxv) at least one nucleic acid including a sequence that is complementary to all or a part of the sequence of the human homolog of mouse miR-423-5p; (xxvi) at least one nucleic acid including a sequence that is complementary to all or a part of the sequence of the human homolog of mouse miR-30b-5p; (xxvii) at least one nucleic acid including a sequence that is complementary to all or a part of the sequence of the human homolog of mouse miR-191-5p; (xxviii) at least one nucleic acid including a sequence that is complementary to all or a part of the sequence of the human homolog of mouse miR-497a-5p; (xxix) at least one nucleic acid including a sequence that is complementary to all or a part of the sequence of the human homolog of mouse miR-32-5p; (xxx) at least one nucleic acid including a sequence that is complementary to all or a part of the sequence of the human homolog of mouse miR-214-5p; (xxxi) at least one nucleic acid including a sequence that is complementary to all or a part of the sequence of the human homolog of mouse miR-326-3p; (xxxii) at least one nucleic acid including a sequence that is complementary to all or a part of the sequence of the human homolog of mouse miR-1195; (xxxiii) at least one nucleic acid including a sequence that is complementary to all or a part of the sequence of the human homolog of mouse miR-122-5p; (xxxiv) at least one nucleic acid including a sequence that is complementary to all or a part of the sequence of the human homolog of mouse miR-1839-3p; (xxxv) at least one nucleic acid including a sequence that is complementary to all or a part of the sequence of the human homolog of mouse miR-500-3p; (xxxvi) at least one nucleic acid including a sequence that is complementary to all or a part of the sequence of the human homolog of mouse miR-30e-3p; (xxxvii) at least one nucleic acid including a sequence that is complementary to all or a part of the sequence of the human homolog of mouse miR-322-3p; (xxxviii) at least one nucleic acid including a sequence that is complementary to all or a part of the sequence of the human homolog of mouse miR-709; (xxxix) at least one nucleic acid including a sequence that is complementary to all or a part of the sequence of the human homolog of mouse miR-486a-3p; (xxxx) at least one nucleic acid including a sequence that is complementary to all or a part of the sequence of the human homolog of mouse miR-133a-3p; (xxxxi) at least one nucleic acid including a sequence that is complementary to all or a part of the sequence of the human homolog of mouse miR-676-3p; (xxxxii) at least one nucleic acid including a sequence that is complementary to all or a part of the sequence of the human homolog of mouse miR-744-5p; (xxxxiii) at least one nucleic acid including a sequence that is complementary to all or a part of the sequence of the human homolog of mouse miR-29a-3p; (xxxxiv) at least one nucleic acid including a sequence that is complementary to all or a part of the sequence of the human homolog of mouse miR-1839-5p; (xxxxv) at least one nucleic acid including a sequence that is complementary to all or a part of the sequence of the human homolog of mouse miR-30a-5p; (xxxxvi) at least one nucleic acid including a sequence that is complementary to all or a part of the sequence of the human homolog of mouse miR-199b-5p; (xxxxvii) at least one nucleic acid including a sequence that is complementary to all or a part of the sequence of the human homolog of mouse miR-125a-5p; (xxxxviii) at least one nucleic acid including a sequence that is complementary to all or a part of the sequence of the human homolog of mouse miR-133b-3p; (il) at least one nucleic acid including a sequence that is complementary to all or a part of the sequence of the human homolog of mouse miR-24-3p; (l) at least one nucleic acid including a sequence that is complementary to all or a part of the sequence of the human homolog of mouse miR-21a-5p; (li) at least one nucleic acid including a sequence that is complementary to all or a part of the sequence of the human homolog of mouse miR-503-5p; (lii) at least one nucleic acid including a sequence that is complementary to all or a part of the sequence of the human homolog of mouse miR-328-3p; (liii) at least one nucleic acid including a sequence that is complementary to all or a part of the sequence of the human homolog of mouse miR-let-7g-5p; (liv) at least one nucleic acid including a sequence that is complementary to all or a part of the sequence of the human homolog of mouse miR-362-3p; (lv) at least one nucleic acid including a sequence that is complementary to all or a part of the sequence of the human homolog of mouse miR-199a-5p; (lvi) at least one nucleic acid including a sequence that is complementary to all or a part of the sequence of the human homolog of mouse miR-15a-3p; (lvii) at least one nucleic acid including a sequence that is complementary to all or a part of the sequence of the human homolog of mouse miR-139-5p; (lviii) at least one nucleic acid including a sequence that is complementary to all or a part of the sequence of the human homolog of mouse miR-149-5p; (lix) at least one nucleic acid including a sequence that is complementary to all or a part of the sequence of the human homolog of mouse miR-29b-3p; (lx) at least one nucleic acid including a sequence that is complementary to all or a part of the sequence of the human homolog of mouse miR-1a-3p; (lxi) at least one nucleic acid including a sequence that is complementary to all or a part of the sequence of the human homolog of mouse miR-23b-3p; (lxii) at least one nucleic acid including a sequence that is complementary to all or a part of the sequence of the human homolog of mouse miR-215-5p; (lxiii) at least one nucleic acid including a sequence that is complementary to all or a part of the sequence of the human homolog of mouse miR-204-5p; (lxiv) at least one nucleic acid including a sequence that is complementary to all or a part of the sequence of the human homolog of mouse miR-200b-5p; (lxv) at least one nucleic acid including a sequence that is complementary to all or a part of the sequence of the human homolog of mouse miR-25-3p; (lxvi) at least one nucleic acid including a sequence that is complementary to all or a part of the sequence of the human homolog of mouse miR-338-3p; and (lxvii) at least one nucleic acid including a sequence that is complementary to all or a part of the sequence of the human homolog of mouse miR-196b-5p.

In some embodiments of any of the kits described herein, one or more of the nucleic acid of (i) through (lxvii) is bound to a substrate. In some embodiments of any of the kits described herein, the substrate is a chip, slide, or film.

As used herein, the word "a" before a noun represents one or more of the particular noun. For example, the phrase "a level" represents "one or more levels."

The term "subject" means any mammal, e.g., such as a human, a monkey, a mouse, a rat, a rabbit, or a goat. A subject can be, e.g., a subject suspected of being exposed to a significant dose of radiation or a subject known to have been exposed to a significant dose of radiation. Additional examples of subjects are described herein.

The term "biological fluid" refers to any fluid produced by the body of a subject (e.g., any of the subjects described herein). Non-limiting examples of biological fluids include serum, plasma, blood, urine, feces, saliva, lymph, sweat, tears, bile, cerebrospinal fluid, chyle, aqueous humour, endolymph, perilymph, exudate, and mucus.

The phrase "level of exposure to radiation" represents the cumulative dose of radiation that a subject has been exposed to during a specific period of time (e.g., a period of time that includes a suspected or confirmed leakage of a high level of radiation into the environment or includes a suspected or confirmed exposure of a subject to a high level of radiation). For example, a specific period of time can include a period of time between about 1 minute and about four weeks, between about 1 minute to about three weeks, between about 5 minutes to about two weeks, between about 1 minute to about one week, between about 1 minute to about 6 days, between about 1 minute to about 5 days, between about 1 minute to about 4 days, between about 1 minute to about 3 days, between about 1 minute to about 2 days, between about 1 minute to about 1 day, between about 1 minute to about 12 hours, between about 1 minute to about 6 hours, between about 1 minute to about 4 hours, between about 1 minute to about 3 hours, between about 1 minute to about 2 hours, between about 1 minute to about 1 hour, between about 1 minute to about 30 minutes, between about 1 minute to about 20 minutes, between about 1 minute to about 15 minutes, between about 1 minute to about 10 minutes, or between about 1 minute to about 5 minutes. In some examples, a period of time can includes a suspected or confirmed leakage of a high level of radiation into the environment, e.g., as a result of detonation of a nuclear bomb, a leakage of a high level of radiation from a nuclear energy facility, irradiation of the body of a subject having a disease (e.g., cancer) in order to treat the disease (e.g., cancer), or as a result of working or living near a nuclear energy facility or a nuclear waste site.

The phrase "significant dose of radiation" is art known and refers to a cumulative dose of radiation over a specific period of time (e.g., a period of time that includes a suspected or confirmed leakage of a high level of radiation into the environment or includes a suspected or confirmed exposure of a subject to a high level of radiation) that is greater than a cumulative dose of background radiation from radioisotopes in the natural environment (e.g., radioisotopes present in the earth and radioisotopes present in the earth's atmosphere) that a subject has been exposed to over a similar control period of time (e.g., a period of time that does not include a suspected or confirmed leakage of a high level of radiation into the environment and does not include a suspected or confirmed exposure of a subject to a high level of radiation).

The phrase "treatment for reducing radiation-induced damage" is art known and means a treatment administered to a subject for the purpose of reducing the number, severity, development, and/or rate of development of one or more (e.g., two, three, four, or five) symptoms of radiation disease in a subject. Examples of symptoms of radiation disease are described herein. Non-limiting examples of treatments for reducing radiation-induced damage are described herein. Additional examples of treatments for reducing radiation-induced damage are known in the art. Exemplary methods for determining the efficacy of treatment for reducing radiation-induced damage in a subject exposed to a significant dose of radiation are also provided herein.

The phrase "risk of poor prognosis from radiation exposure" is art known and means a subject's risk of developing a severe form of radiation disease in the future (e.g., between 1 day and 5 years, between 1 day and 4 years, between 1 day and 3 years, between 1 day and 2 years, between 1 day and 1 year, between 1 day and 10 months, between 1 day and 8 months, between 1 day and 6 months, between 1 day and 5 months, between 1 day and 4 months, between 1 day and 3 months, between 1 day and 2 months, between 1 day and 7 weeks, between 1 day and 6 weeks, between 1 day and 5 weeks, between 1 day and 1 month, between 1 day and 3 weeks, between 1 day and 2 weeks, or between 1 day and 1 week) as compared to the risk in a control subject (e.g., a subject not exposed to a significant dose of radiation). Symptoms of a severe form of radiation disease include, e.g., one or more of a decrease in the number of bone marrow stromal cells, a decrease in the number of hematopoietic progenitor cells (HPCs), a decrease in the number of hematopoietic stem cells (HSCs), a decrease in the number of T-cells, a decrease in the number of B-cells, a decrease in the number of neutrophils, a decrease in the level of platelets, a decrease in the level of hemoglobin, a decrease in the complete blood count (CBC), a decrease in the colony-forming units in culture (CFU-C), a decrease in the bone marrow mononuclear cells (BM-MNCs), a decrease in total white blood cell count, an increase in the risk of infection, and an increased in the risk of death, e.g., as compared to the numbers/levels of bone marrow stromal cells, HPCs, HSCs, T-cells, B-cells, neutrophils, platelets, hemoglobin, CBC, CFUs, CFU-C, BM-MNCs, and total white blood cell count, and the risk of infection and risk of death in a control subject (e.g., a subject not exposed to a significant dose of radiation). Exemplary methods of determining a subject's risk of poor prognosis from radiation exposure are described herein.

The phrase "risk of subsequent development of radiation disease" is art known and means a subject's later risk (e.g., between 1 day and 5 years, between 1 day and 4 years, between 1 day and 3 years, between 1 day and 2 years, between 1 day and 1 year, between 1 day and 10 months, between 1 day and 8 months, between 1 day and 6 months, between 1 day and 5 months, between 1 day and 4 months, between 1 day and 3 months, between 1 day and 2 months, between 1 day and 7 weeks, between 1 day and 6 weeks, between 1 day and 5 weeks, between 1 day and 1 month, between 1 day and 3 weeks, between 1 day and 2 weeks, or between 1 day and 1 week) of developing radiation disease as compared to the risk in a control subject (e.g., a subject not exposed to a significant dose of radiation) (e.g., over a similar time period). Exemplary methods for determining a subject's risk of subsequent development of radiation disease are described herein.

The term "triaging" is art known and means evaluating a plurality of subjects in order to prioritize the subjects for treatment by a physician. Triaging can, e.g., be based on the severity of each subject's exposure to radiation (e.g., as determined using any of the methods described herein). Exemplary methods for triaging a plurality of subjects having been exposed or suspected of having been exposed to radiation are described herein.

The phrase "efficacy of treatment" is art known and means the absence or a reduction in the level of one or more (e.g., two, three, or four) of the number, severity, development, and/or rate of development of one or more (e.g., two, three, four, or five) symptoms of radiation disease in a subject and/or the absence or a reduction in a subject's risk of subsequent development of radiation disease (e.g., as compared to a subject that has been exposed to a similar level of radiation and has received a different treatment or no treatment). Exemplary methods for determining the efficacy of a treatment for reducing radiation-induced damage in a subject are described herein.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

not significant, n.s.

Figure 14:
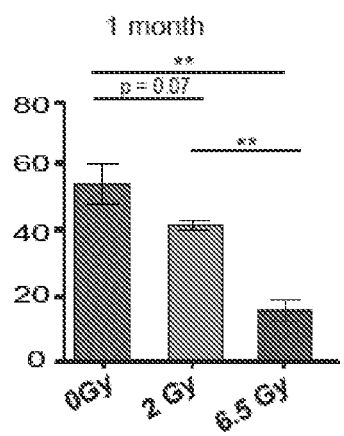

FIG. 14 is a graph showing the number of CFU-Cs (in thousands) per hind limb in bone marrow collected from mice one month after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.01, **.

Figure 15:
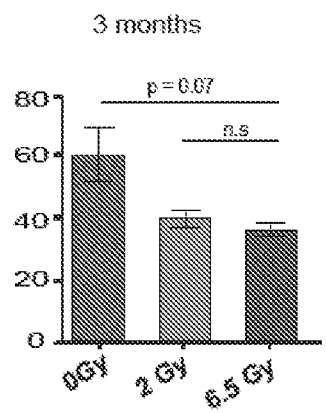

FIG. 15 is a graph showing the number of CFU-Cs (in thousands) per hind limb in bone marrow collected from mice three months after 0 Gy-, 2 Gy-, 6.5 Gy-, or 8 Gy-total body irradiation. The error bars represent ±standard error of the mean. All pairwise comparisons were performed by one-way ANOVA followed by Tukey's test. Not significant, n.s.

Figure 16:
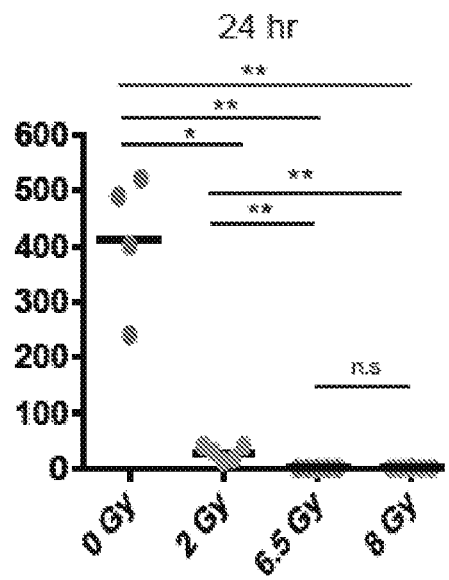

FIG. 16 is a graph showing the number of lineage-negative, Sca-1-positive, c-kit-negative (LSK−) cells (in thousands) per hind limb in bone marrow collected from mice 24 hours after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.05, *; p<0.01, **; not significant, n.s.

Figure 17:
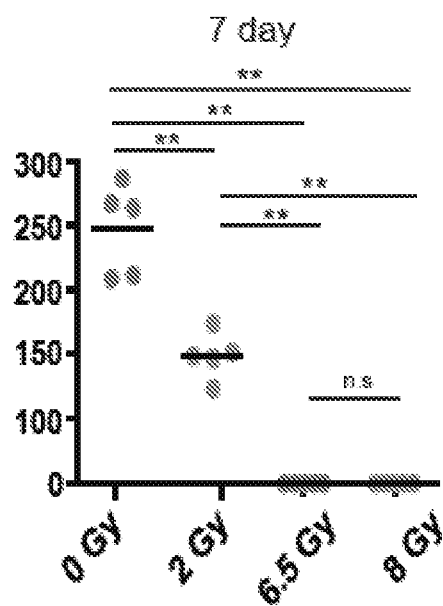

FIG. 17 is a graph showing the number of LSK− cells (in thousands) per hind limb in bone marrow collected from mice 7 days after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.01, **; not significant, n.s.

Figure 18:
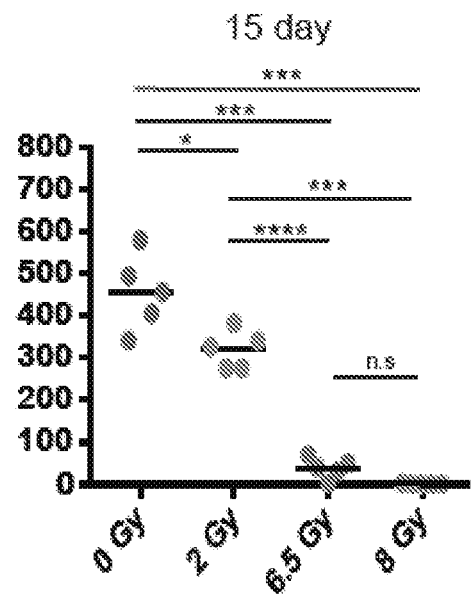

FIG. 18 is a graph showing the number of LSK− cells (in thousands) per hind limb in bone marrow collected from mice 15 days after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.05, *; p<0.001, *; p<0.0001, **; not significant, n.s.

Figure 19:
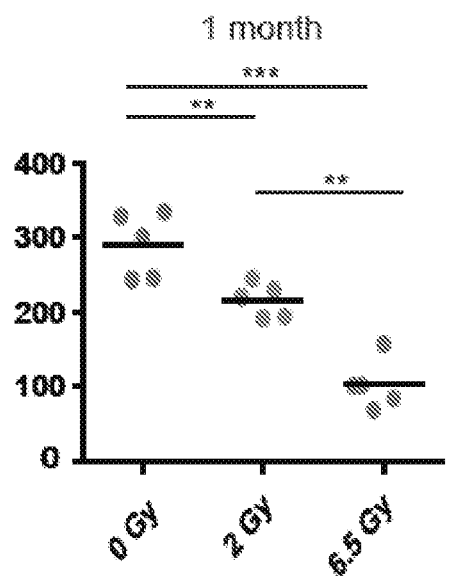

FIG. 19 is a graph showing the number of LSK− cells (in thousands) per hind limb in bone marrow collected from mice one month after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.01, ; p<0.001, *.

Figure 20:
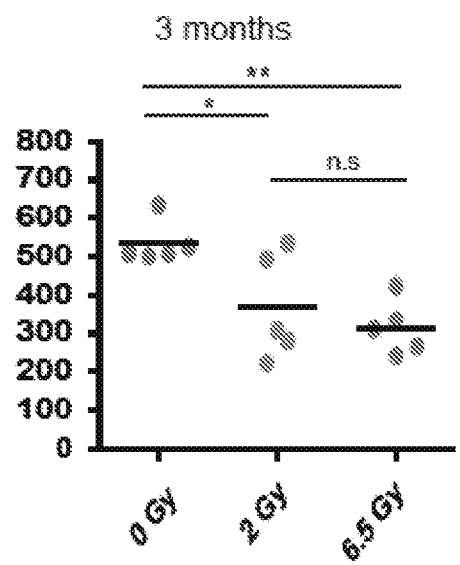

FIG. 20 is a graph showing the number of LSK− cells (in thousands) per hind limb in bone marrow collected from mice three months after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.05, *; p<0.01, **; not significant, n.s.

Figure 21:
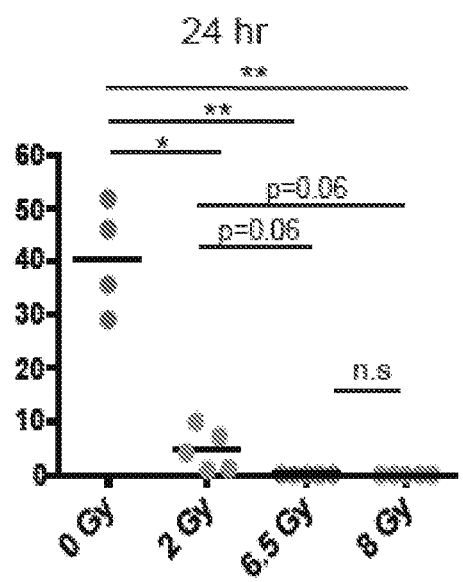

FIG. 21 is a graph showing the number of LSK$^+$ cells (in thousands) per hind limb in bone marrow collected from mice 24 hours after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.05, *; p<0.01, **; not significant, n.s.

Figure 22:
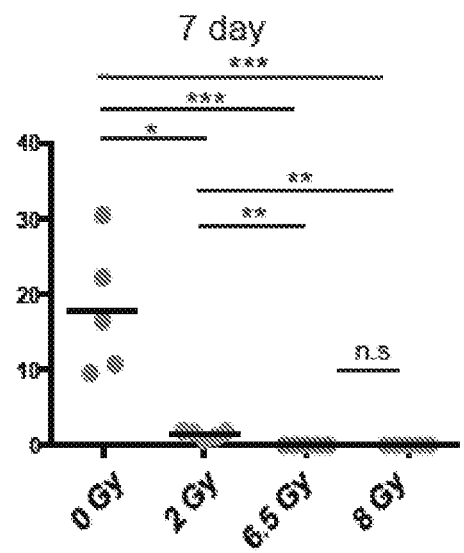

FIG. 22 is a graph showing the number of LSK$^+$ cells (in thousands) per hind limb in bone marrow collected from mice 7 days after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.05, *; p<0.01, ; p<0.001, *; not significant, n.s.

Figure 23:
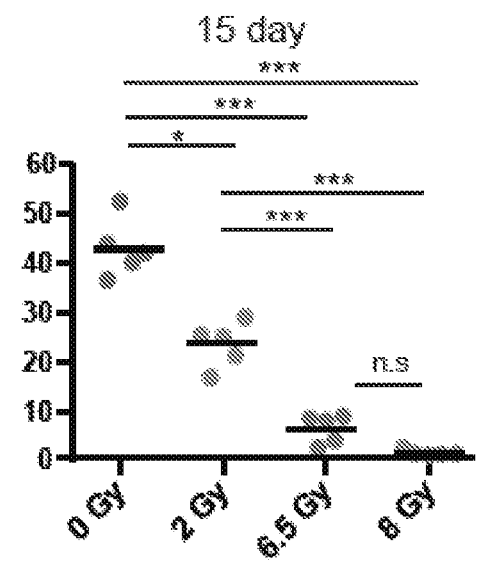

FIG. 23 is a graph showing the number of LSK$^+$ cells (in thousands) per hind limb in bone marrow collected from mice 15 days after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.05, *; p<0.001, ***; not significant, n.s.

Figure 24:
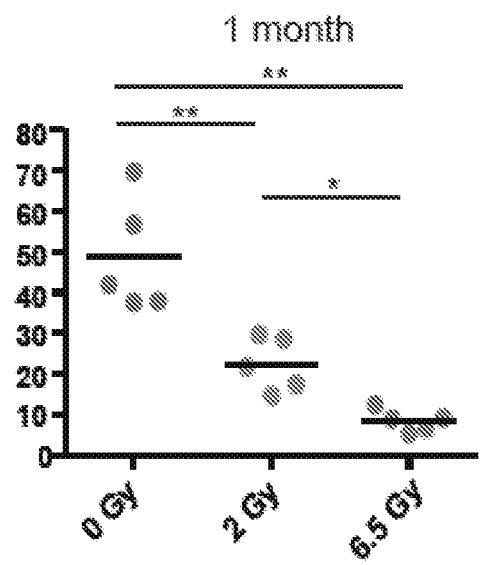

FIG. 24 is a graph showing the number of LSK$^+$ cells (in thousands) per hind limb in bone marrow collected from mice one month after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.05, *; p<0.01, **.

Figure 25:
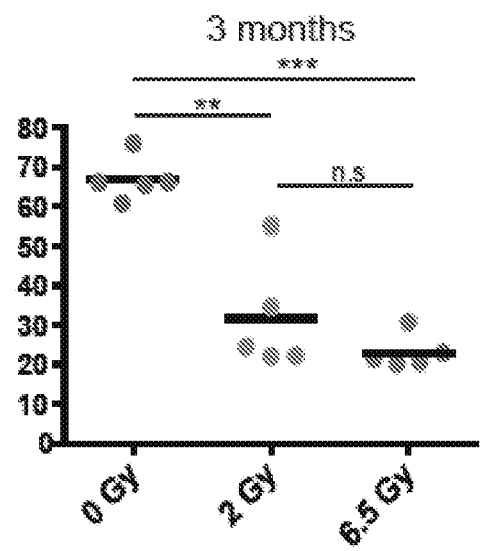

FIG. 25 is a graph showing the number of LSK$^+$ cells (in thousands) per hind limb in bone marrow collected from mice three months after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.01, ; p<0.001, *; not significant, n.s.

Figure 26:
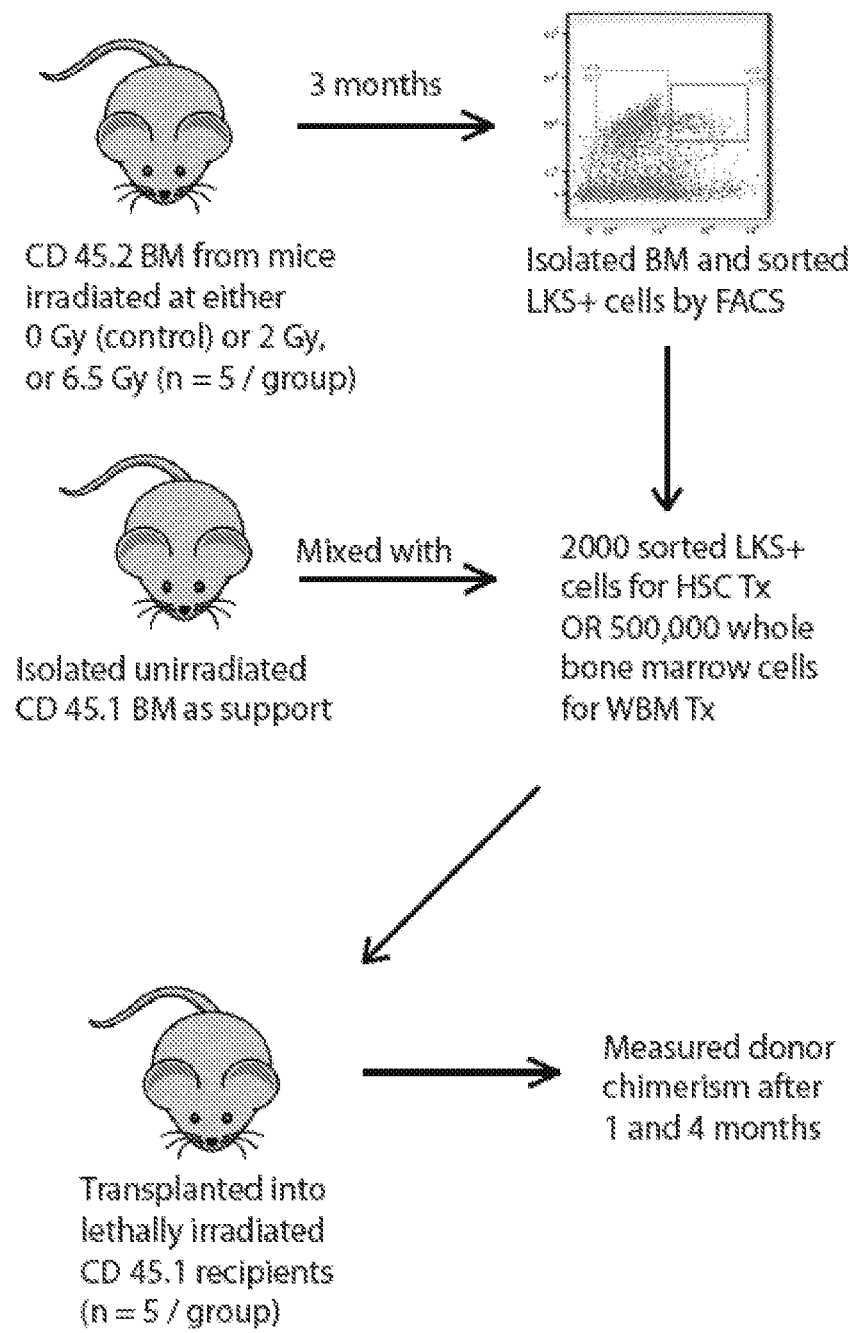

FIG. 26 is a schematic of an experiment where CD 45.2$^+$ bone marrow is collected from mice three months after exposure to 0 Gy-, 2 Gy-, or 6.5 Gy-total body irradiation, the LKS$^+$ cells were isolated from the bone marrow by fluorescence-assisted cell sorting (FACS), 2000 sorted LKS$^+$ cells or 500,000 whole bone marrow cells were mixed with CD45.1$^+$ bone marrow support cells from non-experimentally-irradiated mice, the mixture transplanted into lethally-irradiated CD45.1$^+$ recipient mice (n=5 per group), and the chimerism of CD45.1$^+$ and CD45.2$^+$ leukocytes determined at 1 and 4 months after transplantation of the mixture into the lethally-irradiated recipient mice.

Figure 27:
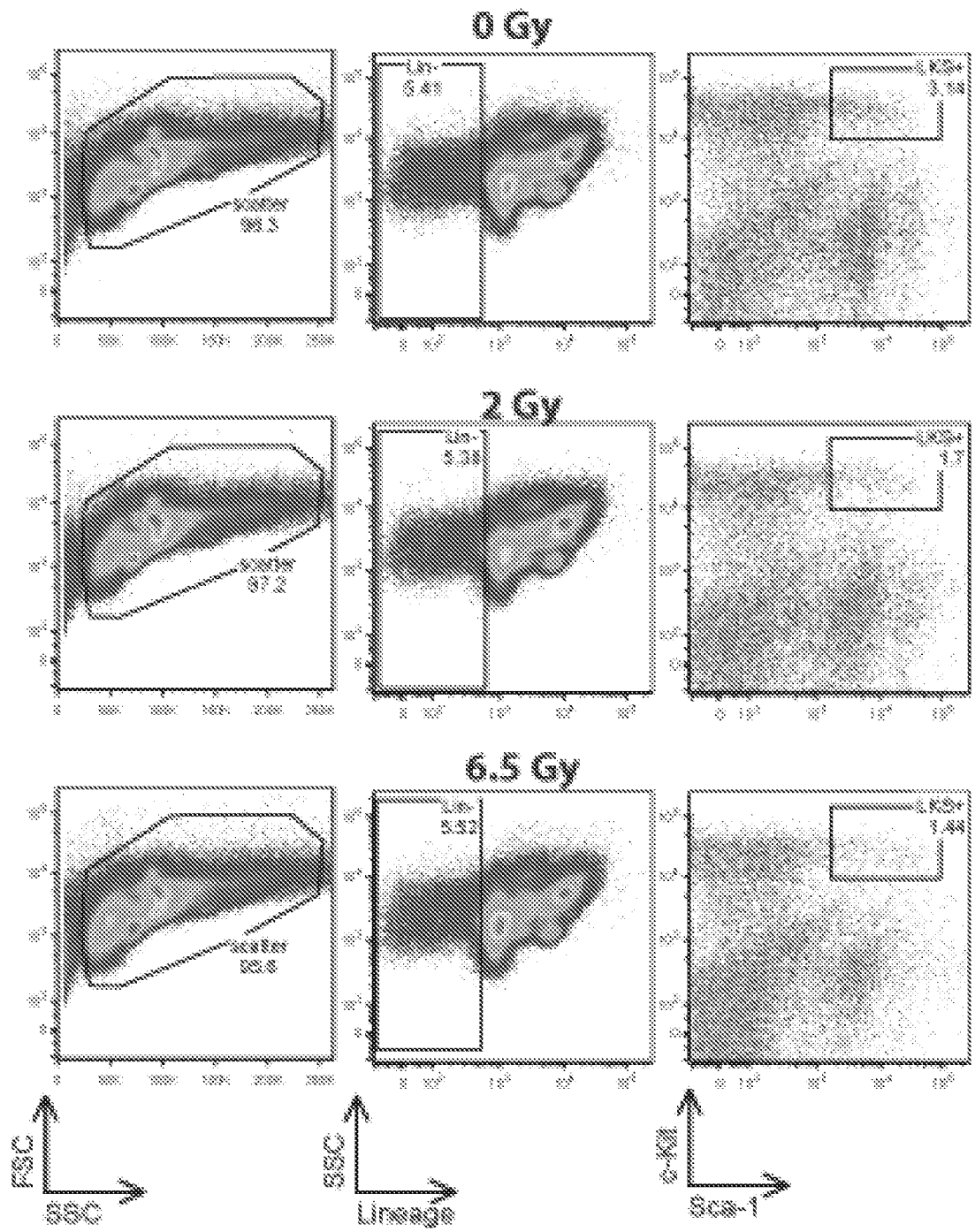

FIG. 27 shows a set of three, two-dimensional FACS profiles of stained bone marrow collected from donor CD45.2+ mice three months after their exposure to 0 Gy-, 2 Gy-, or 6.5 Gy-total body irradiation (and later used to sort LKS+ or whole bone marrow cells for transplantation). Each horizontal set of three, two-dimensional FACS profiles show, from left to right, the total scatter (side scatter and forward scatter), lineage-, and LKS+ gates. For LKS (lineage, cKit, Sca-1) staining to visualize hematopoietic precursor cells and hematopoietic stem cells, whole bone marrow was stained with biotinylated anti-lineage cocktail (anti-Mac1, Gr-1, CD3e, B220, and Ter119), APC-conjugated anti-cKit (clone 2B8), and PECy7-conjugated anti Sca-1

Figure 28:
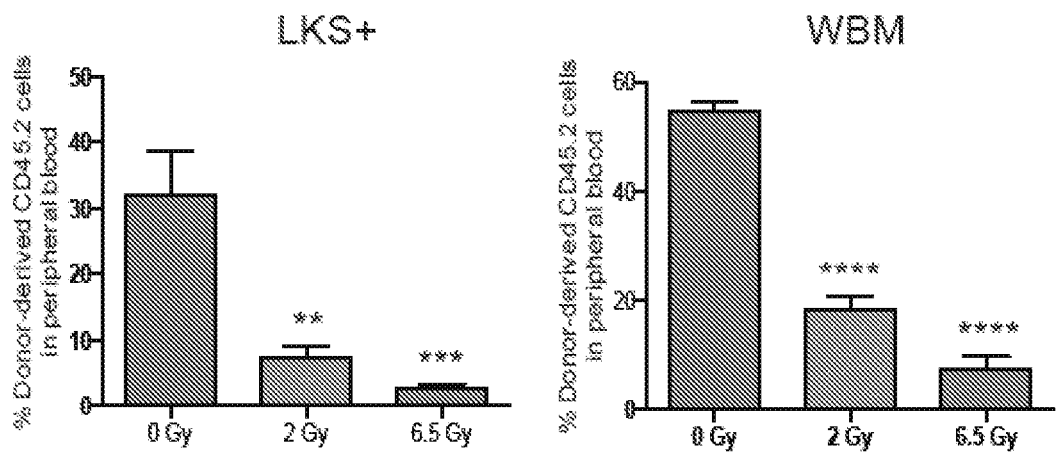

FIG. 28 is a pair of graphs showing the number of donor-derived (CD45.2$^+$) LKS$^+$ cells and the number of donor-derived (CD45.2$^+$) whole bone marrow cells in the peripheral blood of lethally-irradiated CD45.1$^+$ recipient mice one month after transplantation with a mixture of (1) 2000 sorted LKS$^+$ cells or 500,000 whole bone marrow cells obtained from a CD45.2$^+$ donor mouse three months after exposure to 0 Gy-, 2 Gy-, or 6.5-Gy irradiation, and (2) bone marrow support cells from non-irradiated CD45.1$^+$ mice. The error bars represent ±the standard error of the mean. All pairwise comparisons were computed using one-way ANOVA followed by Tukey's test. Asterisks represent statistically significant comparisons. P<0.01, ; p<0.001, *; p<0.0001, ****.

Figure 29:
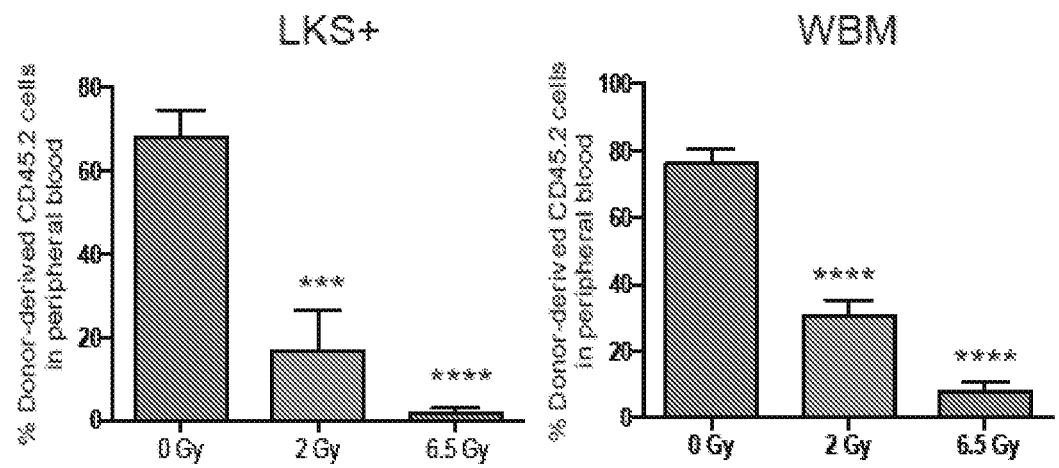

FIG. 29 is a pair of graphs showing the number of donor-derived (CD45.2$^+$) LKS$^+$ cells and the number of donor-derived (CD45.2$^+$) whole bone marrow cells in the peripheral blood of lethally-irradiated CD45.1$^+$ recipient mice four months after transplantation with a mixture of (1) 2000 sorted LKS$^+$ cells or 500,000 whole bone marrow cells obtained from a CD45.2$^+$ donor mouse three months after exposure to 0 Gy-, 2 Gy-, or 6.5 Gy-total body irradiation, and (2) bone marrow support cells from non-irradiated CD45.1$^+$ mice. The error bars represent ±the standard error of the mean. All pairwise comparisons were computed using one-way ANOVA followed by Tukey's test. Asterisks represent statistically significant comparisons. P<0.001, *; p<0.0001, **.

Figure 30:
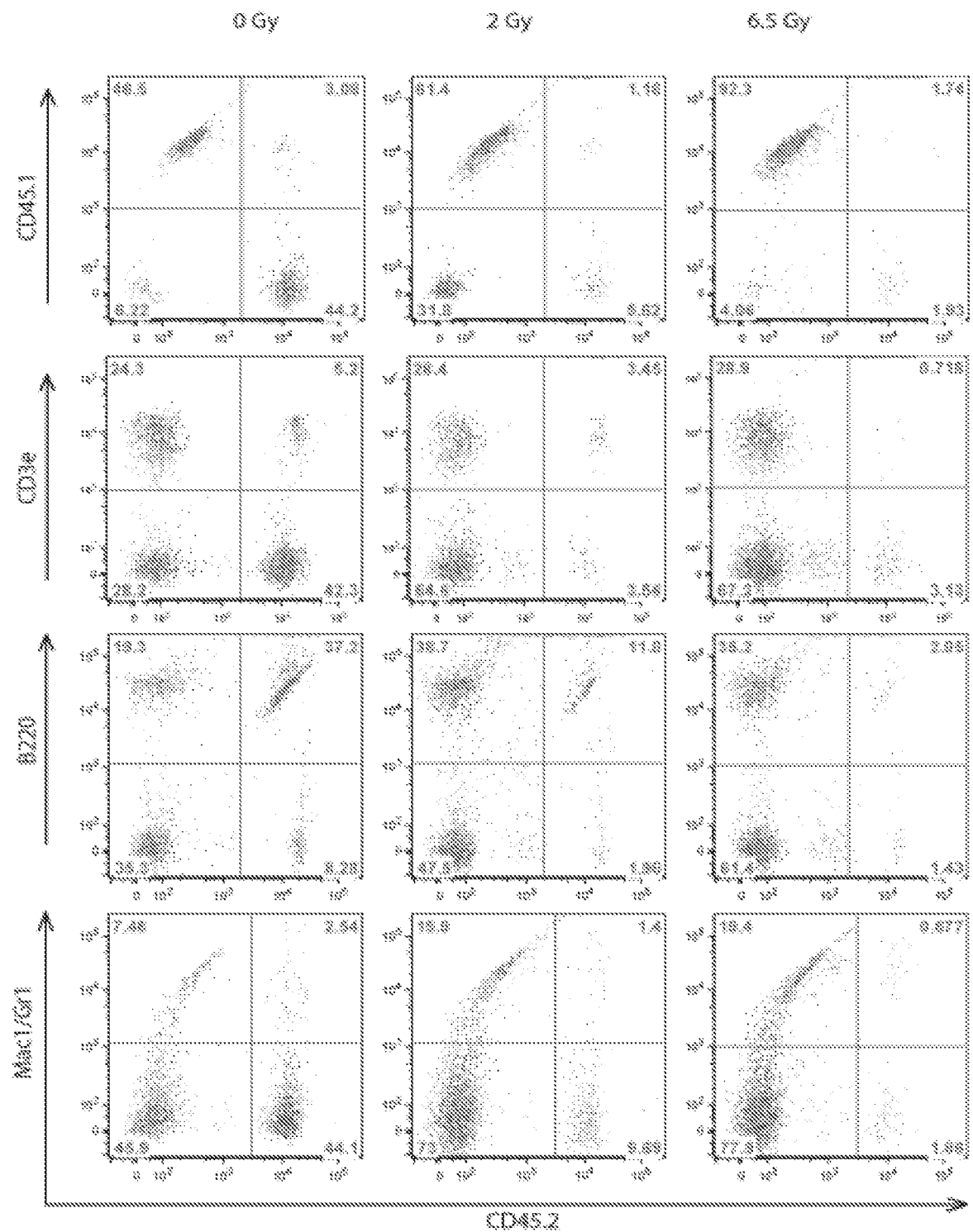

FIG. 30 is three sets of two-dimensional FACS profiles of total leukocytes, T-cells, B-cells, and myeloid cells (recipient leukocytes, CD45.1$^+$; T-cells, CD3e$^+$; B-cells, B220$^+$; and myeloid cells, Mac1/Gr1$^+$) (top to bottom, respectively) in the peripheral blood of recipient mice one month after transplantation with a mixture of (1) 2000 sorted LKS$^+$ cells collected from donor CD45.2$^+$ mice three months after exposure to 0 Gy-, 2 Gy-, or 6.5 Gy-total body irradiation (left to right, respectively) and (2) 250,000 CD45.1$^+$ bone marrow support cells (right panels, middle panels, and left panels, respectively).

Figure 31:
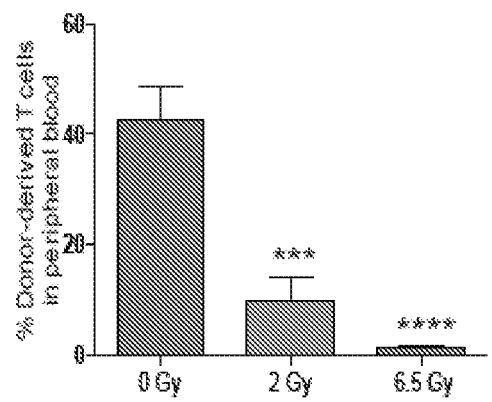

FIG. 31 is a graph showing the percentage of donor-derived CD45.2$^+$ T-cells in a recipient CD45.1$^+$ mouse one month after transplantation with a mixture of (1) 2000 sorted LKS$^+$ cells collected from donor CD45.2$^+$ mice three months after exposure to 0 Gy-, 2 Gy-, or 6.5 Gy-total body irradiation and (2) 250,000 CD45.1$^+$ bone marrow support cells. Error bars represent ±the standard error of the mean. All pairwise comparisons were computed using one-way ANOVA followed by Tukey's test. Asterisks represent significant comparisons. P<0.001, *; p<0.0001, **.

Figure 32:
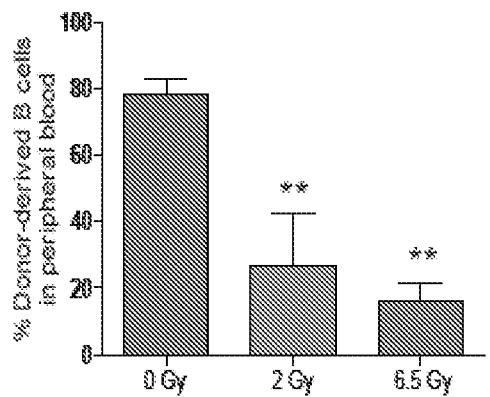

FIG. 32 is a graph showing the percentage of donor-derived CD45.2$^+$ B-cells in a recipient CD45.1$^+$ mouse one month after transplantation with a mixture of (1) 2000 sorted LKS$^+$ cells collected from donor CD45.2$^+$ mice three months after exposure to 0 Gy-, 2 Gy-, or 6.5 Gy-total body irradiation and (2) 250,000 CD45.1$^+$ bone marrow support cells. Error bars represent ±the standard error of the mean. All pairwise comparisons were computed using one-way ANOVA followed by Tukey's test. Asterisks represent significant comparisons. P<0.01, **.

Figure 33:
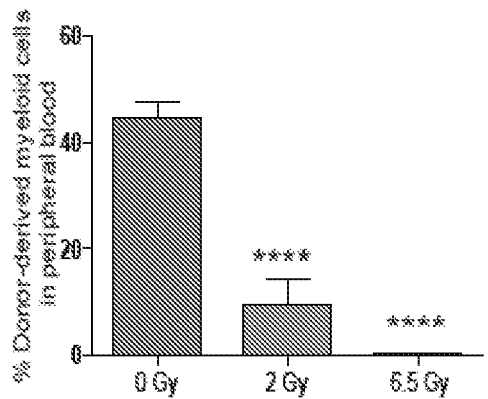

FIG. 33 is a graph showing the percentage of donor-derived CD45.2$^+$ myeloid cells in a recipient CD45.1$^+$ mouse one month after transplantation with a mixture of (1) 2000 sorted LKS$^+$ cells collected from donor CD45.2$^+$ mice three months after exposure to 0 Gy-, 2 Gy-, or 6.5 Gy-total body irradiation and (2) 250,000 CD45.1$^+$ bone marrow support cells. Error bars represent ±the standard error of the mean. All pairwise comparisons were computed using one-way ANOVA followed by Tukey's test. Asterisks represent significant comparisons. P<0.0001, ****.

Figure 34:
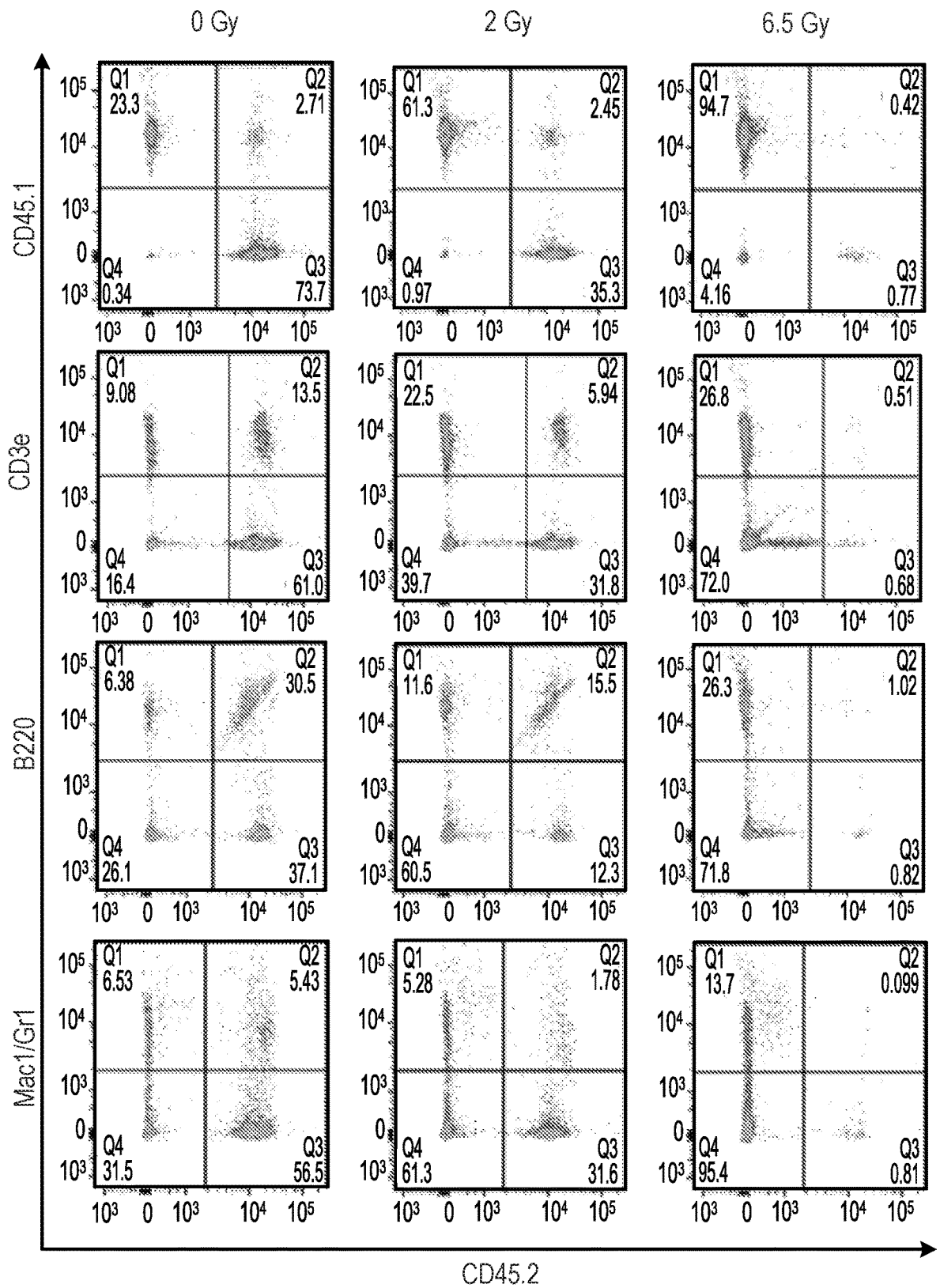

FIG. 34 is three sets of two-dimensional FACS profiles of total leukocytes, T-cells, B-cells, and myeloid cells (recipient leukocytes, CD45.1$^+$; T-cells, CD3e; B-cells, B220$^+$; and myeloid cells, Mac1/Gr1$^+$) (top to bottom, respectively) in the peripheral blood of recipient CD45.1$^+$ mice four months after transplantation with a mixture of (1) 2000 sorted LKS$^+$ cells collected from donor CD45.2$^+$ mice three months after exposure to 0 Gy-, 2 Gy-, or 6.5 Gy-total body irradiation (left to right, respectively) and (2) 250,000 CD45.1+ bone marrow support cells.

Figure 35:
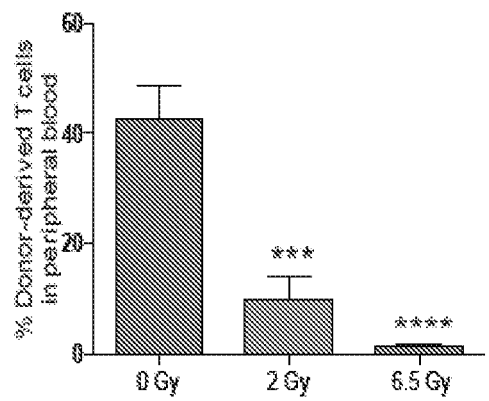

FIG. 35 is a graph showing the percentage of donor-derived CD45.2$^+$ T-cells in a recipient CD45.1$^+$ mouse four months after transplantation with a mixture of (1) 2000 sorted LKS$^+$ cells collected from donor CD45.2$^+$ mice three months after exposure to 0 Gy-, 2 Gy-, or 6.5 Gy-total body irradiation and (2) 250,000 CD45.1$^+$ bone marrow support cells. Error bars represent ±the standard error of the mean. All pairwise comparisons were computed using one-way ANOVA followed by Tukey's test. Asterisks represent significant comparisons. P<0.001, *; p<0.0001, **.

Figure 36:
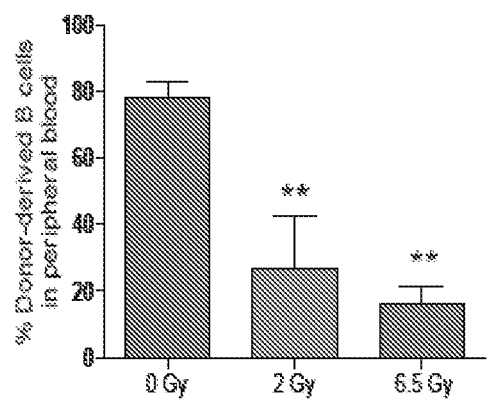

FIG. 36 is a graph showing the percentage of donor-derived CD45.2$^+$ B-cells in a recipient CD45.1$^+$ mouse four months after transplantation with a mixture of (1) 2000 sorted LKS$^+$ cells collected from donor CD45.2$^+$ mice three months after exposure to 0 Gy-, 2 Gy-, or 6.5 Gy-total body irradiation and (2) 250,000 CD45.1$^+$ bone marrow support cells. Error bars represent ±the standard error of the mean. All pairwise comparisons were computed using one-way ANOVA followed by Tukey's test. Asterisks represent significant comparisons. P<0.01, **.

Figure 37:
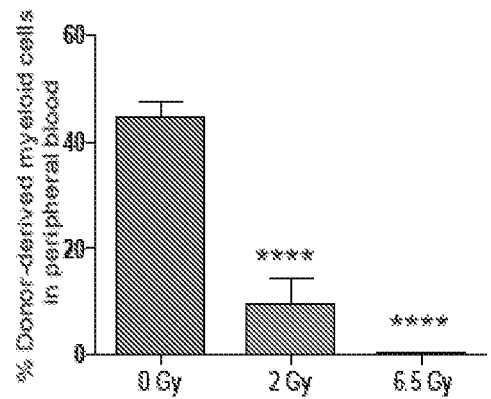

FIG. 37 is a graph showing the percentage of donor-derived CD45.2$^+$ myeloid cells in a recipient CD45.1$^+$ mouse four months after transplantation with a mixture of (1) 2000 sorted LKS$^+$ cells collected from donor CD45.2$^+$ mice three months after exposure to 0 Gy-, 2 Gy-, or 6.5 Gy-total body irradiation and (2) 250,000 CD45.1$^+$ bone marrow support cells. Error bars represent ±the standard error of the mean. All pairwise comparisons were computed using one-way ANOVA followed by Tukey's test. Asterisks represent significant comparisons. P<0.0001, ****.

Figure 38:
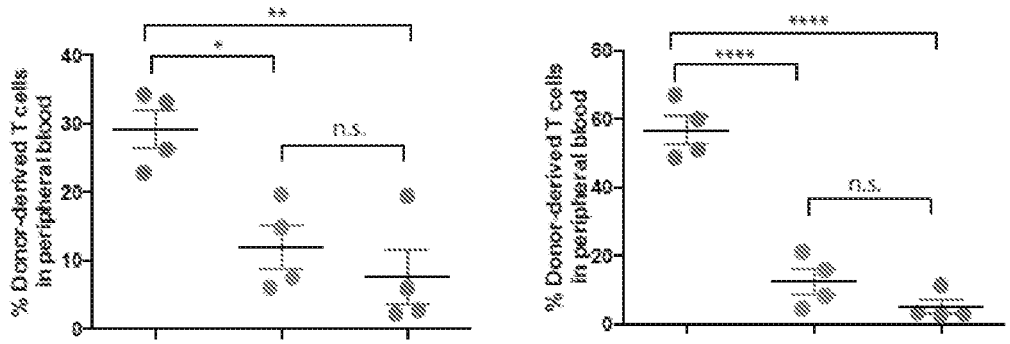

FIG. 38 is a pair of graphs of the percentage of donor-derived CD45.2$^+$ T-cells in the peripheral blood of a recipient CD45.1$^+$ mouse one month (left graph) or four months (right graph) after transplantation with a mixture of (1) 500,000 bone marrow support cells from a donor CD45.2$^+$ mouse three months after exposure to 0 Gy-, 2 Gy-, or 6.5 Gy-total body irradiation and (2) 250,000 CD45.1$^+$ bone marrow support cells. Asterisks represent statistically significant comparisons. One-way ANOVA followed by Tukey's test for multiple comparisons was used to assess statistical significance. P<0.05, *; p<0.01, ; p<0.0001, **; not significant, n.s.

Figure 39:
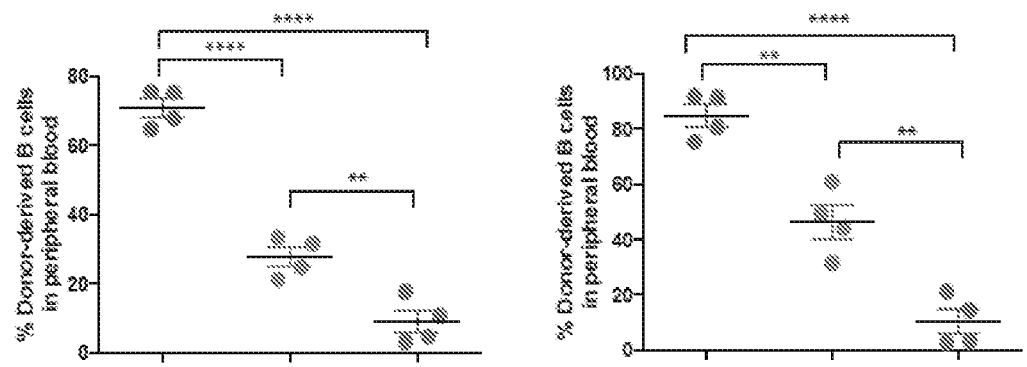

FIG. 39 is a pair of graphs of the percentage of donor-derived CD45.2$^+$ B-cells in the peripheral blood of a recipient CD45.1$^+$ mouse one month (left graph) or four months (right graph) after transplantation with a mixture of (1) 500,000 whole bone marrow cells from a donor CD45.2$^+$ mouse three months after exposure to 0 Gy-, 2 Gy-, or 6.5 Gy-total body irradiation and (2) 250,000 CD45.1$^+$ bone marrow support cells. Asterisks represent statistically significant comparisons. One-way ANOVA followed by Tukey's test for multiple comparisons was used to assess statistical significance. P<0.01, ; p<0.0001, **.

Figure 40:
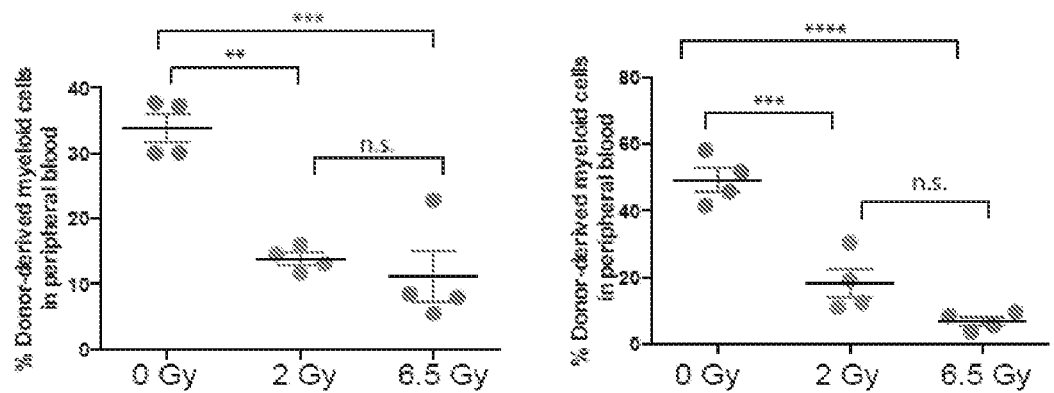

FIG. 40 is a pair of graphs of the percentage of donor-derived CD45.2$^+$ myeloid cells in the peripheral blood of a recipient CD45.1$^+$ mouse one month (left graph) or four months (right graph) after transplantation with a mixture of (1) 500,000 whole bone marrow cells from a donor CD45.2$^+$ mouse three months after exposure to 0 Gy-, 2 Gy-, or 6.5 Gy-total body irradiation and (2) 250,000 CD45.1$^+$ bone marrow support cells. Asterisks represent statistically significant comparisons. One-way ANOVA followed by Tukey's test for multiple comparisons was used to assess statistical significance. P<0.01, ; p<0.001, *; p<0.0001, ****; not significance, n.s.

Figure 41:
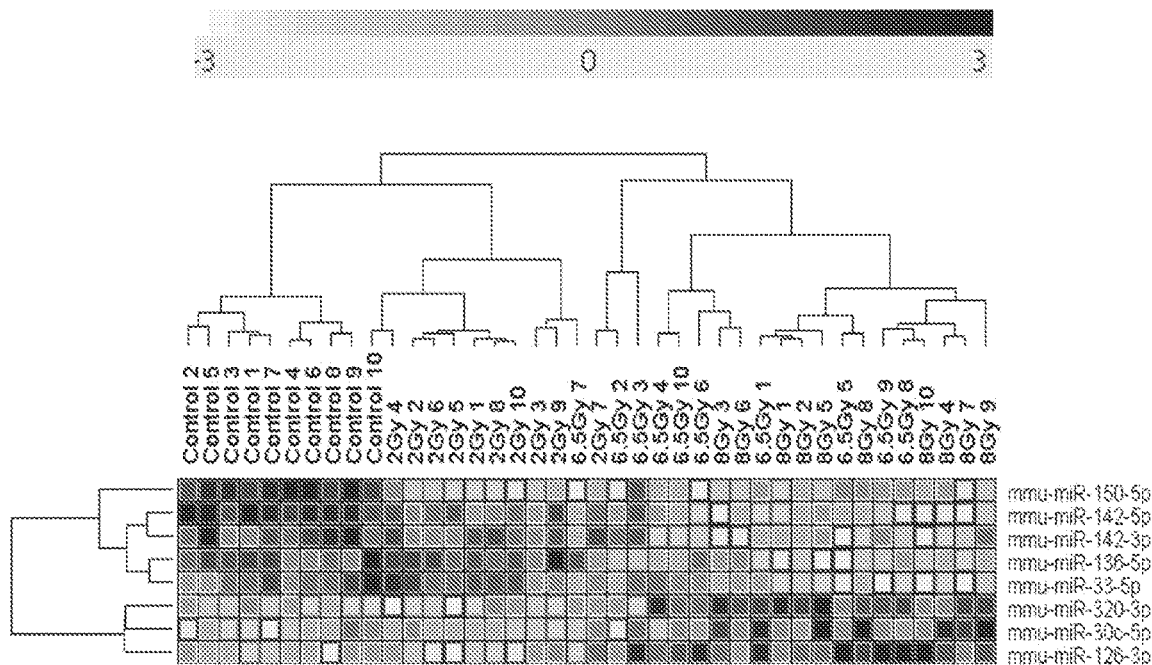

FIG. 41 is a heatmap showing the changes in expression levels of serum miRNAs that are significantly altered in samples from mice exposed to 2 Gy-, 6.5 Gy-, or 8 Gy-total body irradiation as compared to non-irradiated controls (0 Gy). Hierarchical clustering was performed to depict the relationship between the samples.

Figure 42:
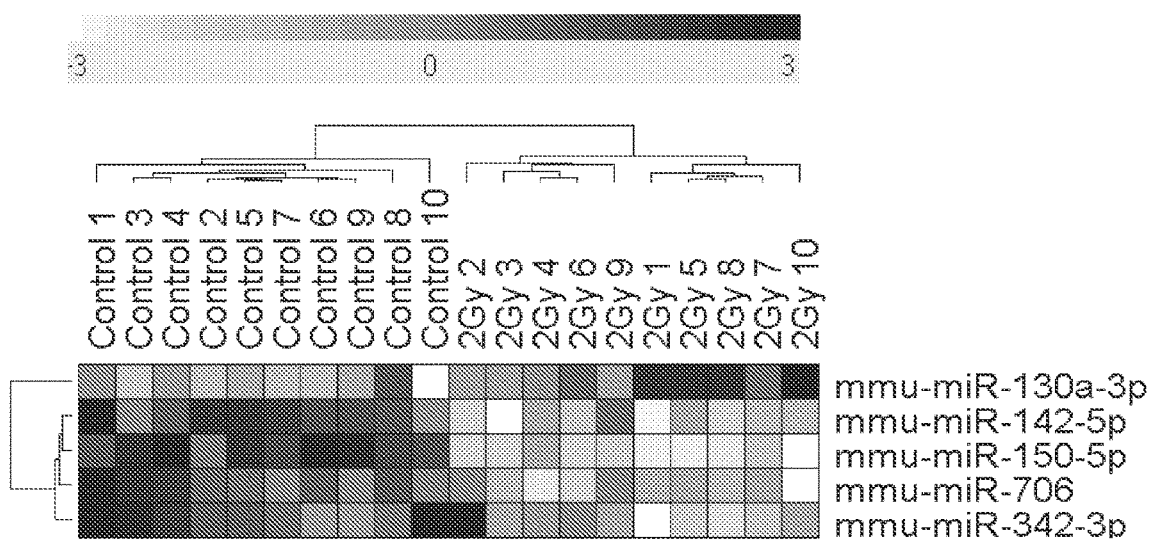

FIG. 42 is a heatmap showing the changes in expression levels of serum miRNAs that are significantly altered in samples from mice exposed to 2 Gy-total body irradiation as compared to non-irradiated controls (0 Gy). Hierarchical clustering was performed to depict the relationship between the samples. Normalization of profiling data was performed by computing the global mean of 170 miRNAs expressed in all samples.

Figure 43:
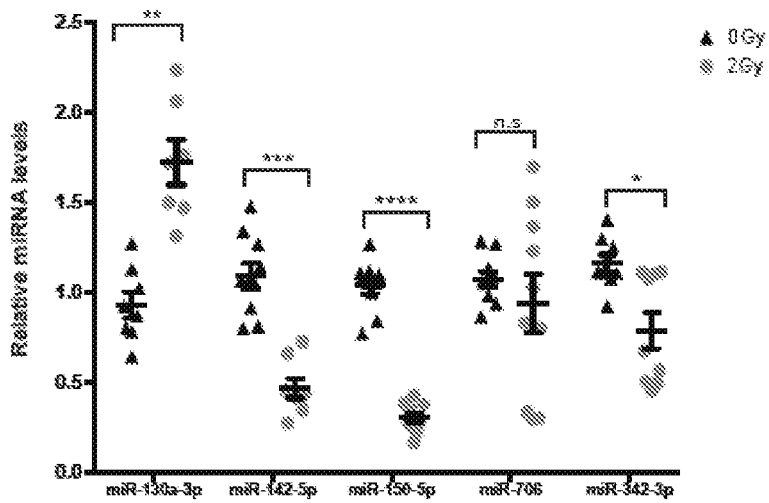

FIG. 43 is a graph showing the relative levels of mouse miR-130a-3p, miR-142-5p, miR-150-5p, miR-706, and miR-342-3p in serum samples harvested from mice 24 hours after exposure to 0 Gy- or 2 Gy-whole body irradiation. The data are representative of three experiments. Error bars represent ±the standard error of the mean. Asterisks represent statistically significant comparisons. Statistical significance was assessed using two-tailed Student's t test. P<0.05, *; p<0.01, ; p<0.001, *; p<0.0001, ****; not significant, n.s.

Figure 44:
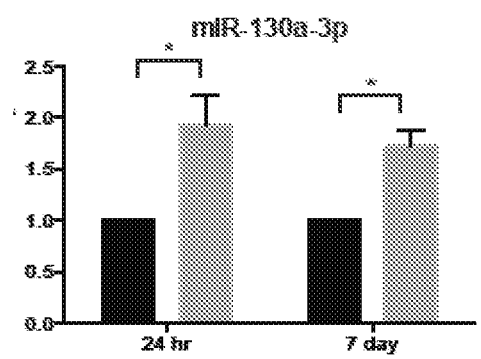

FIG. 44 is a graph showing the relative levels of mouse miR-130a-3p in serum samples harvested from mice 24 hours or 7 days after exposure to 0 Gy- or 2 Gy-total body irradiation. The data are representative of three experiments. Error bars represent ±the standard error of the mean. Asterisks represent statistically significant comparisons. Statistical significance was assessed using two-tailed Student's t test. P<0.05, *.

Figure 45:
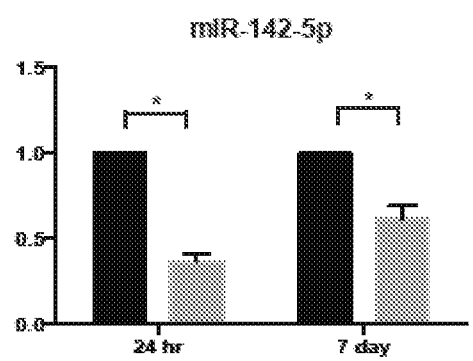

FIG. 45 is a graph showing the relative levels of mouse miR-142-5p in serum samples harvested from mice 24 hours or 7 days after exposure to 0 Gy- or 2 Gy-total body irradiation. The data are representative of three experiments. Error bars represent ±the standard error of the mean. Asterisks represent statistically significant comparisons. Statistical significance was assessed using two-tailed Student's t test. P<0.05, *.

Figure 46:
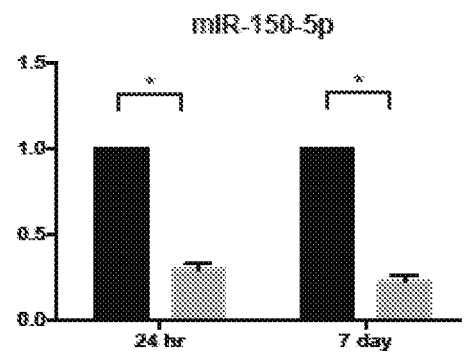

FIG. 46 is a graph showing the relative levels of mouse miR-150-5p in serum samples harvested from mice 24 hours or 7 days after exposure to 0 Gy- or 2 Gy-total body irradiation. The data are representative of three experiments. Error bars represent ±the standard error of the mean. Asterisks represent statistically significant comparisons. Statistical significance was assessed using two-tailed Student's t test. P<0.05, *.

Figure 47:
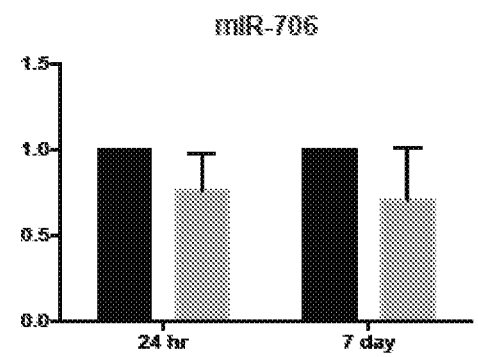

FIG. 47 is a graph showing the relative levels of mouse miR-706 in serum samples harvested from mice 24 hours or 7 days after exposure to 0 Gy- or 2 Gy-total body irradiation. The data are representative of three experiments. Error bars represent ±the standard error of the mean.

Figure 48:
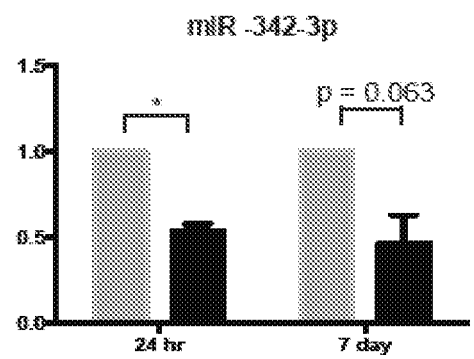

FIG. 48 is a graph showing the relative levels of mouse miR-342-3p in serum samples harvested from mice 24 hours or 7 days after exposure to 0 Gy- or 2 Gy-total body irradiation. The data are representative of three experiments. Error bars represent ±the standard error of the mean. The asterisk represents a statistically significant comparison. Statistical significance was assessed using two-tailed Student's t test. P<0.05, *.

Figure 49:
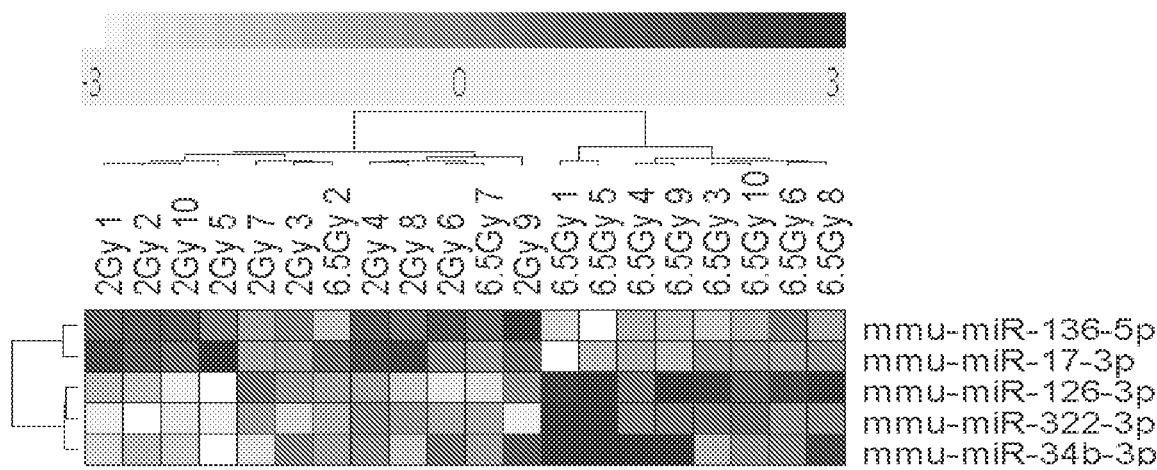

FIG. 49 is a heatmap showing the changes in expression levels of miRNAs that are significantly altered in serum samples from mice exposed to 6.5 Gy-total body irradiation as compared to mice exposed to 2 Gy-total body irradiation. Hierarchical clustering was performed to depict the relationship between the samples. Normalization of profiling data was performed by computing the global mean of 170 miRNAs expressed in all serum samples.

Figure 50:
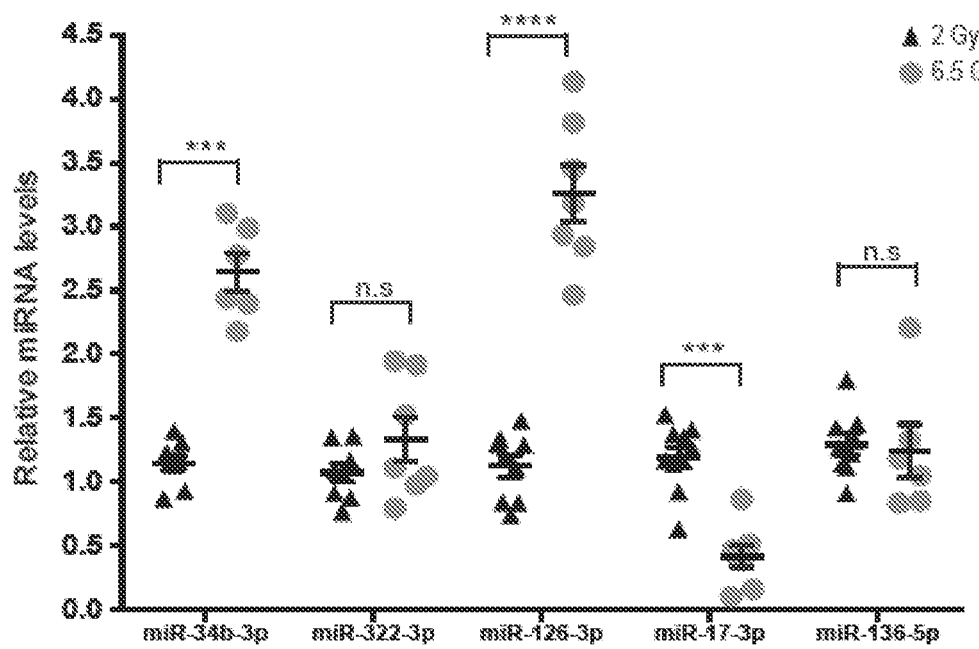

FIG. 50 is a graph showing the relative levels of mouse miR-34b-3p, miR-322-3p, miR-126-3p, miR-17-3p, and miR-136-5p in serum samples harvested from mice 24 hours after exposure to 2 Gy- or 6.5 Gy-whole body irradiation. The data are representative of three experiments. Error bars represent ±the standard error of the mean. Asterisks represent statistically significant comparisons. Statistical significance was assessed using two-tailed Student's t test. P<0.001, *; p<0.0001, **; not significant, n.s.

Figure 51:
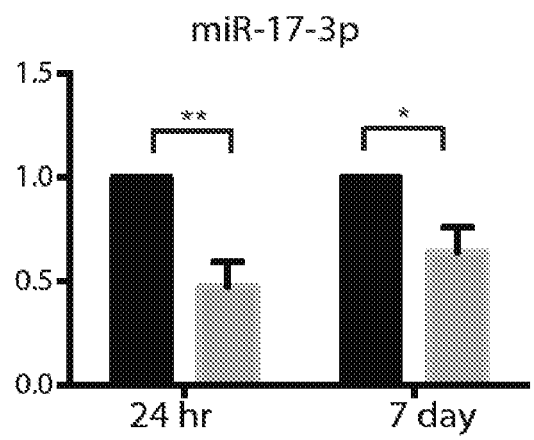

FIG. 51 is a graph showing the relative levels of mouse miR-17-3p in serum samples harvested from mice 24 hours or 7 days after exposure to 2 Gy- or 6.5 Gy-total body irradiation. The data are representative of three experiments. Error bars represent ±the standard error of the mean. Statistical significance was assessed using two-tailed Student's t test. P<0.01, **; p<0.05, *.

Figure 52:
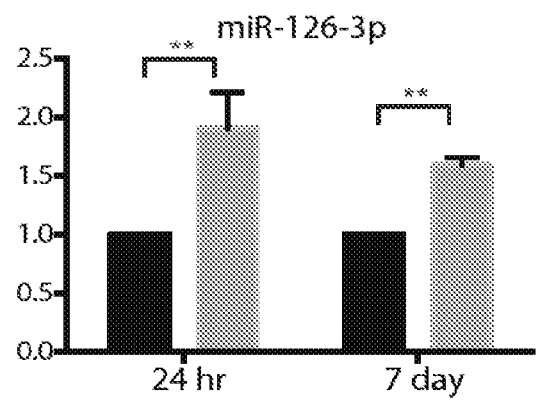

FIG. 52 is a graph showing the relative levels of mouse miR-126-3p in serum samples harvested from mice 24 hours or 7 days after exposure to 2 Gy- or 6.5 Gy-total body irradiation. The data are representative of three experiments. Error bars represent ±the standard error of the mean. Statistical significance was assessed using two-tailed Student's t test. P<0.01, **.

Figure 53:
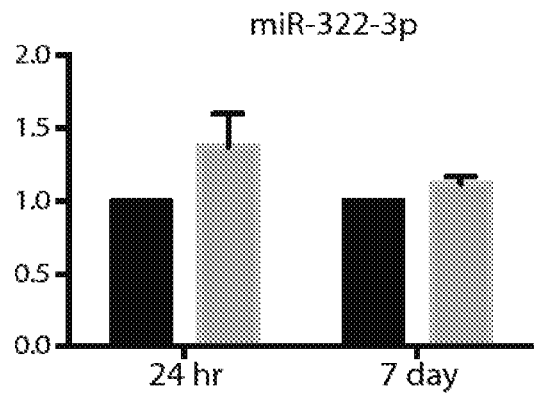

FIG. 53 is a graph showing the relative levels of mouse miR-322-3p in serum samples harvested from mice 24 hours or 7 days after exposure to 2 Gy- or 6.5 Gy-total body irradiation. The data are representative of three experiments. Error bars represent ±the standard error of the mean.

Figure 54:
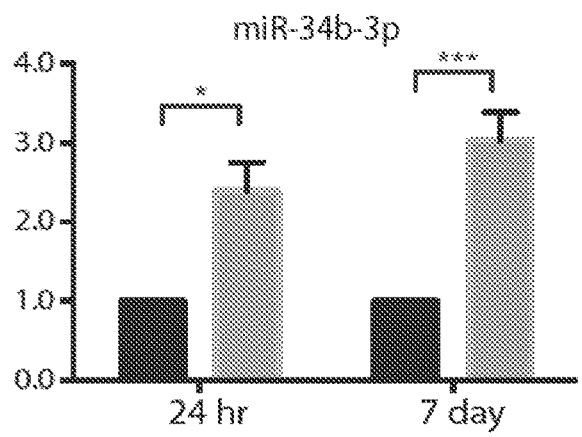

FIG. 54 is a graph showing the relative levels of mouse miR-34b-3p in serum samples harvested from mice 24 hours or 7 days after exposure to 2 Gy- or 6.5 Gy-total body irradiation. The data are representative of three experiments. Error bars represent ±the standard error of the mean. Statistical significance was assessed using two-tailed Student's t test. P<0.001, ***; p<0.05, *.

Figure 55:
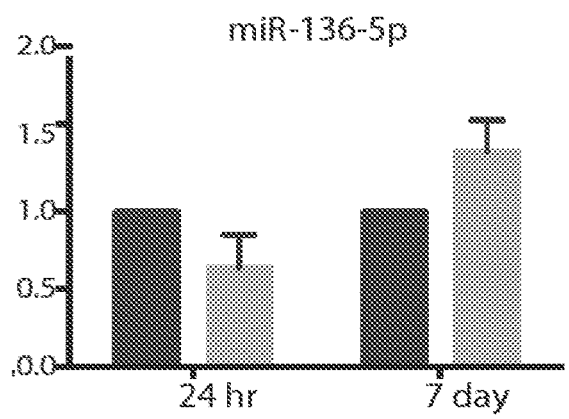

FIG. 55 is a graph showing the relative levels of mouse miR-136-5p in serum samples harvested from mice 24 hours or 7 days after exposure to 2 Gy- or 6.5 Gy-total body irradiation. The data are representative of three experiments. Error bars represent ±the standard error of the mean.

Figure 56:
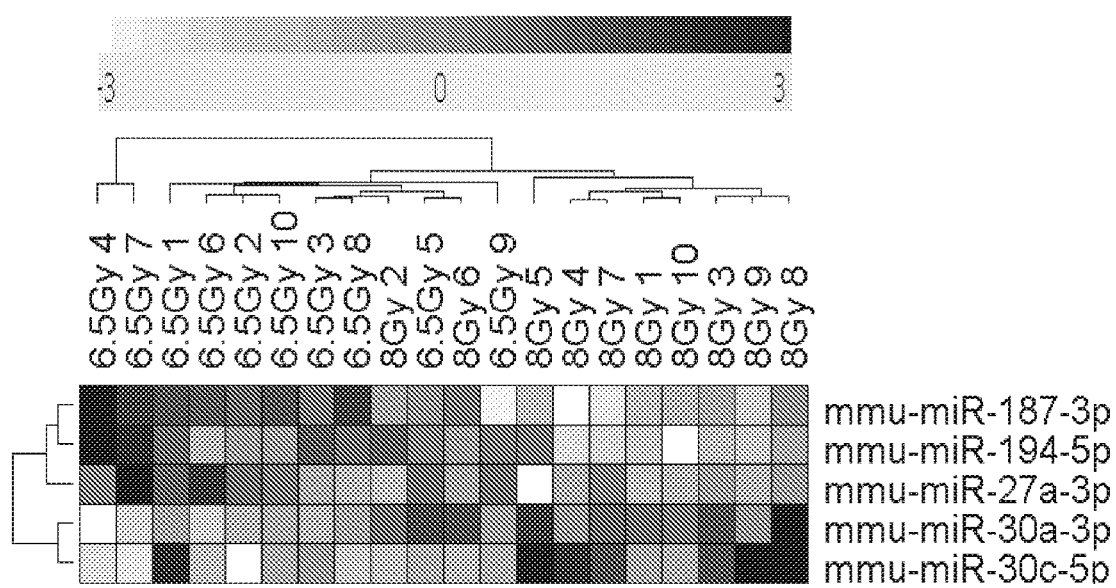

FIG. 56 is a heatmap showing the changes in the expression levels of miRNAs that are significantly altered in serum samples from mice exposed to 8.0 Gy-total body irradiation as compared to mice exposed to 6.5 Gy-total body irradiation. Hierarchical clustering was performed to depict the relationship between the samples. Normalization of profiling data was performed by computing the global mean of 170 miRNAs expressed in all serum samples.

Figure 57:
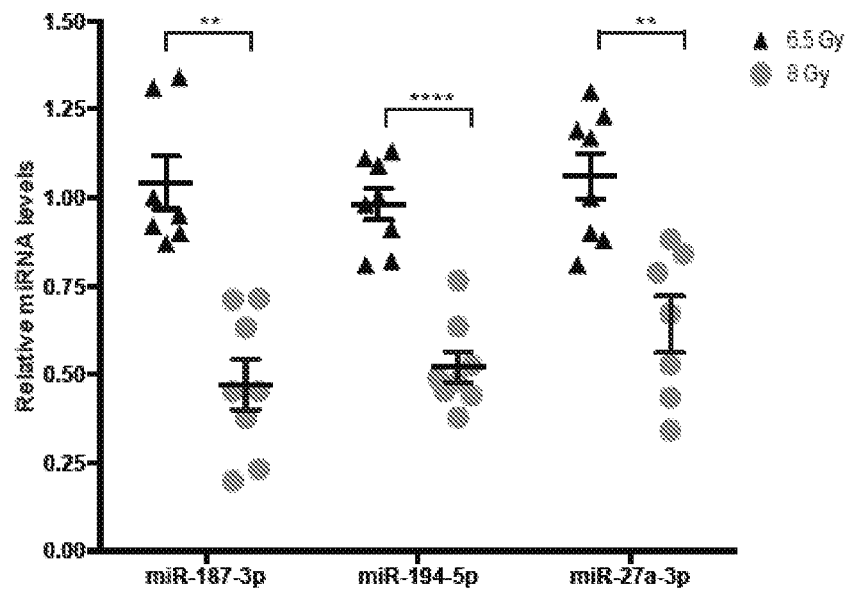

FIG. 57 is a graph showing the relative levels of mouse miR-187-3p, miR-194-5p, and miR-27a-3p in serum samples harvested from mice 24 hours after exposure to 6.5 Gy- or 8 Gy-whole body irradiation. The data are representative of three experiments. Error bars represent ±the standard error of the mean. Asterisks represent statistically significant comparisons. Statistical significance was assessed using two-tailed Student's t test. $P<0.01$, ; $p<0.001$, **.

Figure 58:
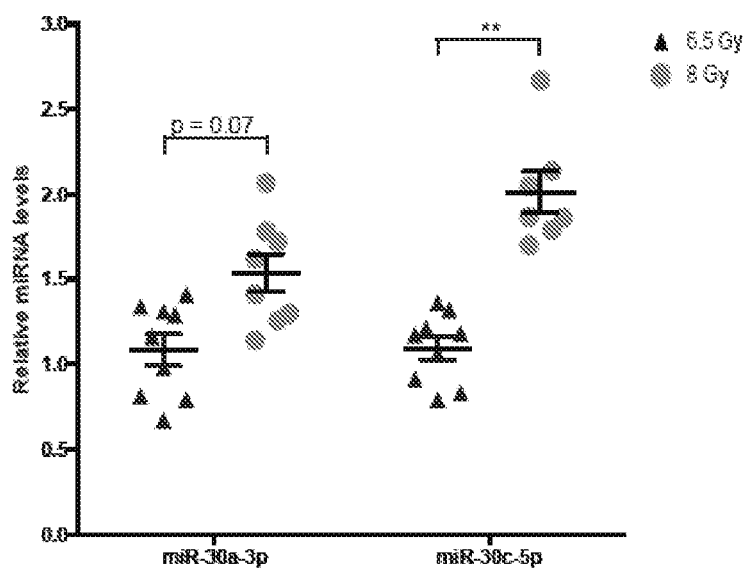

FIG. 58 is a graph showing the relative levels of mouse miR-30a-3p and miR-30c-5p in serum samples harvested from mice 24 hours after exposure to 6.5 Gy- or 8 Gy-whole body irradiation. The data are representative of three experiments. Error bars represent ±the standard error of the mean. The asterisk represents a statistically significant comparison. Statistical significance was assessed using two-tailed Student's t test. $P<0.01$, **.

Figure 59:
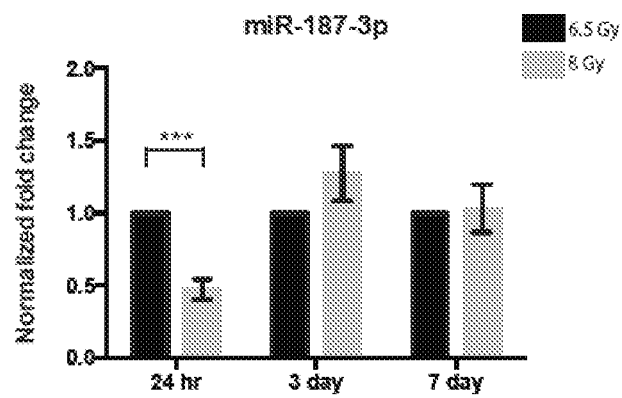

FIG. 59 is a graph showing the relative levels of mouse miR-187-3p in samples harvested from mice 24 hours, 3 days, or 7 days after exposure to 6.5 Gy- or 8 Gy-total body irradiation. The data are representative of three experiments. Error bars represent ±the standard error of the mean. The asterisk represents a statistically significant comparison. Statistical significance was assessed using two-tailed Student's t test. $P<0.001$, ***.

Figure 60:
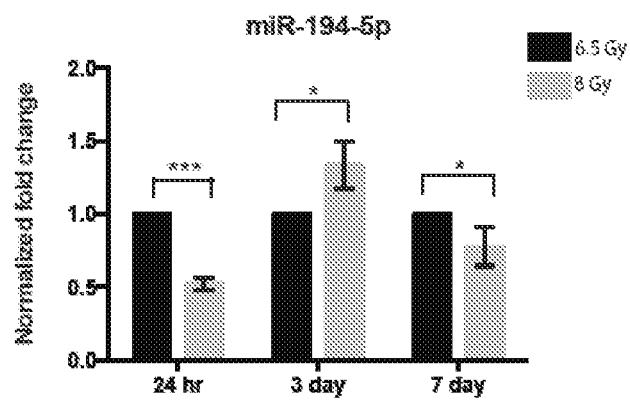

FIG. 60 is a graph showing the relative levels of mouse miR-194-5p in serum samples harvested from mice 24 hours, 3 days, or 7 days after exposure to 6.5 Gy- or 8 Gy-total body irradiation. The data are representative of three experiments. Error bars represent ±the standard error of the mean. Asterisks represent statistically significant comparisons. Statistical significance was assessed using two-tailed Student's t test. $P<0.05$, *; $p<0.001$, ***.

Figure 61:
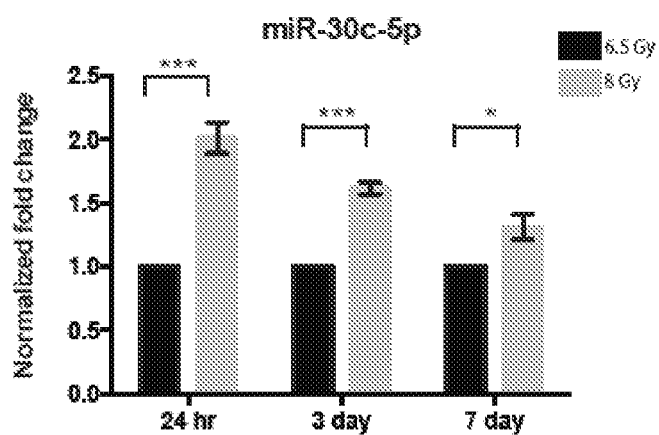

FIG. 61 is a graph showing the relative levels of mouse miR-30c-5p in serum samples harvested from mice 24 hours, 3 days, or 7 days after exposure to 6.5 Gy- or 8 Gy-total body irradiation. The data are representative of three experiments. Error bars represent ±the standard error of the mean. Asterisks represent statistically significant comparisons. Statistical significance was assessed using two-tailed Student's t test. $P<0.05$, *; $P<0.001$, ***.

Figure 62:
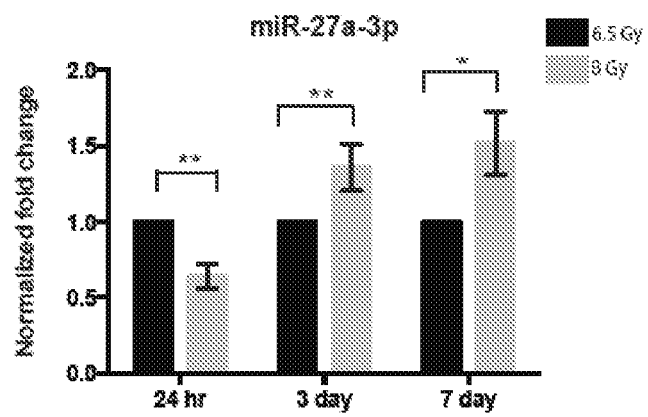

FIG. 62 is a graph showing the relative levels of mouse miR-27a-3p in samples harvested from mice 24 hours, 3 days, or 7 days after exposure to 6.5 Gy- or 8 Gy-total body irradiation. The data are representative of three experiments. Error bars represent ±the standard error of the mean. Asterisks represent statistically significant comparisons. Statistical significance was assessed using two-tailed Student's t test. $P<0.05$, *; $p<0.01$, **.

Figure 63:
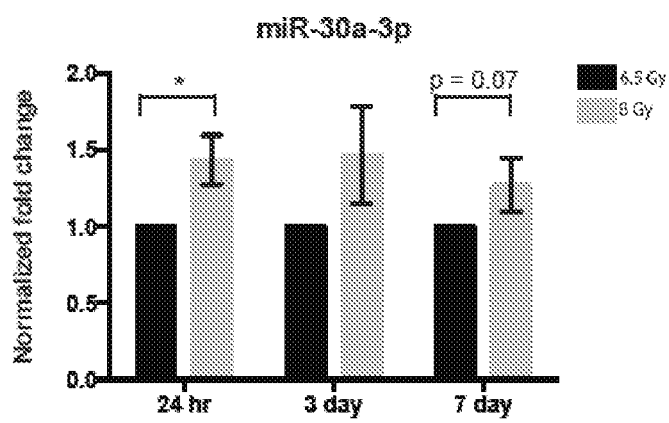

FIG. 63 is a graph showing the relative levels of mouse miR-30a-3p in serum samples harvested from mice 24 hours, 3 days, or 7 days after exposure to 6.5 Gy- or 8 Gy-total body irradiation. The data are representative of three experiments. Error bars represent ±the standard error of the mean. The asterisk represents a statistically significant comparison. Statistical significance was assessed using two-tailed Student's t test. $P<0.05$, *.

Figure 64:
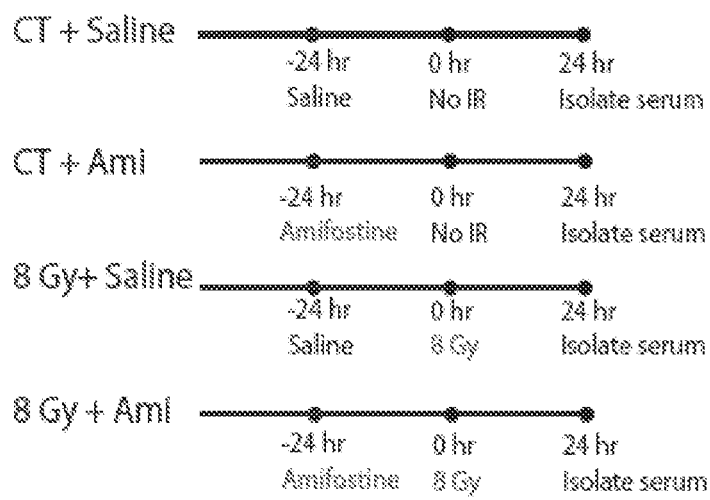

FIG. 64 is a schematic of an experiment where mice are intraperitoneally administered saline or amifostine (250 mg/kg) 24 hours prior to exposure to 0 Gy- to 8 Gy-total body irradiation, serum collected from the mice 24 hours later, and the expression levels of serum miRNAs determined.

Figure 65:
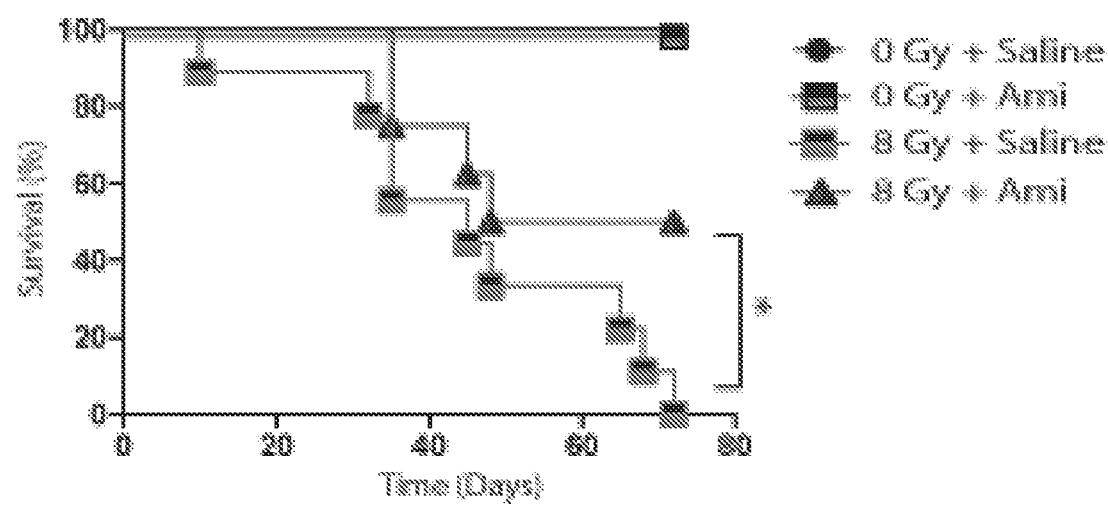

FIG. 65 is a Kaplan-Meier survival curve of mice treated with saline 24 hours prior to exposure to 0 Gy- to 8 Gy-total body irradiation, or mice treated with amifostine (250 mg/kg) 24 hours prior to exposure to 0 Gy- to 8 Gy-total body irradiation. The asterisk represents a statistically significant comparison. $P>0.05$, *.

Figure 66:
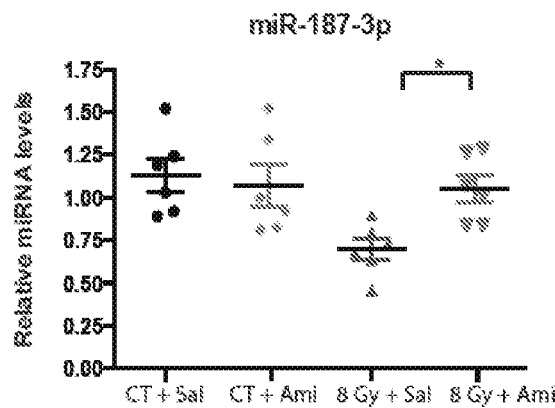

FIG. 66 is a graph showing the levels of mouse miR-187-3p in serum from mice treated with saline 24 hours prior to exposure to 0 Gy- or 8 Gy-total body irradiation, or in serum from mice treated with amifostine (250 mg/kg) 24 hours prior to exposure to 0 Gy- to 8 Gy-total body irradiation. Serum was collected 48 hours after administration of saline or amifostine to the mice. The data shown are the mean±the standard error of the mean. Statistical significance was measured by one-way ANOVA followed by Dunnett's test. The asterisk identifies a statistically significant comparison. $P<0.05$, *.

Figure 67:
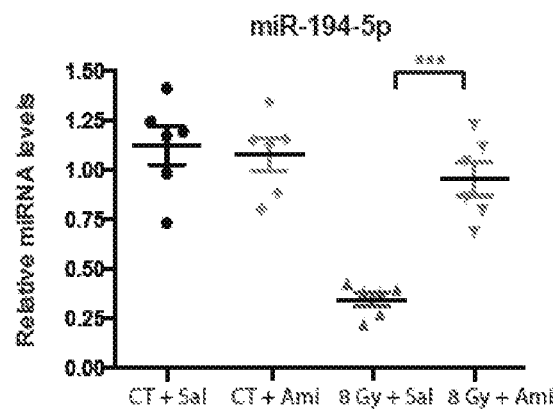

FIG. 67 is a graph showing the levels of mouse miR-194-5p in serum from mice treated with saline 24 hours prior to exposure to 0 Gy- or 8 Gy-total body irradiation, or mice treated with amifostine (250 mg/kg) 24 hours prior to exposure to 0 Gy- to 8 Gy-total body irradiation. Serum was collected 48 hours after administration of saline or amifostine to the mice. The data shown are the mean±the standard error of the mean. Statistical significance was measured by one-way ANOVA followed by Dunnett's test. The asterisk identifies a statistically significant comparison. $P<0.001$, ***.

Figure 68:
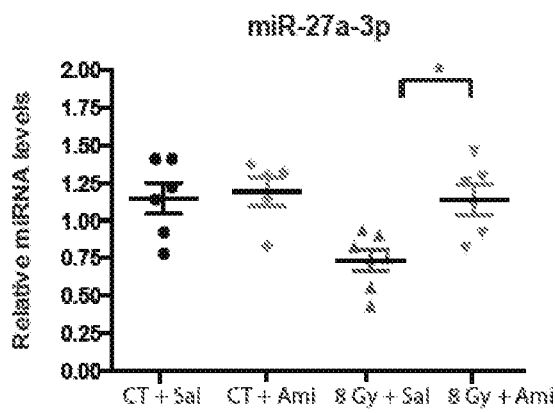

FIG. 68 is a graph showing the levels of mouse miR-27a-3p in serum from mice treated with saline 24 hours prior to exposure to 0 Gy- or 8 Gy-total body irradiation, or mice treated with amifostine (250 mg/kg) 24 hours prior to exposure to 0 Gy- to 8 Gy-total body irradiation. Serum was collected 48 hours after administration of saline or amifostine to the mice. The data shown are the mean±the standard error of the mean. Statistical significance was measured by one-way ANOVA followed by Dunnett's test. The asterisk identifies a statistically significant comparison. $P<0.05$, *.

Figure 69:
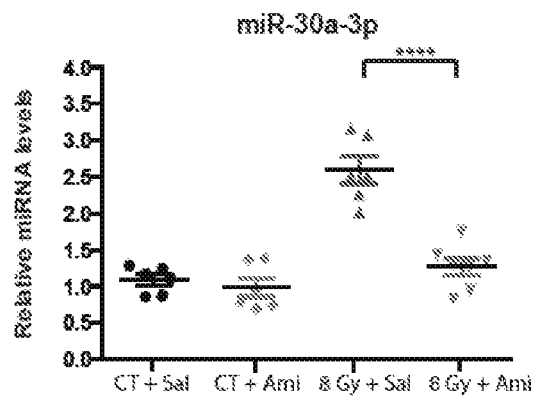

FIG. 69 is a graph showing the levels of mouse miR-30a-3p in serum from mice treated with saline 24 hours prior to exposure to 0 Gy- or 8 Gy-total body irradiation, or mice treated with amifostine (250 mg/kg) 24 hours prior to exposure to 0 Gy- to 8 Gy-total body irradiation. Serum was collected 48 hours after administration of saline or amifostine to the mice. The data shown are the mean±the standard error of the mean. Statistical significance was measured by one-way ANOVA followed by Dunnett's test. The asterisk identifies a statistically significant comparison. $P<0.0001$, ****.

Figure 70:
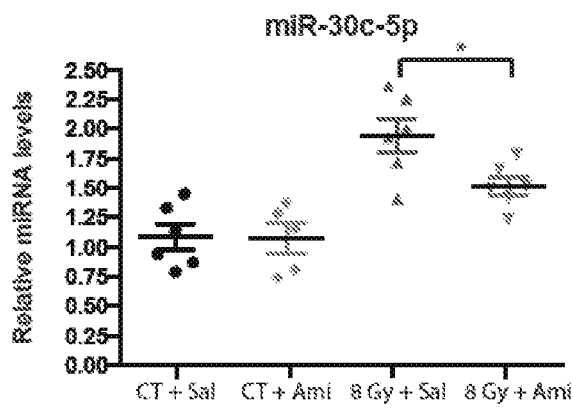

FIG. 70 is a graph showing the levels of mouse miR-30c-5p in serum from mice treated with saline 24 hours prior to exposure to 0 Gy- or 8 Gy-total body irradiation, or mice treated with amifostine (250 mg/kg) 24 hours prior to exposure to 0 Gy- to 8 Gy-total body irradiation. Serum was collected 48 hours after administration of saline or amifostine to the mice. The data shown are the mean±the standard error of the mean. Statistical significance was measured by one-way ANOVA followed by Dunnett's test. The asterisk identifies a statistically significant comparison. $P<0.05$, *.

Figure 71:
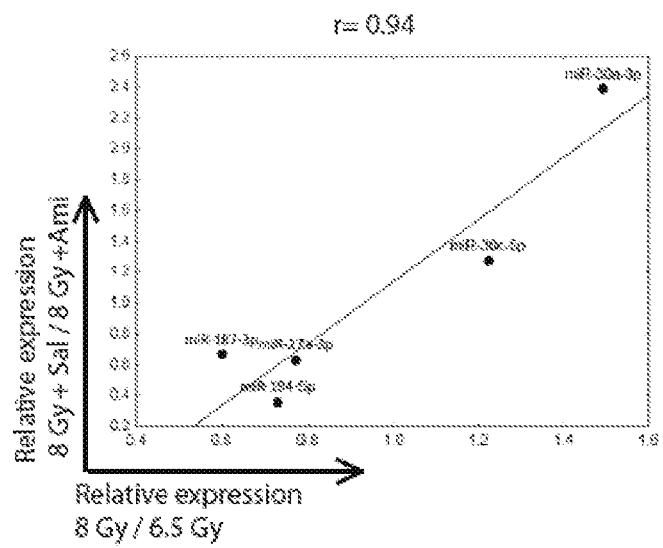

FIG. 71 is a graph showing the comparison of the relative expression ratios of miRNAs in serum samples from mice exposed to 6.5 Gy- or 8.0 Gy-from two separate experiments (the data in FIGS. 56-53 and FIGS. 59-65).

Figure 72:
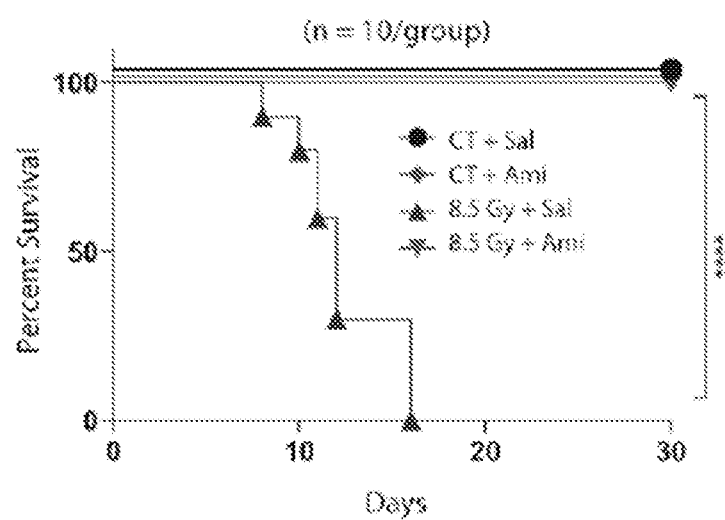

FIG. 72 is a Kaplan-Meier survival curve of mice treated with saline 45 minutes prior to exposure to 0 Gy- to 8.5 Gy-total body irradiation, or mice treated with amifostine (200 mg/kg) 45 minutes prior to exposure to 0 Gy- to 8.5

Gy-total body irradiation. Ten mice were included in each group. The asterisk represents a statistically significant comparison. P<0.0001, ****.

Figure 73:
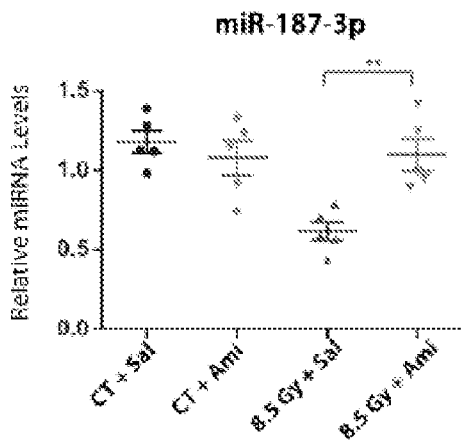

FIG. 73 is a graph showing the levels of mouse miR-187-3p in serum from mice exposed to 0 Gy- or 8.5 Gy-total body irradiation 45 minutes after administration of saline or 200 mg/kg amifostine. The mean±the standard error of the mean are shown. The asterisk represents a statistically significant comparison. P<0.01, **. Statistical significance was measured by one-way ANOVA followed by Dunnett's test.

Figure 74:
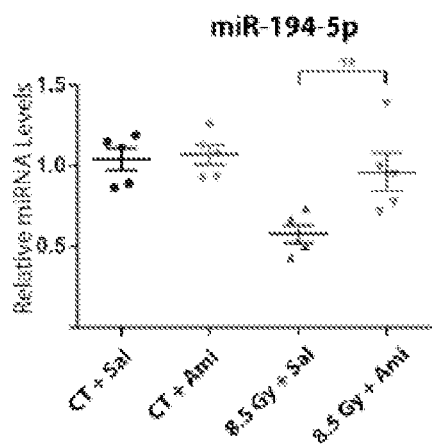

FIG. 74 is a graph showing the levels of mouse miR-194-5p in serum from mice exposed to 0 Gy- or 8.5 Gy-total body irradiation 45 minutes after administration of saline or 200 mg/kg amifostine. The mean±the standard error of the mean are shown. The asterisk represents a statistically significant comparison. P<0.01, **. Statistical significance was measured by one-way ANOVA followed by Dunnett's test.

Figure 75:
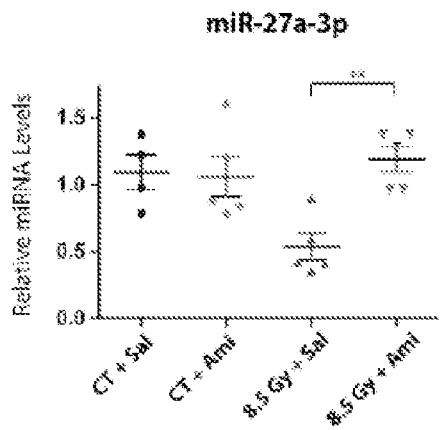

FIG. 75 is a graph showing the levels of mouse miR-27a-3p in serum from mice exposed to 0 Gy- or 8.5 Gy-total body irradiation 45 minutes after administration of saline or 200 mg/kg amifostine. The mean±the standard error of the mean are shown. The asterisk represents a statistically significant comparison. P<0.01, **. Statistical significance was measured by one-way ANOVA followed by Dunnett's test.

Figure 76:
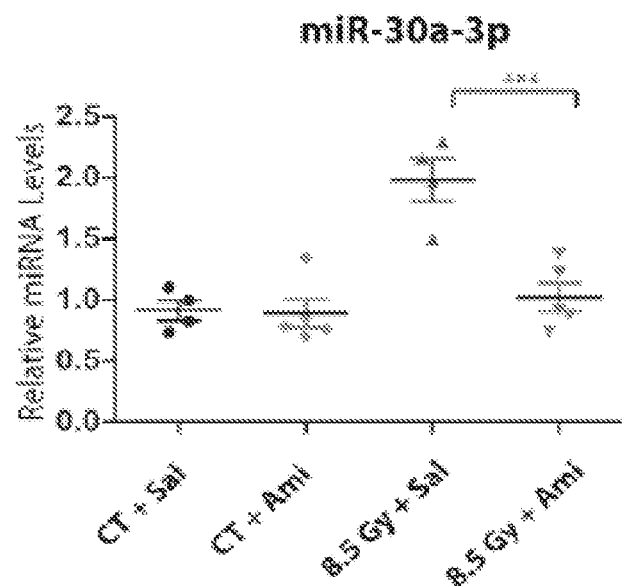

FIG. 76 is a graph showing the levels of mouse miR-30a-3p in serum from mice exposed to 0 Gy- or 8.5 Gy-total body irradiation 45 minutes after administration of saline or 200 mg/kg amifostine. The mean±the standard error of the mean are shown. The asterisk represents a statistically significant comparison. P<0.001, ***. Statistical significance was measured by one-way ANOVA followed by Dunnett's test.

Figure 77:
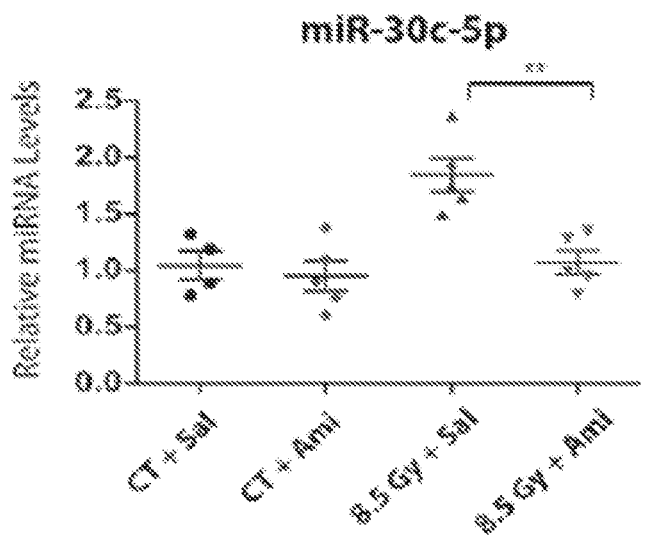

FIG. 77 is a graph showing the levels of mouse miR-30c-5p in serum from mice exposed to 0 Gy- or 8.5 Gy-total body irradiation 45 minutes after administration of saline or 200 mg/kg amifostine. The mean±the standard error of the mean are shown. The asterisk represents a statistically significant comparison. P<0.01, **. Statistical significance was measured by one-way ANOVA followed by Dunnett's test.

Figure 78:
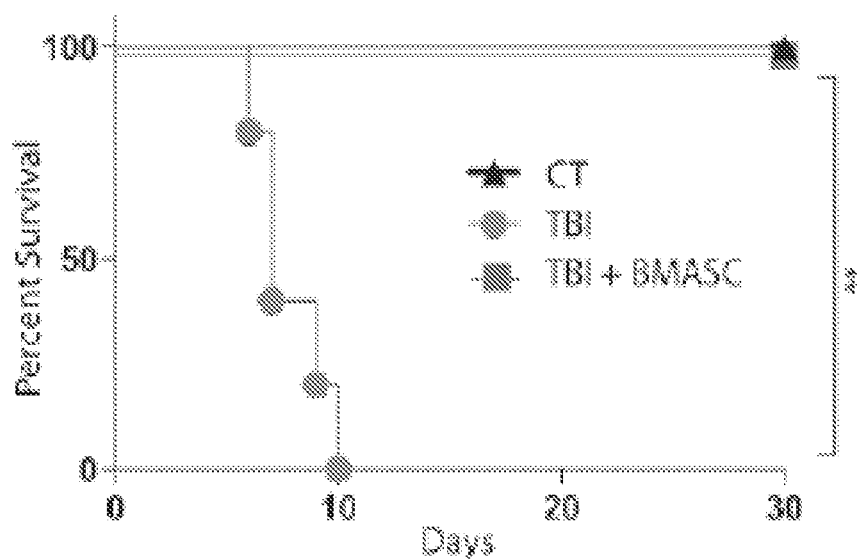

FIG. 78 is a Kaplan-Meier survival curve of mice exposed to 0 Gy-total body irradiation and untreated, or mice exposed to 10.4 Gy-total body irradiation and left untreated or treated with two doses with 2 million bone marrow stromal cells per mouse (24 hours and 72 hours after total body irradiation). Survival was monitored for up to 30 days. The asterisk represents a statistically significant comparison. P<0.01, **.

Figure 79:
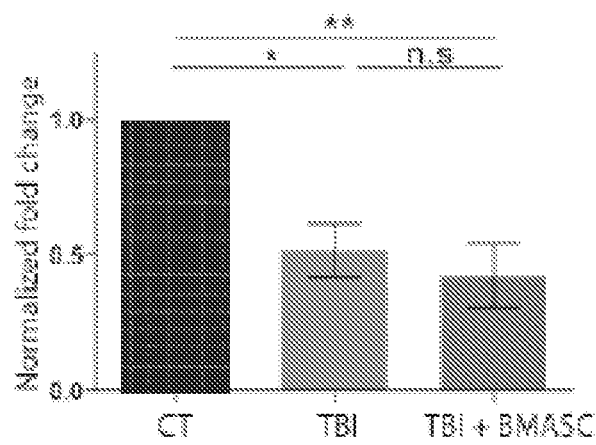

FIG. 79 is a graph showing the levels of mouse miR-150-5p in mice exposed to 0 Gy-total body irradiation and untreated, or mice exposed to 10.4 Gy-total body irradiation and left untreated or treated with two doses of 2 million bone marrow stromal cells per mouse (24 hours and 72 hours after total body irradiation). Serum samples were obtained 48 hours after the second administration of bone marrow stromal cells. The mean±the standard error of the mean are shown. Statistical significance assessed using one-way ANOVA followed by Tukey's test for multiple comparisons. Asterisks identify statistically significant comparisons. P<0.05, *; p<0.01, **; not significant, n.s.

Figure 80:
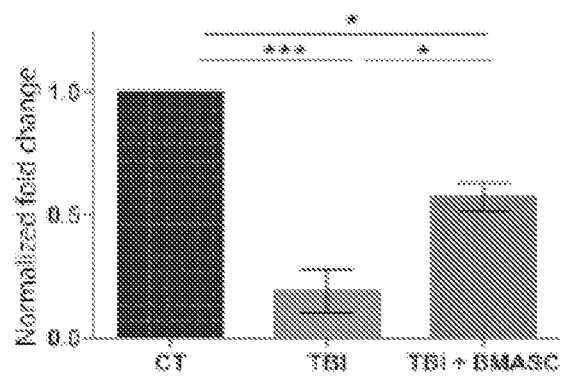

FIG. 80 is a graph showing the levels of mouse miR-27a-3p in mice exposed to 0 Gy-total body irradiation and untreated, or mice exposed to 10.4 Gy-total body irradiation and left untreated or treated with two doses of 2 million bone marrow stromal cells per mouse (24 hours and 72 hours after total body irradiation). Serum samples were obtained 48 hours after the second administration of bone marrow stromal cells. The mean±the standard error of the mean are shown. Statistical significance assessed using one-way ANOVA followed by Tukey's test for multiple comparisons. Asterisks identify statistically significant comparisons. P<0.05, *; p<0.001, ***; not significant, n.s.

Figure 81:
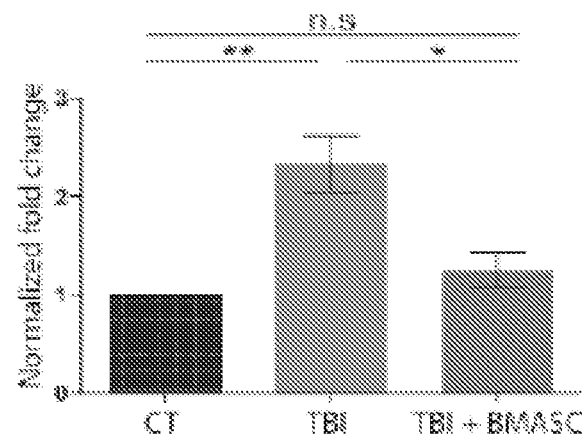

FIG. 81 is a graph showing the levels of mouse miR-30a-3p in mice exposed to 0 Gy-total body irradiation and untreated, or mice exposed to 10.4 Gy-total body irradiation and left untreated or treated with two doses of 2 million bone marrow stromal cells per mouse (24 hours and 72 hours after total body irradiation). Serum samples were obtained 48 hours after the second administration of bone marrow stromal cells. The mean±the standard error of the mean are shown. Statistical significance assessed using one-way ANOVA followed by Tukey's test for multiple comparisons. Asterisks identify statistically significant comparisons. P<0.05, *; p<0.001, ***; not significant, n.s.

Figure 82:
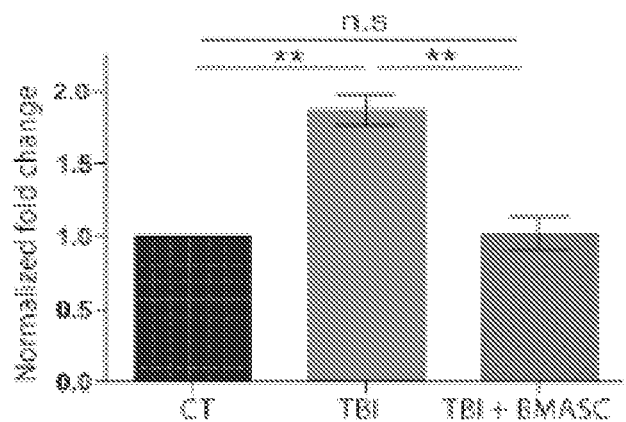

FIG. 82 is a graph showing the levels of mouse miR-30c-5p in mice exposed to 0 Gy-total body irradiation and untreated, or mice exposed to 10.4 Gy-total body irradiation and left untreated or treated with two doses of 2 million bone marrow stromal cells per mouse (24 hours and 72 hours after total body irradiation). Serum samples were obtained 48 hours after the second administration of bone marrow stromal cells. The mean±the standard error of the mean are shown. Statistical significance assessed using one-way ANOVA followed by Tukey's test for multiple comparisons. Asterisks identify statistically significant comparisons. P<0.01, **; not significant, n.s.

Figure 83:
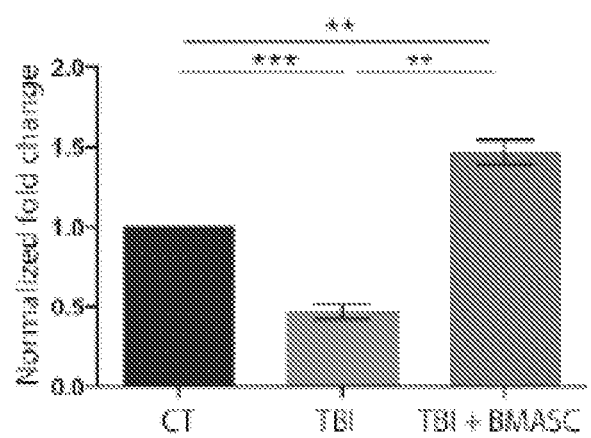

FIG. 83 is a graph showing the levels of mouse miR-187-3p in mice exposed to 0 Gy-total body irradiation and untreated, or mice exposed to 10.4 Gy-total body irradiation and left untreated or treated with two doses of 2 million bone marrow stromal cells per mouse (24 hours and 72 hours after total body irradiation). Serum samples were obtained 48 hours after the second administration of bone marrow stromal cells. The mean±the standard error of the mean are shown. Statistical significance assessed using one-way ANOVA followed by Tukey's test for multiple comparisons. Asterisks identify statistically significant comparisons. P<0.01, ; p<0.001, *; not significant, n.s.

Figure 84:
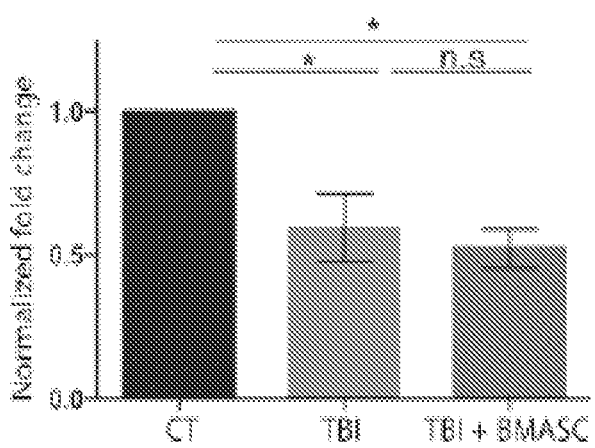

FIG. 84 is a graph showing the levels of mouse miR-194-3p in mice exposed to 0 Gy-total body irradiation and untreated, or mice exposed to 10.4 Gy-total body irradiation and left untreated or treated with two doses of 2 million bone marrow stromal cells per mouse (24 hours and 72 hours after total body irradiation). Serum samples were obtained 48 hours after the second administration of bone marrow stromal cells. The mean±the standard error of the mean are shown. Statistical significance assessed using one-way ANOVA followed by Tukey's test for multiple comparisons. Asterisks identify statistically significant comparisons. P<0.05, *; not significant, n.s.

Figure 85:
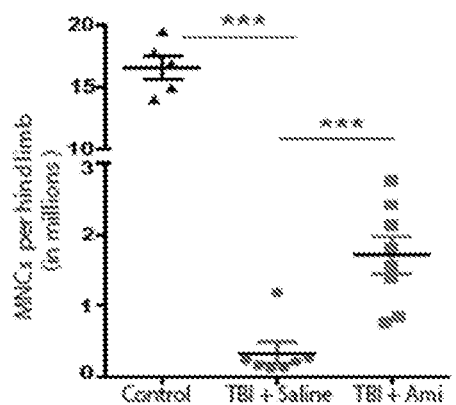

FIG. 85 is a graph showing the number of BM-MNCs (in millions) per hind limb in untreated control humanized mice and in humanized mice treated with saline or amifostine prior to irradiation with 4.0 Gy or 4.5 Gy of total body irradiation.

Figure 86:
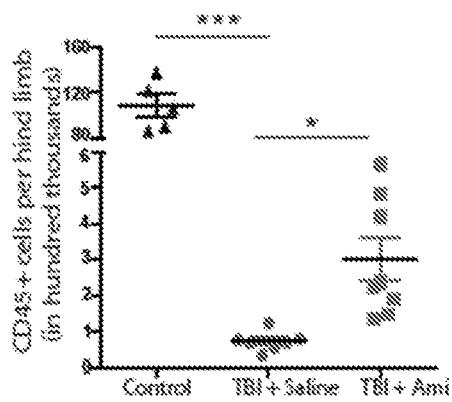

FIG. 86 is a graph showing the number of CD45 positive cells (in hundred thousands) per hind limb in untreated control humanized mice and in humanized mice treated with saline or amifostine prior to irradiation with 4.0 Gy or 4.5 Gy of total body irradiation.

Figure 87:
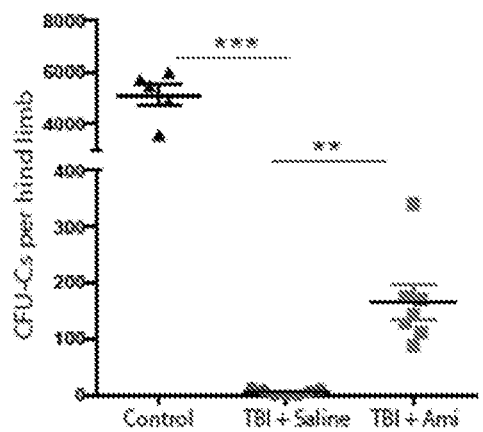

FIG. 87 is a graph showing the number of CFU-Cs per hind limb in untreated control humanized mice and in humanized mice treated with saline or amifostine prior to irradiation with 4.0 Gy or 4.5 Gy of total body irradiation.

Figure 88:
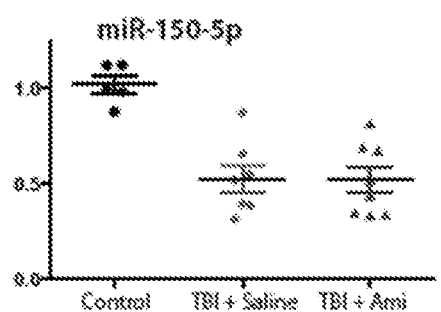

FIG. 88 is a graph showing the relative level of miR-150-5p in serum of humanized mice treated with saline or amifostine, irradiated with 4.0 Gy or 4.5 Gy of total body irradiation, and allowed to recover for 24 hours, as compared to the level of miR-150-5p in the serum of untreated control humanized mice.

Figure 89:
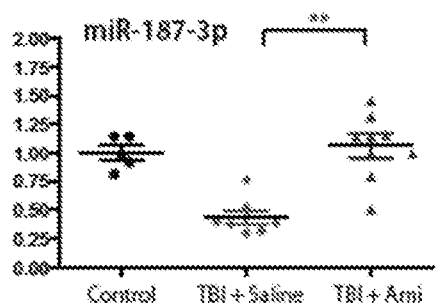

FIG. 89 is a graph showing the relative level of miR-187-3p in serum of humanized mice treated with saline or amifostine, irradiated with 4.0 Gy or 4.5 Gy of total body irradiation, and allowed to recover for 24 hours, as compared to the level of miR-187-3p in the serum of untreated control humanized mice.

Figure 90:
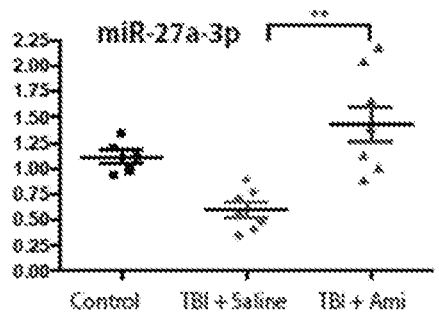

FIG. 90 is a graph showing the relative level of miR-27a-3p in serum of humanized mice treated with saline or amifostine, irradiated with 4.0 Gy or 4.5 Gy of total body irradiation, and allowed to recover for 24 hours, as compared to the level of miR-27a-3p in the serum of untreated control humanized mice.

Figure 91:
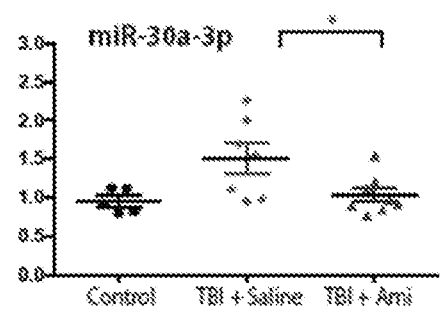

FIG. 91 is a graph showing the relative level of miR-30a-3p in serum of humanized mice treated with saline or amifostine, irradiated with 4.0 Gy or 4.5 Gy of total body irradiation, and allowed to recover for 24 hours, as compared to the level of miR-30a-3p in the serum of untreated control humanized mice.

Figure 92:
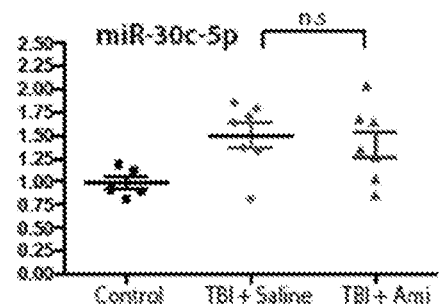

FIG. 92 is a graph showing the relative level of miR-30c-5p in serum of humanized mice treated with saline or amifostine, irradiated with 4.0 Gy or 4.5 Gy of total body irradiation, and allowed to recover for 24 hours, as compared to the level of miR-30c-5p in the serum of untreated control humanized mice.

Figure 93:
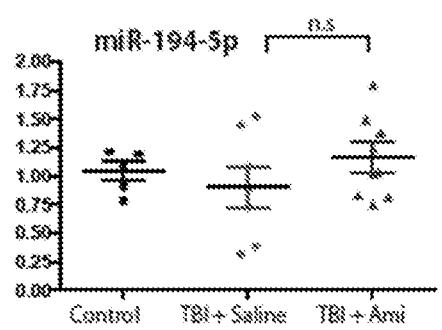

FIG. 93 is a graph showing the relative level of miR-194-5p in serum of humanized mice treated with saline or amifostine, irradiated with 4.0 Gy or 4.5 Gy of total body irradiation, and allowed to recover for 24 hours, as compared to the level of miR-194-5p in the serum of untreated control humanized mice.

DETAILED DESCRIPTION

Subjects exposed to tissue damaging levels of radiation often do not experience some symptoms of radiation disease until one to three weeks, and it is difficult for medical professionals to quickly estimate a subject's level of exposure to radiation. Often, a subject's level of exposure to radiation is determined once the subject's begins to show signs and symptoms of radiation disease (e.g., as a result of damage to hematopoietic system or gastrointestinal system). In order to increase the efficacy of a treatment for reducing radiation-induced damage, the treatment must be administered shortly after the subject has been exposed to a significant level of radiation.

Provided herein are methods of determining a subject's level of exposure to radiation, methods of determining whether a subject has been exposed to a radiation dose of 2 Gy or more, methods of determining a subject's risk of poor prognosis from radiation exposure, methods of determining a subject's risk of subsequent development of radiation disease, methods of selecting a treatment for reducing radiation-induced damage for a subject, methods of selecting a subject for treatment of radiation disease, methods of triaging a plurality of subjects exposed or suspected of being exposed to radiation, and methods of determining the efficacy of a treatment (e.g., a treatment for reducing radiation-induced damage) administered to a subject exposed to a significant dose of radiation that are based on the discovery that changes in the serum levels of specific miRNAs (e.g., changes in the serum levels of one or more (e.g., two or more, three or more, four or more, five or more, six or more, seven or more, eight or more, nine or more, ten or more, eleven or more, twelve or more, thirteen or more, fifteen or more, sixteen or more, seventeen or more, eighteen or more, nineteen or more, or twenty or more) of, e.g., mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p, and human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p) occur in subjects that have been exposed to total body irradiation, and that the changes in the levels of these specific miRNAs are radiation dose-dependent and also correlate with a subject's future risk of developing radiation disease, a subject's future risk of poor prognosis from radiation exposure, and the effectiveness of a treatment (e.g., a treatment for reducing radiation-induced damage) in a subject exposed to radiation (e.g., a subject exposed to a significant level of radiation). Also provided are kits that can be used, e.g., to perform any of the methods described herein.

The methods and kits provided herein allow for a physician to quickly (e.g., between 30 minutes and 48 hours, between 30 minutes and 36 hours, between 30 minutes and 24 hours, between 30 minutes and 20 hours, between 30 minutes and 15 hours, between 30 minutes and 12 hours, between 30 minutes and 10 hours, between 30 minutes and 8 hours, between 30 minutes and 6 hours, between 30 minutes and 4 hours, between 30 minutes and 3 hours, or between 30 minutes and 2 hours) and accurately determine a subject's exposure to radiation. The methods and kits provided herein also allow for a physician to quickly (e.g., between 30 minutes and 48 hours, between 30 minutes and 36 hours, between 30 minutes and 24 hours, between 30 minutes and 20 hours, between 30 minutes and 15 hours, between 30 minutes and 12 hours, between 30 minutes and 10 hours, between 30 minutes and 8 hours, between 30 minutes and 6 hours, between 30 minutes and 4 hours, between 30 minutes and 3 hours, or between 30 minutes and 2 hours) triage subjects exposed or suspected of being exposed to radiation, and to quickly (e.g., between 30 minutes and 48 hours, between 30 minutes and 36 hours, between 30 minutes and 24 hours, between 30 minutes and 20 hours, between 30 minutes and 15 hours, between 30 minutes and 12 hours, between 30 minutes and 10 hours, between 30 minutes and 8 hours, between 30 minutes and 6 hours, between 30 minutes and 4 hours, between 30 minutes and 3 hours, or between 30 minutes and 2 hours) select an appropriate treatment for a subject (e.g., a subject suspected of or known to have been exposed to radiation).

Exemplary aspects of the methods and kits provided herein are described below. As one of skill in the art would appreciate, the various aspects of the methods and kits described below can be used in any combination.

Radiation Disease

Radiation disease is a disease caused by exposure to a significant dose of radiation. As used herein, "radiation" refers to the following types of radiation: x-radiation, gamma-radiation, alpha particle radiation, beta particle radiation, and neutron radiation (e.g., a dose of radiation of 1 Gy or more, a dose of radiation of 1.5 Gy or more, a dose of radiation of 2 Gy or more, a dose of radiation of 2.5 Gy or more, or a dose of radiation of 3 Gy or more). The severity of radiation disease in a subject depends on the level of radiation the subject was exposed to. Radiation disease often is typified by damage to the subject's hematopoietic system (Mauch et al., *Int. J. Radiat. Oncol. Biol. Phys.* 31:1319-1339, 1995), but subjects with radiation disease can also have damage to their gastrointestinal tract and cerebrovascular system (Waselenko et al., *Ann. Intern. Med.* 140:1037-1051, 2004). Damage to the subject's hematopoietic system can result, e.g., in a rapid decrease in the levels of lymphocytes (T-cells and/or B-cells), bone marrow stromal cells, neutrophils, platelets, BM-MSCs, CFU-Cs, HPCs, and HSCs, and a decrease in total white blood cell count (WBC) and complete blood count (CBC). The decrease in the levels of these cells and cell counts can result in an increased risk of infection in the subject. Exposure to high doses of radiation can result in a severe, non-recoverable bone marrow damage, which results in pancytopenia (due to the complete loss of hematopoietic stem cells in the subject) and death. A 2 Gy- to 6 Gy-dose of radiation results in damage to the hematopoietic system of a subject, the symptoms of which appear in a few weeks to 2 months after the subject's exposure to radiation. At higher doses of radiation of about 8 Gy to about 12 Gy, lethal gastrointestinal and bone marrow toxicity is observed and death is probable in one to three weeks (Waselenko et al., *Ann. Intern. Med.* 140:1037-1051, 2004; Coleman et al., Science 304:693-694, 2004).

Non-limiting examples of symptoms of radiation disease can include nausea and vomiting, loss of appetite, diarrhea, headache, fever, fatigue and weakness, purpura, hemorrhage, increased risk of infections, hair loss, cognitive impairment, electrolyte disturbance, shock, seizures, tremor, ataxia, decreased levels of platelets, decreased levels of neutrophils, decreased levels of B-cells, decreased levels of T-cells, decreased levels of bone marrow stromal cells, decreased levels of CFU-Cs, decreased levels of CBCs, decreased levels of WBCs, decreased levels of BM-MNCs, decreased levels of HPCs (e.g., LKS$^-$ cells), decreased levels of HSCs (e.g., LKS$^+$ cells), decreased levels of hemoglobin, and lung fibrosis. Methods for detecting the levels of platelets, neutrophils, B-cells, T-cells, CFU-Cs, BM-MNCs, HPCs, HSCs, and hemoglobin, and CBCs and WBCs are well known in the art. Exemplary methods for determining the levels of B-cells, T-cells, CFU-Cs, BM-MNCs, HPCs, and HSCs, and determining CMCs are also described herein.

A subject having radiation sickness can have, e.g., present with, one or more (e.g., two, three, four, five, six, seven, eight, nine, ten, eleven, twelve, thirteen, fourteen, or fifteen) of any of the symptoms of radiation disease described herein (in any combination), e.g., at substantially the same time, or at different times following exposure to a significant dose of radiation.

Once diagnosed, a subject having radiation disease is typically first decontaminated before treatment by a physician. The decontamination can include the removal of articles of clothing that contain a radioactive isotope. The decontamination can also include removing radioactive isotopes from a subject's skin and endothelium.

After decontamination, a subject can be administered a treatment for reducing radiation-induced damage (e.g., one or more of any of the exemplary treatments for reducing radiation-induced damage described herein).

Subjects

A subject as described herein can be a male or a female. The subject can be a juvenile (e.g., an infant or toddler) or an adult. Where the subjects is a juvenile, he or she may be between 1 day and 18 years old, inclusive (e.g., between 1 day and 17 years old, between 1 day and 16 years old, between 1 day and 15 years old, between 1 day and 14 years old, between 1 day and 13 years old, between 1 day and 12 years old, between 1 day and 11 years old, between 1 day and 10 years old, between 1 day and 9 years old, between 1 day and 8 years old, between 1 day and 7 years old, between 1 day and 6 years old, between 1 day and 5 years old, between 1 day and 4 years old, between 1 day and 3 years old, between 1 day and 2 years old, between 1 day and 1 year old, between 1 day and 6 months old, between 6 months and 4 years old, between 1 month and 5 years old, between 3 years and 13 years old, or between 13 years and 18 years old). When the subject is an adult, the subject may be, e.g., between 18 to 20 years old, inclusive, or at least or about 20, 25, 30, 35, 40, 45, 50, 55, 60, 65, 70, 75, 80, 85, 90, 95, or at least or about 100 years old.

In some embodiments of any of the methods described herein, the subject has been exposed or is suspected of having been exposed to a significant dose of radiation. In some embodiments of any of the methods described herein, the subject has been identified as being exposed to radiation (e.g., a significant dose of radiation) or as being likely to have been exposed to radiation (e.g., a significant dose of radiation). In some embodiments, the subject has a disease (e.g., cancer) and has been irradiated with a significant dose of radiation in order to treat the disease (e.g., a tumor) in the subject. In some embodiments of any of the methods described herein, the subject is or was previously at a location having or suspected of having a significant level of radiation (e.g., the site of a nuclear attack or a site proximal to the site of a nuclear attack, the site of radiation release from a nuclear weapon or site proximal to the site of radiation release from a nuclear weapon, a nuclear energy facility or a site proximal to a nuclear energy facility, a nuclear waste facility or proximal to a nuclear waste facility, or a nuclear medicine facility or a site proximal to a nuclear medicine facility). In some examples of any of the methods described herein, the subject has already been diagnosed as having radiation disease or having been exposed to a significant level of radiation (e.g., using any of the methods provided herein).

In some embodiments of any of the methods described herein, the sample including a biological fluid is obtained from the subject within 5 minutes to one week (e.g., within 5 minutes to six days, within 5 minutes to five days, within 5 minutes to 96 hours, within 5 minutes to three days, within 5 minutes to two days, within 5 minutes to one day, within 5 minutes to 20 hours, within 5 minutes to 16 hours, within 5 minutes to 12 hours, within 5 minutes to 10 hours, within 5 minutes to 8 hours, within 5 minutes to 6 hours, within 5 minutes to 4 hours, within 5 minutes to 3 hours, within 5 minutes to 2 hours, within 10 minutes to one week, within 10 minutes to six days, within 10 minutes to five days, within 10 minutes to 96 hours, within 10 minutes to three days, within 10 minutes to two days, within 10 minutes to one day, within 10 minutes to 20 hours, within 10 minutes to 16 hours, within 10 minutes to 12 hours, within 10 minutes to 10 hours, within 10 minutes to 8 hours, within 10 minutes to 6 hours, within 10 minutes to 4 hours, within 10 minutes to 3 hours, within 10 minutes to 2 hours, within 20 minutes to one week, within 20 minutes to six days, within 20 minutes to five days, within 20 minutes to 96 hours, within 20 minutes to three days, within 20 minutes to two days, within 20 minutes to one day, within 20 minutes to 20 hours, within 20 minutes to 16 hours, within 20 minutes to 12 hours, within 20 minutes to 10 hours, within 20 minutes to 8 hours, within 20 minutes to 6 hours, within 20 minutes to 4 hours, within 20 minutes to 3 hours, within 20 minutes to 2 hours, within 30 minutes to one week, within 30 minutes to six days, within 30 minutes to five days, within 30 minutes to 96 hours, within 30 minutes to three days, within 30 minutes to two days, within 30 minutes to one day, within 30 minutes to 20 hours, within 30 minutes to 16 hours, within 30 minutes to 12 hours, within 30 minutes to 10 hours, within 30 minutes to 8 hours, within 30 minutes to 6 hours, within 30 minutes to 4 hours, within 30 minutes to 3 hours, within 30 minutes to 2 hours, within 1 hour to one week, within 1 hour to six days, within 1 hour to five days, within 1 hour to 96 hours, within 1 hour to three days, within 1 hour to two days, within 1 hour to one day, within 1 hour to 20 hours, within 1 hour to 16 hours, within 1 hour to 12 hours, within 1 hour to 10 hours, within 1 hour to 8 hours, within 1 hour to 6 hours, within 1 hour to 4 hours, within 1 hour to 3 hours, or within 1 hour to 2 hours). In some embodiments of any of the methods described herein, the sample includes a biological fluid selected from the group of blood, plasma, serum, saliva, or urine. Some embodiments of any of the methods described herein further include obtaining a sample including a biological fluid (e.g., serum) from a subject.

MiRNAs and Methods of Determining Levels of miRNAs

The methods described herein include determining a level(s) of one or more of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p and human homologues of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p in a sample(s) including a biological fluid from a subject.

The sequences of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p are well known in the art. Exemplary sequences for mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p are listed below.

```
Mouse miR-130a-3p (mmu-miR-130a-3p)
CAGUGCAAUGUUAAAAGGGCAU      (SEQ ID NO: 19)

Mouse miR-150-5p (mmu-miR-150-3p)
UCUCCCAACCCUUGUACCAGUG      (SEQ ID NO: 20)

Mouse miR-17-3p (mmu-miR-17-3p)
ACUGCAGUGAGGGCACUUGUAG      (SEQ ID NO: 21)

Mouse miR-187-3p (mmu-miR-187-3p)
UCGUGUCUUGUGUUGCAGCCGG      (SEQ ID NO: 22)

Mouse miR-194-5p (mmu-miR-194-5p)
UGUAACAGCAACUCCAUGUGGA      (SEQ ID NO: 23)

Mouse miR-27a-3p (mmu-miR-27a-3p)
UUCACAGUGGCUAAGUUCCGC       (SEQ ID NO: 24)
```

Mouse miR-30a-3p (mmu-miR-30a-3p)
CUUUCAGUCGGAUGUUUGCAGC        (SEQ ID NO: 25)

Mouse miR-30c-5p (mmu-miR-30c-5p)
UGUAAACAUCCUACACUCUCAGC       (SEQ ID NO: 26)

Mouse miR-142-5p (mmu-miR-142-5p)
CAUAAAGUAGAAAGCACUACU         (SEQ ID NO: 27)

Mouse miR-342-3p (mmu-miR-342-3p)
UCUCACACAGAAAUCGCACCCGU       (SEQ ID NO: 28)

Mouse miR-34b-3p (mmu-miR-34b-3p)
AAUCACUAACUCCACUGCCAUC        (SEQ ID NO: 29)

Mouse miR-126-3p (mmu-miR-126-3p)
UCGUACCGUGAGUAAUAAUGCG        (SEQ ID NO: 30)

Mouse miR-320-3p (mmu-miR-320-3p)
AAAAGCUGGGUUGAGAGGGCGA        (SEQ ID NO: 31)

Mouse miR-136-5p (mmu-miR-136-5p)
ACUCCAUUUGUUUUGAUGAUGG        (SEQ ID NO: 32)

Mouse miR-33-5p (mmu-miR-33-5p)
GUGCAUUGUAGUUGCAUUGCA         (SEQ ID NO: 33)

Mouse miR-142a-3p (mmu-miR-142a-3p)
UGUAGUGUUUCCUACUUUAUGGA       (SEQ ID NO: 34)

Mouse miR-706 (mmu-miR-706)
AGAGAAACCCUGUCUCAAAAAA        (SEQ ID NO: 35)

Mouse miR-375-3p (mmu-miR-375-3p)
UUUGUUCGUUCGGCUCGCGUGA        (SEQ ID NO: 36)

Mouse miR-29a-5p (mmu-miR-29a-5p)
ACUGAUUUCUUUUGGUGUUCAG        (SEQ ID NO: 37)

Mouse miR-193a-3p (mmu-miR-193a-3p)
AACUGGCCUACAAAGUCCCAGU        (SEQ ID NO: 38)

Mouse miR-99b-5p (mmu-miR-99b-5p)
CACCCGUAGAACCGACCUUGCG        (SEQ ID NO: 39)

Mouse miR-151-3p (mmu-miR-151-3p)
CUAGACUGAGGCUCCUUGAGG         (SEQ ID NO: 40)

Mouse miR-let-7d-3p (mmu-miR-let-7d-3p)
CUAUACGACCUGCUGCCUUUCU        (SEQ ID NO: 41)

Mouse miR-486-5p (mmu-miR-486-5p)
UCCUGUACUGAGCUGCCCCGAG        (SEQ ID NO: 42)

Mouse miR-423-5p (mmu-miR-423-5p)
UGAGGGGCAGAGAGCGAGACUUU       (SEQ ID NO: 43)

Mouse miR-30b-5p (mmu-miR-30b-5p)
UGUAAACAUCCUACACUCAGCU        (SEQ ID NO: 44)

Mouse miR-191-5p (mmu-miR-191-5p)
CAACGGAAUCCCAAAAGCAGCUG       (SEQ ID NO: 45)

Mouse miR-497a-5p (mmu-miR-497a-5p)
CAGCAGCACACUGUGGUUUGUA        (SEQ ID NO: 46)

Mouse miR-32-5p (mmu-miR-32-5p)
UAUUGCACAUUACUAAGUUGCA        (SEQ ID NO: 47)

Mouse miR-214-5p (mmu-miR-214-5p)
UGCCUGUCUACACUUGCUGUGC        (SEQ ID NO: 48)

Mouse miR-326-3p (mmu-miR-326-3p)
CCUCUGGGCCCUUCCUCCAGU         (SEQ ID NO: 49)

Mouse miR-1195 (mmu-miR-1195)
UGAGUUCGAGGCCAGCCUGCUCA       (SEQ ID NO: 50)

Mouse miR-122-5p (mmu-miR-122-5p)
UGGAGUGUGACAAUGGUGUUUG        (SEQ ID NO: 51)

Mouse miR-1839-3p (mmu-miR-1839-3p)
AGACCUACUUAUCUACCAACAGC       (SEQ ID NO: 52)

Mouse miR-500-3p (mmu-miR-500-3p)
AAUGCACCUGGGCAAGGGUUCA        (SEQ ID NO: 53)

Mouse miR-30e-3p (mmu-miR-30e-3p)
CUUUCAGUCGGAUGUUUACAGC        (SEQ ID NO: 54)

Mouse miR-322-3p (mmu-miR-322-3p)
AAACAUGAAGCGCUGCAACAC         (SEQ ID NO: 55)

Mouse miR-709 (mmu-miR-709)
GGAGGCAGAGGCAGGAGGA           (SEQ ID NO: 56)

Mouse miR-486a-3p (mmu-miR-486a-3p)
CGGGGCAGCUCAGUACAGGAU         (SEQ ID NO: 57)

Mouse miR-133a-3p (mmu-miR-133a-3p)
UUUGGUCCCCUUCAACCAGCUG        (SEQ ID NO: 58)

Mouse miR-676-3p (mmu-miR-676-3p)
CCGUCCUGAGGUUGUUGAGCU         (SEQ ID NO: 59)

Mouse miR-744-5p (mmu-miR-744-5p)
UGCGGGGCUAGGGCUAACAGCA        (SEQ ID NO: 60)

Mouse miR-29a-3p (mmu-miR-29a-3p)
UAGCACCAUCUGAAAUCGGUUA        (SEQ ID NO: 61)

Mouse miR-1839-5p (mmu-miR-1839-5p)
AAGGUAGAUAGAACAGGUCUUG        (SEQ ID NO: 62)

Mouse miR-30a-5p (mmu-miR-30a-5p)
UGUAAACAUCCUCGACUGGAAG        (SEQ ID NO: 63)

Mouse miR-199b-5p (mmu-miR-199b-5p)
CCCAGUGUUUAGACUACCUGUUC       (SEQ ID NO: 64)

Mouse miR-125a-5p (mmu-miR-125a-5p)
UCCCUGAGACCCUUUAACCUGUGA      (SEQ ID NO: 65)

Mouse miR-133b-3p (mmu-miR-133b-3p)
UUUGGUCCCCUUCAACCAGCUA        (SEQ ID NO: 66)

Mouse miR-24-3p (mmu-miR-24-3p)
UGGCUCAGUUCAGCAGGAACAG        (SEQ ID NO: 67)

Mouse miR-21a-5p (mmu-miR-21a-5p)
UAGCUUAUCAGACUGAUGUUGA        (SEQ ID NO: 68)

Mouse miR-503-5p (mmu-miR-503-5p)
UAGCAGCGGGAACAGUACUGCAG       (SEQ ID NO: 69)

Mouse miR-328-3p (mmu-miR-328-3p)
CUGGCCCUCUCUGCCCUUCCGU        (SEQ ID NO: 70)

Mouse miR-let-7g-5p (mmu-miR-let-7g-5p)
UGAGGUAGUAGUUUGUACAGUU        (SEQ ID NO: 71)

Mouse miR-362-3p (mmu-miR-362-3p)
AACACACCUGUUCAAGGAUUCA        (SEQ ID NO: 72)

Mouse miR-199a-5p (mmu-miR-199a-5p)
CCCAGUGUUCAGACUACCUGUUC       (SEQ ID NO: 73)

Mouse miR-15a-3p (mmu-miR-15a-3p)
CAGGCCAUACUGUGCUGCCUCA        (SEQ ID NO: 74)

Mouse miR-139-5p (mmu-miR-139-5p)
UCUACAGUGCACGUGUCUCCAG        (SEQ ID NO: 75)

Mouse miR-149-5p (mmu-miR-149-5p)
UCUGGCUCCGUGUCUUCACUCCC       (SEQ ID NO: 76)

Mouse miR-29b-3p (mmu-miR-29b-3p)
UAGCACCAUUUGAAAUCAGUGUU       (SEQ ID NO: 77)

Mouse miR-1a-3p (mmu-miR-1a-3p)
UGGAAUGUAAAGAAGUAUGUAU        (SEQ ID NO: 78)

-continued

```
Mouse miR-23b-3p (mmu-miR-23b-3p)
AUCACAUUGCCAGGGAUUACC         (SEQ ID NO: 79)

Mouse miR-215-5p (mmu-miR-215-5p)
AUGACCUAUGAUUUGACAGAC         (SEQ ID NO: 80)

Mouse miR-204-5p (mmu-miR-204-5p)
UUCCCUUUGUCAUCCUAUGCCU        (SEQ ID NO: 81)

Mouse miR-200b-5p (mmu-miR-200b-5p)
CAUCUUACUGGGCAGCAUUGGA        (SEQ ID NO: 82)

Mouse miR-25-3p (mmu-miR-25-3p)
CAUUGCACUUGUCUCGGUCUGA        (SEQ ID NO: 83)

Mouse miR-338-3p (mmu-miR-338-3p)
UCCAGCAUCAGUGAUUUUGUUG        (SEQ ID NO: 84)

Mouse miR-196b-5p (mmu-miR-196b-5p)
UAGGUAGUUUCCUGUUGUUGGG        (SEQ ID NO: 85)
```

A variety of websites are available which allow for the identification of human homologues (or other mammalian homologues) of a mouse miRNA based on sequence identity or a high degree of sequence similarity between the mouse and human miRNA sequences (e.g., the miRBase website). For example, exemplary human homologues of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-122-5p, miR-500-3p, miR-30e-3p, miR-322-3p, miR-709, miR-486a-3p, miR-133a-3p, miR-676-3p, miR-744-5p, miR-29a-3p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p were identified by performing a sequence alignment between each mouse miRNA and a database of human miRNAs. An exemplary human homologue identified for each of mouse miR-130a-3p, miR-150-5p, miR-17-3p, miR-187-3p, miR-194-5p, miR-27a-3p, miR-30a-3p, miR-30c-5p, miR-142-5p, miR-342-3p, miR-34b-3p, miR-126-3p, miR-320-3p, miR-136-5p, miR-33-5p, miR-142a-3p, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-122-5p, miR-500-3p, miR-30e-3p, miR-322-3p, miR-709, miR-486a-3p, miR-133a-3p, miR-676-3p, miR-744-5p, miR-29a-3p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p is listed below, along with an alignment of the cDNA of the exemplary human homologue with the cDNA of its corresponding mouse miRNA.

Given the high level of nucleotide sequence homology between the miRNAs of two very taxonomically different mammals (e.g., humans and mice) (see below), it is understood that other mammals (e.g., non-human primates (such as chimpanzees, monkeys, gorillas, and baboons), bovine mammals, horses, dogs, cats, sheep, goats, rabbits, guinea pigs, rats, hamsters, and gerbils) would have miRNA homologues that are identical, or almost identical (e.g., greater than 90%, about 95%, or greater than 95% identical) to the mouse and human miRNAs whose nucleotide sequences are provided below.

```
Human miR-130a-3p (hsa-miR-130a-3p)
   CAGUGCAAUGUUAAAAGGGCAU                                     (SEQ ID NO: 86)

Alignment of Mouse and Human miR-130a-3p (100% Identical)
1 CAGTGCAATGTTAAAAGGGCAT    22  Mouse mmu-miR-130a-3p cDNA    (SEQ ID NO: 87)
  ||||||||||||||||||||||
1 CAGTGCAATGTTAAAAGGGCAT    22  Human hsa-miR-130a-3p cDNA    (SEQ ID NO: 88)

Human miR-150-5p (hsa-miR-150-5p)
   UCUCCCAACCCUUGUACCAGUG                                     (SEQ ID NO: 89)

Alignment of Mouse and Human miR-150-5p (100% Identical)
1 TCTCCCAACCCTTGTACCAGTG    22  Mouse mmu-miR-150-5p cDNA     (SEQ ID NO: 90)
  ||||||||||||||||||||||
1 TCTCCCAACCCTTGTACCAGTG    22  Human hsa-miR-150-5p cDNA     (SEQ ID NO: 91)

Human miR-17-3p (hsa-miR-17-3p)
   ACUGCAGUGAAGGCACUUGUAG                                     (SEQ ID NO: 92)

Alignment of Mouse and Human miR-17-3p (95% Identical)
1 ACTGCAGTGAGGGCACTTGTAG    22  Mouse mmu-miR-17-3p cDNA      (SEQ ID NO: 93)
  |||||||||| |||||||||||
1 ACTGCAGTGAAGGCACTTGTAG    22  Human hsa-miR-17-3p cDNA      (SEQ ID NO: 94)

Human miR-187-3p (hsa-miR-187-3p)
   UCGUGUCUUGUGUUGCAGCCGG                                     (SEQ ID NO: 95)

Alignment of Mouse and Human miR-187-3p (100% identical)
1 TCGTGTCTTGTGTTGCAGCCGG    22  Mouse mmu-miR-187-3p cDNA     (SEQ ID NO: 96)
  ||||||||||||||||||||||
1 TCGTGTCTTGTGTTGCAGCCGG    22  Human hsa-miR-187-3p cDNA     (SEQ ID NO: 97)

Human miR-194-5p (hsa-miR-194-5p)
   UGUAACAGCAACUCCAUGUGGA                                     (SEQ ID NO: 98)
```

-continued

```
Alignment of Mouse and Human miR-194-5p (100%)
1 TGTAACAGCAACTCCATGTGGA   22  Mouse mmu-miR-194-5p cDNA   (SEQ ID NO: 99)
  ||||||||||||||||||||||
1 TGTAACAGCAACTCCATGTGGA   22  Human hsa-miR-194-5p cDNA   (SEQ ID NO: 100)

Human miR-27a-3p (hsa-miR-27a-3p)
  UUCACAGUGGCUAAGUUCCGC                                    (SEQ ID NO: 101)

Alignment of Mouse and Human miR-27a-3p (100% identical)
1 TTCACAGTGGCTAAGTTCCGC    21  Mouse mmu-miR-27a-3p cDNA   (SEQ ID NO: 102)
  |||||||||||||||||||||
1 TTCACAGTGGCTAAGTTCCGC    21  Human hsa-miR-27a-3p cDNA   (SEQ ID NO: 103)

Human miR-30a-3p (hsa-miR-30a-3p)
  CUUUCAGUCGGAUGUUUGCAGC                                   (SEQ ID NO: 104)

Alignment of Mouse and Human miR-30a-3p (100% identical)
1 CTTTCAGTCGGATGTTTGCAGC   22  Mouse mmu-miR-30a-3p cDNA   (SEQ ID NO: 105)
  ||||||||||||||||||||||
1 CTTTCAGTCGGATGTTTGCAGC   22  Human hsa-miR-30a-3p cDNA   (SEQ ID NO: 106)

Human miR-30c-5p (hsa-miR-30c-5p)
  UGUAAACAUCCUACACUCUCAGC                                  (SEQ ID NO: 107)

Alignment of Mouse and Human miR-30c-5p (100% identical)
1 TGTAAACATCCTACACTCTCAGC  23  Mouse mmu-miR-30c-5p cDNA   (SEQ ID NO: 108)
  |||||||||||||||||||||||
1 TGTAAACATCCTACACTCTCAGC  23  Human hsa-miR-30c-5p cDNA   (SEQ ID NO: 109)

Human miR-142-5p (hsa-miR-142-5p)
  CAUAAAGUAGAAAGCACUACU                                    (SEQ ID NO: 110)

Alignment of Mouse and Human miR-142-5p (100% identical)
1 CATAAAGTAGAAAGCACTACT    21  Mouse mmu-miR-142-5p cDNA   (SEQ ID NO: 111)
  |||||||||||||||||||||
1 CATAAAGTAGAAAGCACTACT    21  Human hsa-miR-142-5p cDNA   (SEQ ID NO: 112)

Human miR-342-3p (hsa-miR-342-3p)
  UCUCACACAGAAAUCGCACCCGU                                  (SEQ ID NO: 113)

Alignment of Mouse and Human miR-342-3p (100% identical)
1 TCTCACACAGAAATCGCACCCGT  23  Mouse mmu-miR-342-3p cDNA   (SEQ ID NO: 114)
  |||||||||||||||||||||||
1 TCTCACACAGAAATCGCACCCGT  23  Human hsa-miR-342-3p cDNA   (SEQ ID NO: 115)

Human miR-34b-3p (hsa-miR-34b-3p)
  CAAUCACUAACUCCACUGCCAU                                   (SEQ ID NO: 116)

Alignment of Mouse and Human miR-34b-3p (100% identical)
1 AATCACTAACTCCACTGCCAT    21  Mouse mmu-miR-34b-3p cDNA   (SEQ ID NO: 117)
  |||||||||||||||||||||
2 AATCACTAACTCCACTGCCAT    22  Human hsa-miR-34b-3p cDNA   (SEQ ID NO: 118)

Human miR-126-3p (hsa-miR-126-3p)
  UCGUACCGUGAGUAAUAAUGCG                                   (SEQ ID NO: 119)

Alignment of Mouse and Human miR-126-3p (100% identical)
1 TCGTACCGTGACTAATAATGCG   22  Mouse mmu-miR-126-3p cDNA   (SEQ ID NO: 120)
  ||||||||||||||||||||||
1 TCGTACCGTGAGTAATAATGCG   22  Human hsa-miR-126-3p cDNA   (SEQ ID NO: 121)

Human homologue of mouse miR-320-3p (hsa-miR-320a)
  AAAAGCUGGGUUGAGAGGGCGA                                   (SEQ ID NO: 122)

Alignment of Mouse miR-320-3p and Human miR-320a (100% identical)
1 AAAAGCTGGGTTGAGAGGGCGA   22  Mouse mmu-miR-320-3p cDNA   (SEQ ID NO: 123)
  ||||||||||||||||||||||
1 AAAAGCTGGGTTGAGAGGGCGA   22  Human hsa-miR-320a cDNA     (SEQ ID NO: 124)

Human miR-136-5p (hsa-miR-136-5p)
  ACUCCAUUUGUUUUGAUGAUGGA                                  (SEQ ID NO: 125)

Alignment of Mouse and Human miR-136-5p (100% identical)
1 ACTCCATTTGTTTTGATGATGG   22  Mouse mmu-miR-136-5p cDNA   (SEQ ID NO: 126)
  ||||||||||||||||||||||
1 ACTCCATTTGTTTTGATGATGG   22  Human hsa-miR-136-5p cDNA   (SEQ ID NO: 127)

Human homologue of mouse miR-33-5p (hsa-miR-33a-5p)
  GUGCAUUGUAGUUGCAUUGCA                                    (SEQ ID NO: 128)
```

```
-continued
Alignment of Mouse miR-33-5p and Human miR-33a-5p (100% identical)
1 GTGCATTGTAGTTGCATTGCA   21  Mouse mmu-miR-33-5p cDNA     (SEQ ID NO: 129)
  |||||||||||||||||||||
1 GTGCATTGTAGTTGCATTGCA   21  Human hsa-miR-33a-5p cDNA    (SEQ ID NO: 130)

Human homologue of mouse miR-142a-3p (hsa-miR-142-3p)
    UGUAGUGUUUCCUACUUUAUGGA                                (SEQ ID NO: 131)

Alignment of Mouse miR-142a-3p and Human miR-142-3p (100% identical)
1 TGTAGTGTTTCCTACTTTATGGA 23  Mouse mmu-miR-142a-3p cDNA   (SEQ ID NO: 132)
  |||||||||||||||||||||||
1 TGTAGTGTTTCCTACTTTATGGA 23  Human hsa-miR-142-3p cDNA    (SEQ ID NO: 133)

Human homologue of mouse miR-375-3p (hsa-miR-375)
    UUUGUUCGUUCGGCUCGCGUGA                                 (SEQ ID NO: 134)

Alignment of Mouse miR-375-3p and Human miR-375 (100% identical)
1 TTTGTTCGTTCGGCTCGCGTGA  22  Mouse mmu-miR-375-3p cDNA    (SEQ ID NO: 135)
  ||||||||||||||||||||||
1 TTTGTTCGTTCGGCTCGCGTGA  22  Human hsa-miR-375 cDNA       (SEQ ID NO: 136)

Human miR-29a-5p (hsa-miR-29a-5p)
    ACUGAUUUCUUUUGGUGUUCAG                                 (SEQ ID NO: 137)

Alignment of Mouse and Human miR-29a-5p (100% identical)
1 ACTGATTTCTTTTGGTGTTCAG  22  Mouse mmu-miR-29a-5p cDNA    (SEQ ID NO: 138)
  ||||||||||||||||||||||
1 ACTGATTTCTTTTGGTGTTCAG  22  Human hsa-miR-29a-5p cDNA    (SEQ ID NO: 139)

Human miR-193a-3p (hsa-miR-193a-3p)
    AACUGGCCUACAAAGUCCCAGU                                 (SEQ ID NO: 140)

Alignment of Mouse and Human miR-193a-3p (100% identical)
1 AACTGGCCTACAAAGTCCCAGT  22  Mouse mmu-miR-193a-3p cDNA   (SEQ ID NO: 141)
  ||||||||||||||||||||||
1 AACTGGCCTACAAAGTCCCAGT  22  Human hsa-miR-193a-3p cDNA   (SEQ ID NO: 142)

Human miR-99b-5p (hsa-miR-99b-5p)
    CACCCGUAGAACCGACCUUGCG                                 (SEQ ID NO: 143)

Alignment of Mouse and Human miR-99b-5p (100% identical)
1 CACCCGTAGAACCGACCTTGCG  22  Mouse mmu-miR-99b-5p cDNA    (SEQ ID NO: 144)
  ||||||||||||||||||||||
1 CACCCGTAGAACCGACCTTGCG  22  Human hsa-miR-99b-5p cDNA    (SEQ ID NO: 145)

Human homologue of mouse miR-151-3p (hsa-miR-151a-3p)
    CUAGACUGAAGCUCCUUGAGG                                  (SEQ ID NO: 146)

Alignment of Mouse miR-151-3p and Human miR-151a-3p (95% identical)
1 CTAGACTGAGGCTCCTTGAGG   21  Mouse mmu-miR-151-3p cDNA    (SEQ ID NO: 147)
  |||||||||| |||||||||
1 CTAGACTGAAGCTCCTTGAGG   21  Human hsa-miR-151a-3p cDNA   (SEQ ID NO: 148)

Human miR-let-7d-3p (hsa-miR-let-7d-3p)
    CUAUACGACCUGCUGCCUUUCU                                 (SEQ ID NO: 149)

Alignment of Mouse and Human miR-let-7d-3p (100% identical)
1 CTATACGACCTGCTGCCTTTCT  22  Mouse mmu-miR-let-7d-3p cDNA (SEQ ID NO: 150)
  ||||||||||||||||||||||
1 CTAT4CGACCTGCTGCCTTTCT  22  Human hsa-miR-let-7d-3p cDNA (SEQ ID NO: 151)

Human miR-486-5p (hsa-miR-486-5p)
    UCCUGUACUGAGCUGCCCCGAG                                 (SEQ ID NO: 152)

Alignment of Mouse and Human miR-486-5p (100% identical)
1 TCCTGTACTGAGCTGCCCCGAG  22  Mouse mmu-miR-486-5p cDNA    (SEQ ID NO: 153)
  ||||||||||||||||||||||
1 TCCTGTACTGAGCTGCCCCGAG  22  Human hsa-miR-486-5p cDNA    (SEQ ID NO: 154)

Human miR-423-5p (hsa-miR-423-5p)
    UGAGGGGCAGAGAGCGAGACUUU                                (SEQ ID NO: 155)

Alignment of Mouse and Human miR-423-5p (100% identical)
1 TGAGGGGCAGAGAGCGAGACTTT 23  Mouse mmu-miR-423-5p cDNA    (SEQ ID NO: 156)
  |||||||||||||||||||||||
1 TGAGGGGCAGAGAGCGAGACTTT 23  Human hsa-miR-423-5p cDNA    (SEQ ID NO: 157)

Human miR-30b-5p (hsa-miR-30b-5p)
    UGUAAACAUCCUACACUCAGCU                                 (SEQ ID NO: 158)
```

```
-continued
Alignment of Mouse and Human miR-30b-5p (100% identical)
1 TGTAAACATCCTACACTCAGCT   22 Mouse mmu-miR-30b-5p cDNA     (SEQ ID NO: 159)
  ||||||||||||||||||||||
1 TGTAAACATCCTACACTCAGCT   22 Human hsa-miR-30b-5p cDNA     (SEQ ID NO: 160)

Human miR-191-5p (hsa-miR-191-5p)
  CAACGGAAUCCCAAAAGCAGCUG                                   (SEQ ID NO: 161)

Alignment of Mouse and Human miR-191-5p (100% identical)
1 CAACGGAATCCCAAAAGCAGCTG  23 Mouse mmu-miR-191-5p cDNA     (SEQ ID NO: 162)
  |||||||||||||||||||||||
1 CAACGGAATCCCAAAAGCAGCTG  23 Human hsa-miR-191-5p cDNA     (SEQ ID NO: 163)

Human homologue of mouse miR-497a-5p (hsa-miR-497)
  CAGCAGCACACUGUGGUUUGU                                     (SEQ ID NO: 164)

Alignment of Mouse and Human miR-497a-5p (100% identical)
1 CAGCAGCACACTGTGGTTTGT    21 Mouse mmu-miR-497a-5p cDNA    (SEQ ID NO: 165)
  |||||||||||||||||||||
1 CAGCAGCACACTGTGGTTTGT    21 Human hsa-miR-497 cDNA        (SEQ ID NO: 166)

Human miR-32-5p (hsa-miR-32-5p)
  UAUUGCACAUUACUAAGUUGCA                                    (SEQ ID NO: 167)

Alignment of Mouse and Human miR-32-5p (100% identical)
1 TATTGCACATTACTAAGTTGCA   22 Mouse mmu-miR-32-5p cDNA      (SEQ ID NO: 168)
  ||||||||||||||||||||||
1 TATTGCACATTACTAAGTTGCA   22 Human hsa-miR-32-5p cDNA      (SEQ ID NO: 169)

Human miR-214-5p (hsa-miR-214-5p)
  UGCCUGUCUACACUUGCUGUGC                                    (SEQ ID NO: 170)

Alignment of Mouse and Human miR-214-5p (100% identical)
1 TGCCTGTCTACACTTGCTGTGC   22 Mouse mmu-miR-214-5p cDNA     (SEQ ID NO: 171)
  ||||||||||||||||||||||
1 TGCCTGTCTACACTTGCTGTGC   22 Human hsa-miR-214-5p cDNA     (SEQ ID NO: 172)

Human miR-326-3p (hsa-miR-326-3p)
  CCUCUGGGCCCUUCCUCCAG                                      (SEQ ID NO: 173)

Alignment of Mouse and Human miR-326-3p (100% identical)
1 CCTCTGGGCCCTTCCTCCAG     20 Mouse mmu-miR-326-3p cDNA     (SEQ ID NO: 174)
  ||||||||||||||||||||
1 CCTCTGGGCCCTTCCTCCAG     20 Human hsa-miR-326-3p cDNA     (SEQ ID NO: 175)

Human miR-122-5p (hsa-miR-122-5p)
  UGGAGUGUGACAAUGGUGUUUG                                    (SEQ ID NO: 176)

Alignment of Mouse and Human miR-122-5p (100% identical)
1 TGGAGTGTGACAATGGTGTTTG   22 Mouse mmu-miR-122-5p cDNA     (SEQ ID NO: 177)
  ||||||||||||||||||||||
1 TGGAGTGTGACAATGGTGTTTG   22 Human hsa-miR-122-5p cDNA     (SEQ ID NO: 178)

Human homologue of mouse miR-500-3p (hsa-miR-502-3p)
  AAUGCACCUGGGCAAGGAUUCA                                    (SEQ ID NO: 179)

Alignment of Mouse miR-500-3p and Human miR-502-3p (95% identical)
1 AATGCACCTGGGCAAGGGTTCA   22 Mouse mmu-miR-500-3p cDNA     (SEQ ID NO: 180)
  |||||||||||||||||| ||||
1 AATGCACCTGGGCAAGGATTCA   22 Human hsa-miR-502-3p cDNA     (SEQ ID NO: 181)

Human miR-30e-3p (hsa-miR-30e-3p)
  CUUUCAGUCGGAUGUUUACAGC                                    (SEQ ID NO: 182)

Alignment of Mouse and Human miR-30e-3p (100% identical)
1 CTTTCAGTCGGATGTTTACAGC   22 Mouse mmu-miR-30e-3p cDNA     (SEQ ID NO: 183)
  ||||||||||||||||||||||
1 CTTTCAGTCGGATGTTTACAGC   22 Human hsa-miR-30e-3p cDNA     (SEQ ID NO: 184)

Human homologue of mouse miR-322-3p (hsa-miR-424-3p)
  AAACAUGAAGCGCUGCAACAC                                     (SEQ ID NO: 185)

Alignment of Mouse and Human miR-322-3p (88% identical)
1 AAACATGAAGCGCTGC         16 Mouse mmu-miR-322-3p cDNA     (SEQ ID NO: 186)
  ||||  |||  |||||||
3 AAACGTGAGGCGCTGC         18 Human hsa-miR-424-3p cDNA     (SEQ ID NO: 187)

Human homologue of mouse miR-709 (hsa-miR-1910-3p)
  GAGGCAGAAGCAGGAUGACA                                      (SEQ ID NO: 188)
```

-continued

```
Alignment of Mouse miR-709 and Human miR-1910-3p (93% identical)
2 GAGGCAGAGGCAGGA        16  Mouse mmu-miR-709 cDNA      (SEQ ID NO: 189)
  ||||||||| ||||||
1 GAGGCAGAAGCAGGA        15  Human hsa-miR-1910-3p cDNA  (SEQ ID NO: 190)

Human homolog of mouse miR-486a-3p (hsa-miR-486-3p)
   CGGGGCAGCUCAGUACAGGAU                                (SEQ ID NO: 191)

Alignment of Mouse miR-486a-3p and Human miR-486-3p (100% identical)
1 CGGGGCAGCTCAGTACAGGAT  21  Mouse mmu-miR-486a-3p cDNA (SEQ ID NO: 192)
  |||||||||||||||||||||
1 CGGGGCAGCTCAGTACAGGAT  21  Human hsa-miR-486-3p cDNA  (SEQ ID NO: 193)

Human miR-133a-3p (hsa-miR-133a-3p)
   UUUGGUCCCCUUCAACCAGCUG                               (SEQ ID NO: 194)

Alignment of Mouse and Human miR-133a-3p (100% identical)
1 TTTGGTCCCCTTCAACCAGTCG  22  Mouse mmu-miR-133a-3p cDNA (SEQ ID NO: 195)
  ||||||||||||||||||||||
1 TTTGGTCCCCTTCAACCAGCTG  22  Human hsa-miR-133a-3p cDNA (SEQ ID NO: 196)

Human miR-676-3p (hsa-miR-676-3p)
   CUGUCCUAAGGUUGUUGAGUU                                (SEQ ID NO: 197)

Alignment of Mouse and Human miR-676-3p (94% identical)
3 GTCCTGAGGTTGTTGAG      19  Mouse mmu-miR-676-3p cDNA  (SEQ ID NO: 198)
  ||||| |||||||||||
3 GTCCTAAGGTTGTTGAG      19  Human hsa-miR-676-3p cDNA  (SEQ ID NO: 199)

Human miR-744-5p (hsa-miR-744-5p)
   UGCGGGGCUAGGGCUAACAGCA                               (SEQ ID NO: 200)

Alignment of Mouse and Human miR-744-5p (100% identical)
1 TGCGGGGCTAGGGCTAACAGCA 22  Mouse mmu-miR-744-5p cDNA  (SEQ ID NO: 201)
  ||||||||||||||||||||||
1 TGCGGGGCTAGGGCTAACAGCA 22  Human hsa-miR-744-5p cDNA  (SEQ ID NO: 202)

Human miR-29a-3p (hsa-miR-29a-3p)
   UAGCACCAUCUGAAAUCGGUUA                               (SEQ ID NO: 203)

Alignment of Mouse and Human miR-29a-3p (100% identical)
1 TAGCACCATCTGAAATCGGTTA 22  Mouse mmu-miR-29a-3p cDNA  (SEQ ID NO: 204)
  ||||||||||||||||||||||
1 TAGCACCATCTGAAATCGGTTA 22  Human hsa-miR-29a-3p cDNA  (SEQ ID NO: 205)

Human miR-30a-5p (hsa-miR-30a-5p)
   UGUAAACAUCCUCGACUGGAAG                               (SEQ ID NO: 206)

Alignment of Mouse and Human miR-30a-5p (100% identical)
2 TGTAAACATCCTCGACTGGAAG 22  Mouse mmu-miR-30a-5p cDNA  (SEQ ID NO: 207)
  ||||||||||||||||||||||
1 TGTAAACATCCTCGACTGGAAG 22  Human hsa-miR-30a-5p cDNA  (SEQ ID NO: 208)

Human miR-199b-5p (hsa-miR-199b-5p)
   CCCAGUGUUUAGACUAUCUGUUC                              (SEQ ID NO: 209)

Alignment of Mouse and Human miR-199b-5p (100% identical)
1 CCCAGTGTTTAGACTACCTGTTC 23 Mouse mmu-miR-199b-5p cDNA (SEQ ID NO: 210)
  ||||||||||||||||| ||||||
1 CCCAGTGTTTAGACTATCTGTTC 23 Human hsa-miR-199b-5p cDNA (SEQ ID NO: 211)

Human miR-125a-5p (hsa-miR-125a-5p)
   UCCCUGAGACCCUUUAACCUGUGA                             (SEQ ID NO: 212)

Alignment of Mouse and Human miR-125a-5p (100% identical)
1 TCCCTGAGACCCTTTAACCTGTGA 24 Human hsa-miR-125a-5p cDNA (SEQ ID NO: 213)
  ||||||||||||||||||||||||
1 TCCCTGAGACCCTTTAACCTGTGA 24 Mouse mma-miR-125a-5p cDNA (SEQ ID NO: 214)

Human homologue of mouse miR-133b-3p (hsa-miR-133b)
   UUUGGUCCCCUUCAACCAGCUA                               (SEQ ID NO: 215)

Alignment of Mouse and Human miR-133b-3p (100% identical)
1 TTTGGTCCCCTTCAACCAGCTA 22  Mouse mmu-miR-133b-g3p cDNA (SEQ ID NO: 216)
  ||||||||||||||||||||||
1 TTTGGTCCCCTTCAACCAGCTA 22  Human mmu-miR-133b cDNA    (SEQ ID NO: 217)

Human miR-24-3p (hsa-miR-24-3p)
   UGGCUCAGUUCAGCAGGAACAG                               (SEQ ID NO: 218)
```

-continued

```
Alignment of Mouse and Human miR-24-3p (100% identical)
1 TGGCTCAGTTCAGCAGGAACAG   22 Mouse mmu-miR-24-3p cDNA    (SEQ ID NO: 219)
  |||||||||||||||||||||
1 TGGCTCAGTTCAGCAGGAACAG   22 Human hsa-miR-24-3p cDNA    (SEQ ID NO: 220)

Human homologue of mouse miR-21a-5p (hsa-miR-21-5p)
  UAGCUUAUCAGACUGAUGUUGA                                  (SEQ ID NO: 221)

Alignment of Mouse miR-21a-5p and Human miR-21-5p (100% identical)
1 TAGCTTATCAGACTGATGTTGA   22 Mouse mmu-miR-21a-5p cDNA   (SEQ ID NO: 222)
  ||||||||||||||||||||||
1 TAGCTTATCAGACTGATGTTGA   22 Human hsa-miR-21-5p cDNA    (SEQ ID NO: 223)

Human miR-503-5p (hsa-miR-503-5p)
  UAGCAGCGGGAACAGUUCUGCAG                                 (SEQ ID NO: 224)

Alignment of Mouse and Human miR-503-5p (100% identical)
1 TAGCAGCGGGAACAGTACTGCAG  23 Mouse mmu-miR-503-5p cDNA   (SEQ ID NO: 225)
  |||||||||||||||| ||||||
1 TAGCAGCGGGAACAGTTCTGCAG  23 Human hsa-miR-503-5p cDNA   (SEQ ID NO: 226)

Human miR-328-3p (hsa-miR-328-3p)
  CUGGCCCUCUCUGCCCUUCCGU                                  (SEQ ID NO: 227)

Alignment of Mouse and Human miR-328-3p (100% identical)
1 CTGGCCCTCTCTGCCCTTCCGT   22 Mouse mmu-miR-328-3p cDNA   (SEQ ID NO: 228)
  ||||||||||||||||||||||
1 CTGGCCCTCTCTGCCCTTCCGT   22 Human hsa-miR-328-3p cDNA   (SEQ ID NO: 229)

Human miR-let-7g-5p (hsa-miR-let-7g-5p)
  UGAGGUAGUAGUUUGUACAGUU                                  (SEQ ID NO: 230)

Alignment of Mouse and Human miR-let-7g-5p (100% identical)
1 TGAGGTAGTAGTTTGTACAGTT   22 Mouse mmu-miR-let-7g-5p cDNA(SEQ ID NO: 231)
  ||||||||||||||||||||||
1 TGAGGTAGTAGTTTGTACAGTT   22 Human hsa-miR-let-7g-5p cDNA(SEQ ID NO: 232)

Human miR-362-3p (hsa-miR-362-3p)
  AACACACCUAUUCAAGGAUUCA                                  (SEQ ID NO: 233)

Alignment of Mouse and Human miR-362-3p (95% identical)
1 AACACACCTGTTCAAGGATTCA   22 Mouse mmu-miR-362-3p cDNA   (SEQ ID NO: 234)
  |||||||||  |||||||||||
1 AACACACCTATTCAAGGATTCA   22 Human hsa-miR-362-3p cDNA   (SEQ ID NO: 235)

Human miR-199a-5p (hsa-miR-199a-5p)
  CCCAGUGUUCAGACUACCUGUUC                                 (SEQ ID NO: 236)

Alignment of Mouse and Human miR-199a-5p (100% identical)
1 CCCAGTGTTCAGACTACCTGTTC  23 Mouse mmu-miR-199a-5p cDNA  (SEQ ID NO: 237)
  |||||||||||||||||||||||
1 CCCAGTGTTCAGACTACCTGTTC  23 Human hsa-miR-199a-5p cDNA  (SEQ ID NO: 238)

Human miR-15a-3p (hsa-miR-15a-3p)
  CAGGCCAUAUUGUGCUGCCUCA                                  (SEQ ID NO: 239)

Alignment of Mouse and Human miR-15a-3p (95% identical)
1 CAGGCCATACTGTGCTGCCTCA   22 Mouse mmu-miR-15a-3p cDNA   (SEQ ID NO: 240)
  ||||||||| ||||||||||||
1 CAGGCCATATTGTGCTGCCTCA   22 Human hsa-miR-15a-3p cDNA   (SEQ ID NO: 241)

Human miR-139-5p (hsa-miR-139-5p)
  UCUACAGUGCACGUGUCUCCAGU                                 (SEQ ID NO: 242)

Alignment of Mouse and Human miR-139-5p (100% identical
1 TCTACAGTGCACGTGTCTCCAG   22 Mouse mmu-miR-139-5p cDNA   (SEQ ID NO: 243
  ||||||||||||||||||||||
1 TCTACAGTGCACGTGTCTCCAG   22 Human hsa-miR-139-5p cDNA   (SEQ ID NO: 244)

Human miR-149-5p (hsa-miR-149-5p)
  UCUGGCUCCGUGUCUUCACUCCC                                 (SEQ ID NO: 245)

Alignment of Mouse and Human miR-149-5p (100% identical)
1 TCTGGCTCCGTGTCTTCACTCCC  23 Mouse mmu-miR-149-5p cDNA   (SEQ ID NO: 246)
  |||||||||||||||||||||||
1 TCTGGCTCCGTGTCTTCACTCCC  23 Human hsa-miR-149-5p cDNA   (SEQ ID NO: 247)

Human miR-29b-3p (hsa-miR-29b-3p)
  UAGCACCAUUUGAAAUCAGUGUU                                 (SEQ ID NO: 248)
```

```
Alignment of Mouse and Human miR-29b-3p (100% identical)
1 TAGCACCATTTGAAATCAGTGTT  23 Mouse mmu-miR-29b-3p cDNA     (SEQ ID NO: 249)
  |||||||||||||||||||||||
1 TAGCACCATTTGAAATCAGTGTT  23 Human hsa-miR-23b-3p cDNA     (SEQ ID NO: 250)

Human homologue of mouse miR-1a-3p (hsa-miR-1-3p)
  UGGAAUGUAAAGAAGUAUGUAU                                   (SEQ ID NO: 251)

Alignment of Mouse and Human miR-1a-3p)
1 TGGAATGTAAAGAAGTATGTAT   22 Mouse mmu-miR-1a-3p cDNA     (SEQ ID NO: 252)
  ||||||||||||||||||||||
1 TGGAATGTAAAGAAGTATGTAT   22 Human hsa-miR-1-3p cDNA      (SEQ ID NO: 253)

Human miR-23b-3p (hsa-miR-23b-3p)
  AUCACAUUGCCAGGGAUUACC                                    (SEQ ID NO: 254)

Alignment of Mouse and Human miR-23b-3p (100% identical)
1 ATCACATTGCCAGGGATTACC    21 Mouse mmu-miR-23b-3p cDNA    (SEQ ID NO: 255)
  |||||||||||||||||||||
1 ATCACATTGCCAGGGATTACC    21 Human hsa-miR-23b-3p cDNA    (SEQ ID NO: 256)

Human miR-215-5p (hsa-miR-215-5p)
  AUGACCUAUGAAUUGACAGAC                                    (SEQ ID NO: 257)

Alignment of Mouse and Human miR-215-5p (95% identical)
1 ATGACCTATGATTTGACAGAC    21 Mouse mmu-miR-215-5p cDNA    (SEQ ID NO: 258)
  ||||||||||   |||||||||
1 ATGACCTATGAATTGACAGAC    21 Human hsa-miR-215-5p cDNA    (SEQ ID NO: 259)

Human miR-204-5p (hsa-miR-204-5p)
  UUCCCUUUGUCAUCCUAUGCCU                                   (SEQ ID NO: 260)

Alignment of Mouse and Human miR-204-5p (100% identical)
1 TTCCCTTTGTCATCCTATGCCT   22 Mouse mmu-miR-204-5p cDNA    (SEQ ID NO: 261)
  ||||||||||||||||||||||
1 TTCCCTTTGTCATCCTATGCCT   22 Human hsa-204-5p cDNA        (SEQ ID NO: 262)

Human miR-200b-5p (hsa-miR-200b-5p)
  CAUCUUACUGGGCAGCAUUGGA                                   (SEQ ID NO: 263)

Alignment of Mouse and Human miR-200b-5p (100% identical)
1 CATCTTACTGGGCAGCATTGGA   22 Mouse mmu-miR-200b-5p cDNA   (SEQ ID NO: 264)
  ||||||||||||||||||||||
1 CATCTTACTGGGCAGCATTGGA   22 Human hsa-miR-200b-5p cDNA   (SEQ ID NO: 265)

Human miR-25-3p (hsa-miR-25-3p)
  CAUUGCACUUGUCUCGGUCUGA                                   (SEQ ID NO: 266)

Alignment of Mouse and Human miR-25-3p (100% identical)
1 CATTGCACTTGTCTCGGTCTGA   22 Mouse mmu-miR-25-3p cDNA     (SEQ ID NO: 267)
  ||||||||||||||||||||||
1 CATTGCACTTGTCTCGGTCTGA   22 Human hsa-miR-25-3p cDNA     (SEQ ID NO: 268)

Human miR-338-3p (hsa-miR-338-3p)
  UCCAGCAUCAGUGAUUUUGUUG                                   (SEQ ID NO: 269)

Alignment of Mouse and Human miR-338-3p (100% identical)
1 TCCAGCATCAGTGATTTTGTTG   22 Mouse mmu-miR-338-3p cDNA    (SEQ ID NO: 270)
  ||||||||||||||||||||||
1 TCCAGCATCAGTGATTTTGTTG   22 Human hsa-miR-338-3p cDNA    (SEQ ID NO: 271)

Human miR-196b-5p (hsa-miR-196b-5p)
  UAGGUAGUUUCCUGUUGUUGGG                                   (SEQ ID NO: 272)

Alignment of Mouse and Human miR-196b-5p (100% identical)
1 TAGGTAGTTTCCTGTTGTTGGG   22 Mouse mmu-miR-196b-5p cDNA   (SEQ ID NO: 273)
  ||||||||||||||||||||||
1 TAGGTAGTTTCCTGTTGTTGGG   22 Human hsa-miR-196b-5p cDNA   (SEQ ID NO: 274)
```

A variety of methods for isolating miRNA from blood or serum are known in the art. Not all methods of detecting and/or measuring miRNAs include isolating relevant miRNAs from a blood or serum sample. See, e.g., Shaffer et al., Li et al., *Anal. Biochem.* 431:69-75, 2012. A variety of methods for determining the presence or absence, or a level of a target miRNA are well-known in the art. For example, the presence or absence, or level(s) of one or more miRNAs in a sample(s) can be determined by amplifying the miRNAs present in the sample(s) to generate amplification products, contacting the amplified products to a substrate, and detecting the amplified products bound to the substrate. For example, the presence or absence, or levels of a target miRNA can be determined using quantitative RT-PCR (qPCR) using stem-loop reverse transcriptase primers combined with TaqMan PCR (Applied Biosystems, Foster City, Calif.) analysis (Chen et al., *Nucleic Acids Res.* 33:e179, 2005; Liang et al., *BMC Genomics* 8:166, 2007), qPCR with locked nucleic acid primers (Exiqon, Vedbaek, Denmark) (Raymond et al., *RNA* 11:1737-1744, 2005), qPCR using poly(A) tailing (Qiagen, Valencia, Calif.) (RT miRNA qPCR Assay), high-throughput sequencing of small RNA libraries (Landgraf et al., *Cell* 129:1401-1414, 2007), and microarray analysis (Mattie et al., *Mol. Cancer* 5:24, 2006; Bloomston et al., *JAMA* 297:1901-1908, 2007; Porkka et al., *Cancer Res.* 67:6130-6135, 2007; Calin et al., *Proc. Natl. Acad. Sci. U.S.A.* 101:11755-11760, 2004; Volinia et al., *Proc. Natl. Acad. Sci. U.S.A.* 103:2257-2261, 2006; Wang et al., *RNA* 13:151-159, 2007). Additional exemplary methods for determining the presence or absence, or a level of miRNA in a sample, including a biological fluid, are described herein.

Treatments for Reducing Radiation-Induced Damage

A variety of treatments for reducing radiation-induced damage are known in the art. Non-limiting examples of treatments for reducing radiation-induced damage include administering one or more of a cytokine (e.g., granulocyte colony-stimulating factor, filgrastim, and pegfilgrastim), potassium iodide, Prussian blue, and diethylenetriamine pentaacetic acid to a subject exposed to a significant level of radiation, and/or performing bone marrow transplantation, blood transfusion, and/or surgery to remove damaged tissues from a subject exposed to a significant level of radiation. In some examples, treatment for reducing radiation-induced damage includes administering of two or more doses of one or more of a cytokine (e.g., granulocyte colony-stimulating factor, filgrastim, and pegfilgrastim), potassium iodide, Prussian blue, and diethylenetriamine pentaacetic acid to a subject exposed to a significant level of radiation. In some examples, treatment for reducing radiation-induced damage includes performing one or more bone marrow transplantations and/or one or more blood transfusions on a subject exposed to a significant level of radiation. In some examples, treatment for reducing radiation-induced damage includes hospitalizing a subject exposed to a significant level of radiation. In some embodiments, treatment for reducing radiation-induced damage includes performing outpatient treatment on a subject determined to have been exposed to a low dose of radiation (e.g., less than 2 Gy, less than 1.5 Gy, less than 1 Gy, less than 0.5 Gy of radiation).

Some embodiments of any of the methods described herein further include administering a treatment for reducing radiation-induced damage (e.g., any of the treatments for reducing radiation-induced damage described herein) to the subject.

Methods of Determining a Subject's Level of Exposure to Radiation

Provided herein are methods of determining a subject's level of exposure to radiation that include determining a level of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) miRNAs selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p and human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p in a sample including biological fluid from the subject; comparing the level(s) of the one or more miRNAs in the sample to a reference level(s) of the one or more miRNAs; and determining the subject's level of exposure to radiation based on the comparison of the level(s) of one or more miRNAs in the sample to the reference level(s) of the one or more miRNAs.

In some examples, the reference level(s) is the level(s) of the one or more miRNAs in a sample including a biological fluid from a subject not exposed to a significant dose of radiation, a subject exposed to 0.2 Gy or less of radiation, a subject exposed to 0.4 Gy or less of radiation, a subject exposed to 0.6 Gy or less of radiation, a subject exposed to 0.8 Gy or less of radiation, or a subject exposed to 1 Gy or less of radiation. Additional examples of reference levels of the one or more miRNAs are described below.

In some examples, the subject is a mouse and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of: mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In these examples, e.g., one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of mouse miR-150-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to the reference level(s) (e.g., the level(s) in a sample including a biological fluid from a subject not exposed to a significant dose of radiation), indicates that the subject's exposure to radiation is equal to or less than 2 Gy; one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference level(s) (e.g., a level in a sample including a biological fluid from a subject not exposed to a significant dose of radiation or exposed to about 2 Gy or exposed to about 2 Gy or less of radiation), indicates that the subject's exposure to radiation is between greater than 2 Gy and about 6.5 Gy; and/or one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s) (e.g., the level(s) of in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation), indicates that the subject's exposure to radiation is greater than about 6.5 Gy.

In some examples, the subject is a human, and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In these examples, e.g., one or more one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue or mouse miR-130a-3p, miR-136-5p, miR-30c-

5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of the human homologue of mouse miR-150-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to the reference level(s) (e.g., the level(s) in a sample including a biological fluid from a subject not exposed to a significant dose of radiation), indicates that the subject's exposure to radiation is equal to or less than 2 Gy; one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue of mouse miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of the human homologue of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference level(s) (e.g., a level in a sample including a biological fluid from a subject not exposed to a significant dose of radiation or exposed to about 2 Gy or exposed to about 2 Gy or less of radiation), indicates that the subject's exposure to radiation is between greater than 2 Gy and about 6.5 Gy; and/or one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue of mouse miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologue of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s) (e.g., the level(s) of in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation), indicates that the subject's exposure to radiation is greater than about 6.5 Gy.

The level(s) of the one or more miRNAs can be measured using any of the methods described herein or known in the art. The subject can be any subject described herein or known in the art.

Some examples of these methods include administering (and optionally both selecting and administering) a treatment to the subject based on the subject's determined level of exposure to radiation. For example, the methods can include hospitalizing a subject determined to have been exposed to greater than 2 Gy of radiation (e.g., about or greater than 6.5 Gy of radiation, or greater than 8 Gy of radiation), or treating a subject determined to have been exposed to about 2 Gy or less of radiation on an outpatient basis.

Some examples further include recording the subject's determined exposure to radiation into the subject's clinical file (e.g., a computer readable medium). Some examples further include communicating the subject's determined exposure to radiation to a governmental agency or a health organization. Some examples further include informing and isolating a subject determined to have been exposed to greater than 2 Gy of radiation (e.g., about or greater than 6.5 Gy of radiation, or about or greater than 8 Gy of radiation). Some examples further include informing one or more of the subject's physician, family, and employer of the subject's determined exposure to radiation. Some examples further include triaging a subject based on his or her determined exposure to radiation.

Methods of Determining Whether a Subject has been Exposed to 2 Gy or More of Radiation Also provided herein are methods of determining whether a subject has been exposed to a radiation dose of 2 Gy or more that include determining a level of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) miRNAs selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p and human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p in a sample including a biological fluid from the subject; comparing the level(s) of the one or more (e.g., two or more, three or more, four or more, five or more, six or more, seven or more, eight or more, nine or more, ten or more, eleven or more, twelve or more, thirteen or more, fifteen or more, sixteen or more, seventeen or more, eighteen or more, nineteen or more, or twenty or more) miRNAs in the sample with reference level(s) of the one or more miRNAs; and determining whether the subject has been exposed to a radiation dose of 2 Gy or more based on the comparison of the level(s) of the one or more mRNAs in the sample with the reference level(s) of the one or more miRNAs.

In some examples, the reference level(s) is the level(s) of the one or more miRNAs in a sample including a biological fluid from a subject not exposed to a significant dose of radiation, a subject exposed to 0.2 Gy or less of radiation, a subject exposed to 0.4 Gy or less of radiation, a subject exposed to 0.6 Gy or less of radiation, a subject exposed to 0.8 Gy or less of radiation, or a subject exposed to 1 Gy or less of radiation. Additional examples of reference levels of the one or more miRNAs are described below.

In some examples, the subject is a mouse and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p. In these examples, one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-130a-3p, miR-30a-3p, miR-30c-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p, and/or and a decreased level of one or more of mouse miR-150-5p, miR-17-3p, miR-187-3p, miR-194-5p, miR-27a-3p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, and miR-204-5p in the sample, as compared to the reference level(s) (e.g., any of the reference levels described herein), indicates that the subject has been exposed to 2 Gy or more of radiation. For example, the reference level(s) for mouse miR-130a-3p, miR-150-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p are the level(s) of mouse miR-130a-5p, miR-150-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p in a sample including a biological fluid from a subject not exposed to a significant dose of radiation; the reference level for mouse miR-17-3p is the level of mouse miR-17-3p in a sample including a biological fluid from a subject not exposed to a significant dose of radiation or exposed to about 2 Gy or exposed to about 2 Gy or less of radiation; and/or the reference level(s) for mouse miR-187-3p, miR-194-5p, miR-27a-3p, miR-30a-3p, and miR-30c-5p is the level(s) of mouse miR-187-3p, miR-194-5p, miR-27a-3p, miR-30a-3p, and miR-30c-5p in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation.

In some examples, the subject is a human and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p. In these examples, one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologues of mouse miR-130a-3p, miR-30a-3p, miR-30c-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p, and/or a decreased level of one or more of the human homologues of mouse miR-150-5p, miR-17-3p, miR-187-3p, miR-194-5p, miR-27a-3p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, and miR-204-5p in the sample, as compared to the reference level(s) (e.g., any of the reference levels described herein), indicates that the subject has been exposed to 2 Gy or more of radiation. For example, the reference level(s) for the human homologues of mouse miR-130a-3p and miR-150-5p are the levels of the human homologues of mouse miR-130a-5p, miR-150-5p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p in a sample including a biological fluid from a subject not exposed to a significant dose of radiation; the reference level for the human homologue of mouse miR-17-3p is the level of the human homologue of mouse miR-17-3p in a sample including a biological fluid from a subject not exposed to a significant dose of radiation or exposed to about 2 Gy or exposed to about 2 Gy or less of radiation; and/or the reference level(s) for the human homologues of mouse miR-187-3p, miR-194-5p, miR-27a-3p, miR-30a-3p, and miR-30c-5p are the levels of the human homologues of mouse miR-187-3p, miR-194-5p, miR-27a-3p, miR-30a-3p, and miR-30c-5p in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation.

The level(s) of the one or more miRNAs can be measured using any of the methods described herein or known in the art. The subject can be any subject described herein or known in the art.

Some examples of these methods include administering (and optionally both selecting and administering) a treatment for reducing radiation-induced damage to the subject determined to have been exposed to 2 Gy or more of radiation. For example, the methods include hospitalizing a subject determined to have been exposed to greater than 2 Gy of radiation (e.g., about or greater than 6.5 Gy of radiation, or greater than 8 Gy of radiation), and/or performing bone marrow transplantation, performing blood transfusion, administering a cytokine (e.g., any of the cytokines described herein) and/or performing surgery to remove damaged tissues on a subject determined to have been exposed to 2 Gy or more of radiation.

Some examples further include recording the determination that the subject has been exposed to 2 Gy or more of radiation into the subject's clinical file (e.g., a computer readable medium). Some examples further include communicating the determination that the subject has been exposed to 2 Gy or more of radiation to a governmental agency or a health organization. Some examples further include informing and isolating a subject determined to have been exposed to 2 Gy or more of radiation (e.g., about or greater than 6.5 Gy of radiation, or greater than 8 Gy of radiation). Some examples further include informing one or more of the subject's physician, family, and employer of the determination that the subject has been exposed to 2 Gy or more of radiation. Some examples further include triaging a subject based on the determination that the subject has been exposed to 2 Gy or more of radiation.

Methods of Determining a Subject's Risk of Poor Prognosis from Radiation Exposure Also provided are methods of determining a subject's risk of poor prognosis from radiation exposure that include determining a level of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs in a sample including a biological fluid from a subject; comparing the level(s) of the one or more miRNAs in the sample to reference level(s) of the one or more miRNAs; and determining the subject's risk of poor prognosis from radiation exposure based on the comparison of the level(s) of the one or more miRNAs in the sample to the reference level(s) of the one or more miRNAs.

In some examples, the reference level(s) is the level(s) of the one or more miRNAs in a sample including a biological fluid from a subject not exposed to a significant dose of radiation, a subject exposed to 0.2 Gy or less of radiation, a subject exposed to 0.4 Gy or less of radiation, a subject exposed to 0.6 Gy or less of radiation, a subject exposed to 0.8 Gy or less of radiation, or a subject exposed to 1 Gy or less of radiation. Additional examples of reference levels of the one or more miRNAs are described below.

In some examples, the subject is a mouse, and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, miR-30c-5p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In these examples, one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of mouse miR-142-5p, miR-150-5p, miR-342-3p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in the sample, as compared to the reference level(s) (e.g., the level(s) in a sample including a biological fluid from a subject not exposed to a significant dose of radiation), indicates that the subject's risk of poor prognosis from radiation exposure is moderate (e.g., less than the risk of poor prognosis from radiation exposure in a subject determined to have been exposed to a dose of between greater than 2 Gy and about 6.5 Gy and less than the risk of poor prognosis from radiation exposure in a subject determined to have been exposed to a dose of greater than about 6.5 Gy); one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-34b-3p, miR-126-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference level(s) (e.g., a level in a sample including a biological fluid from a subject not exposed to a significant dose of radiation or exposed to about 2 Gy or exposed to about 2 Gy or less of radiation), indicates that the subject's risk of poor prognosis from radiation exposure is high (e.g., greater than the risk of poor prognosis from radiation exposure in a subject determined to have been exposed to 2 Gy or less of radiation and less than the risk of poor prognosis from radiation exposure in a subject determined to have been exposed to greater than about 6.5 Gy (e.g., about 8 Gy or more) radiation); and/or one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s) (e.g., the level(s) in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation), indicates that the subject's risk of poor prognosis from radiation exposure is very high (e.g., greater than the risk of poor prognosis from radiation exposure in a subject determined to have been exposed to 2 Gy or less of radiation and greater than the risk of poor prognosis from radiation exposure in a subject determined to have been exposed to about 6.5 Gy of radiation).

In some examples, the subject is a human, and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of the human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, miR-30c-5p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In these examples, one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of the human homologue of mouse miR-142-5p, miR-150-5p, miR-342-3p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in the sample, as compared to the reference level(s) (e.g., the level(s) in a sample including a biological fluid from a subject not exposed to a significant dose of radiation), indicates that the subject's risk of poor prognosis from radiation exposure is moderate (e.g., less than the risk of poor prognosis from radiation exposure in a subject determined to have been exposed to a dose of between greater than 2 Gy and about 6.5 Gy and less than the risk of poor prognosis from radiation exposure in a subject determined to have been exposed to a dose of greater than about 6.5 Gy); one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue of mouse miR-34b-3p, miR-126-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of the human homologue of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference level(s) (e.g., a level in a sample including a biological fluid from a subject not exposed to a significant dose of radiation or exposed to about 2 Gy or exposed to about 2 Gy or less of radiation), indicates that the subject's risk of poor prognosis from radiation exposure is high (e.g., greater than the risk of poor prognosis from radiation exposure in a subject determined to have been exposed to 2 Gy or less of radiation and less than the risk of poor prognosis from radiation exposure in a subject determined to have been exposed to greater than about 6.5 Gy (e.g., about 8 Gy or more) radiation); and/or one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue of mouse miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologue of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s) (e.g., the level(s) of in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation), indicates that the subject's risk of poor prognosis from radiation exposure is very high (e.g., greater than the risk of poor prognosis from radiation exposure in a subject determined to have been exposed to 2 Gy or less of radiation and greater than the risk of poor prognosis from radiation exposure in a subject determined to have been exposed to about 6.5 Gy of radiation).

The level(s) of the one or more miRNAs can be measured using any of the methods described herein or known in the art. The subject can be any subject described herein. Some examples of these methods include administering (and optionally both selecting and administering) a treatment for reducing radiation-induced damage to the subject identified as having a very high risk or high risk of poor prognosis from radiation exposure. For example, the methods can include hospitalizing a subject identified as having a very high risk or high risk of poor prognosis from radiation exposure, and/or performing bone marrow transplantation and/or performing blood transfusion, and/or administering a cytokine (e.g., any of the cytokines described herein), and/or performing surgery to remove damaged tissues on a subject identified as having a very high risk or high risk of poor prognosis from radiation exposure. Some embodiments further include treating a subject identified as having a moderate risk of poor prognosis from radiation exposure on an outpatient basis.

Some examples further include recording the subject's identified risk of poor prognosis from radiation exposure in the subject's clinical file (e.g., a computer readable medium). Some examples further include communicating the subject's identified risk of poor prognosis from radiation exposure to a governmental agency or a health organization. Some examples further include informing and isolating a subject identified as having a very high risk or high risk of poor prognosis from radiation exposure. Some examples further include informing one or more of the subject's physician, family, and employer of the subject's identified risk of poor prognosis from radiation exposure. Some examples further include triaging a subject based on his or her identified risk of poor prognosis from radiation exposure.

Poor prognosis from radiation exposure can include one or more of death resulting from radiation exposure (e.g., death within 1 day to 5 years, 1 day to 4 years, 1 day to 3 years, 1 day to 2 years, 1 day to 1 year, 1 day to 6 months, 1 day to 2 months, 1 day to 7 weeks, 1 day to 6 weeks, 1 day to 5 weeks, 1 day to 4 weeks, 1 day to 3 weeks, 1 day to 2 weeks, or 1 day to 1 week), hospitalization resulting from radiation exposure (e.g., death within 1 day to 5 years, 1 day to 4 years, 1 day to 3 years, 1 day to 2 years, 1 day to 1 year, 1 day to 6 months, 1 day to 2 months, 1 day to 7 weeks, 1 day to 6 weeks, 1 day to 5 weeks, 1 day to 4 weeks, 1 day to 3 weeks, 1 day to 2 weeks, or 1 day to 1 week), leukopenia resulting from radiation exposure, infection resulting from radiation exposure, requirement of bone marrow transplantation, and requirement of surgery to remove damaged tissues.

Methods of Assessing a Subject's Risk of Subsequent Development of Radiation Disease Also provided are methods of assessing a subject's risk of subsequent development of radiation disease that include determining a level of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs in a sample including a biological fluid from a subject; comparing the level(s) of the one or more miRNAs in the sample to reference level(s) of the one or more miRNAs; and determining the subject's risk of subsequent development of radiation disease based on the comparison of the level(s) of the one or more miRNAs in the sample to the reference level(s) of the one or more miRNAs.

In some examples, the reference level(s) is the level(s) of the one or more miRNAs in a sample including a biological fluid from a subject not exposed to a significant dose of radiation, a subject exposed to 0.2 Gy or less of radiation, a subject exposed to 0.4 Gy or less of radiation, a subject exposed to 0.6 Gy or less of radiation, a subject exposed to 0.8 Gy or less of radiation, or a subject exposed to 1 Gy or less of radiation. Additional examples of reference levels of the one or more miRNAs are described below.

In some examples, the subject is a mouse, and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of mouse miR-130a-3p, miR-142-5p, miR-150-5p, miR-342-3p, miR- 34b-3p, miR-126-3p, miR-17-3p, miR-187-3p, miR-194-5p, miR-27a-3p, miR-30a-3p, miR-30c-5p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In these examples, one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of mouse miR-142-5p, miR-150-5p, miR-342-3p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in the sample, as compared to the reference level(s) (e.g., the level(s) in a sample including a biological fluid from a subject not exposed to a significant dose of radiation), indicates that the subject's risk of subsequent development of radiation disease is moderate (e.g., less than the risk of subsequent development of radiation disease in a subject determined to have been exposed to a dose of between greater than 2 Gy and about 6.5 Gy and less than the risk of subsequent development of radiation disease in a subject determined to have been exposed to a dose of greater than about 6.5 Gy); one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-34b-3p, miR-126-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference level(s) (e.g., level(s) in a sample including a biological fluid from a subject not exposed to a significant dose of radiation or exposed to about 2 Gy or exposed to about 2 Gy or less of radiation), indicates that the subject's risk of subsequent development of radiation disease is high (e.g., greater than the risk of subsequent development of radiation disease in a subject determined to have been exposed to 2 Gy or less of radiation and less than the risk of subsequent development of radiation disease in a subject determined to have been exposed to greater than about 6.5 Gy (e.g., about 8 Gy or more) radiation)); and/or one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s) (e.g., the level(s) of in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation), indicates that the subject's risk of subsequent development of radiation disease is very high (e.g., greater than the risk of subsequent development of radiation disease in a subject determined to have been exposed to 2 Gy or less of radiation and greater than the risk of subsequent development of radiation disease in a subject determined to have been exposed to about 6.5 Gy of radiation).

In some examples, the subject is a human, and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of the human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, miR-30c-5p, miR-320-3p, miR-136-5p, miR-33-5p, miR-142a-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In these examples, one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of the human homologue of mouse miR-142-5p, miR-150-5p, miR-342-3p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-34b-3p, miR-139-5p, miR-149-5p, miR-1a-3p, miR-23b-3p, miR-215-5p, miR-204-5p, and miR-187-3p in the sample, as compared to the reference level(s) (e.g., the level(s) in a sample including a biological fluid from a subject not exposed to a significant dose of radiation), indicates that the subject's risk of subsequent development of radiation disease is moderate (e.g., less than the risk of subsequent development of radiation disease in a subject determined to have been exposed to a dose of between greater than 2 Gy and about 6.5 Gy and less than the risk of subsequent development of radiation disease in a subject determined to have been exposed to a dose of greater than about 6.5 Gy); one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue of mouse miR-34b-3p, miR-126-3p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of the human homologue of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference level(s) (e.g., level(s) in a sample including a biological fluid from a subject not exposed to a significant dose of radiation or exposed to about 2 Gy or exposed to about 2 Gy or less of radiation), indicates that the subject's risk of subsequent development of radiation disease is high (e.g., greater than the risk of subsequent development of radiation disease in a subject determined to have been exposed to 2 Gy or less of radiation and less than the risk of subsequent development of radiation disease in a subject determined to have been exposed to greater than about 6.5 Gy (e.g., about 8 Gy or more) radiation)); and/or one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologue of mouse miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologue of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s) (e.g., the level(s) of in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation), indicates that the subject's risk of subsequent development of radiation disease is very high (e.g., greater than the risk of subsequent development of radiation disease in a subject determined to have been exposed to 2 Gy or less of radiation and greater than the risk of subsequent development of radiation disease in a subject determined to have been exposed to about 6.5 Gy of radiation).

The level(s) of the one or more miRNAs can be measured using any of the methods described herein or known in the art. The subject can be any subject described herein or known in the art.

Some examples of these methods include administering (and optionally both selecting and administering) a treatment for reducing radiation-induced damage to the subject identified as having a very high risk or high risk of subsequent development of radiation disease. For example, the methods can include hospitalizing a subject identified as having a very high risk or high risk of subsequent development of radiation disease, and/or performing bone marrow transplantation, performing blood transfusion, administering a cytokine (e.g., any of the cytokines described herein) and/or performing surgery to remove damaged tissues on a subject identified as having a very high risk or high risk of subsequent development of radiation disease. Some embodiments further include treating a subject identified as having a moderate risk of subsequent development of radiation disease on an outpatient basis.

Some examples further include recording the subject's identified risk of subsequent development of radiation disease in the subject's clinical file (e.g., a computer readable medium). Some examples further include communicating the subject's identified risk of subsequent development of radiation disease to a governmental agency or a health organization. Some examples further include informing and isolating a subject identified as having a very high risk or high risk of subsequent development of radiation disease. Some examples further include informing one or more of the subject's physician, family, and employer of the subject's identified risk of subsequent development of radiation disease. Some examples further include triaging a subject based on his or her identified risk of subsequent development of radiation disease.

Methods of Selecting a Treatment for a Subject

Also provided herein are methods of selecting a treatment for a subject that include determining a level(s) of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs selected from the group of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p and human homologues of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p, in a sample including a biological fluid from the subject; comparing the level(s) of the one or more miRNAs in the sample to reference level(s) of the one or more miRNAs; and selecting a treatment for reducing radiation-induced damage (e.g., any of the exemplary treatments for reducing radiation-induced damage described herein or known in the art) for a subject based on the comparison of the level(s) of the one or more miRNAs in the sample to the reference level(s) of the one or more miRNAs.

Non-limiting examples of treatments for reducing radiation-induced damage include administration of one or more of a cytokine (e.g., granulocyte colony-stimulating factor, filgrastim, and pegfilgrastim), potassium iodide, Prussian blue, and diethylenetriamine pentaacetic acid, and performance of bone marrow transplantation, blood transfusion, and surgery to remove damaged tissues. In some examples, the selected treatment includes inpatient treatment.

In some examples, the reference level(s) is the level(s) of the one or more miRNAs in a sample including a biological fluid from a subject not exposed to a significant dose of radiation, a subject exposed to 0.2 Gy or less of radiation, a subject exposed to 0.4 Gy or less of radiation, a subject exposed to 0.6 Gy or less of radiation, a subject exposed to 0.8 Gy or less of radiation, or a subject exposed to 1 Gy or less of radiation. Additional examples of reference levels of the one or more miRNAs are described below.

In some examples, the subject is a mouse and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p. In some examples, a treatment for reducing radiation-induced damage is selected for a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s) (e.g., any of the reference levels described herein). In some examples, a treatment for reducing radiation-induced damage is not selected for a subject having a non-elevated level of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and a non-decreased level of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s) (e.g., any of the reference levels described herein). In some examples, the reference level(s) for mouse miR-130a-3p, miR-150-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p is the level(s) in a sample including a biological fluid from a subject not exposed to a significant dose of radiation; the reference level for mouse miR-17-3p is the level of mouse miR-17-3p in a sample including a biological fluid from a subject not exposed to a significant dose of radiation or exposed to about 2 Gy or exposed to about 2 Gy or less of radiation; and/or the reference level(s) of mouse miR-187-3p, miR-194-5p, miR-27a-3p, miR-30a-3p, and miR-30c-5p is the level(s) of mouse miR-187-3p, miR-194-5p, miR-27a-3p, miR-30a-3p, and miR-30c-5p in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation.

In some examples, the subject is a human and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of the human homologues of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p. In some examples, a treatment for reducing radiation-induced damage is selected for a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologues of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologues of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-

3p, miR-215-5p, and miR-338-3p in the sample, as compared to reference level(s) (e.g., any of the reference levels described herein). In some examples, a treatment for reducing radiation-induced damage is not selected for a subject having a non-elevated level of the human homologues of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and a non-decreased level of the human homologues of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s) (e.g., any of the reference levels described herein). In some examples, the reference level(s) for the human homologues of mouse miR-130a-3p, miR-150-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p is the level(s) in a sample including a biological fluid from a subject not exposed to a significant dose of radiation; the reference level for the human homologue of mouse miR-17-3p is the level of the human homologue of mouse miR-17-3p in a sample including a biological fluid from a subject not exposed to a significant dose of radiation or exposed to about 2 Gy or exposed to about 2 Gy or less of radiation; and/or the reference level(s) of the human homologue of mouse miR-187-3p, miR-194-5p, miR-27a-3p, miR-30a-3p, and miR-30c-5p is the level(s) of the human homologue of mouse miR-187-3p, miR-194-5p, miR-27a-3p, miR-30a-3p, and miR-30c-5p in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation.

The level(s) of the one or more miRNAs can be measured using any of the methods described herein or known in the art. The subject can be any subject described herein or known in the art.

Some embodiments of any of the methods described herein further include administering the selected treatment to the subject.

Some examples further include recording the selected treatment in the subject's clinical file (e.g., a computer readable medium). Some examples further include communicating the selected treatment to a governmental agency or a health organization. Some examples further include informing a subject of the treatment selected for him or her. Some examples further include informing one or more of the subject's physician, family, and employer of the treatment selected for the subject.

Methods of Selecting a Subject for Treatment

Also provided herein are methods of selecting a subject for treatment of radiation disease that include determining a level(s) of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs selected from the group of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p and human homologues of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p, in a sample including a biological fluid from the subject; comparing the level(s) of the one or more miRNAs in the sample to reference level(s) of the one or more miRNAs (e.g., any of the exemplary reference levels described herein); and selecting a subject for treatment of radiation disease based on the comparison of the level(s) of the one or more miRNAs in the sample to the reference level(s) of the one or more miRNAs.

Non-limiting examples of treatments for radiation disease (e.g., a treatment for reducing radiation-induced damage) include administration of one or more of a cytokine (e.g., granulocyte colony-stimulating factor, filgrastim, and pegfilgrastim), potassium iodide, Prussian blue, and diethylenetriamine pentaacetic acid, and/or performance of bone marrow transplantation, blood transfusion, and/or surgery to remove tissues damaged by radiation exposure. In some examples, treatment for radiation disease includes inpatient treatment.

In some examples, the reference level(s) is the level(s) of the one or more miRNAs in a sample including a biological fluid from a subject not exposed to a significant dose of radiation, a subject exposed to 0.2 Gy or less of radiation, a subject exposed to 0.4 Gy or less of radiation, a subject exposed to 0.6 Gy or less of radiation, a subject exposed to 0.8 Gy or less of radiation, or a subject exposed to 1 Gy or less of radiation. Additional examples of reference levels of the one or more miRNAs are described below.

In some examples, the subject is a mouse and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p. In some examples, a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s) (e.g., any of the reference levels described herein) is selected for treatment of radiation disease; or a subject not having an elevated level of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and not having a decreased level of one or more of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s) (e.g., any of the reference levels described herein) is not selected for treatment of radiation disease. In some examples, the reference levels for mouse miR-130a-3p, miR-150-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p is the level(s) in a sample including a biological fluid from a subject not exposed to a significant dose of radiation; the reference level for mouse miR-17-3p is the level of mouse miR-17-3p in a sample including a biological fluid from a subject not exposed to a significant dose of radiation or exposed to about 2 Gy or exposed to about 2 Gy or less of radiation; and/or the reference level(s) of mouse miR-187-3p, miR-194-5p, miR-27a-3p, miR-30a-3p, and miR-30c-5p is the level(s) of mouse miR-187-3p, miR-194-5p, miR-27a-3p, miR-30a-3p, and miR-30c-5p in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation.

In some examples, the subject is a human and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of the human homologues of mouse miR-130a-3p, miR-150-5p, miR-17-3p, miR-187-3p, miR-194-5p, miR-27a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR- 200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p. In some examples, a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologues of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more the human homologues of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s) (e.g., any of the reference levels described herein) is selected for treatment of radiation disease; or a subject not having an elevated level of the human homologues of mouse miR-130a-3p, miR-30a-3p, miR-30c-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and not having a decreased level of one or more of the human homologues of mouse miR-150-5p, miR-17-3p, miR-187-3p, miR-194-5p, miR-27a-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p in the sample, as compared to reference level(s) (e.g., any of the reference levels described herein) is not selected for treatment of radiation disease. In some examples, the reference level(s) of the human homologues of mouse miR-130a-3p, miR-150-5p, miR-320-3p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, miR-142-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-29b-3p, miR-215-5p, and miR-338-3p is the level(s) in a sample including a biological fluid from a subject not exposed to a significant dose of radiation; the reference level of the human homologue of mouse miR-17-3p is the level of the human homologue of mouse miR-17-3p in a sample including a biological fluid from a subject not exposed to a significant dose of radiation or exposed to about 2 Gy or exposed to about 2 Gy or less of radiation; and/or the reference level(s) of the human homologues of mouse miR-187-3p, miR-194-5p, miR-27a-3p, miR-30a-3p, and miR-30c-5p is the level(s) of the human homologues of mouse miR-187-3p, miR-194-5p, miR-27a-3p, miR-30a-3p, and miR-30c-5p in a sample including a biological fluid from a subject not exposed to a significant dose of radiation, exposed to about 2 Gy or exposed to about 2 Gy or less of radiation, or exposed to about 6.5 Gy or exposed to about 6.5 Gy or less of radiation.

The level(s) of the one or more miRNAs can be measured using any of the methods described herein or known in the art. The subject can be any subject described herein or known in the art.

Some embodiments of any of the methods described herein further include administering a treatment for radiation disease (e.g., any of the treatments for reducing radiation-induced damage) to the subject selected for treatment of radiation disease. Some examples further include recording in the subject's clinical file (e.g., a computer readable medium) that he or she has been selected for treatment of radiation disease or has not been selected for treatment of radiation disease. Some examples further include communicating to a governmental agency or a health organization that the subject has been selected for treatment of radiation disease or has not been selected for treatment of radiation disease. Some examples further include informing the subject that he or she has been selected for treatment of radiation disease or that he or she has not been selected for treatment of radiation disease. Some examples further include informing one or more of the subject's physician, family, and employer that the subject has been selected for treatment of radiation disease or that the subject has not been selected for treatment of radiation disease.

Methods of Triaging Subjects Exposed or Suspected of Being Exposed to Radiation

Also provided herein are methods of triaging a plurality of subjects exposed or suspected of being exposed to radiation that include determining a level of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p and human homologues of one or more of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p in a sample including a biological fluid from the subject; comparing the level(s) of the one or more miRNAs in the sample to reference level(s) of the one or more miRNAs (e.g., any of the reference levels described herein); and triaging the subject based on the comparison of the level(s) of the one or more miRNAs in the sample to the reference level(s) of the one or more miRNAs.

In some examples, the reference level(s) is the level(s) of the one or more miRNAs in a sample including a biological fluid from a subject not exposed to a significant dose of radiation, a subject exposed to 0.2 Gy or less of radiation, a subject exposed to 0.4 Gy or less of radiation, a subject exposed to 0.6 Gy or less of radiation, a subject exposed to 0.8 Gy or less of radiation, or a subject exposed to 1 Gy or less of radiation. Additional examples of reference levels of the one or more miRNAs are described below.

In some examples, the subject is a mouse and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-3p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In such examples, a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of mouse miR-150-5p, miR-142-5p, miR-320-3p, miR-142a-3p, miR-126-3p, miR-706, miR-29a-5p, miR-30a-3p, miR-194-5p, miR-let-7d-3p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to the reference level(s) (e.g., the level(s) in a sample including a biological fluid from a subject not exposed to a significant dose of radiation), is given low priority in triaging (e.g., subjects having high priority and medium priority are seen by a physician or treated before subjects having low priority); a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-320-3p, miR-30c-5p, miR-126-3p, miR-375-3p, miR-99b-5p, miR-30a-3p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference level(s), (e.g., a level in a sample including a biological fluid from a subject not exposed to a significant dose of radiation or exposed to about 2 Gy or exposed to about 2 Gy or less of radiation), is given medium priority in triaging (e.g., subjects having high priority are seen by a physician or treated before subjects having medium priority, and subjects having medium priority are seen by a physician or treated before subjects having low priority); and/or a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of mouse miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s) (e.g., a level(s) in a sample including a biological fluid from a subject not exposed to a significant dose of radiation or exposed to about 2 Gy or exposed to about 2 Gy or less of radiation), is given high priority in triaging (e.g., subjects having high priority are seen by a physician or treated before subjects having medium or low priority).

In some examples, the subject is a human and the one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) miRNAs are selected from the group of the human homologues of mouse miR-130a-3p, miR-150-5p, miR-17-3p, miR-187-3p, miR-194-5p, miR-27a-3p, miR-30a-3p, miR-30c-5p, miR-142-5p, miR-320-3p, miR-136-5p, miR-33-5p, miR-142a-3p, miR-126-3p, miR-706, miR-375-3p, miR-29a-5p, miR-193a-3p, miR-99b-5p, miR-151-3p, miR-let-7d-5p, miR-486-5p, miR-423-5p, miR-30b-5p, miR-191-5p, miR-497a-5p, miR-32-5p, miR-214-5p, miR-326-3p, miR-1195, miR-122-5p, miR-1839-3p, miR-500-3p, miR-30e-3p, miR-322-3p, miR-709, miR-486a-3p, miR-133a-3p, miR-676-3p, miR-744-5p, miR-29a-3p, miR-1839-5p, miR-30a-5p, miR-199b-5p, miR-125a-5p, miR-133b-3p, miR-24-3p, miR-21a-5p, miR-503-5p, miR-328-3p, miR-let-7g-5p, miR-362-3p, miR-199a-5p, miR-342-3p, miR-34b-3p, miR-15a-3p, miR-139-5p, miR-149-5p, miR-29b-3p, miR-1a-3p, miR-23b-3p, miR-215-5p, miR-204-5p, miR-200b-5p, miR-25-3p, miR-338-3p, and miR-196b-5p. In such examples, a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologues of mouse miR-130a-3p, miR-136-5p, miR-30c-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-17-3p, miR-29a-3p, miR-200b-5p, miR-25-3p, miR-338-3p, and miR-196b-5p, and/or a decreased level of one or more of the human homologues of mouse miR-150-5p, miR-142-5p, miR-320-3p, miR-142a-3p, miR-126-3p, miR-706, miR-29a-5p, miR-30a-3p, miR-194-5p, miR-let-7d-5p, miR-497a-5p, miR-214-5p, miR-1195, miR-122-5p, miR-500-3p, miR-322-3p, miR-133a-3p, miR-24-3p, miR-362-3p, miR-199a-5p, miR-342-3p, miR-34b-3p, miR-139-5p, miR-149-5p, miR-1a-3p, miR-23b-3p, miR-215-5p, miR-204-5p, and miR-187-3p in the sample, as compared to the reference level(s) (e.g., the level(s) in a sample including a biological fluid from a subject not exposed to a significant dose of radiation), is given low priority in triaging (e.g., subjects having high priority and medium priority are seen by a physician or treated before subjects having low priority); a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologues of mouse miR-320-3p, miR-30c-5p, miR-126-3p, miR-375-3p, miR-99b-5p, miR-30a-3p, miR-151-3p, miR-let-7d-5p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, miR-25-3p, and miR-196b-5p, and/or a decreased level of one or more of the human homologues of mouse miR-17-3p, miR-142-5p, miR-150-5p, miR-136-5p, miR-33-5p, miR-142a-3p, miR-706, miR-29a-5p, miR-193a-3p, miR-194-5p, miR-497a-5p, miR-32-5p, miR-214-5p, miR-326-3p, miR-122-5p, miR-500-3p, miR-27a-3p, miR-29a-3p, miR-199b-5p, miR-21a-5p, miR-503-5p, miR-362-3p, miR-199a-5p, miR-15a-3p, miR-29b-3p, miR-215-5p, miR-187-3p, and miR-338-3p in the sample, as compared to the reference level(s), (e.g., a level in a sample including a biological fluid from a subject not exposed to a significant dose of radiation or exposed to about 2 Gy or exposed to about 2 Gy or less of radiation), is given medium priority in triaging (e.g., subjects having high priority are seen by a physician or treated before subjects having medium priority, and subjects having medium priority are seen by a physician or treated before subjects having low priority); and/or a subject having one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, or 64) of: an elevated level of one or more of the human homologues of mouse miR-30a-3p, miR-30c-5p, miR-320-3p, miR-30c-5p, miR-126-3p, miR-375-3p, miR-99b-5p, miR-151-3p, miR-let-7d-3p, miR-486-5p, miR-423-5p, miR-30b-5p, miR-191-5p, miR-1195, miR-1839-3p, miR-30e-3p, miR-322-3p, miR-709, miR-486a-3p, miR-133a-3p, miR-676-3p, miR-744-5p, miR-1839-5p, miR-30a-5p, miR-125a-5p, miR-133b-3p, miR-24-3p, miR-328-3p, miR-let-7g-5p, miR-342-3p, miR-34b-3p, miR-139-5p, miR-149-5p, miR-1a-3p, miR-23b-3p, miR-204-5p, miR-200b-5p, and miR-25-3p, and/or a decreased level of one or more of the human homologues of mouse miR-187-3p, miR-194-5p, miR-27a-3p, miR-142-5p, miR-150-5p, miR-136-5p, miR-33-5p, miR-142a-3p, miR-706, miR-29a-5p, miR-193a-3p, miR-497a-5p, miR-32-5p, miR-214-5p, miR-326-3p, miR-122-5p, miR-500-3p, miR-32-5p, miR-214-5p, miR-326-3p, miR-122-5p, miR-500-3p, miR-29a-3p, miR-199b-5p, miR-21a-5p, miR-503-5p, miR-362-3p, miR-199a-5p, miR-15a-3p, miR-17-3p, miR-130a-3p, miR-29b-3p, miR-215-5p, miR-338-3p, and miR-196b-5p in the sample, as compared to the reference level(s) (e.g., a level(s) in a sample including a biological fluid from a subject not exposed to a significant dose of radiation or exposed to about 2 Gy or exposed to about 2 Gy or less of radiation), is given high priority in triaging (e.g., subjects having high priority are seen by a physician or treated before subjects having medium or low priority).

The level(s) of the one or more miRNAs can be measured using any of the methods described herein or known in the art. The subject can be any subject described herein or known in the art. In some examples, the plurality of subjects are subjects in an emergency room or housed in an emergency trauma facility.

Some embodiments of any of the methods described herein further include administering a treatment (e.g., any of the treatments for reducing radiation-induced damage) to a subject given high priority in triaging. Some examples further include recording into a computer system that the subject has been given low, medium, or high priority in triaging. Some examples further include communicating to a governmental agency or a health organization that the subject has been given low, medium, or high priority in triaging. Some examples further include informing the subject that he or she has been given low, medium, or high priority in triaging. Some examples further include informing one or more of the subject's physician, family, and employer that the subject has been given low, medium, or high priority in triaging.

Methods of Determining Efficacy of a Treatment Administered to a Subject Exposed or Suspected of being Exposed to a Significant Dose of Radiation Also provided are methods of determining the efficacy of a treatment administered to a subject exposed to a significant dose of radiation that include (a) determining a first level of one or more (e.g., two or more, three or more, four or more, five or more, six or more, seven or more, eight or more, nine or more, ten or more, eleven or more, 2, 3, 4, 5, 6, 7, 8, 9, 10, 11, or 12) miRNAs in a sample including a biological fluid obtained from the subject exposed to a significant dose of radiation at a first time point; (b) after the first time point and before a second time point, administering a treatment for reducing radiation-induced damage to the subject (e.g., any of the treatments for reducing radiation-induced damage described herein); (c) determining a second level of the one or more (e.g., two or more, three or more, four or more, five or more, six or more, seven or more, eight or more, nine or more, ten or more, eleven or more, 2, 3, 4, 5, 6, 7, 8, 9, 10, 11, or 12) miRNAs in a sample including a biological fluid obtained from the subject at the second time point; and (d) determining the efficacy of the treatment administered to the subject based on a comparison of the second level(s) of the one or more miRNAs to the first level(s) of the one or more miRNAs.

In some examples, the subject is a mouse and the one or more (e.g., two or more, three or more, four or more, five or more, six or more, seven or more, eight or more, nine or more, ten or more, eleven or more, 2, 3, 4, 5, 6, 7, 8, 9, 10, 11, or 12) miRNAs are selected from the group of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p. In some examples, one or more (e.g., two, three, four, five, six, seven, eight, nine, ten, eleven, or twelve) of: an elevation in the second level of one or more of mouse miR-142-5p, miR-150-5p, miR-342-3p, miR-17-3p, miR-187-3p, miR-194-5p, and miR-27a-3p, and/or a decrease in the second level of one or more of mouse miR-130a-3p, miR-126-3p, miR-346-3p, miR-30a-3p, and miR-30c-5p, as compared to the first level(s) of one or more of mouse miR-142-5p, miR-150-5p, miR-342-3p, miR-17-3p, miR-187-3p, miR-194-5p, miR-27a-3p, miR-130a-3p, miR-126-3p, miR-346-3p, miR-30a-3p, and miR-30c-5p, indicates that the treatment administered to the subject was effective.

In some examples, the subject is a human and the one or more (e.g., two or more, three or more, four or more, five or more, six or more, seven or more, eight or more, nine or more, ten or more, eleven or more, 2, 3, 4, 5, 6, 7, 8, 9, 10, 11, or 12) miRNAs are selected from the group of human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p. In some examples, one or more (e.g., two, three, four, five, six, seven, eight, nine, ten, eleven, or twelve) of: an elevation in the second level of one or more of the human homologues of mouse miR-142-5p, miR-150-5p, miR-342-3p, miR-17-3p, miR-187-3p, miR-194-5p, and miR-27a-3p, and/or a decrease in the second level of one or more of the human homologues of mouse miR-130a-3p, miR-126-3p, miR-346-3p, miR-30a-3p, and miR-30c-5p, as compared to the first level(s) of one or more of the human homologues of mouse miR-142-5p, miR-150-5p, miR-342-3p, miR-17-3p, miR-187-3p, miR-194-5p, miR-27a-3p, miR-130a-3p, miR-126-3p, miR-346-3p, miR-30a-3p, and miR-30c-5p, indicates that the treatment administered to the subject was effective.

Also provided are methods including determining the efficacy of a treatment for reducing radiation-induced damage in a subject exposed to a significant level of radiation that includes (a) determining a level of one or more (e.g., two or more, three or more, four or more, five or more, six or more, seven or more, eight or more, nine or more, ten or more, eleven or more, 2, 3, 4, 5, 6, 7, 8, 9, 10, 11, or 12) miRNAs in a sample including a biological fluid from a subject previously exposed to a significant level of radiation and thereafter administered a treatment for reducing radiation-induced damage; (b) comparing the level(s) of the one or more miRNAs in the sample to reference level(s) of the one or more miRNAs (e.g., any of the reference levels described herein); and (c) determining the efficacy of the treatment for reducing radiation-induced damage in the subject based on the comparison of the level(s) of the one or more miRNAs in the sample to the reference level(s) of the one or more miRNAs.

Non-limiting examples of treatments for reducing radiation-induced damage is selected from the group of cytokines (e.g., granulocyte colony-stimulating factor, filgrastim, and pegfilgrastim), potassium iodide, Prussian blue, diethylenetriamine pentaacetic acid, bone marrow transplantation, blood transfusion, and surgery to remove damaged tissues.

In some examples, the reference level(s) is the level(s) of the one or more miRNAs in a sample including a biological fluid from a subject not exposed to a significant dose of radiation, a subject exposed to 0.2 Gy or less of radiation, a subject exposed to 0.4 Gy or less of radiation, a subject exposed to 0.6 Gy or less of radiation, a subject exposed to 0.8 Gy or less of radiation, or a subject exposed to 1 Gy or less of radiation. Additional examples of reference levels of the one or more miRNAs are described below.

In some examples, the subject is a mouse and the one or more (e.g., two or more, three or more, four or more, five or more, six or more, seven or more, eight or more, nine or more, ten or more, eleven or more, 2, 3, 4, 5, 6, 7, 8, 9, 10, 11, or 12) mRNAs are selected from the group of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p. In some examples, one or more (e.g., two, three, four, five, six, seven, eight, nine, ten, eleven, or twelve) of: an elevated level of one or more of mouse miR-130a-3p, miR-34-3p, miR-126-3p, miR-30a-3p, and miR-30c-5p, and/or a decreased level of one or more of mouse miR-142-5p, miR-150-5p, miR-342-3p, miR-17-3p, miR-187-3p, miR-194-5p, and miR-27a-3p, in the sample, as compared to the reference level(s) (e.g., levels in a sample including biological fluid from a subject not exposed to a significant dose of radiation, a subject exposed to a significant level of radiation and not administered a treatment or not administered an effective treatment, a subject exposed to about 2 Gy or exposed to about 2 Gy or less of radiation, or a subject exposed to about 6.5 Gy or exposed to about 6.5 Gy or less of radiation or levels in a sample including a biological fluid from a control subject that was exposed to a significant level of radiation and administered an effective treatment), indicates that treatment was not effective; or one or more (e.g., two or more, three or more, four or more, five or more, six or more, seven or more, eight or more, nine or more, ten or more, eleven or more, 2, 3, 4, 5, 6, 7, 8, 9, 10, 11, or 12) of a non-elevated level of mouse miR-130a-3p, miR-34-3p, miR-126-3p, miR-30a-3p, and miR-30c-5p, and a non-decreased level of mouse miR-142-5p, miR-150-5p, miR-342-3p, miR-17-3p, miR-187-3p, miR-194-5p, and miR-27a-3p, in the sample, as compared to the reference level(s) (e.g., levels in a sample including biological fluid from a subject not exposed to a significant dose of radiation, a subject exposed to a significant level of radiation and not administered a treatment or not administered an effective treatment, a subject exposed to about 2 Gy or exposed to about 2 Gy or less of radiation, or a subject exposed to about 6.5 Gy or exposed to about 6.5 Gy or less of radiation or levels in a sample including a biological fluid from a control subject that was exposed to a significant level of radiation and administered an effective treatment), indicates that treatment was effective.

In some examples, the subject is a human and the one or more (e.g., two or more, three or more, four or more, five or more, six or more, seven or more, eight or more, nine or more, ten or more, eleven or more, 2, 3, 4, 5, 6, 7, 8, 9, 10, 11, or 12) mRNAs are selected from the group of the human homologues of mouse miR-130a-3p, miR-142-5p, miR-150-5p, miR-342-3p, miR-34b-3p, miR-126-3p, miR-17-3p, miR-187-3p, miR-194-5p, miR-27a-3p, miR-30a-3p, and miR-30c-5p. In some examples, one or more (e.g., two, three, four, five, six, seven, eight, nine, ten, eleven, or twelve) of: an elevated level of one or more of the human homologue of mouse miR-130a-3p, miR-34-3p, miR-126-3p, miR-30a-3p, and miR-30c-5p, and/or a decreased level of one or more of the human homologue of mouse miR-142-5p, miR-150-5p, miR-342-3p, miR-17-3p, miR-187-3p, miR-194-5p, and miR-27a-3p, in the sample, as compared to the reference level(s) (e.g., levels in a sample including biological fluid from a subject not exposed to a significant dose of radiation, a subject exposed to a significant level of radiation and not administered a treatment or not administered an effective treatment, a subject exposed to about 2 Gy or exposed to about 2 Gy or less of radiation, or a subject exposed to about 6.5 Gy or exposed to about 6.5 Gy or less of radiation or levels in a sample including a biological fluid from a control subject that was exposed to a significant level of radiation and administered an effective treatment), indicates that treatment was not effective; or one or more (e.g., two or more, three or more, four or more, five or more, six or more, seven or more, eight or more, nine or more, ten or more, eleven or more, 2, 3, 4, 5, 6, 7, 8, 9, 10, 11, or 12) of a non-elevated level of the human homologues of mouse miR-130a-3p, miR-34-3p, miR-126-3p, miR-30a-3p, and miR-30c-5p, and a non-decreased level of the human homologues of mouse miR-142-5p, miR-150-5p, miR-342-3p, miR-17-3p, miR-187-3p, miR-194-5p, and miR-27a-3p, in the sample, as compared to the reference level(s) (e.g., levels in a sample including biological fluid from a subject not exposed to a significant dose of radiation, a subject exposed to a significant level of radiation and not administered a treatment or not administered an effective treatment, a subject exposed to about 2 Gy or exposed to about 2 Gy or less of radiation, or a subject exposed to about 6.5 Gy or exposed to about 6.5 Gy or less of radiation or levels in a sample including a biological fluid from a control subject that was exposed to a significant level of radiation and administered an effective treatment), indicates that treatment was effective.

The level(s) of the one or more miRNAs can be measured using any of the methods described herein or known in the art. For example, the first and second level(s) of the one or more miRNAs in the samples are determined in steps (a) and (c) by amplifying the miRNAs present in the sample(s) to generate amplification products, contacting the amplified products to a substrate, and detecting the amplified products bound to the substrate. The subject can be any subject described herein or known in the art.

Some embodiments further include administering one or more additional doses of a treatment identified as being effective. Some embodiments, where the treatment was identified as not being effective, further include administering an alternate treatment to the subject.

Methods of Treating a Subject Having Radiation Disease

Also provided are methods of treating a subject having radiation disease (e.g., a subject that has been identified or has been diagnosed as having radiation disease) or a subject identified as having been exposed to a significant level of radiation (e.g., using any of the methods described herein) that include administering a therapeutically effective dose of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) of mouse miR-150-5p, miR-17-3p, miR-187-3p, miR-194-5p, miR-27a-3p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, and miR-204-5p, and human homologues of mouse miR-150-5p, miR-17-3p, miR-187-3p, miR-194-5p, miR-27a-3p, miR-142-5p, miR-320-3p, miR-142a-3p, miR-126-3p, miR-706, miR-29a-5p, miR-let-7d-3p, miR-497a-5p, miR-214-5p, miR-1195, miR-122-5p, miR-500-3p, miR-322-3p, miR-133a-3p, miR-29a-3p, miR-199b-5p, miR-125a-5p, miR-133b-3p, miR-24-3p, miR-362-3p, miR-199a-5p, miR-342-3p, miR-34b-3p, miR-139-5p, miR-149-5p, miR-1a-3p, miR-23b-3p, miR-215-5p, and miR-204-5p, and/or a therapeutically effective dose of one or more (e.g., two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty of more) (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30) of an inhibitory nucleic acid that decreases the levels of one or more of mouse miR-130a-3p, miR-30a-3p, miR-30c-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p, and human homologues of mouse miR-130a-3p, miR-30a-3p, miR-30c-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p in a subject. Non-limiting examples of an inhibitory nucleic acid include siRNAs, shRNAs, and antisense nucleic acids which contain a sequence that is complementary to a sequence present in one of mouse miR-130a-3p, miR-30a-3p, miR-30c-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p, and human homologues of mouse miR-130a-3p, miR-30a-3p, miR-30c-5p, miR-136-5p, miR-375-3p, miR-193a-3p, miR-151-3p, miR-486-5p, miR-423-5p, miR-30b-5p, miR-191-5p, miR-32-5p, miR-326-3p, miR-1839-3p, miR-709, miR-486a-3p, miR-676-3p, miR-744-5p, miR-1839-5p, miR-30a-5p, miR-21a-5p, miR-503-5p, miR-328-3p, miR-let-7g-5p, miR-15a-3p, miR-29b-3p, miR-200b-5p, miR-25-3p, miR-338-3p, and miR-1966-5p.

Kits

Also provided herein are kits that consist or consist essentially of one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, or 67) of: (i) at least one nucleic acid including a sequence (e.g., a sequence of between about 5 nucleotides to 25 nucleotides) that is complementary to all or a part of the sequence of the human homolog of mouse miR-130a-3p; (ii) at least one nucleic acid including a sequence (e.g., a sequence of between about 5 nucleotides to 25 nucleotides) that is complementary to all or a part of the sequence of the human homolog of mouse miR-150-5p; (iii) at least one nucleic acid including a sequence (e.g., a sequence of between about 5 nucleotides to 25 nucleotides) that is complementary to all or a part of the sequence of the human homolog of mouse miR-17-3p; (iv) at least one nucleic acid including a sequence (e.g., a sequence of between about 5 nucleotides to 25 nucleotides) that is complementary to all or a part of the sequence of the human homolog of mouse miR-187-3p; (v) at least one nucleic acid including a sequence (e.g., a sequence of between about 5 nucleotides to 25 nucleotides) that is complementary to all or a part of the sequence of the human homolog of mouse miR-194-5p; (vi) at least one nucleic acid including a sequence (e.g., a sequence of between about 5 nucleotides to 25 nucleotides) that is complementary to all or a part of the sequence of the human homolog of mouse miR-27a-3p; (vii) at least one nucleic acid including a sequence (e.g., a sequence of between about 5 nucleotides to 25 nucleotides) that is complementary to all or a part of the sequence of the human homolog of mouse miR-30a-3p; (viii) at least one nucleic acid including a sequence (e.g., a sequence of between about 5 nucleotides to 25 nucleotides) that is complementary to all or a part of the sequence of the human homolog of mouse miR-30c-5p; (ix) at least one nucleic acid including a sequence (e.g., a sequence of between about 5 nucleotides to 25 nucleotides) that is complementary to all or a part of the sequence of the human homolog of mouse miR-142-5p; (x) at least one nucleic acid including a sequence (e.g., a sequence of between about 5 nucleotides to 25 nucleotides) that is complementary to all or a part of the sequence of the human homolog of mouse miR-342-3p; (xi) at least one nucleic acid including a sequence (e.g., a sequence of between about 5 nucleotides to 25 nucleotides) that is complementary to all or a part of the sequence of the human homolog of mouse miR-34b-3p; (xii) at least one nucleic acid including a sequence (e.g., a sequence of between about 5 nucleotides to 25 nucleotides) that is complementary to all or a part of the sequence of the human homolog of mouse miR-126-3p; (xiii) at least one nucleic acid comprising a sequence (e.g., a sequence of between about 5 nucleotides to 25 nucleotides) that is complementary to all or a part of the sequence of the human homolog of mouse miR-320-3p; (xiv) at least one nucleic acid comprising a sequence (e.g., a sequence of between about 5 nucleotides to 25 nucleotides) that is complementary to all or a part of the sequence of the human homolog of mouse miR-136-5p; (xv) at least one nucleic acid comprising a sequence (e.g., a sequence of between about 5 nucleotides to 25 nucleotides) that is complementary to all or a part of the sequence of the human homolog of mouse miR-33-5p; (xvi) at least one nucleic acid comprising a sequence (e.g., a sequence of between about 5 nucleotides to 25 nucleotides) that is complementary to all or a part of the sequence of the human homolog of mouse miR-142a-3p; (xvii) at least one nucleic acid comprising a sequence (e.g., a sequence of between about 5 nucleotides to 25 nucleotides) that is complementary to all or a part of the sequence of the human homolog of mouse miR-706; (xviii) at least one nucleic acid comprising a sequence (e.g., a sequence of between about 5 nucleotides to 25 nucleotides) that is complementary to all or a part of the sequence of the human homolog of mouse miR-375-3p; (xix) at least one nucleic acid comprising a sequence (e.g., a sequence of between about 5 nucleotides to 25 nucleotides) that is complementary to all or a part of the sequence of the human homolog of mouse miR-29a-5p; (xx) at least one nucleic acid comprising a sequence (e.g., a sequence of between about 5 nucleotides to 25 nucleotides) that is complementary to all or a part of the sequence of the human homolog of mouse miR-193a-3p; (xxi) at least one nucleic acid comprising a sequence (e.g., a sequence of between about 5 nucleotides to 25 nucleotides) that is complementary to all or a part of the sequence of the human homolog of mouse miR-99b-5p; (xxii) at least one nucleic acid comprising a sequence (e.g., a sequence of between about 5 nucleotides to 25 nucleotides) that is complementary to all or a part of the sequence of the human homolog of mouse miR-151-3p; (xxiii) at least one nucleic acid comprising a sequence (e.g., a sequence of between about 5 nucleotides to 25 nucleotides) that is complementary to all or a part of the sequence of the human homolog of mouse miR-let-7d-3p; (xxiv) at least one nucleic acid comprising a sequence (e.g., a sequence of between about 5 nucleotides to 25 nucleotides) that is complementary to all or a part of the sequence of the human homolog of mouse miR-486-5p; (xxv) at least one nucleic acid comprising a sequence (e.g., a sequence of between about 5 nucleotides to 25 nucleotides) that is complementary to all or a part of the sequence of the human homolog of mouse miR-423-5p; (xxvi) at least one nucleic acid comprising a sequence (e.g., a sequence of between about 5 nucleotides to 25 nucleotides) that is complementary to all or a part of the sequence of the human homolog of mouse miR-30b-5p; (xxvii) at least one nucleic acid comprising a sequence (e.g., a sequence of between about 5 nucleotides to 25 nucleotides) that is complementary to all or a part of the sequence of the human homolog of mouse miR-191-5p; (xxviii) at least one nucleic acid comprising a sequence (e.g., a sequence of between about 5 nucleotides to 25 nucleotides) that is complementary to all or a part of the sequence of the human homolog of mouse miR-497a-5p; (xxix) at least one nucleic acid comprising a sequence (e.g., a sequence of between about 5 nucleotides to 25 nucleotides) that is complementary to all or a part of the sequence of the human homolog of mouse miR-32-5p; (xxx) at least one nucleic acid comprising a sequence (e.g., a sequence of between about 5 nucleotides to 25 nucleotides) that is complementary to all or a part of the sequence of the human homolog of mouse miR-214-5p; (xxxi) at least one nucleic acid comprising a sequence (e.g., a sequence of between about 5 nucleotides to 25 nucleotides) that is complementary to all or a part of the sequence of the human homolog of mouse miR-326-3p; (xxxii) at least one nucleic acid comprising a sequence (e.g., a sequence of between about 5 nucleotides to 25 nucleotides) that is complementary to all or a part of the sequence of the human homolog of mouse miR-1195; (xxxiii) at least one nucleic acid comprising a sequence (e.g., a sequence of between about 5 nucleotides to 25 nucleotides) that is complementary to all or a part of the sequence of the human homolog of mouse miR-122-5p; (xxxiv) at least one nucleic acid comprising a sequence (e.g., a sequence of between about 5 nucleotides to 25 nucleotides) that is complementary to all or a part of the sequence of the human homolog of mouse miR-1839-3p; (xxxv) at least one nucleic acid comprising a sequence (e.g., a sequence of between about 5 nucleotides to 25 nucleotides) that is complementary to all or a part of the sequence of the human homolog of mouse miR-500-3p; (xxxvi) at least one nucleic acid comprising a sequence (e.g., a sequence of between about 5 nucleotides to 25 nucleotides) that is complementary to all or a part of the sequence of the human homolog of mouse miR-30e-3p; (xxxvii) at least one nucleic acid comprising a sequence (e.g., a sequence of between about 5 nucleotides to 25 nucleotides) that is complementary to all or a part of the sequence of the human homolog of mouse miR-322-3p; (xxxviii) at least one nucleic acid comprising a sequence (e.g., a sequence of between about 5 nucleotides to 25 nucleotides) that is complementary to all or a part of the sequence of the human homolog of mouse miR-709; (xxxix) at least one nucleic acid comprising a sequence (e.g., a sequence of between about 5 nucleotides to 25 nucleotides) that is complementary to all or a part of the sequence of the human homolog of mouse miR-486a-3p; (xxxx) at least one nucleic acid comprising a sequence (e.g., a sequence of between about 5 nucleotides to 25 nucleotides) that is complementary to all or a part of the sequence of the human homolog of mouse miR-133a-3p; (xxxxi) at least one nucleic acid comprising a sequence (e.g., a sequence of between about 5 nucleotides to 25 nucleotides) that is complementary to all or a part of the sequence of the human homolog of mouse miR-676-3p; (xxxxii) at least one nucleic acid comprising a sequence (e.g., a sequence of between about 5 nucleotides to 25 nucleotides) that is complementary to all or a part of the sequence of the human homolog of mouse miR-744-5p; (xxxxiii) at least one nucleic acid comprising a sequence (e.g., a sequence of between about 5 nucleotides to 25 nucleotides) that is complementary to all or a part of the sequence of the human homolog of mouse miR-29a-3p; (xxxxiv) at least one nucleic acid comprising a sequence (e.g., a sequence of between about 5 nucleotides to 25 nucleotides) that is complementary to all or a part of the sequence of the human homolog of mouse miR-1839-5p; (xxxxv) at least one nucleic acid comprising a sequence (e.g., a sequence of between about 5 nucleotides to 25 nucleotides) that is complementary to all or a part of the sequence of the human homolog of mouse miR-30a-5p; (xxxxvi) at least one nucleic acid comprising a sequence (e.g., a sequence of between about 5 nucleotides to 25 nucleotides) that is complementary to all or a part of the sequence of the human homolog of mouse miR-199b-5p; (xxxxvii) at least one nucleic acid comprising a sequence (e.g., a sequence of between about 5 nucleotides to 25 nucleotides) that is complementary to all or a part of the sequence of the human homolog of mouse miR-125a-5p; (xxxxviii) at least one nucleic acid comprising a sequence (e.g., a sequence of between about 5 nucleotides to 25 nucleotides) that is complementary to all or a part of the sequence of the human homolog of mouse miR-133b-3p; (il) at least one nucleic acid comprising a sequence (e.g., a sequence of between about 5 nucleotides to 25 nucleotides) that is complementary to all or a part of the sequence of the human homolog of mouse miR-24-3p; (1) at least one nucleic acid comprising a sequence (e.g., a sequence of between about 5 nucleotides to 25 nucleotides) that is complementary to all or a part of the sequence of the human homolog of mouse miR-21a-5p; (li) at least one nucleic acid comprising a sequence (e.g., a sequence of between about 5 nucleotides to 25 nucleotides) that is complementary to all or a part of the sequence of the human homolog of mouse miR-503-5p; (lii) at least one nucleic acid comprising a sequence (e.g., a sequence of between about 5 nucleotides to 25 nucleotides) that is complementary to all or a part of the sequence of the human homolog of mouse miR-328-3p; (liii) at least one nucleic acid comprising a sequence (e.g., a sequence of between about 5 nucleotides to 25 nucleotides) that is complementary to all or a part of the sequence of the human homolog of mouse miR-let-7g-5p; (liv) at least one nucleic acid comprising a sequence (e.g., a sequence of between about 5 nucleotides to 25 nucleotides) that is complementary to all or a part of the sequence of the human homolog of mouse miR-362-3p; (lv) at least one nucleic acid comprising a sequence (e.g., a sequence of between about 5 nucleotides to 25 nucleotides) that is complementary to all or a part of the sequence of the human homolog of mouse miR-199a-5p; (lvi) at least one nucleic acid comprising a sequence (e.g., a sequence of between about 5 nucleotides to 25 nucleotides) that is complementary to all or a part of the sequence of the human homolog of mouse miR-15a-3p; (lvii) at least one nucleic acid comprising a sequence (e.g., a sequence of between about 5 nucleotides to 25 nucleotides) that is complementary to all or a part of the sequence of the human homolog of mouse miR-139-5p; (lviii) at least one nucleic acid comprising a sequence (e.g., a sequence of between about 5 nucleotides to 25 nucleotides) that is complementary to all or a part of the sequence of the human homolog of mouse miR-149-5p; (lix) at least one nucleic acid comprising a sequence (e.g., a sequence of between about 5 nucleotides to 25 nucleotides) that is complementary to all or a part of the sequence of the human homolog of mouse miR-29b-3p; (lx) at least one nucleic acid comprising a sequence (e.g., a sequence of between about 5 nucleotides to 25 nucleotides) that is complementary to all or a part of the sequence of the human homolog of mouse miR-1a-3p; (lxi) at least one nucleic acid comprising a sequence (e.g., a sequence of between about 5 nucleotides to 25 nucleotides) that is complementary to all or a part of the sequence of the human homolog of mouse miR-23b-3p; (lxii) at least one nucleic acid comprising a sequence (e.g., a sequence of between about 5 nucleotides to 25 nucleotides) that is complementary to all or a part of the sequence of the human homolog of mouse miR-215-5p; (lxiii) at least one nucleic acid comprising a sequence (e.g., a sequence of between about 5 nucleotides to 25 nucleotides) that is complementary to all or a part of the sequence of the human homolog of mouse miR-204-5p; (lxiv) at least one nucleic acid comprising a sequence (e.g., a sequence of between about 5 nucleotides to 25 nucleotides) that is complementary to all or a part of the sequence of the human homolog of mouse miR-200b-5p; (lxv) at least one nucleic acid comprising a sequence (e.g., a sequence of between about 5 nucleotides to 25 nucleotides) that is complementary to all or a part of the sequence of the human homolog of mouse miR-25-3p; (lxvi) at least one nucleic acid comprising a sequence (e.g., a sequence of between about 5 nucleotides to 25 nucleotides) that is complementary to all or a part of the sequence of the human homolog of mouse miR-338-3p; and (lxvii) at least one nucleic acid comprising a sequence (e.g., a sequence of between about 5 nucleotides to 25 nucleotides) that is complementary to all or a part of the sequence of the human homolog of mouse miR-196b-5p.

The at least one nucleic acid can include an alternate backbone chemistry, such as phosphorothioate bond-based chemistries, and alternative nucleoside residues, such as modified residues, that are capable of pairing with multiple nucleoside base residues.

In some examples, one or more (e.g., two, three, four, five, six, seven, eight, nine, ten, eleven, or twelve) of the nucleic acid of (i) through (lxvii) is bound to a substrate (e.g., a glass chip, a chip or microchip, slides, a bead, or a film). Some examples of the kits further include one or more nucleic acids that act as spiked in DNA or RNA loading controls. Non-limiting examples of spiked in DNA or RNA loading controls are described in the Examples, and additional examples are well known in the art. Some examples of the kits further include instructions to performing any of the methods described herein.

In some embodiments, the one or more nucleic acids of (i) through (lxvii) bound to a substrate is an array. Arrays typically contain addressable moieties that can detect the presence of an entity in a sample including a biological fluid, e.g., via the binding event.

In some examples, the substrate in the kits can be a surface-derivatized glass or silica, or a polymer membrane surface (see e.g., Guo, et al., *Nucleic Acids Res.* 22:5456-5465, 1994; Maskos et al., *Nucleic Acids Res.* 20:1679-1684, 1992; and Southern, et al., *Nucleic Acids Res.* 22:1368-1373, 1994). Modification of the surface of the substrate can be accomplished any of the techniques known in the art. For example, siliceous or metal oxide surfaces can be derivatized with bifunctional silanes, i.e., silanes having a first functional group enabling covalent binding to the surface (e.g., Si-halogen or Si-alkoxy group, as in —$SiCl_3$ or —$Si(OCH_3)_3$, respectively) and a second functional group that can impart the desired chemical and/or physical modifications to the surface to covalently or non-covalently attach the one or more nucleic acids of (i) through (lxvii). Silylated derivatizations and other surface derivatizations are known in the art (see, e.g., U.S. Pat. Nos. 5,624,711; 5,266,222; and 5,137,765). Other processes for preparing arrays are described in U.S. Pat. No. 6,649,348.

Polymer array synthesis is also described extensively in the literature including in the following: WO 00/58516 and U.S. Pat. Nos. 5,143,854; 5,242,974; 5,252,743; 5,324,633; 5,384,261; 5,405,783; 5,424,186; 5,451,683; 5,482,867; 5,491,074; 5,527,681; 5,550,215; 5,571,639; 5,578,832; 5,593,839; 5,599,695; 5,624,711; 5,631,734; 5,795,716; 5,831,070; 5,837,832; 5,856,101; 5,858,659; 5,936,324; 5,968,740; 5,974,164; 5,981,185; 5,981,956; 6,025,601; 6,033,860; 6,040,193; 6,090,555; 6,136,269; 6,269,846; 6,428,752; 5,412,087; 6,147,205; 6,262,216; 6,310,189; 5,889,165; and 5,959,098, and WO 99/36760 and WO 01/58593.

EXAMPLES

Several general protocols are described below, which may be used in any of the methods described herein and do not limit the scope of the invention described in the claims.

Example 1. Characterization of Hematopoietic Injury in C57BL/6J Mice Following Exposure to Different Doses of Total Body Irradiation An initial set of experiments was performed to test the effect of total body irradiation on the hematopoietic system in mice.

Materials and Methods

Mice and Total Body Irradiation

C57BL/6J male mice (10 weeks old) were obtained from Jackson Labs (Bar Harbor, Me.) and the mice were used in the experiments at an age of 12-13 weeks. Animals were exposed to total body irradiation in an irradiation pie cage (Braintree Scientific, Braintree, Mass.) at various doses. Irradiation was performed using a 137Cs source (Gamma Cell® 40 Exactor, Best Theratronics, Ottawa, Ontario).

Bone Marrow Harvest and Flow Cytometry

Bone marrow was harvested as per protocols described in Parmar et al. (*Stem Cells* 28:1186-1195, 2010). Briefly, animals were dissected to isolate the femurs and tibia from the mouse hind limb. The extracted bones were flushed with a 23-gauge needle using Hank's Balanced Salt Solution (HBSS, Life Technologies, Grand Island, N.Y.) supplemented with 2% fetal bovine serum (FBS) and 1% 10 mM HEPES (Life Technologies) to obtain bone marrow. The cells were then passed through an 18 gauge needle to obtain a single cell suspension. The bone marrow mononuclear cell count (BM-MNC) was determined by counting cells using 3% acetic acid with methylene blue solution (Stem Cell Technologies, Vancouver, British Columbia). For LKS (lineage, cKit, Sca-1) staining to visualize hematopoietic progenitor cells (HPCs) and hematopoietic stem cells (HSCs), whole bone marrow was stained with biotinylated anti-lineage cocktail (anti-Mac1, Gr-1, CD3e, B220, and Ter119), APC-conjugated anti-cKit (clone 2B8), and PECy7-conjugated anti Sca-1 (clone D7) antibodies. Following primary antibody staining, the cells were washed and incubated in PE-conjugated streptavidin secondary antibody to visualize lineage-positive cells. All primary and secondary antibodies were obtained from BD Biosciences (San Jose, Calif.). The samples were acquired using an LSR Fortessa instrument (Becton Dickinson, Franklin Lakes, N.J.) and data was analyzed using FlowJo software (Tree-Star, Ashland, Oreg.).

Colony Assays

To assess colony-forming ability, whole bone marrow isolated after flushing mouse femurs and tibiae was plated in 12-well plates at a density of 20,000 to 100,000 cells/well in methylcellulose medium (Methocult CF M3434, Stem Cell Technologies, Vancouver, British Columbia) containing recombinant murine IL-3, recombinant murine IL-6, and recombinant human erythropoietin. Cells from all samples were plated in triplicates and incubated at 37° C. in 5% $CO_2$ for 7 days at which time hematopoietic colonies formed (colony-forming units in culture, CFU-Cs) were scored.

Complete Blood Counts (CBCs)

Blood collection for CBCs (100 µL) was performed by retro-orbital bleeding after anesthesia in EDTA-coated tubes (BD Biosciences, San Jose, Calif.). CBCs were recorded with a Hemavet 950 FS hematology analyzer (Drew Scientific, Dallas, Tex.).

Results

Figure 1:
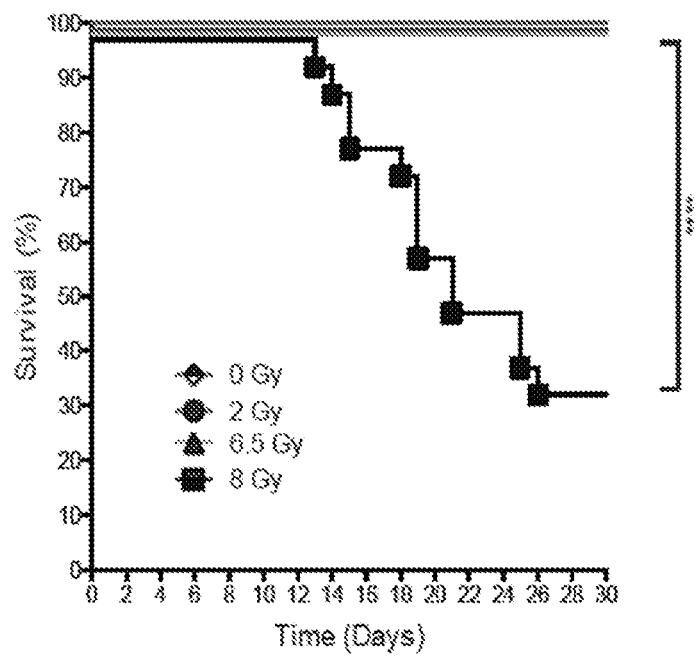
FIG. 1 is a Kaplan-Meier survival curve of C57BL/6J male mice (n=20 per group) exposed to 0 Gy- (control), 2 Gy-, 6.5 Gy-, or 8 Gy-total body irradiation. The data were analyzed by Log-rank (Mantel-Cox) test.
Figure 2:
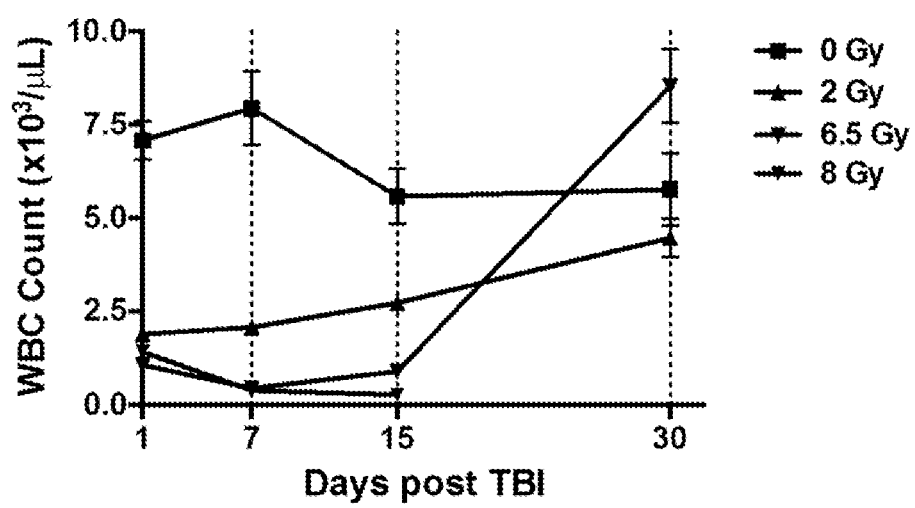
FIG. 2 is a graph showing the total white blood cell count in C57BL/6J mice at 1 day, 7 days, 15 days, or 30 days after 0 Gy- (control), 2 Gy-, 6.5 Gy-, or 8 Gy-total body irradiation (n=5 mice per group per time point).
Figure 3:
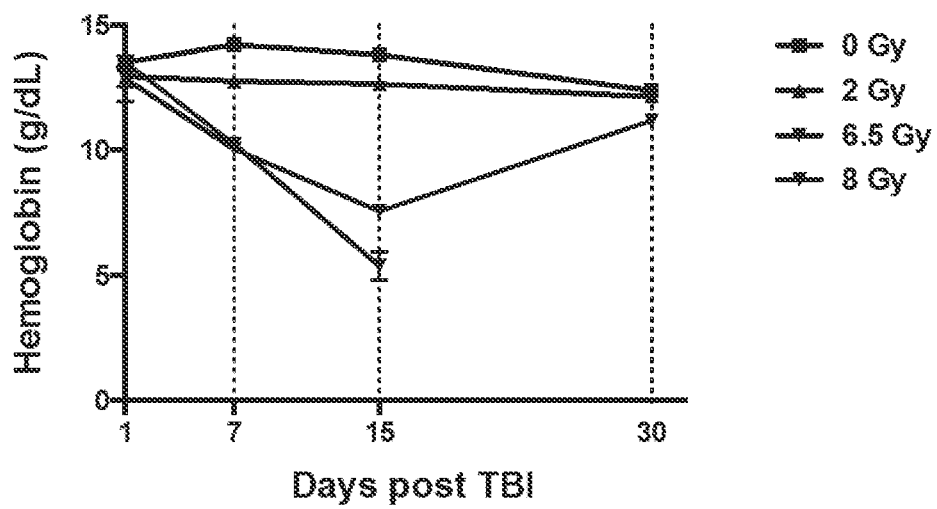
FIG. 3 is a graph showing the hemoglobin levels in C57BL/6J mice at 1 day, 7 days, 15 days, or 30 days after 0 Gy- (control), 2 Gy-, 6.5 Gy-, or 8 Gy-total body irradiation (n=5 mice per group per time point).
Figure 4:
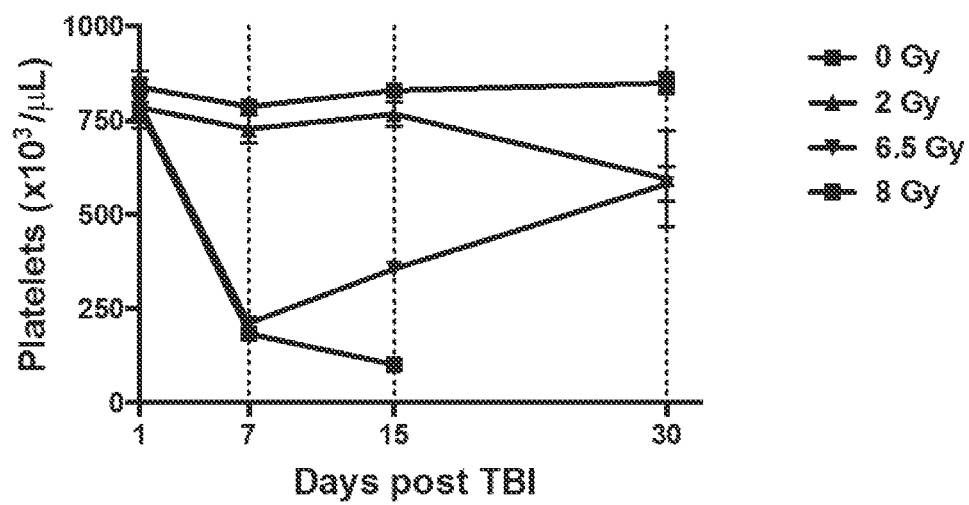
FIG. 4 is a graph showing the platelet levels in C57BL/6J mice at 1 day, 7 days, 15 days, or 30 days after 0 Gy- (control), 2 Gy-, 6.5 Gy-, or 8 Gy-total body irradiation (n=5 mice per group per time point).
Figure 5:
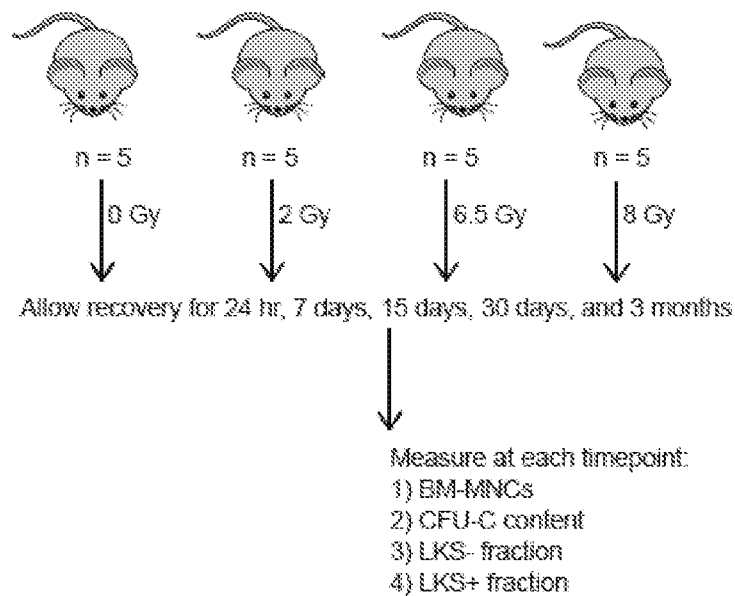
FIG. 5 is a schematic of an experiment where C57BL/6J mice were exposed to total body irradiation at 0 Gy- (control), 2 Gy-, 6.5 Gy-, or 8 Gy-, and sacrificed 24 hours, 7 days, 15 days, 30 days, or 3 months later. Bone marrow was collected from each sacrificed mouse and the levels of bone marrow-mononuclear cells (BM-MNCs), colony forming units in culture (CFU-C), lineage-negative, Sca-1-positive, c-kit-negative (LSK−) cells, and LKS+ cells were determined in the collected bone marrow.
Figure 6:
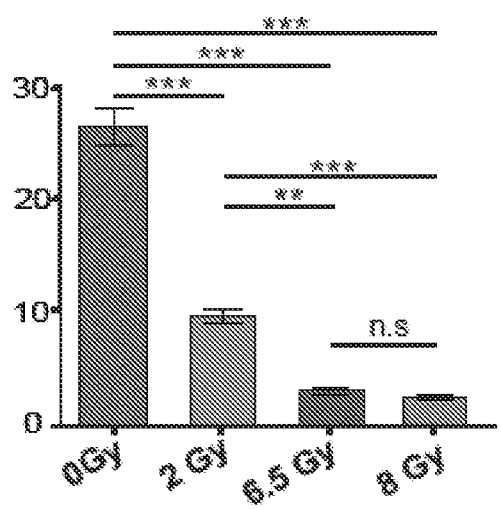
FIG. 6 is a graph showing the number of bone marrow mononuclear cells (BM-MNCs) in millions per hind limb in bone marrow collected from mice 24 hours after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. $P<0.01$, ; $p<0.001$, *; not significant, n.s.
Figure 7:
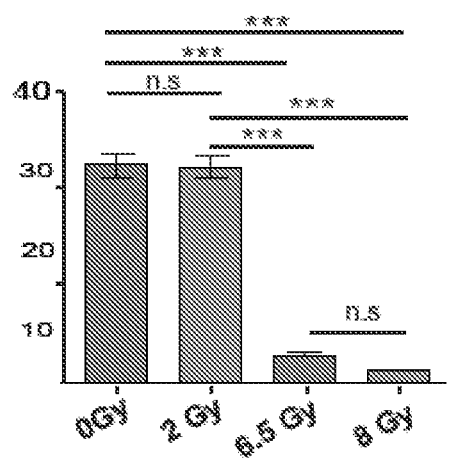
FIG. 7 is a graph showing the number of BM-MNCs (in millions) per hind limb in bone marrow collected from mice 7 days after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. $P<0.001$, ***; not significant, n.s.
Figure 8:
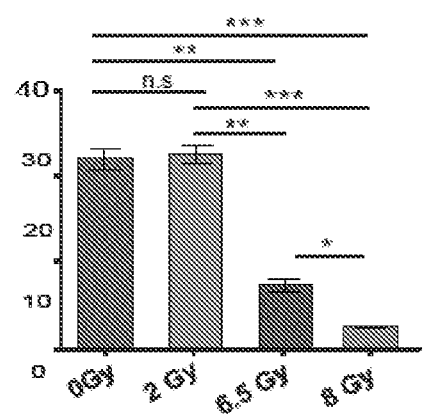
FIG. 8 is a graph showing the number of BM-MNCs (in millions) per hind limb in bone marrow collected from mice 15 days after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. $P<0.05$, *; $p<0.01$, ; $p<0.001$, *; not significant, n.s.
Figure 9:
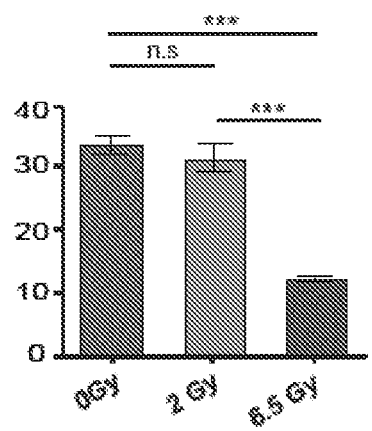
FIG. 9 is a graph showing the number of BM-MNCs (in millions) per hind limb in bone marrow collected from mice one month after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. $P<0.001$, ***; not significant, n.s.
Figure 10:
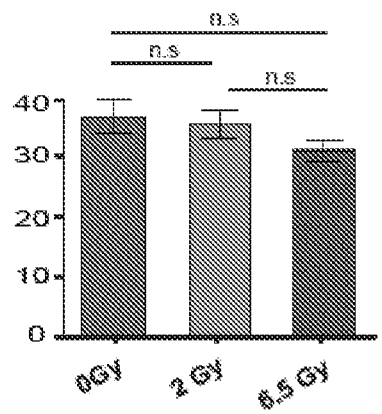
FIG. 10 is a graph showing the number of BM-MNCs (in millions) per hind limb in bone marrow collected from mice three months after 0 Gy-, 2 Gy-, 6.5 Gy-, or 8 Gy-total body irradiation. The error bars represent ±standard error of the mean. All pairwise comparisons were performed by one-way ANOVA followed by Tukey's test. Not significant, n.s.
Figure 11:
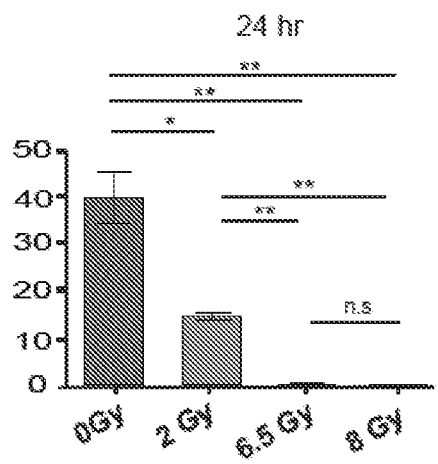
FIG. 11 is a graph showing the number of colony forming units in culture (CFU-Cs) (in thousands) per hind limb in bone marrow collected from mice 24 hours after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. $P<0.05$, *; $p<0.01$, **; not significant, n.s.
Figure 12:
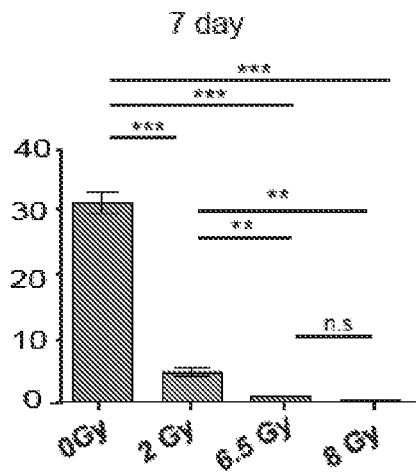
FIG. 12 is a graph showing the number of CFU-Cs (in thousands) per hind limb in bone marrow collected from mice 7 days after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.01, ; p<0.001, *; not significant, n.s.
Figure 13:
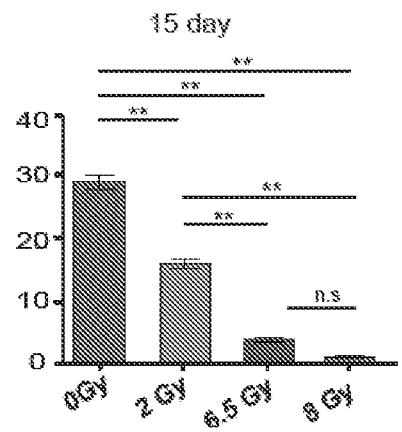
FIG. 13 is a graph showing the number of CFU-Cs (in thousands) per hind limb in bone marrow collected from mice 15 days after 0 Gy-, 2 Gy-, 6.5 Gy-, or 8 Gy-total body irradiation. The error bars represent ±standard error of the mean. All pairwise comparisons were performed by one-way ANOVA followed by Tukey's test. The horizontal bars with asterisks represent statistically significant comparisons. P<0.01, **.

The data in FIG. 1 show that mice exposed to 2 Gy- or 6.5 Gy-total body radiation survive, while the majority of mice exposed to 8 Gy-total body irradiation (65%) are not viable. Thus, 2 Gy and 6.5 Gy were chosen as the sub-lethal low and sub-lethal high doses, respectively, and 8 Gy was considered the lethal dose for subsequent experiments. Complete blood count of peripheral blood showed a reduction in white blood cells (WBCs), red blood cells (RBCs), platelets, and hemoglobin at all tested doses of irradiation (FIGS. 2-4). By day 7, severe lymphopenia and anemia are observed in the 6.5 Gy- and 8 Gy-irradiated mice and there was no significant difference in the peripheral blood parameters at day 15 between the two cohorts of animals (FIGS. 2-4).

Decrease in bone marrow cellularity is an important measure of injury caused to the hematopoietic system following irradiation. At 24 hours post-radiation, a radiation dose-dependent reduction in the cellularity of bone marrow was observed. A dose of 2 Gy caused a ~2.5-fold decrease in BM-BMCs relative to non-irradiated controls while at higher doses, an 8-10-fold reduction decrease was observed (FIGS. 6-10). By day 7 and day 15, a complete recovery of BM-MNCs was observed in mice exposed to 2 Gy of radiation, whereas the BM-MNC count remained very low and indistinguishable for the mice exposed to 6.5 Gy and 8 Gy of radiation, respectively. The mice exposed to 6.5 Gy of radiation showed significant recovery of BM-MNCs by 30 days, and a complete recovery of BM-MNCs by 3 months (FIGS. 6-10).

The CFU-C count following irradiation was significantly decreased for all doses, and the 6.5 Gy- and 8 Gy-cohorts were indistinguishable, both with very low CFU-C counts at day 15 (FIGS. 11-15). At subsequent time points, the bone marrow from both the 2 Gy- and 6.5 Gy-groups displayed improvement in hematopoietic progenitor cell function, but mice in the 8 Gy-group failed to recover. Flow cytometry was used to evaluate the bone marrow hematopoietic progenitor cell population in control and irradiated mice. The $LKS^-$ (lineage$^-$, c-Kit$^+$, Sca-1$^-$) population is enriched in hematopoietic progenitor cells (HPCs) and the $LKS^+$ (lineage$^-$, c-Kit$^+$, Sca-1$^+$) population is enriched in hematopoietic stem cells (HSCs). A severe reduction in the HPC content was observed at 24 hours after total body irradiation in all of the irradiated groups (FIGS. 16-20). The kinetics of recovery for the HPC population ($LKS^-$ cells) in the weeks and months after total body irradiation was similar to the CFU-C levels (FIGS. 11-20). The numbers of HPCs in the 6.5 Gy- and 8 Gy-irradiated mice remained comparably low and indistinguishable at 15 days after total body irradiation. The data reveal that dose dependent hematopoietic injury occurs after total body irradiation, but animals exposed to sub-lethal high- (6.5 Gy) or lethal (8 Gy)-total body irradiation doses remain largely indistinguishable up to 15 days post-total body irradiation.

The data described above show that sub-lethal doses of total body irradiation cause a severe reduction, but not complete depletion of HPCs in the 2 Gy- and 6.5 Gy-irradiated animals. A similar trend in the HSC population ($LKS^+$ cells) was observed, with a striking ablation until 7 days in all total body irradiation cohorts, and detectable recovery at the 15-day time point occurs in the 2 Gy-irradiated animals (FIGS. 21-25). On the other hand, HSC levels in the 6.5 Gy- and 8 Gy-irradiated animals at 15 days post-total body irradiation remained significantly low. These data show that sub-lethal doses of total body irradiation cause permanent damage to stem cells, which can lead to stem cell senescence and a decrease in the engraftment potential of HSCs.

Example 2. Residual HSCs in Sub-Lethally Irradiated Mice Retain the Capacity to Repopulate Bone Marrow A set of experiments were performed to determine whether recovered residual HSCs from 2 Gy- or 6.5 Gy-irradiated mice would be able to repopulate the hematopoietic system.

Materials and Methods

The methods used to irradiate mice, collect bone marrow, perform flow cytometry, and determine CFU-Cs and CBCs are described in Example 1.

HSC and Bone Marrow Transplantation

Short-term and long-term repopulating ability was assessed by transplantation of either sorted HSCs or unfractionated whole bone marrow from donor mice (C56BL/6J CD45.2 congenic) into lethally irradiated (10 Gy) recipients (B6.SJL-Ptprc$^a$ Pep3$^b$/BoyJ CD45.1 congenic) as described in Parmar et al. (*Stem Cells* 28:1886-1195, 2010). Donor mice were exposed to 0 Gy-, 2 Gy-, or 6.5 Gy-total body irradiation and allowed to recover for three months, at which time the animals were sacrificed, and bone marrow was isolated by flushing, and HSCs were sorted using a FACS Aria (BD Biosciences, San Jose, Calif.). For transplants involving sorted HSCs, a total of 2000 LKS$^+$ cells from CD45.2$^+$ donor mice were mixed with 250,000 CD45.1$^+$ bone marrow support cells and injected intravenously to a lethally irradiated CD45.1 recipient mouse. For transplants involving unfractionated bone marrow, a total of 500,000 whole bone marrow cells from CD45.2$^+$ donor mice were mixed with 250,000 CD45.1$^+$ bone marrow support cells and injected intravenously to lethally an irradiated CD45.1$^+$ recipient mouse. Five mice were transplanted per total body irradiation dose group for the HSC transplants, while four mice were transplanted per total body irradiation dose group for the whole bone marrow transplants. Peripheral blood samples were collected at 1 month and four months post-transplantation and were used to assess short-term and long-term repopulation of cells in the recipient mouse, respectively. Donor cell chimerism in recipients was assessed by staining peripheral blood with FITC-conjugated anti-CD45.2 (clone 104) and PE-conjugated anti-CD45.1 (clone A20) antibodies. To measure the extent of multi-lineage reconstitution, the percentage of donor-derived (CD45.2$^+$) B-cells, T-cells, and myeloid cells are calculated by co-staining with PE-conjugated anti-B220 (clone RA3-6B2), PE-anti-CD3e (clone 145-2C11), and PE-anti-Mac1/anti-Gr1 (clones M1/70 and RB6-8C5), respectively. All antibodies were obtained from BD Biosciences (San Jose, Calif.). The stained samples were analyzed using a LSR Fortessa instrument (Becton Dickinson, Franklin Lakes, N.J.) and FlowJo software (TreeStar, Ashland, Oreg.).

Results

HSC transplantation studies were performed to determine whether the recovered residual HSCs from 2 Gy- or 6.5 Gy-irradiated samples would be able to repopulate the hematopoietic system of a lethally radiated mouse. Specifically, engraftment of HSCs from CD45.2$^+$ donor mice (harvested three-months following irradiation with 2 Gy or 6.5 Gy) were transplanted into lethally irradiated CD45.1$^+$ recipient mice, and peripheral blood chimerism was determined at 1 month and 4 months post-transplantation (FIGS. 26-29). Donor cell engraftment (total leukocytes) at 1 month and 4 months post-transplantation showed an approximate 4-fold decrease in the irradiated recipients transplanted with sorted HSCs from the 2 Gy-irradiated donors. Moreover, a 10-20-fold decrease was observed in recipients transplanted with HSCs from 6.5 Gy-irradiated donor mice as compared to a control (FIGS. 28 and 29). When multi-lineage reconstitution of T-cells, B-cells, and myeloid cells was investigated, a similar defect in peripheral blood chimerism was observed (FIGS. 30-37). Competitive repopulation assays performed with unfractionated whole bone marrow showed similar defects in the chimerism of total leukocytes (FIGS. 28 and 29), and lineage-restricted cells in peripheral blood (FIGS. 38-40). Taken together, these data suggest that although most of the HSCs in sub-lethally-irradiated animals are severely impaired in their repopulating potential, rare functional HSCs do exist and maintain the hematopoietic system in sub-lethally-irradiated animals. The ability of mice exposed to sub-lethal doses of radiation to remain viable may be due to the reconstitution potential of the residual functional HSCs.

Example 3. Radiation Dose-Specific Serum miRNAs

A set of radiation dose-specific serum miRNAs were identified.

Materials and Methods

Serum Preparation

Peripheral blood was collected by retro-orbital bleeding after anesthesia. Up to 200 μL of blood was collected in DNAse/RNAse-free Eppendorf tubes and incubated at room temperature for 2 hours to allow clotting. Blood samples were then centrifuged in an Eppendorf 5415C centrifuge at 14000 RPM (15996 g) for 5 minutes at room temperature. The supernatant was collected and re-centrifuged at the above conditions to remove any remaining cellular contamination. The resulting supernatant (serum) was stored in aliquots at −80° C.

Murine mRNA Profiling

A miRCURY LNA™ Universal RT miRNA PCR Rodent Panel 1&II kit containing 742 assays was used to profile miRNAs differentially expressed in mouse serum from animals exposed to 0 Gy (control), 2 Gy, 6.5 Gy, or 8 Gy doses of total body irradiation (Exiqon, Vedbaek, Denmark). Ten mice were profiled per group for a total of 40 samples. On average, 339 miRNAs were detected per sample, with at least 170 miRNAs detected in each samples, and 68 of these miRNAs were identified as being differentially expressed with a p value below 0.05. The data quality for samples across different groups was determined by comparing the number of detected miRNAs with overall Cp values, and was found to be very similar. Normalization of the data was performed using the global mean of 170 of the most-commonly expressed miRNAs in all samples. The levels of a set of RNA and DNA spiked-in controls and hemolysis controls were also determined in order to ascertain the technical performance of each sample. Spiked-in controls were also used throughout the study for profiling and validation. RNA spiked-in controls were also used to test the efficiency of the cDNA synthesis reaction, while DNA spiked-in controls were also used to test the efficiency of the qPCR amplification. In order to negate the possibility of hemolysis, ΔCp for miR-451 (expressed in red blood cells) and miR-23a-3p (relatively stable in serum) was computed for each sample as previously reported (Blondal et al., *Methods* 59:S1-S6, 2013). ΔCp values lower than 7 suggest minimal levels of red blood cell contamination.

RNA Extraction and cDNA Synthesis

Total RNA was isolated from serum samples by using the miRCURY™ RNA Isolation Kit—Biofluids from 50 μL mouse serum as per the manufacturer's manual. Total RNA was eluted in 50 μL mouse serum as per the manufacturer's manual. Total RNA was eluted in 50 μL of RNAse-free H$_2$O and stored at −80° C. Per the manufacturer's recommendations, input volumes for serum RNA were optimized for the cDNA synthesis reaction. cDNA was synthesized in 10 μL reactions using the Universal cDNA Synthesis Kit II and was diluted 50-fold in RNAse/DNAse-free H$_2$O for use in quantitative PCR. The reagents for RNA extraction and cDNA synthesis were obtained from Exiqon (Vedbaek, Denmark).

Quantitative PCR

Diluted cDNA was subjected to quantitative PCR analysis in Pick-N-Mix plates designed in a 96-well format. SYBR® Green qPCR MasterMix was mixed 1:1 with diluted cDNA and added to specific wells in pre-designed Pick-N-Mix plates containing dried-down LNA primers specific for selected miRNAs (see Table 1 for a list of miRNA target sequences). The Pick-N-Mix plates also contained a number of controls including miR-101a and miR-19b (normalization controls), UniSp6 (proprietary RNA spiked-in control), and UniSp3 (proprietary DNA spiked-in control). Built-in interpolate calibrator (IPC) reactions were used to control for inter-plate variability. Pick-N-Mix qPCR plates were run on an Applied Biosystems 7500 FAST Real-Time PCR System. The data were generally normalized using miR-101a. However, normalization using miR-19b levels produced similar results. MiR-451 and miR-23a levels were used to assess the extent of hemolysis. All reagents used for quantitative PCR were obtained from Exiqon (Vedbaek, Denmark).

TABLE 1

Target Sequences of Individual miRNAs Detected in Pick-N-Mix Plates (SEQ ID NOs: 1-18)

| mIRNA | Target Sequence |
| --- | --- | --- |
| Control miRNA | mmu-miR-101a-3p | UACAGUACUGUGAUAACUGAA |
| Control miRNA | mmu-miR-19b-3p | UGUGCAAAUCCAUGCAAAACUGA |
| RNA Spike-in | UniSp6 | Exiqon Proprietary Sequence |
| DNA Spike-in | UniSp3 | Exiqon Proprietary Sequence |
| 0 Gy v. 2 Gy Signature | mmu-miR-130a-3p | CAGUGCAAUGUUAAAAGGGCAU |
|  | mmu-miR-142-5p | CAUAAAGUAGAAAGCACUACU |
|  | mmu-miR-150-5p | UCUCCCAACCCUUGUACCAGUG |
|  | mmu-miR-706 | AGAGAAACCCUGUCUCAAAAAA |
|  | mmu-miR-342-3p | UCUCACACAGAAAUCGCACCCGU |
| 2 Gy v. 6.5 Gy Signature | mmu-miR-34b-3p | AAUCACUAACUCCACUGCCAUC |
|  | mmu-miR-322-3p | AAACAUGAAGCGCUGCAACAC |
|  | mmu-miR-126-3p | UCGUACCGUGAGUAAUAAUGCG |
|  | mmu-miR-17-3p | ACUGCAGUGAGGGCACUUGUAG |
|  | mmu-miR-136-5p | ACUCCAUUUGUUUUGAUGAUGG |
| 6.5 Gy v. 8 Gy Signature | mmu-miR-187-3p | UCGUGUCUUGUGUUGCAGCCGG |
|  | mmu-miR-194-5p | UGUAACAGCAACUCCAUGUGGA |
|  | mmu-miR-27a-3p | UUCACAGUGGCUAAGUUCCGC |
|  | mmu-miR-29a-3p | UAGCACCAUCUGAAAUCGGUUA |
|  | mmu-miR-30a-3p | CUUUCAGUCGGAUGUUUGCAGC |
|  | mmu-miR-30c-5P | UGUAAACAUCCUACACUCUCAGC |

Statistical Analysis

MicroRNA Profiling: Normalization of miRNA serum levels was performed using 170 commonly expressed miRNAs. Analysis of variance (ANOVA) was used to determine which miRNAs differed significantly between groups. To adjust for multiple comparisons testing, the Benjamini-Hochberg correction was applied. A threshold of p<0.05 in ANOVA was selected as the level of statistical significance. MiRNAs with p values of <0.05 in ANOVA was used in hierarchical-clustering analysis to visualize expression patterns. Differentially-expressed miRNAs were tested in pairwise comparisons with a Benjamini-Hochberg adjusted Student's t-test to determine between-group differences.

Power Analysis: Power analysis was performed using the Hierarchical Clustering Explorer 3.5 tool (Seo et al., *Bioinformatics* 22:808-814, 2006). The number of samples was estimated to be sufficient to provide statistical power of at least 80% needed to obtain a p value of less than 0.01 for differentially expressed miRNAs with a fold change of 0>1.5 or <0.67 in between group comparisons. The p value threshold was lowered from 0.05 to account for multi-group post-hoc testing. A sample size of 10 per group was thus calculated to allow us to confirm statistically significant differences for the top 95 differentially expressed miRNAs with the predetermined effect sizes. P levels lower than 0.05 were considered as statistically significant.

Results

Serum miRNAs were profiled in mice 24 hours after exposure to 0 Gy-, 2 Gy-, 6.5 Gy-, or 8 Gy-total body irradiation (10 mice per group). A comparison of expression levels revealed eight miRNAs that allow for the discrimination between samples from control mice and samples from irradiated mice (FIG. 41). Signatures pertaining to specific comparisons between radiation groups are presented in FIGS. 42-53. All miRNAs represented in the heatmaps were found to be statistically significant (p<0.05). Significance between the groups was computed using analysis of variance (ANOVA) corrected for multiple hypothesis testing.

Relative to samples from control mice, the samples from mice irradiated with 2 Gy show a significant drop in complete blood counts (CBCs) and BM-MNC counts at 24 hours post-irradiation, but these blood cell values were almost completely restored by 7 days. However, the HPC and HSC counts remained significantly lower in samples from 2 Gy-irradiated mice as compared to samples from the control mice at 7 days (FIGS. 11-25).

The miRNA profiling data show that five serum miRNAs were effective in distinguishing between the control or 2 Gy-irradiated mice 24 hours after radiation exposure (FIGS. 42 and 43). MiR-130a-3p was increased in the 2 Gy-irradiated mice as compared to the levels in the control mice, while the levels of miR-150-5p, miR-142-5p, miR-706, and miR-342-3p were decreased in the 2 Gy-irradiated mice as compared to the levels in the control mice. This signature was validated using an independent set of animals that were left untreated or exposed to a total body irradiation dose of 2 Gy, and the miRNA levels determined in samples collected from the mice at 24 hours post-irradiation. The serum miRNA pattern continues to distinguish the control mice from the 2 Gy-irradiated mice when the samples were collected 7 days after irradiation (FIGS. 44-48). These data are also consistent with the diminished numbers of HSCs and HPCs in the 2 Gy-irradiated cohort at 7 days post-irradiation. As BM-MNC counts a week after radiation exposure are not significantly different in the control mice and the 2 Gy-irradiated mice, these data suggest that serum miRNA expression can be used to quantitatively and accurately identify individuals exposed to 2 Gy radiation.

A subsequent set of experiments was performed to determine whether miRNA expression levels can be used to distinguish between patients that have been exposed to a low sub-lethal or high sub-lethal doses of radiation. The data show that the levels of five different miRNAs, miR-136-5p, miR-17-3p, miR-126-3p, miR-322-3p, and miR-34b-3p, can be used to accurately distinguish between individuals exposed to a low sub-lethal or high sub-lethal doses of radiation (FIGS. 49-55).

Similar to the untreated- and 2 Gy-irradiated mice, analysis of hematopoietic damage is unable to differentiate between animals exposed to high sub-lethal (6.5 Gy) irradiation and lethal (8 Gy) total body irradiation (FIGS. 1 and 5-29). The data in FIGS. 56-58 show that the levels of specific serum miRNAs can also be used to accurately differentiate between 6.5 Gy- and 8.0 Gy-irradiated mice by using samples obtained as early as 24 hours after irradiation (FIGS. 56-58). The levels of miR-187-3p, miR-194-5p, and miR-27a-3p were decreased in the 8 Gy-irradiated mice as compared to the levels in the 6.5 Gy-irradiated mice, while the levels of miR-30a and miR-30c were increased in the 8 Gy-irradiated mice as compared to the levels in the 6.5 Gy-irradiated mice (FIGS. 56-58).

An additional set of experiments were performed to determine whether levels of the identified miRNAs can be used to accurately identify the dose of radiation that mice have been exposed to when the serum samples are collected at later time points, e.g., 24 hours, three days, and one week after irradiation. In these experiments, mice were treated to a total body irradiation dose of 6.5 Gy or 8 Gy. Consistent with the above described data, the levels of serum miRNAs can be used to distinguish between lethal- versus sub-lethal-doses of radiation (FIGS. 59-63). Serum levels of miR-30a-3p and miR-30c-5p continued to differentiate between the 6.5 Gy- and 8.0 Gy-irradiated mice when samples were collected at three days and seven days post-irradiation (FIGS. 59-63).

Table 2 shows the fold change in the levels of 68 serum miRNAs in 2 Gy-, 6.5 Gy-, or 8 Gy-irradiated mice as compared to non-experimentally irradiated mice.

In sum, these data show that the levels of the different specific miRNAs described in this Example (in the text or figures) can be used to determine the level or dose of radiation that a subject has been exposed to.

TABLE 2

Fold Changes in 68 Different miRNAs in Mice Irradiated with 2 Gy-, 6.5 Gy-, or 8 Gy- Total Body Irradiation as Compared to Untreated Mice

| miRNA | Rank | Benjamini-Hochberg Corrected p-value | Fold Change | | |
|---|---|---|---|---|---|
| | | | 2 Gy vs 0 Gy | 6.5 Gy vs 0 Gy | 8 Gy vs 0 Gy |
| mmu-miR-142-5p | 1 | 6.14552E−10 | 0.74424399 | 0.549934615 | 0.467752484 |
| mmu-miR-150-5p | 2 | 6.41729E−10 | 0.33485287 | 0.360400719 | 0.346659291 |
| mmu-miR-320-3p | 3 | 6.83112E−06 | 0.96224966 | 1.187536684 | 1.32071546 |
| mmu-miR-136-5p | 4 | 8.17096E−06 | 1.03771902 | 0.464873503 | 0.411761228 |
| mmu-miR-33-5p | 5 | 4.8463E−05 | 1.00605562 | 0.547886821 | 0.412110487 |
| mmu-miR-142-3p | 6 | 4.8463E−05 | 0.91027254 | 0.578995013 | 0.512969604 |
| mmu-miR-30c-5p | 7 | 0.000365421 | 1.04125706 | 1.124307627 | 1.374873802 |
| mmu-miR-126-3p | 8 | 0.000365421 | 0.96088497 | 1.52362955 | 1.397680627 |
| mmu-miR-706 | 9 | 0.000466025 | 0.39885132 | 0.355518689 | 0.633605238 |
| mmu-miR-375-3p | 10 | 0.000466244 | 1.23386818 | 2.136008605 | 2.283729398 |
| mmu-miR-29a-5p | 11 | 0.000466244 | 0.88815734 | 0.965287846 | 0.709055154 |
| mmu-miR-193a-3p | 12 | 0.000529968 | 1.16807721 | 0.648857482 | 0.436360524 |
| mmu-miR-99b-5p | 13 | 0.000529968 | 0.99604663 | 1.343865649 | 1.512510076 |
| mmu-miR-30a-3p | 14 | 0.001068664 | 0.98962715 | 1.062153376 | 1.586158278 |
| mmu-miR-194-5p | 15 | 0.001068664 | 0.81191712 | 0.610441938 | 0.445697163 |
| mmu-miR-151-3p | 16 | 0.001068664 | 1.13039179 | 1.466557685 | 1.309094574 |
| mmu-let-7d-3p | 17 | 0.001068664 | 0.97075842 | 1.220688226 | 1.202449856 |
| mmu-miR-486-5p | 18 | 0.001406802 | 1.18781032 | 1.463315368 | 2.065511432 |
| mmu-miR-423-5p | 19 | 0.001406802 | 1.04859246 | 1.296138995 | 1.433861551 |
| mmu-miR-30b-5p | 20 | 0.002090685 | 1.03949322 | 1.118894183 | 1.226753205 |
| mmu-miR-191-5p | 21 | 0.002342556 | 1.13886399 | 1.431738514 | 1.633205493 |
| mmu-miR-497-5p | 22 | 0.003354593 | 0.93721128 | 0.749399546 | 0.620269054 |
| mmu-miR-32-5p | 23 | 0.003528045 | 1.08012807 | 0.628353232 | 0.60521677 |
| mmu-miR-214-5p | 24 | 0.003991952 | 0.7250106 | 0.703128367 | 0.472213492 |
| mmu-miR-326-3p | 25 | 0.005363873 | 1.23852539 | 0.851291436 | 0.795937744 |
| mmu-miR-1195 | 26 | 0.00547774 | 0.96775855 | 1.091070893 | 1.828845971 |
| mmu-miR-122-5p | 27 | 0.00547774 | 0.9331905 | 0.347893687 | 0.148560227 |
| mmu-miR-1839-3p | 28 | 0.006649678 | 1.31726438 | 1.533746054 | 2.030902658 |
| mmu-miR-500-3p | 29 | 0.007061575 | 0.98538558 | 0.798727717 | 0.576675503 |
| mmu-miR-30e-3p | 30 | 0.008842863 | 0.99620407 | 1.118186905 | 1.447594383 |
| mmu-miR-191-5p | 31 | 0.008475716 | 1.11075355 | 1.336579832 | 1.549260059 |
| mmu-miR-322-3p | 32 | 0.008828838 | 0.84830107 | 1.319445753 | 1.179301198 |
| mmu-miR-709 | 33 | 0.012398254 | 1.17074719 | 1.283596703 | 2.015808092 |
| mmu-miR-486-3p | 34 | 0.012398254 | 1.15572492 | 1.26343094 | 2.007373735 |
| mmu-miR-133a-3p | 35 | 0.01300781 | 0.8577409 | 1.808599164 | 2.388619602 |
| mmu-miR-676-3p | 36 | 0.013062937 | 1.02467973 | 1.200464931 | 1.261017633 |
| mmu-miR-744-5p | 37 | 0.013450652 | 1.11874039 | 1.206177008 | 1.300646391 |
| mmu-miR-27a-3p | 38 | 0.013750505 | 0.897455 | 0.907534042 | 0.701532751 |
| mmu-miR-29a-3p | 39 | 0.014568628 | 0.93057734 | 0.846667907 | 0.759548456 |
| mmu-miR-1839-5p | 40 | 0.014568628 | 1.08694504 | 1.276875982 | 1.316700195 |
| mmu-miR-30a-5p | 41 | 0.014568628 | 1.05482542 | 1.181824227 | 1.346126285 |
| mmu-miR-199b-5p | 42 | 0.016705178 | 0.86410859 | 0.513797016 | 0.632615767 |

TABLE 2-continued

Fold Changes in 68 Different miRNAs in Mice Irradiated with 2 Gy-, 6.5 Gy-, or 8 Gy- Total Body Irradiation as Compared to Untreated Mice

| miRNA | Rank | Benjamini-Hochberg Corrected p-value | Fold Change 2 Gy vs 0 Gy | 6.5 Gy vs 0 Gy | 8 Gy vs 0 Gy |
|---|---|---|---|---|---|
| mmu-miR-125a-5p | 43 | 0.022628544 | 0.95885072 | 1.091894886 | 1.262232335 |
| mmu-miR-133b-3p | 44 | 0.024815118 | 0.87153511 | 1.658615981 | 2.115999503 |
| mmu-miR-24-3p | 45 | 0.024815118 | 0.98024783 | 1.184038592 | 1.119192515 |
| mmu-miR-21a-5p | 46 | 0.024815118 | 1.11453515 | 0.83129145 | 0.789893731 |
| mmu-miR-503-5p | 47 | 0.024815118 | 1.17062491 | 0.805712381 | 0.783530294 |
| mmu-mi-328-3p | 48 | 0.024815118 | 1.13325302 | 1.308132313 | 1.338479397 |
| mmu-let-7g-5p | 49 | 0.024815118 | 1.0988627 | 1.139369002 | 1.416967729 |
| mmu-miR-362-3p | 50 | 0.024815118 | 0.88814566 | 0.804011505 | 0.662542946 |
| mmu-miR-199a-5p | 51 | 0.025154963 | 0.90437047 | 0.601503597 | 0.631100613 |
| mmu-miR-342-3p | 52 | 0.02747761 | 0.74026498 | 1.131865806 | 1.05831998 |
| mmu-miR-34b-3p | 53 | 0.028987297 | 0.72634533 | 1.610402809 | 1.543163375 |
| mmu-miR-15a-3p | 54 | 0.028987297 | 1.1168344 | 0.719823542 | 0.588058284 |
| mmu-miR-139a-5p | 55 | 0.033183048 | 0.89176006 | 1.179771672 | 1.070031762 |
| mmu-miR-17-3p | 56 | 0.033183048 | 1.20541903 | 0.631158748 | 0.880193062 |
| mmu-miR-130a-3p | 57 | 0.033183048 | 1.23030213 | 0.993397276 | 0.942905848 |
| mmu-miR-149-5p | 58 | 0.033183048 | 0.91083128 | 1.293986617 | 1.527284883 |
| mmu-miR-29b-3p | 59 | 0.033183048 | 1.02341004 | 0.816190497 | 0.738902258 |
| mmu-miR-1a-3p | 60 | 0.035135178 | 0.70860665 | 1.329943292 | 2.129491746 |
| mmu-miR-23b-3p | 61 | 0.036567207 | 0.96591806 | 1.179012129 | 1.113184704 |
| mmu-miR-215-5p | 62 | 0.036567207 | 0.74514845 | 0.695719558 | 0.474670243 |
| mmu-miR-204b-5p | 63 | 0.040650135 | 0.85603509 | 1.631185521 | 1.807800285 |
| mmu-miR-187-3p | 64 | 0.041980065 | 0.938443632 | 0.938443632 | 0.562868937 |
| mmu-miR-200b-5p | 65 | 0.041980065 | 1.1873809 | 1.538043311 | 1.668073737 |
| mmu-miR-25-3p | 66 | 0.041980065 | 1.0929659 | 1.170620915 | 1.537301555 |
| mmu-miR-338-3p | 67 | 0.046950851 | 1.09509996 | 0.857254876 | 0.812354606 |
| mmu-miR-196b-5p | 68 | 0.049109597 | 1.31602496 | 1.065034064 | 0.733581783 |

Example 4. Serum miRNAs Predict Severity of Radiation Disease

An experiment was performed to test whether the levels of the specific miRNAs described in these Examples can be used to predict the severity of radiation disease in a subject.
Materials and Methods Irradiation, serum collection, and miRNA profiling were performed as described in Example 3.
Radioprotection with Amifostine Saline or amifostine was given to mice intraperitoneally at 250 mg/kg body weight 24 hours prior to 0 Gy- or 8 Gy-total body irradiation in a first set of experiments. In a second set of experiments, mice were left untreated or mice were administered saline or 200 mg/kg amifostine 45 minutes prior to 0 Gy- or 8.5 Gy-total body irradiation. Serum was collected from all mice at 24 hours after irradiation or a time point in the non-irradiated mice that would correspond to 24 hours after irradiation in the treated mice.
Statistical Analysis Validation with real-time qPCR: One-way ANOVA was used to confirm global significance. Dunnett's post-hoc testing procedure was used to compare miRNA levels in the irradiated+saline-group against three other experimental groups. Univariate comparisons were performed using the Student's t-test or the Student's t-test for paired samples. Pearson's correlation coefficient was used for correlation testing. Survival analysis was performed using the log-rank (Mantel-Cox) test.
Results Cohorts of mice were treated with saline or amifostine 24-hours prior to exposure to 8 Gy-total body irradiation, and sera were collected 24 hours post-irradiation (FIG. 64). To confirm the protective effect of amifostine on the survival of the lethally-irradiated mice, Kaplan-Meier analysis was performed on the same set of animals (FIG. 65). While all mice injected with saline and irradiated with 8 Gy died at about day 70, animals administered amifostine prior to 8 Gy-irradiation displayed a 50 percent improvement in survival (n=8 per group; p=0.0452). The sera collected from these mice at 24 hours after irradiation show that the levels of miRNAs are significantly altered when comparing the differences between the groups and when the 8 Gy-irradiated+saline-administered group was compared to the other three groups (Table 3). The serum miRNA signature responded to amifostine treatment only in the context of lethal radiation (FIGS. 66-70). The degree of change in response to radiation and amifostine was however of different magnitude for each miRNA. MiR-194-5p and miR-30a-3p displayed the most dramatic alterations, while miR-187-3p, miR-27a, and miR-30c-3p showed more moderate changes (FIGS. 66-70). The analysis in FIG. 71 shows a very high correlation (r=0.94; p=0.02) indicates that the five miRNAs (miR-187-3p, miR-194-5p, miR-27a-3p, miR-30a-3p, and miR-30c-5p) can serve as markers of risk of poor prognosis from radiation exposure (e.g., risk of mortality from radiation exposure) and markers of risk of developing radiation disease.

TABLE 3

Statistical Comparison of the Saline Treated and 8 Gy-Irradiated Mice Data to the Other Experimental Groups

| mRNA | CT + Saline | CT + Ami | 8 Gy 4 + Ami |
|---|---|---|---|
| miR-187-3p IR | 0.0085 | 0.0266 | 0.0360 |
| miR-194-5p IR | <0.0001 | <0.0001 | 0.0001 |
| miR-30a-3p IR | <0.0001 | <0.0001 | <0.0001 |
| miR-27a-3p IR | 0.0066 | 0.0048 | 0.0108 |
| miR-30c-5p IR | 0.0001 | 0.0002 | 0.0414 |

An additional set of experiments was performed to test whether the levels of miR-187-3p, miR-194-5p, miR-30a-

3p, miR-27a-3p, and miR-30c-5p can be used to predict a subject's future risk of developing radiation disease. In these experiments, mice where either left untreated or were administered saline or 200 mg/kg amifostine 45 minutes prior to 0 Gy- or 8 Gy-irradiation.

The data show that mice administered 200 mg/kg amifostine 45 minutes prior to 8.5-Gy-total body irradiation had prolonged survival than mice who received saline 45 minutes prior to 8.5 Gy-total body irradiation (FIG. 72). The data show a significant difference in the levels of miR-187-3p, miR-194-5p, miR-27a-3p, miR-30a-3p, and miR-30c-5p in mice administered saline and 45 minutes later treated with 8.5 Gy-total body irradiation as compared to mice administered amifostine and 45 minutes later treated with 8.5 Gy-total body irradiation (FIGS. 73-77, respectively). These data indicate that the levels of miR-187-3p, miR-194-5p, miR-27a-3p, miR-30a-3p, and miR-30c-5p can be used to determine a subject's risk of poor prognosis from radiation exposure and can also be used to predict a subject's risk of subsequently developing radiation disease.

Example 5. Serum miRNAs can Indicate Effective Treatment of Radiation Disease

An additional set of experiments was performed to determine whether levels of miRNAs can indicate effective treatment in a subject previously exposed to total body irradiation.
Materials and Methods Irradiation, serum collection, and miRNA profiling were performed as described in Example 3.
Treatment with Bone Marrow Transplantation after Irradiation In this set of experiments, C57BL/6J mice were left untreated (n=5), were treated with 10.4 Gy-total body irradiation and left untreated (n=5), or were treated with 10.4 Gy-total body irradiation and administered two doses of 2 million bone marrow stromal cells (BMASC) per mouse at 24 hours and 72 hours after irradiation (n=5).
Results The data show that mice administered two doses of 2 million bone marrow stromal cells after 10.4 Gy-total body irradiation had prolonged survival than mice who did not receive bone marrow stromal cells after 10.4 Gy-total body irradiation (FIG. 78). The data show a significant difference in the levels of miR-150, miR-27a, miR-30a, miR-30c, miR-187-3p, and miR-194-3p in mice that received 10.4 Gy-total body irradiation and no bone marrow stromal cells as compared to mice that received two transplants of bone marrow stromal cells after 10.4 Gy-total body irradiation (FIGS. 79-84, respectively). These data show that the levels of miR-150, miR-27a, miR-30a, miR-30c, miR-187-3p, and miR-194-3p can be used to determine the efficacy of a treatment for reducing radiation-induced damage administered to a subject previously exposed to a significant level of radiation.

Example 6. Validation of Serum miRNA Signature in Humanized Mice

A set of experiments was performed to verify if the same miRNA(s) could be used to determine a human's level of exposure to radiation. These experiments utilized a humanized mouse model.
Materials and Methods Irradiation, serum collection, and miRNA profiling were performed as described in Example 3.

HuCD34+ "humanized" NSG mice were obtained from Jackson Labs, Bar Harbor, Me. These mice were generated by irradiating each mouse at 1.4 Gy to deplete their bone marrow and injecting each mouse with CD34+ human HSC. Each mouse was tested for engraftment of human CD45+ cells and murine CD45+ cells at 12 weeks following transplantation. Prior to the experiments described herein, the presence of human CD45+ cells was confirmed in the peripheral blood and bone marrow from untreated control mice using an anti-human CD45 FITC antibody.

The HuCD34+ mice were treated with saline or amifostine (200 mg/kg of body weight 45 min-1 hr before radiation exposure) and were subsequently treated with 4 Gy to 4.5 Gy of total body irradiation, or were left untreated. Following these treatments, total bone cellularity and the levels of serum miRNAs were determined in the mice. Both CD45 staining of peripheral blood and engraftment analysis of bone marrow was performed when animals became moribund (between 9-14 days after total body radiation) and were sacrificed. The mice were irradiated at approximately 12 weeks after initial assessment of engraftment.
Results The initial engraftment percentages of human CD45+ cells in the peripheral blood and bone marrow were determined (prior to administration of saline or amifostine, and prior to experimental irradiation). The percentage of human CD45+ cells in the bone marrow of two exemplary untreated control humanized mice was 71.8% and 63% respectively, and the percentage of human CD45+ cells in the peripheral blood of two exemplary untreated control humanized mice was 83.2% and 70.6%, respectively.

The humanized mice were treated with saline or amifostine, and subsequently treated with 4.0 Gy to 4.5 Gy of total body irradiation, or were left untreated (control group). The percentage of human CD45 positive cell engraftment, the percentage of human CD45 positive cells in the peripheral blood, the bone marrow cellularity, the human CD45 positive cell number, and the CFU-Cs were determined in each mouse, and the levels of six serum miRNAs were also determined. The percentage of human CD45 positive cell engraftment and the percentage of human CD45 positive cells in the peripheral blood of the mice are shown in Tables 4 and 5 below.

TABLE 4

Percentage of Human CD45 Positive Cell Engraftment in Human CD34-positive NSG Humanized Mice

| Mouse # | % hCD45+ engraftment in mouse peripheral blood | Treatment |
| --- | --- | --- |
| 1 | 75.2 | TBI + Saline |
| 2 | 49.8 | TBI + Saline |
| 3 | 52.1 | TBI + Saline |
| 4 | 60.2 | TBI + Saline |
| 5 | 50.9 | TBI + Saline |
| 6 | 65 | TBI + Saline |
| 7 | 55.8 | TBI + Saline |
| 8 | 58.2 | TBI + Amifostine |
| 9 | 52.5 | TBI + Amifostine |
| 10 | 62.1 | TBI + Amifostine |
| 11 | 74.3 | TBI + Amifostine |
| 12 | 67.5 | TBI + Amifostine |
| 13 | 52.1 | TBI + Amifostine |
| 14 | 49.6 | TBI + Amifostine |
| 15 | 61.4 | TBI + Amifostine |
| 16 | 51.8 | Control |
| 17 | 50.8 | Control |
| 18 | 55.9 | Control |
| 19 | 58.8 | Control |
| 20 | 65.8 | Control |

TABLE 5

Peripheral Blood CBC Levels in Human CD34-positive NSG Humanized Mice

| Group | Mouse # | CBC at euthanasia | | | | |
|---|---|---|---|---|---|---|
| | | WBC (K/uL) | RBC (M/uL) | Hb (g/dL) | HCT (%) | PLT (K/uL) |
| TBI + Saline | 2 | 1.20 | 0.24 | 1.90 | 1.60 | 20 |
| | 5 | 1.30 | 0.19 | 2.80 | 1.20 | 4 |
| | 7 | 0.56 | 1.64 | 2.80 | 3.00 | 88 |
| | Avg | 1.02 | 0.69 | 2.50 | 1.93 | 37.33 |
| | SEM | 0.23 | 0.48 | 0.30 | 0.55 | 25.75 |
| TBI + Amifostine | 8 | 1.28 | 2.55 | 4.80 | 17.00 | 213 |
| | 9 | 1.19 | 1.65 | 3.20 | 11.00 | 44 |
| | 13 | 1.20 | 2.92 | 4.80 | 4.80 | 56 |
| | Avg | 1.22 | 2.37 | 4.27 | 10.93 | 104.33 |
| | SEM | 0.03 | 0.38 | 0.53 | 3.52 | 54.44 |
| Control | 16 | 1.20 | 4.75 | 11.00 | 38.50 | 345 |
| | 17 | 1.32 | 5.35 | 10.50 | 39.60 | 609 |
| | 18 | 2.16 | 5.66 | 12.40 | 42.20 | 686 |
| | 19 | 1.77 | 5.89 | 11.60 | 45.30 | 645 |
| | 20 | 1.44 | 5.41 | 10.70 | 40.60 | 577 |
| | Avg | 1.58 | 5.41 | 11.24 | 41.24 | 572.40 |
| | SEM | 0.17 | 0.19 | 0.34 | 1.18 | 59.69 |

The data in FIGS. 85-87 show that treatment of the humanized mice with amifostine prior to irradiation results in an increase in the total bone marrow cellularity, the number of human CD45 positive cells in the bone marrow, and the number of CFU-Cs as compared to the corresponding levels in a mouse administered saline prior to irradiation.

The data in FIGS. 88-93 show that several miRNAs show a similar change in serum levels in response to irradiation. These data indicate that the levels of the miRNAs described herein can be used to determine a human's level of exposure to radiation and the effectiveness of a treatment administered to a subject exposed to radiation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject in need thereof, the method comprising:
   (a) determining a level of miRNAs miR-187-3p, miR-27a-3p, and miR-30a-3p in a serum sample from the human subject;
   (b) comparing the levels of the miRNAs in the serum sample from the human subject to reference levels of the miRNAs, wherein the reference levels of the miR-NAs are levels of the miRNAs in a reference serum sample from a human subject not exposed to a significant dose of radiation;
   (c) determining that the level of miR-30a-3p is increased and the levels of miR-187-3p and miR-27a-3p are decreased in the serum sample from the human subject compared to the reference levels of the miRNAs;
   (d) selecting a treatment for reducing damage induced by a lethal dose of radiation for the subject; and
   (e) administering a treatment for reducing damage induced by a lethal dose of radiation to the human subject.

2. The method of claim 1, wherein the treatment for reducing damage induced by a lethal dose of radiation is selected from the group consisting of: administration of one or more of a cytokine, potassium iodide, Prussian blue, and diethylenetriamine pentaacetic acid, bone marrow transplantation, blood transfusion, and surgery to remove damaged tissues.

3. The method of claim 2, wherein the cytokine is selected from the group consisting of granulocyte colony-stimulating factor, filgrastim, and pegfilgrastim.

4. The method of claim 1, wherein the sample is obtained from the human subject within 30 minutes to 96 hours after the possible exposure of the human subject to radiation.

5. The method of claim 1, wherein the lethal dose of radiation is radiation of about 8 Gy to about 12 Gy.

6. The method of claim 1, wherein the human subject not exposed to a significant dose of radiation is exposed to less than or equal to 0.2 Gy, 0.4 Gy, 0.6 Gy, or 0.8 Gy of radiation.

7. The method of claim 1, wherein the significant dose of radiation is radiation of about 8 Gy to about 12 Gy.

8. The method of claim 1, wherein the significant dose of radiation is a lethal dose of radiation.

9. The method of claim 8, wherein the lethal dose of radiation is radiation of about 8 Gy to about 12 Gy.

10. A method of treating a human subject in need thereof, wherein the human subject is or has previously been determined to have an increased serum level of miR-30a-3p and decreased serum levels of miR-187-3p and miR-27a-3p relative to reference levels of the miRNAs, wherein the reference levels of the miRNAs are levels of the miRNAs in a reference serum sample from a human subject not exposed to a significant dose of radiation, the method comprising administering to the human subject a treatment for radiation disease.

11. The method of claim 10, wherein the treatment for radiation disease is selected from the group consisting of: administration of one or more of a cytokine, potassium iodide, Prussian blue, and diethylenetriamine pentaacetic acid, bone marrow transplantation, blood transfusion, and surgery to remove damaged tissues.

12. The method of claim 11, wherein the cytokine is selected from the group consisting of granulocyte colony-stimulating factor, filgrastim, and pegfilgrastim.

13. The method of claim 10, wherein the serum levels of miR-30a-3p, miR-187-3p, and miR-27a-3p are from a serum sample obtained from the human subject within 30 minutes to 96 hours after possible exposure of the subject to radiation.

14. The method of claim 10, wherein the treatment is for radiation disease caused by exposure to a lethal dose of radiation.

15. The method of claim 14, wherein the lethal dose of radiation is a dose of about 8 Gy to about 12 Gy.

16. The method of claim 10, wherein the human subject not exposed to a significant dose of radiation is exposed to less than or equal to 0.2 Gy, 0.4 Gy, 0.6 Gy, or 0.8 Gy of radiation.

17. The method of claim 10, wherein the significant dose of radiation is radiation of about 8 Gy to about 12 Gy.

18. The method of claim 10, wherein the significant dose of radiation is a lethal dose of radiation.

19. The method of claim 18, wherein the lethal dose of radiation is radiation of about 8 Gy to about 12 Gy.

\* \* \* \* \*

SEQUENCE LISTING

```
<160> NUMBER OF SEQ ID NOS: 274

<210> SEQ ID NO 1
<211> LENGTH: 21
<212> TYPE: RNA
<213> ORGANISM: Mus musculus

<400> SEQUENCE: 1
uacaguacug ugauaacuga a                                        21

<210> SEQ ID NO 2
<211> LENGTH: 23
<212> TYPE: RNA
<213> ORGANISM: Mus musculus

<400> SEQUENCE: 2
ugugcaaauc caugcaaaac uga                                      23

<210> SEQ ID NO 3
<211> LENGTH: 22
<212> TYPE: RNA
<213> ORGANISM: Mus musculus

<400> SEQUENCE: 3
cagugcaaug uuaaaagggc au                                       22

<210> SEQ ID NO 4
<211> LENGTH: 21
<212> TYPE: RNA
<213> ORGANISM: Mus musculus

<400> SEQUENCE: 4
cauaaaguag aaagcacuac u                                        21

<210> SEQ ID NO 5
<211> LENGTH: 22
<212> TYPE: RNA
<213> ORGANISM: Mus musculus
```

```
<400> SEQUENCE: 5
ucucccaacc cuuguaccag ug                                          22

<210> SEQ ID NO 6
<211> LENGTH: 22
<212> TYPE: RNA
<213> ORGANISM: Mus musculus

<400> SEQUENCE: 6
agagaaaccc ugucucaaaa aa                                          22

<210> SEQ ID NO 7
<211> LENGTH: 23
<212> TYPE: RNA
<213> ORGANISM: Mus musculus

<400> SEQUENCE: 7
ucucacacag aaaucgcacc cgu                                         23

<210> SEQ ID NO 8
<211> LENGTH: 22
<212> TYPE: RNA
<213> ORGANISM: Mus musculus

<400> SEQUENCE: 8
aaucacuaac uccacugcca uc                                          22

<210> SEQ ID NO 9
<211> LENGTH: 21
<212> TYPE: RNA
<213> ORGANISM: Mus musculus

<400> SEQUENCE: 9
aaacaugaag cgcugcaaca c                                           21

<210> SEQ ID NO 10
<211> LENGTH: 22
<212> TYPE: RNA
<213> ORGANISM: Mus musculus

<400> SEQUENCE: 10
ucguaccgug aguaauaaug cg                                          22

<210> SEQ ID NO 11
<211> LENGTH: 22
<212> TYPE: RNA
<213> ORGANISM: Mus musculus

<400> SEQUENCE: 11
acugcaguga gggcacuugu ag                                          22

<210> SEQ ID NO 12
<211> LENGTH: 22
<212> TYPE: RNA
<213> ORGANISM: Mus musculus

<400> SEQUENCE: 12
acuccauuug uuuugaugau gg                                          22

<210> SEQ ID NO 13
<211> LENGTH: 22
<212> TYPE: RNA
<213> ORGANISM: Mus musculus
```

```
<400> SEQUENCE: 13
ucgugucuug uguugcagcc gg                                           22

<210> SEQ ID NO 14
<211> LENGTH: 22
<212> TYPE: RNA
<213> ORGANISM: Mus musculus

<400> SEQUENCE: 14
uguaacagca acuccaugug ga                                           22

<210> SEQ ID NO 15
<211> LENGTH: 21
<212> TYPE: RNA
<213> ORGANISM: Mus musculus

<400> SEQUENCE: 15
uucacagugg cuaaguuccg c                                            21

<210> SEQ ID NO 16
<211> LENGTH: 22
<212> TYPE: RNA
<213> ORGANISM: Mus musculus

<400> SEQUENCE: 16
uagcaccauc ugaaaucggu ua                                           22

<210> SEQ ID NO 17
<211> LENGTH: 22
<212> TYPE: RNA
<213> ORGANISM: Mus musculus

<400> SEQUENCE: 17
cuuucagucg gauguuugca gc                                           22

<210> SEQ ID NO 18
<211> LENGTH: 23
<212> TYPE: RNA
<213> ORGANISM: Mus musculus

<400> SEQUENCE: 18
uguaaacauc cuacacucuc agc                                          23

<210> SEQ ID NO 19
<211> LENGTH: 22
<212> TYPE: RNA
<213> ORGANISM: Mus musculus

<400> SEQUENCE: 19
cagugcaaug uuaaaagggc au                                           22

<210> SEQ ID NO 20
<211> LENGTH: 22
<212> TYPE: RNA
<213> ORGANISM: Mus musculus

<400> SEQUENCE: 20
ucucccaacc cuuguaccag ug                                           22

<210> SEQ ID NO 21
<211> LENGTH: 22
<212> TYPE: RNA
<213> ORGANISM: Mus musculus
```

<400> SEQUENCE: 21
acugcaguga gggcacuugu ag                                    22

<210> SEQ ID NO 22
<211> LENGTH: 22
<212> TYPE: RNA
<213> ORGANISM: Mus musculus

<400> SEQUENCE: 22
ucgugucuug uguugcagcc gg                                    22

<210> SEQ ID NO 23
<211> LENGTH: 22
<212> TYPE: RNA
<213> ORGANISM: Mus musculus

<400> SEQUENCE: 23
uguaacagca acuccaugug ga                                    22

<210> SEQ ID NO 24
<211> LENGTH: 21
<212> TYPE: RNA
<213> ORGANISM: Mus musculus

<400> SEQUENCE: 24
uucacagugg cuaaguuccg c                                     21

<210> SEQ ID NO 25
<211> LENGTH: 22
<212> TYPE: RNA
<213> ORGANISM: Mus musculus

<400> SEQUENCE: 25
cuuucagucg gauguuugca gc                                    22

<210> SEQ ID NO 26
<211> LENGTH: 23
<212> TYPE: RNA
<213> ORGANISM: Mus musculus

<400> SEQUENCE: 26
uguaaacauc cuacacucuc agc                                   23

<210> SEQ ID NO 27
<211> LENGTH: 21
<212> TYPE: RNA
<213> ORGANISM: Mus musculus

<400> SEQUENCE: 27
cauaaaguag aaagcacuac u                                     21

<210> SEQ ID NO 28
<211> LENGTH: 23
<212> TYPE: RNA
<213> ORGANISM: Mus musculus

<400> SEQUENCE: 28
ucucacacag aaaucgcacc cgu                                   23

<210> SEQ ID NO 29
<211> LENGTH: 22
<212> TYPE: RNA
<213> ORGANISM: Mus musculus

```
<400> SEQUENCE: 29
aaucacuaac uccacugcca uc                                              22

<210> SEQ ID NO 30
<211> LENGTH: 22
<212> TYPE: RNA
<213> ORGANISM: Mus musculus

<400> SEQUENCE: 30
ucguaccgug aguaauaaug cg                                              22

<210> SEQ ID NO 31
<211> LENGTH: 22
<212> TYPE: RNA
<213> ORGANISM: Mus musculus

<400> SEQUENCE: 31
aaaagcuggg uugagagggc ga                                              22

<210> SEQ ID NO 32
<211> LENGTH: 22
<212> TYPE: RNA
<213> ORGANISM: Mus musculus

<400> SEQUENCE: 32
acuccauuug uuuugaugau gg                                              22

<210> SEQ ID NO 33
<211> LENGTH: 21
<212> TYPE: RNA
<213> ORGANISM: Mus musculus

<400> SEQUENCE: 33
gugcauugua guugcauugc a                                               21

<210> SEQ ID NO 34
<211> LENGTH: 23
<212> TYPE: RNA
<213> ORGANISM: Mus musculus

<400> SEQUENCE: 34
uguaguguuu ccuacuuuau gga                                             23

<210> SEQ ID NO 35
<211> LENGTH: 22
<212> TYPE: RNA
<213> ORGANISM: Mus musculus

<400> SEQUENCE: 35
agagaaaccc ugucucaaaa aa                                              22

<210> SEQ ID NO 36
<211> LENGTH: 22
<212> TYPE: RNA
<213> ORGANISM: Mus musculus

<400> SEQUENCE: 36
uuuguucguu cggcucgcgu ga                                              22

<210> SEQ ID NO 37
<211> LENGTH: 22
<212> TYPE: RNA
<213> ORGANISM: Mus musculus
```

-continued

```
<400> SEQUENCE: 37
acugauuucu uuugguguuc ag                                        22

<210> SEQ ID NO 38
<211> LENGTH: 22
<212> TYPE: RNA
<213> ORGANISM: Mus musculus

<400> SEQUENCE: 38
aacuggccua caaaguccca gu                                        22

<210> SEQ ID NO 39
<211> LENGTH: 22
<212> TYPE: RNA
<213> ORGANISM: Mus musculus

<400> SEQUENCE: 39
cacccguaga accgaccuug cg                                        22

<210> SEQ ID NO 40
<211> LENGTH: 21
<212> TYPE: RNA
<213> ORGANISM: Mus musculus

<400> SEQUENCE: 40
cuagacugag gcuccuugag g                                         21

<210> SEQ ID NO 41
<211> LENGTH: 22
<212> TYPE: RNA
<213> ORGANISM: Mus musculus

<400> SEQUENCE: 41
cuauacgacc ugcugccuuu cu                                        22

<210> SEQ ID NO 42
<211> LENGTH: 22
<212> TYPE: RNA
<213> ORGANISM: Mus musculus

<400> SEQUENCE: 42
uccuguacug agcugccccg ag                                        22

<210> SEQ ID NO 43
<211> LENGTH: 23
<212> TYPE: RNA
<213> ORGANISM: Mus musculus

<400> SEQUENCE: 43
ugaggggcag agagcgagac uuu                                       23

<210> SEQ ID NO 44
<211> LENGTH: 22
<212> TYPE: RNA
<213> ORGANISM: Mus musculus

<400> SEQUENCE: 44
uguaaacauc cuacacucag cu                                        22

<210> SEQ ID NO 45
<211> LENGTH: 23
<212> TYPE: RNA
<213> ORGANISM: Mus musculus
```

-continued

```
<400> SEQUENCE: 45
caacggaauc ccaaaagcag cug                                            23

<210> SEQ ID NO 46
<211> LENGTH: 22
<212> TYPE: RNA
<213> ORGANISM: Mus musculus

<400> SEQUENCE: 46
cagcagcaca cugugguuug ua                                             22

<210> SEQ ID NO 47
<211> LENGTH: 22
<212> TYPE: RNA
<213> ORGANISM: Mus musculus

<400> SEQUENCE: 47
uauugcacau uacuaaguug ca                                             22

<210> SEQ ID NO 48
<211> LENGTH: 22
<212> TYPE: RNA
<213> ORGANISM: Mus musculus

<400> SEQUENCE: 48
ugccugucua cacuugcugu gc                                             22

<210> SEQ ID NO 49
<211> LENGTH: 21
<212> TYPE: RNA
<213> ORGANISM: Mus musculus

<400> SEQUENCE: 49
ccucugggcc cuuccuccag u                                              21

<210> SEQ ID NO 50
<211> LENGTH: 23
<212> TYPE: RNA
<213> ORGANISM: Mus musculus

<400> SEQUENCE: 50
ugaguucgag gccagccugc uca                                            23

<210> SEQ ID NO 51
<211> LENGTH: 22
<212> TYPE: RNA
<213> ORGANISM: Mus musculus

<400> SEQUENCE: 51
uggaguguga caauggucuu ug                                             22

<210> SEQ ID NO 52
<211> LENGTH: 23
<212> TYPE: RNA
<213> ORGANISM: Mus musculus

<400> SEQUENCE: 52
agaccuacuu aucuaccaac agc                                            23

<210> SEQ ID NO 53
<211> LENGTH: 22
<212> TYPE: RNA
<213> ORGANISM: Mus musculus
```

```
<400> SEQUENCE: 53
aaugcaccug ggcaagggu ca                                              22

<210> SEQ ID NO 54
<211> LENGTH: 22
<212> TYPE: RNA
<213> ORGANISM: Mus musculus

<400> SEQUENCE: 54
cuuucagucg gauguuuaca gc                                             22

<210> SEQ ID NO 55
<211> LENGTH: 21
<212> TYPE: RNA
<213> ORGANISM: Mus musculus

<400> SEQUENCE: 55
aaacaugaag cgcugcaaca c                                              21

<210> SEQ ID NO 56
<211> LENGTH: 19
<212> TYPE: RNA
<213> ORGANISM: Mus musculus

<400> SEQUENCE: 56
ggaggcagag gcaggagga                                                 19

<210> SEQ ID NO 57
<211> LENGTH: 21
<212> TYPE: RNA
<213> ORGANISM: Mus musculus

<400> SEQUENCE: 57
cggggcagcu caguacagga u                                              21

<210> SEQ ID NO 58
<211> LENGTH: 22
<212> TYPE: RNA
<213> ORGANISM: Mus musculus

<400> SEQUENCE: 58
uuuggucccc uucaaccagc ug                                             22

<210> SEQ ID NO 59
<211> LENGTH: 21
<212> TYPE: RNA
<213> ORGANISM: Mus musculus

<400> SEQUENCE: 59
ccguccugag guuguugagc u                                              21

<210> SEQ ID NO 60
<211> LENGTH: 22
<212> TYPE: RNA
<213> ORGANISM: Mus musculus

<400> SEQUENCE: 60
ugcggggcua gggcuaacag ca                                             22

<210> SEQ ID NO 61
<211> LENGTH: 22
<212> TYPE: RNA
<213> ORGANISM: Mus musculus
```

```
<400> SEQUENCE: 61
uagcaccauc ugaaacggu ua                                          22

<210> SEQ ID NO 62
<211> LENGTH: 22
<212> TYPE: RNA
<213> ORGANISM: Mus musculus

<400> SEQUENCE: 62
aagguagaua gaacaggucu ug                                         22

<210> SEQ ID NO 63
<211> LENGTH: 22
<212> TYPE: RNA
<213> ORGANISM: Mus musculus

<400> SEQUENCE: 63
uguaaacauc cucgacugga ag                                         22

<210> SEQ ID NO 64
<211> LENGTH: 23
<212> TYPE: RNA
<213> ORGANISM: Mus musculus

<400> SEQUENCE: 64
cccaguguuu agacuaccug uuc                                        23

<210> SEQ ID NO 65
<211> LENGTH: 24
<212> TYPE: RNA
<213> ORGANISM: Mus musculus

<400> SEQUENCE: 65
ucccugagac ccuuuaaccu guga                                       24

<210> SEQ ID NO 66
<211> LENGTH: 22
<212> TYPE: RNA
<213> ORGANISM: Mus musculus

<400> SEQUENCE: 66 uuugguccccc uucaaccagc ua                                        22

<210> SEQ ID NO 67
<211> LENGTH: 22
<212> TYPE: RNA
<213> ORGANISM: Mus musculus

<400> SEQUENCE: 67
uggcucaguu cagcaggaac ag                                         22

<210> SEQ ID NO 68
<211> LENGTH: 22
<212> TYPE: RNA
<213> ORGANISM: Mus musculus

<400> SEQUENCE: 68
uagcuuauca gacugauguu ga                                         22

<210> SEQ ID NO 69
<211> LENGTH: 23
<212> TYPE: RNA
<213> ORGANISM: Mus musculus
```

-continued

```
<400> SEQUENCE: 69
uagcagcggg aacaguacug cag                                           23

<210> SEQ ID NO 70
<211> LENGTH: 22
<212> TYPE: RNA
<213> ORGANISM: Mus musculus

<400> SEQUENCE: 70
cuggcccucu cugcccuucc gu                                            22

<210> SEQ ID NO 71
<211> LENGTH: 22
<212> TYPE: RNA
<213> ORGANISM: Mus musculus

<400> SEQUENCE: 71
ugagguagua guuuguacag uu                                            22

<210> SEQ ID NO 72
<211> LENGTH: 22
<212> TYPE: RNA
<213> ORGANISM: Mus musculus

<400> SEQUENCE: 72
aacacaccug uucaaggauu ca                                            22

<210> SEQ ID NO 73
<211> LENGTH: 23
<212> TYPE: RNA
<213> ORGANISM: Mus musculus

<400> SEQUENCE: 73
cccaguguuc agacuaccug uuc                                           23

<210> SEQ ID NO 74
<211> LENGTH: 22
<212> TYPE: RNA
<213> ORGANISM: Mus musculus

<400> SEQUENCE: 74
caggccauac ugugcugccu ca                                            22

<210> SEQ ID NO 75
<211> LENGTH: 22
<212> TYPE: RNA
<213> ORGANISM: Mus musculus

<400> SEQUENCE: 75
ucuacagugc acgugucucc ag                                            22

<210> SEQ ID NO 76
<211> LENGTH: 23
<212> TYPE: RNA
<213> ORGANISM: Mus musculus

<400> SEQUENCE: 76
ucuggcuccg ugucuucacu ccc                                           23

<210> SEQ ID NO 77
<211> LENGTH: 23
<212> TYPE: RNA
<213> ORGANISM: Mus musculus
```

```
<400> SEQUENCE: 77
uagcaccauu ugaaaucagu guu                                               23

<210> SEQ ID NO 78
<211> LENGTH: 22
<212> TYPE: RNA
<213> ORGANISM: Mus musculus

<400> SEQUENCE: 78
uggaauguaa agaaguaugu au                                                22

<210> SEQ ID NO 79
<211> LENGTH: 21
<212> TYPE: RNA
<213> ORGANISM: Mus musculus

<400> SEQUENCE: 79
aucacauugc cagggauuac c                                                 21

<210> SEQ ID NO 80
<211> LENGTH: 21
<212> TYPE: RNA
<213> ORGANISM: Mus musculus

<400> SEQUENCE: 80
augaccuaug auuugacaga c                                                 21

<210> SEQ ID NO 81
<211> LENGTH: 22
<212> TYPE: RNA
<213> ORGANISM: Mus musculus

<400> SEQUENCE: 81
uucccuuugu cauccaugc cu                                                 22

<210> SEQ ID NO 82
<211> LENGTH: 22
<212> TYPE: RNA
<213> ORGANISM: Mus musculus

<400> SEQUENCE: 82
caucuuacug ggcagcauug ga                                                22

<210> SEQ ID NO 83
<211> LENGTH: 22
<212> TYPE: RNA
<213> ORGANISM: Mus musculus

<400> SEQUENCE: 83
cauugcacuu gucucggucu ga                                                22

<210> SEQ ID NO 84
<211> LENGTH: 22
<212> TYPE: RNA
<213> ORGANISM: Mus musculus

<400> SEQUENCE: 84
uccagcauca gugauuuugu ug                                                22

<210> SEQ ID NO 85
<211> LENGTH: 22
<212> TYPE: RNA
<213> ORGANISM: Mus musculus
```

```
<400> SEQUENCE: 85
uagguaguuu ccuguuguug gg                                              22

<210> SEQ ID NO 86
<211> LENGTH: 22
<212> TYPE: RNA
<213> ORGANISM: Homo sapiens

<400> SEQUENCE: 86
cagugcaaug uuaaaagggc au                                              22

<210> SEQ ID NO 87
<211> LENGTH: 22
<212> TYPE: DNA
<213> ORGANISM: Mus musculus

<400> SEQUENCE: 87
cagtgcaatg ttaaaagggc at                                              22

<210> SEQ ID NO 88
<211> LENGTH: 22
<212> TYPE: DNA
<213> ORGANISM: Homo sapiens

<400> SEQUENCE: 88
cagtgcaatg ttaaaagggc at                                              22

<210> SEQ ID NO 89
<211> LENGTH: 22
<212> TYPE: RNA
<213> ORGANISM: Homo sapiens

<400> SEQUENCE: 89
ucucccaacc cuuguaccag ug                                              22

<210> SEQ ID NO 90
<211> LENGTH: 22
<212> TYPE: DNA
<213> ORGANISM: Mus musculus

<400> SEQUENCE: 90
tctcccaacc cttgtaccag tg                                              22

<210> SEQ ID NO 91
<211> LENGTH: 22
<212> TYPE: DNA
<213> ORGANISM: Homo sapiens

<400> SEQUENCE: 91
tctcccaacc cttgtaccag tg                                              22

<210> SEQ ID NO 92
<211> LENGTH: 22
<212> TYPE: RNA
<213> ORGANISM: Homo sapiens

<400> SEQUENCE: 92
acugcaguga aggcacuugu ag                                              22

<210> SEQ ID NO 93
<211> LENGTH: 22
<212> TYPE: DNA
<213> ORGANISM: Mus musculus
```

-continued

```
<400> SEQUENCE: 93
actgcagtga gggcacttgt ag                                              22

<210> SEQ ID NO 94
<211> LENGTH: 22
<212> TYPE: DNA
<213> ORGANISM: Homo sapiens

<400> SEQUENCE: 94
actgcagtga aggcacttgt ag                                              22

<210> SEQ ID NO 95
<211> LENGTH: 22
<212> TYPE: RNA
<213> ORGANISM: Homo sapiens

<400> SEQUENCE: 95
ucgugucuug uguugcagcc gg                                              22

<210> SEQ ID NO 96
<211> LENGTH: 22
<212> TYPE: DNA
<213> ORGANISM: Mus musculus

<400> SEQUENCE: 96
tcgtgtcttg tgttgcagcc gg                                              22

<210> SEQ ID NO 97
<211> LENGTH: 22
<212> TYPE: DNA
<213> ORGANISM: Homo sapiens

<400> SEQUENCE: 97
tcgtgtcttg tgttgcagcc gg                                              22

<210> SEQ ID NO 98
<211> LENGTH: 22
<212> TYPE: RNA
<213> ORGANISM: Homo sapiens

<400> SEQUENCE: 98
uguaacagca acuccaugug ga                                              22

<210> SEQ ID NO 99
<211> LENGTH: 22
<212> TYPE: DNA
<213> ORGANISM: Mus musculus

<400> SEQUENCE: 99
tgtaacagca actccatgtg ga                                              22

<210> SEQ ID NO 100
<211> LENGTH: 22
<212> TYPE: DNA
<213> ORGANISM: Homo sapiens

<400> SEQUENCE: 100
tgtaacagca actccatgtg ga                                              22

<210> SEQ ID NO 101
<211> LENGTH: 21
<212> TYPE: RNA
<213> ORGANISM: Homo sapiens
```

```
<400> SEQUENCE: 101
uucacagugg cuaaguuccg c                                              21

<210> SEQ ID NO 102
<211> LENGTH: 21
<212> TYPE: DNA
<213> ORGANISM: Mus musculus

<400> SEQUENCE: 102
ttcacagtgg ctaagttccg c                                              21

<210> SEQ ID NO 103
<211> LENGTH: 21
<212> TYPE: DNA
<213> ORGANISM: Homo sapiens

<400> SEQUENCE: 103
ttcacagtgg ctaagttccg c                                              21

<210> SEQ ID NO 104
<211> LENGTH: 22
<212> TYPE: RNA
<213> ORGANISM: Homo sapiens

<400> SEQUENCE: 104
cuuucagucg gauguuugca gc                                             22

<210> SEQ ID NO 105
<211> LENGTH: 22
<212> TYPE: DNA
<213> ORGANISM: Mus musculus

<400> SEQUENCE: 105
ctttcagtcg gatgtttgca gc                                             22

<210> SEQ ID NO 106
<211> LENGTH: 22
<212> TYPE: DNA
<213> ORGANISM: Homo sapiens

<400> SEQUENCE: 106
ctttcagtcg gatgtttgca gc                                             22

<210> SEQ ID NO 107
<211> LENGTH: 23
<212> TYPE: RNA
<213> ORGANISM: Homo sapiens

<400> SEQUENCE: 107
uguaaacauc cuacacucuc agc                                            23

<210> SEQ ID NO 108
<211> LENGTH: 23
<212> TYPE: DNA
<213> ORGANISM: Mus musculus

<400> SEQUENCE: 108
tgtaaacatc ctacactctc agc                                            23

<210> SEQ ID NO 109
<211> LENGTH: 23
<212> TYPE: DNA
<213> ORGANISM: Homo sapiens
```

-continued

```
<400> SEQUENCE: 109
tgtaaacatc ctacactctc agc                                           23

<210> SEQ ID NO 110
<211> LENGTH: 21
<212> TYPE: RNA
<213> ORGANISM: Homo sapiens

<400> SEQUENCE: 110
cauaaaguag aaagcacuac u                                             21

<210> SEQ ID NO 111
<211> LENGTH: 21
<212> TYPE: DNA
<213> ORGANISM: Mus musculus

<400> SEQUENCE: 111
cataaagtag aaagcactac t                                             21

<210> SEQ ID NO 112
<211> LENGTH: 21
<212> TYPE: DNA
<213> ORGANISM: Homo sapiens

<400> SEQUENCE: 112
cataaagtag aaagcactac t                                             21

<210> SEQ ID NO 113
<211> LENGTH: 23
<212> TYPE: RNA
<213> ORGANISM: Homo sapiens

<400> SEQUENCE: 113
ucucacacag aaaucgcacc cgu                                           23

<210> SEQ ID NO 114
<211> LENGTH: 23
<212> TYPE: DNA
<213> ORGANISM: Mus musculus

<400> SEQUENCE: 114
tctcacacag aaatcgcacc cgt                                           23

<210> SEQ ID NO 115
<211> LENGTH: 23
<212> TYPE: DNA
<213> ORGANISM: Homo sapiens

<400> SEQUENCE: 115
tctcacacag aaatcgcacc cgt                                           23

<210> SEQ ID NO 116
<211> LENGTH: 22
<212> TYPE: RNA
<213> ORGANISM: Homo sapiens

<400> SEQUENCE: 116
caaucacuaa cuccacugcc au                                            22

<210> SEQ ID NO 117
<211> LENGTH: 21
<212> TYPE: DNA
<213> ORGANISM: Mus musculus
```

-continued

```
<400> SEQUENCE: 117
aatcactaac tccactgcca t                                        21

<210> SEQ ID NO 118
<211> LENGTH: 21
<212> TYPE: DNA
<213> ORGANISM: Homo sapiens

<400> SEQUENCE: 118
aatcactaac tccactgcca t                                        21

<210> SEQ ID NO 119
<211> LENGTH: 22
<212> TYPE: RNA
<213> ORGANISM: Homo sapiens

<400> SEQUENCE: 119
ucguaccgug aguaauaaug cg                                       22

<210> SEQ ID NO 120
<211> LENGTH: 22
<212> TYPE: DNA
<213> ORGANISM: Mus musculus

<400> SEQUENCE: 120
tcgtaccgtg agtaataatg cg                                       22

<210> SEQ ID NO 121
<211> LENGTH: 22
<212> TYPE: DNA
<213> ORGANISM: Homo sapiens

<400> SEQUENCE: 121
tcgtaccgtg agtaataatg cg                                       22

<210> SEQ ID NO 122
<211> LENGTH: 22
<212> TYPE: RNA
<213> ORGANISM: Homo sapiens

<400> SEQUENCE: 122
aaaagcuggg uugagagggc ga                                       22

<210> SEQ ID NO 123
<211> LENGTH: 22
<212> TYPE: DNA
<213> ORGANISM: Mus musculus

<400> SEQUENCE: 123
aaaagctggg ttgagagggc ga                                       22

<210> SEQ ID NO 124
<211> LENGTH: 22
<212> TYPE: DNA
<213> ORGANISM: Homo sapiens

<400> SEQUENCE: 124
aaaagctggg ttgagagggc ga                                       22

<210> SEQ ID NO 125
<211> LENGTH: 23
<212> TYPE: RNA
<213> ORGANISM: Homo sapiens
```

```
<400> SEQUENCE: 125
acuccauuug uuuugaugau gga                                        23

<210> SEQ ID NO 126
<211> LENGTH: 22
<212> TYPE: DNA
<213> ORGANISM: Mus musculus

<400> SEQUENCE: 126
actccatttg ttttgatgat gg                                         22

<210> SEQ ID NO 127
<211> LENGTH: 22
<212> TYPE: DNA
<213> ORGANISM: Homo sapiens

<400> SEQUENCE: 127
actccatttg ttttgatgat gg                                         22

<210> SEQ ID NO 128
<211> LENGTH: 21
<212> TYPE: RNA
<213> ORGANISM: Homo sapiens

<400> SEQUENCE: 128
gugcauugua guugcauugc a                                          21

<210> SEQ ID NO 129
<211> LENGTH: 21
<212> TYPE: DNA
<213> ORGANISM: Mus musculus

<400> SEQUENCE: 129
gtgcattgta gttgcattgc a                                          21

<210> SEQ ID NO 130
<211> LENGTH: 21
<212> TYPE: DNA
<213> ORGANISM: Homo sapiens

<400> SEQUENCE: 130
gtgcattgta gttgcattgc a                                          21

<210> SEQ ID NO 131
<211> LENGTH: 23
<212> TYPE: RNA
<213> ORGANISM: Homo sapiens

<400> SEQUENCE: 131
uguaguguuu ccuacuuuau gga                                        23

<210> SEQ ID NO 132
<211> LENGTH: 23
<212> TYPE: DNA
<213> ORGANISM: Mus musculus

<400> SEQUENCE: 132
tgtagtgttt cctactttat gga                                        23

<210> SEQ ID NO 133
<211> LENGTH: 23
<212> TYPE: DNA
<213> ORGANISM: Homo sapiens
```

-continued

<400> SEQUENCE: 133
tgtagtgttt cctactttat gga                                              23

<210> SEQ ID NO 134
<211> LENGTH: 22
<212> TYPE: RNA
<213> ORGANISM: Homo sapiens

<400> SEQUENCE: 134
uuuguucguu cggcucgcgu ga                                               22

<210> SEQ ID NO 135
<211> LENGTH: 22
<212> TYPE: DNA
<213> ORGANISM: Mus musculus

<400> SEQUENCE: 135
tttgttcgtt cggctcgcgt ga                                               22

<210> SEQ ID NO 136
<211> LENGTH: 22
<212> TYPE: DNA
<213> ORGANISM: Homo sapiens

<400> SEQUENCE: 136
tttgttcgtt cggctcgcgt ga                                               22

<210> SEQ ID NO 137
<211> LENGTH: 22
<212> TYPE: RNA
<213> ORGANISM: Homo sapiens

<400> SEQUENCE: 137
acugauuucu uuugguguuc ag                                               22

<210> SEQ ID NO 138
<211> LENGTH: 22
<212> TYPE: DNA
<213> ORGANISM: Mus musculus

<400> SEQUENCE: 138
actgatttct tttggtgttc ag                                               22

<210> SEQ ID NO 139
<211> LENGTH: 22
<212> TYPE: DNA
<213> ORGANISM: Homo sapiens

<400> SEQUENCE: 139
actgatttct tttggtgttc ag                                               22

<210> SEQ ID NO 140
<211> LENGTH: 22
<212> TYPE: RNA
<213> ORGANISM: Homo sapiens

<400> SEQUENCE: 140
aacuggccua caaaguccca gu                                               22

<210> SEQ ID NO 141
<211> LENGTH: 22
<212> TYPE: DNA
<213> ORGANISM: Mus musculus

```
<400> SEQUENCE: 141
aactggccta caaagtccca gt                                           22

<210> SEQ ID NO 142
<211> LENGTH: 22
<212> TYPE: DNA
<213> ORGANISM: Homo sapiens

<400> SEQUENCE: 142
aactggccta caaagtccca gt                                           22

<210> SEQ ID NO 143
<211> LENGTH: 22
<212> TYPE: RNA
<213> ORGANISM: Homo sapiens

<400> SEQUENCE: 143
cacccguaga accgaccuug cg                                           22

<210> SEQ ID NO 144
<211> LENGTH: 22
<212> TYPE: DNA
<213> ORGANISM: Mus musculus

<400> SEQUENCE: 144
cacccgtaga accgaccttg cg                                           22

<210> SEQ ID NO 145
<211> LENGTH: 22
<212> TYPE: DNA
<213> ORGANISM: Homo sapiens

<400> SEQUENCE: 145
cacccgtaga accgaccttg cg                                           22

<210> SEQ ID NO 146
<211> LENGTH: 21
<212> TYPE: RNA
<213> ORGANISM: Homo sapiens

<400> SEQUENCE: 146
cuagacugaa gcuccuugag g                                            21

<210> SEQ ID NO 147
<211> LENGTH: 21
<212> TYPE: DNA
<213> ORGANISM: Mus musculus

<400> SEQUENCE: 147
ctagactgag gctccttgag g                                            21

<210> SEQ ID NO 148
<211> LENGTH: 21
<212> TYPE: DNA
<213> ORGANISM: Homo sapiens

<400> SEQUENCE: 148
ctagactgaa gctccttgag g                                            21

<210> SEQ ID NO 149
<211> LENGTH: 22
<212> TYPE: RNA
<213> ORGANISM: Homo sapiens
```

```
<400> SEQUENCE: 149
cuauacgacc ugcugccuuu cu                                              22

<210> SEQ ID NO 150
<211> LENGTH: 22
<212> TYPE: DNA
<213> ORGANISM: Mus musculus

<400> SEQUENCE: 150
ctatacgacc tgctgccttt ct                                              22

<210> SEQ ID NO 151
<211> LENGTH: 22
<212> TYPE: DNA
<213> ORGANISM: Homo sapiens

<400> SEQUENCE: 151
ctatacgacc tgctgccttt ct                                              22

<210> SEQ ID NO 152
<211> LENGTH: 22
<212> TYPE: RNA
<213> ORGANISM: Homo sapiens

<400> SEQUENCE: 152
uccuguacug agcugccccg ag                                              22

<210> SEQ ID NO 153
<211> LENGTH: 22
<212> TYPE: DNA
<213> ORGANISM: Mus musculus

<400> SEQUENCE: 153
tcctgtactg agctgccccg ag                                              22

<210> SEQ ID NO 154
<211> LENGTH: 22
<212> TYPE: DNA
<213> ORGANISM: Homo sapiens

<400> SEQUENCE: 154
tcctgtactg agctgccccg ag                                              22

<210> SEQ ID NO 155
<211> LENGTH: 23
<212> TYPE: RNA
<213> ORGANISM: Homo sapiens

<400> SEQUENCE: 155
ugaggggcag agagcgagac uuu                                             23

<210> SEQ ID NO 156
<211> LENGTH: 23
<212> TYPE: DNA
<213> ORGANISM: Mus musculus

<400> SEQUENCE: 156
tgaggggcag agagcgagac ttt                                             23

<210> SEQ ID NO 157
<211> LENGTH: 23
<212> TYPE: DNA
<213> ORGANISM: Homo sapiens
```

```
<400> SEQUENCE: 157 tgagggcag agagcgagac ttt                                              23

<210> SEQ ID NO 158
<211> LENGTH: 22
<212> TYPE: RNA
<213> ORGANISM: Homo sapiens

<400> SEQUENCE: 158
uguaaacauc cuacacucag cu                                              22

<210> SEQ ID NO 159
<211> LENGTH: 22
<212> TYPE: DNA
<213> ORGANISM: Mus musculus

<400> SEQUENCE: 159
tgtaaacatc ctacactcag ct                                              22

<210> SEQ ID NO 160
<211> LENGTH: 22
<212> TYPE: DNA
<213> ORGANISM: Homo sapiens

<400> SEQUENCE: 160
tgtaaacatc ctacactcag ct                                              22

<210> SEQ ID NO 161
<211> LENGTH: 23
<212> TYPE: RNA
<213> ORGANISM: Homo sapiens

<400> SEQUENCE: 161
caacggaauc ccaaaagcag cug                                             23

<210> SEQ ID NO 162
<211> LENGTH: 23
<212> TYPE: DNA
<213> ORGANISM: Mus musculus

<400> SEQUENCE: 162
caacggaatc ccaaaagcag ctg                                             23

<210> SEQ ID NO 163
<211> LENGTH: 23
<212> TYPE: DNA
<213> ORGANISM: Homo sapiens

<400> SEQUENCE: 163
caacggaatc ccaaaagcag ctg                                             23

<210> SEQ ID NO 164
<211> LENGTH: 21
<212> TYPE: RNA
<213> ORGANISM: Homo sapiens

<400> SEQUENCE: 164
cagcagcaca cugugguuug u                                               21

<210> SEQ ID NO 165
<211> LENGTH: 21
<212> TYPE: DNA
<213> ORGANISM: Mus musculus
```

<400> SEQUENCE: 165
cagcagcaca ctgtggtttg t                                              21

<210> SEQ ID NO 166
<211> LENGTH: 21
<212> TYPE: DNA
<213> ORGANISM: Homo sapiens

<400> SEQUENCE: 166
cagcagcaca ctgtggtttg t                                              21

<210> SEQ ID NO 167
<211> LENGTH: 22
<212> TYPE: RNA
<213> ORGANISM: Homo sapiens

<400> SEQUENCE: 167
uauugcacau uacuaaguug ca                                             22

<210> SEQ ID NO 168
<211> LENGTH: 22
<212> TYPE: DNA
<213> ORGANISM: Mus musculus

<400> SEQUENCE: 168
tattgcacat tactaagttg ca                                             22

<210> SEQ ID NO 169
<211> LENGTH: 22
<212> TYPE: DNA
<213> ORGANISM: Homo sapiens

<400> SEQUENCE: 169
tattgcacat tactaagttg ca                                             22

<210> SEQ ID NO 170
<211> LENGTH: 22
<212> TYPE: RNA
<213> ORGANISM: Homo sapiens

<400> SEQUENCE: 170
ugccugucua cacuugcugu gc                                             22

<210> SEQ ID NO 171
<211> LENGTH: 22
<212> TYPE: DNA
<213> ORGANISM: Mus musculus

<400> SEQUENCE: 171
tgcctgtcta cacttgctgt gc                                             22

<210> SEQ ID NO 172
<211> LENGTH: 22
<212> TYPE: DNA
<213> ORGANISM: Homo sapiens

<400> SEQUENCE: 172
tgcctgtcta cacttgctgt gc                                             22

<210> SEQ ID NO 173
<211> LENGTH: 20
<212> TYPE: RNA
<213> ORGANISM: Homo sapiens

```
<400> SEQUENCE: 173
ccucugggcc cuuccuccag                                               20

<210> SEQ ID NO 174
<211> LENGTH: 20
<212> TYPE: DNA
<213> ORGANISM: Mus musculus

<400> SEQUENCE: 174
cctctgggcc cttcctccag                                               20

<210> SEQ ID NO 175
<211> LENGTH: 20
<212> TYPE: DNA
<213> ORGANISM: Homo sapiens

<400> SEQUENCE: 175
cctctgggcc cttcctccag                                               20

<210> SEQ ID NO 176
<211> LENGTH: 22
<212> TYPE: RNA
<213> ORGANISM: Homo sapiens

<400> SEQUENCE: 176
uggaguguga caauguguu ug                                             22

<210> SEQ ID NO 177
<211> LENGTH: 22
<212> TYPE: DNA
<213> ORGANISM: Mus musculus

<400> SEQUENCE: 177
tggagtgtga caatggtgtt tg                                            22

<210> SEQ ID NO 178
<211> LENGTH: 22
<212> TYPE: DNA
<213> ORGANISM: Homo sapiens

<400> SEQUENCE: 178
tggagtgtga caatggtgtt tg                                            22

<210> SEQ ID NO 179
<211> LENGTH: 22
<212> TYPE: RNA
<213> ORGANISM: Homo sapiens

<400> SEQUENCE: 179
aaugcaccug ggcaaggauu ca                                            22

<210> SEQ ID NO 180
<211> LENGTH: 22
<212> TYPE: DNA
<213> ORGANISM: Mus musculus

<400> SEQUENCE: 180
aatgcacctg ggcaagggtt ca                                            22

<210> SEQ ID NO 181
<211> LENGTH: 22
<212> TYPE: DNA
<213> ORGANISM: Homo sapiens
```

```
<400> SEQUENCE: 181
aatgcacctg ggcaaggatt ca                                              22

<210> SEQ ID NO 182
<211> LENGTH: 22
<212> TYPE: RNA
<213> ORGANISM: Homo sapiens

<400> SEQUENCE: 182
cuuucagucg gauguuuaca gc                                              22

<210> SEQ ID NO 183
<211> LENGTH: 22
<212> TYPE: DNA
<213> ORGANISM: Mus musculus

<400> SEQUENCE: 183
ctttcagtcg gatgtttaca gc                                              22

<210> SEQ ID NO 184
<211> LENGTH: 22
<212> TYPE: DNA
<213> ORGANISM: Homo sapiens

<400> SEQUENCE: 184
ctttcagtcg gatgtttaca gc                                              22

<210> SEQ ID NO 185
<211> LENGTH: 21
<212> TYPE: RNA
<213> ORGANISM: Homo sapiens

<400> SEQUENCE: 185
aaacaugaag cgcugcaaca c                                               21

<210> SEQ ID NO 186
<211> LENGTH: 16
<212> TYPE: DNA
<213> ORGANISM: Mus musculus

<400> SEQUENCE: 186
aaacatgaag cgctgc                                                     16

<210> SEQ ID NO 187
<211> LENGTH: 16
<212> TYPE: DNA
<213> ORGANISM: Homo sapiens

<400> SEQUENCE: 187
aaacgtgagg cgctgc                                                     16

<210> SEQ ID NO 188
<211> LENGTH: 20
<212> TYPE: RNA
<213> ORGANISM: Homo sapiens

<400> SEQUENCE: 188
gaggcagaag caggaugaca                                                 20

<210> SEQ ID NO 189
<211> LENGTH: 15
<212> TYPE: RNA
<213> ORGANISM: Mus musculus
```

<400> SEQUENCE: 189
gaggcagagg cagga                                                    15

<210> SEQ ID NO 190
<211> LENGTH: 15
<212> TYPE: RNA
<213> ORGANISM: Homo sapiens

<400> SEQUENCE: 190
gaggcagaag cagga                                                    15

<210> SEQ ID NO 191
<211> LENGTH: 21
<212> TYPE: RNA
<213> ORGANISM: Homo sapiens

<400> SEQUENCE: 191
cggggcagcu caguacagga u                                             21

<210> SEQ ID NO 192
<211> LENGTH: 21
<212> TYPE: DNA
<213> ORGANISM: Mus musculus

<400> SEQUENCE: 192
cggggcagct cagtacagga t                                             21

<210> SEQ ID NO 193
<211> LENGTH: 21
<212> TYPE: DNA
<213> ORGANISM: Homo sapiens

<400> SEQUENCE: 193
cggggcagct cagtacagga t                                             21

<210> SEQ ID NO 194
<211> LENGTH: 22
<212> TYPE: RNA
<213> ORGANISM: Homo sapiens

<400> SEQUENCE: 194
uuuggucccc uucaaccagc ug                                            22

<210> SEQ ID NO 195
<211> LENGTH: 22
<212> TYPE: DNA
<213> ORGANISM: Mus musculus

<400> SEQUENCE: 195
tttggtcccc ttcaaccagc tg                                            22

<210> SEQ ID NO 196
<211> LENGTH: 22
<212> TYPE: DNA
<213> ORGANISM: Homo sapiens

<400> SEQUENCE: 196
tttggtcccc ttcaaccagc tg                                            22

<210> SEQ ID NO 197
<211> LENGTH: 21
<212> TYPE: RNA
<213> ORGANISM: Homo sapiens

```
<400> SEQUENCE: 197
cuguccuaag guuguugagu u                                              21

<210> SEQ ID NO 198
<211> LENGTH: 17
<212> TYPE: DNA
<213> ORGANISM: Mus musculus

<400> SEQUENCE: 198
gtcctgaggt tgttgag                                                   17

<210> SEQ ID NO 199
<211> LENGTH: 17
<212> TYPE: DNA
<213> ORGANISM: Homo sapiens

<400> SEQUENCE: 199
gtcctaaggt tgttgag                                                   17

<210> SEQ ID NO 200
<211> LENGTH: 22
<212> TYPE: RNA
<213> ORGANISM: Homo sapiens

<400> SEQUENCE: 200
ugcggggcua gggcuaacag ca                                             22

<210> SEQ ID NO 201
<211> LENGTH: 22
<212> TYPE: DNA
<213> ORGANISM: Mus musculus

<400> SEQUENCE: 201
tgcggggcta gggctaacag ca                                             22

<210> SEQ ID NO 202
<211> LENGTH: 22
<212> TYPE: DNA
<213> ORGANISM: Homo sapiens

<400> SEQUENCE: 202
tgcggggcta gggctaacag ca                                             22

<210> SEQ ID NO 203
<211> LENGTH: 22
<212> TYPE: RNA
<213> ORGANISM: Homo sapiens

<400> SEQUENCE: 203
uagcaccauc ugaaaucggu ua                                             22

<210> SEQ ID NO 204
<211> LENGTH: 22
<212> TYPE: DNA
<213> ORGANISM: Mus musculus

<400> SEQUENCE: 204
tagcaccatc tgaaatcggt ta                                             22

<210> SEQ ID NO 205
<211> LENGTH: 22
<212> TYPE: DNA
<213> ORGANISM: Homo sapiens
```

```
<400> SEQUENCE: 205
tagcaccatc tgaaatcggt ta                                          22

<210> SEQ ID NO 206
<211> LENGTH: 22
<212> TYPE: RNA
<213> ORGANISM: Homo sapiens

<400> SEQUENCE: 206
uguaaacauc cucgacugga ag                                          22

<210> SEQ ID NO 207
<211> LENGTH: 22
<212> TYPE: DNA
<213> ORGANISM: Mus musculus

<400> SEQUENCE: 207
tgtaaacatc ctcgactgga ag                                          22

<210> SEQ ID NO 208
<211> LENGTH: 22
<212> TYPE: DNA
<213> ORGANISM: Homo sapiens

<400> SEQUENCE: 208
tgtaaacatc ctcgactgga ag                                          22

<210> SEQ ID NO 209
<211> LENGTH: 23
<212> TYPE: RNA
<213> ORGANISM: Homo sapiens

<400> SEQUENCE: 209
cccaguguuu agacuaucug uuc                                         23

<210> SEQ ID NO 210
<211> LENGTH: 23
<212> TYPE: DNA
<213> ORGANISM: Mus musculus

<400> SEQUENCE: 210
cccagtgttt agactacctg ttc                                         23

<210> SEQ ID NO 211
<211> LENGTH: 23
<212> TYPE: DNA
<213> ORGANISM: Homo sapiens

<400> SEQUENCE: 211
cccagtgttt agactatctg ttc                                         23

<210> SEQ ID NO 212
<211> LENGTH: 24
<212> TYPE: RNA
<213> ORGANISM: Homo sapiens

<400> SEQUENCE: 212
ucccugagac ccuuuaaccu guga                                        24

<210> SEQ ID NO 213
<211> LENGTH: 24
<212> TYPE: DNA
<213> ORGANISM: Homo sapiens
```

<400> SEQUENCE: 213
tccctgagac cctttaacct gtga                                              24

<210> SEQ ID NO 214
<211> LENGTH: 24
<212> TYPE: DNA
<213> ORGANISM: Mus musculus

<400> SEQUENCE: 214
tccctgagac cctttaacct gtga                                              24

<210> SEQ ID NO 215
<211> LENGTH: 22
<212> TYPE: RNA
<213> ORGANISM: Homo sapiens

<400> SEQUENCE: 215
uuuggucccc uucaaccagc ua                                                22

<210> SEQ ID NO 216
<211> LENGTH: 22
<212> TYPE: DNA
<213> ORGANISM: Mus musculus

<400> SEQUENCE: 216
tttggtcccc ttcaaccagc ta                                                22

<210> SEQ ID NO 217
<211> LENGTH: 22
<212> TYPE: DNA
<213> ORGANISM: Homo sapiens

<400> SEQUENCE: 217
tttggtcccc ttcaaccagc ta                                                22

<210> SEQ ID NO 218
<211> LENGTH: 22
<212> TYPE: RNA
<213> ORGANISM: Homo sapiens

<400> SEQUENCE: 218
uggcucaguu cagcaggaac ag                                                22

<210> SEQ ID NO 219
<211> LENGTH: 22
<212> TYPE: DNA
<213> ORGANISM: Mus musculus

<400> SEQUENCE: 219
tggctcagtt cagcaggaac ag                                                22

<210> SEQ ID NO 220
<211> LENGTH: 22
<212> TYPE: DNA
<213> ORGANISM: Homo sapiens

<400> SEQUENCE: 220
tggctcagtt cagcaggaac ag                                                22

<210> SEQ ID NO 221
<211> LENGTH: 22
<212> TYPE: RNA
<213> ORGANISM: Homo sapiens

```
<400> SEQUENCE: 221
uagcuuauca gacugauguu ga                                    22

<210> SEQ ID NO 222
<211> LENGTH: 22
<212> TYPE: DNA
<213> ORGANISM: Mus musculus

<400> SEQUENCE: 222
tagcttatca gactgatgtt ga                                    22

<210> SEQ ID NO 223
<211> LENGTH: 22
<212> TYPE: DNA
<213> ORGANISM: Homo sapiens

<400> SEQUENCE: 223
tagcttatca gactgatgtt ga                                    22

<210> SEQ ID NO 224
<211> LENGTH: 23
<212> TYPE: RNA
<213> ORGANISM: Homo sapiens

<400> SEQUENCE: 224
uagcagcggg aacaguucug cag                                   23

<210> SEQ ID NO 225
<211> LENGTH: 23
<212> TYPE: DNA
<213> ORGANISM: Mus musculus

<400> SEQUENCE: 225
tagcagcggg aacagtactg cag                                   23

<210> SEQ ID NO 226
<211> LENGTH: 23
<212> TYPE: DNA
<213> ORGANISM: Homo sapiens

<400> SEQUENCE: 226
tagcagcggg aacagttctg cag                                   23

<210> SEQ ID NO 227
<211> LENGTH: 22
<212> TYPE: RNA
<213> ORGANISM: Homo sapiens

<400> SEQUENCE: 227
cuggcccucu cugcccuucc gu                                    22

<210> SEQ ID NO 228
<211> LENGTH: 22
<212> TYPE: DNA
<213> ORGANISM: Mus musculus

<400> SEQUENCE: 228
ctggccctct ctgcccttcc gt                                    22

<210> SEQ ID NO 229
<211> LENGTH: 22
<212> TYPE: DNA
<213> ORGANISM: Homo sapiens
```

```
<400> SEQUENCE: 229
ctggccctct ctgcccttcc gt                                          22

<210> SEQ ID NO 230
<211> LENGTH: 22
<212> TYPE: RNA
<213> ORGANISM: Homo sapiens

<400> SEQUENCE: 230
ugagguagua guuuguacag uu                                          22

<210> SEQ ID NO 231
<211> LENGTH: 22
<212> TYPE: DNA
<213> ORGANISM: Mus musculus

<400> SEQUENCE: 231
tgaggtagta gtttgtacag tt                                          22

<210> SEQ ID NO 232
<211> LENGTH: 22
<212> TYPE: DNA
<213> ORGANISM: Homo sapiens

<400> SEQUENCE: 232
tgaggtagta gtttgtagag tt                                          22

<210> SEQ ID NO 233
<211> LENGTH: 22
<212> TYPE: RNA
<213> ORGANISM: Homo sapiens

<400> SEQUENCE: 233
aacacaccua uucaaggauu ca                                          22

<210> SEQ ID NO 234
<211> LENGTH: 22
<212> TYPE: DNA
<213> ORGANISM: Mus musculus

<400> SEQUENCE: 234
aacacacctg ttcaaggatt ca                                          22

<210> SEQ ID NO 235
<211> LENGTH: 22
<212> TYPE: DNA
<213> ORGANISM: Homo sapiens

<400> SEQUENCE: 235
aacacaccta ttcaaggatt ca                                          22

<210> SEQ ID NO 236
<211> LENGTH: 23
<212> TYPE: RNA
<213> ORGANISM: Homo sapiens

<400> SEQUENCE: 236
cccaguguuc agacuaccug uuc                                         23

<210> SEQ ID NO 237
<211> LENGTH: 23
<212> TYPE: DNA
<213> ORGANISM: Mus musculus
```

```
<400> SEQUENCE: 237
cccagtgttc agactacctg ttc                                            23

<210> SEQ ID NO 238
<211> LENGTH: 23
<212> TYPE: DNA
<213> ORGANISM: Homo sapiens

<400> SEQUENCE: 238
cccagtgttc agactacctg ttc                                            23

<210> SEQ ID NO 239
<211> LENGTH: 22
<212> TYPE: RNA
<213> ORGANISM: Homo sapiens

<400> SEQUENCE: 239
caggccauau ugugcugccu ca                                             22

<210> SEQ ID NO 240
<211> LENGTH: 22
<212> TYPE: DNA
<213> ORGANISM: Mus musculus

<400> SEQUENCE: 240
caggccatac tgtgctgcct ca                                             22

<210> SEQ ID NO 241
<211> LENGTH: 22
<212> TYPE: DNA
<213> ORGANISM: Homo sapiens

<400> SEQUENCE: 241
caggccatat tgtgctgcct ca                                             22

<210> SEQ ID NO 242
<211> LENGTH: 23
<212> TYPE: RNA
<213> ORGANISM: Homo sapiens

<400> SEQUENCE: 242
ucuacagugc acgugucucc agu                                            23

<210> SEQ ID NO 243
<211> LENGTH: 22
<212> TYPE: DNA
<213> ORGANISM: Mus musculus

<400> SEQUENCE: 243
tctacagtgc acgtgtctcc ag                                             22

<210> SEQ ID NO 244
<211> LENGTH: 22
<212> TYPE: DNA
<213> ORGANISM: Homo sapiens

<400> SEQUENCE: 244
tctacagtgc acgtgtctcc ag                                             22

<210> SEQ ID NO 245
<211> LENGTH: 23
<212> TYPE: RNA
<213> ORGANISM: Homo sapiens
```

```
<400> SEQUENCE: 245
ucuggcuccg ugucuucacu ccc                                          23

<210> SEQ ID NO 246
<211> LENGTH: 23
<212> TYPE: DNA
<213> ORGANISM: Mus musculus

<400> SEQUENCE: 246
tctggctccg tgtcttcact ccc                                          23

<210> SEQ ID NO 247
<211> LENGTH: 23
<212> TYPE: DNA
<213> ORGANISM: Homo sapiens

<400> SEQUENCE: 247
tctggctccg tgtcttcact ccc                                          23

<210> SEQ ID NO 248
<211> LENGTH: 23
<212> TYPE: RNA
<213> ORGANISM: Homo sapiens

<400> SEQUENCE: 248
uagcaccauu ugaaaucagu guu                                          23

<210> SEQ ID NO 249
<211> LENGTH: 23
<212> TYPE: DNA
<213> ORGANISM: Mus musculus

<400> SEQUENCE: 249
tagcaccatt tgaaatcagt gtt                                          23

<210> SEQ ID NO 250
<211> LENGTH: 23
<212> TYPE: DNA
<213> ORGANISM: Homo sapiens

<400> SEQUENCE: 250
tagcaccatt tgaaatcagt gtt                                          23

<210> SEQ ID NO 251
<211> LENGTH: 22
<212> TYPE: RNA
<213> ORGANISM: Homo sapiens

<400> SEQUENCE: 251
uggaauguaa agaaguaugu au                                           22

<210> SEQ ID NO 252
<211> LENGTH: 22
<212> TYPE: DNA
<213> ORGANISM: Mus musculus

<400> SEQUENCE: 252
tggaatgtaa agaagtatgt at                                           22

<210> SEQ ID NO 253
<211> LENGTH: 22
<212> TYPE: DNA
<213> ORGANISM: Homo sapiens
```

```
<400> SEQUENCE: 253
tggaatgtaa agaagtatgt at                                              22

<210> SEQ ID NO 254
<211> LENGTH: 21
<212> TYPE: RNA
<213> ORGANISM: Homo sapiens

<400> SEQUENCE: 254
aucacauugc cagggauuac c                                               21

<210> SEQ ID NO 255
<211> LENGTH: 21
<212> TYPE: DNA
<213> ORGANISM: Mus musculus

<400> SEQUENCE: 255
atcacattgc cagggattac c                                               21

<210> SEQ ID NO 256
<211> LENGTH: 21
<212> TYPE: DNA
<213> ORGANISM: Homo sapiens

<400> SEQUENCE: 256
atcacattgc cagggattac c                                               21

<210> SEQ ID NO 257
<211> LENGTH: 21
<212> TYPE: RNA
<213> ORGANISM: Homo sapiens

<400> SEQUENCE: 257
augaccuaug aauugacaga c                                               21

<210> SEQ ID NO 258
<211> LENGTH: 21
<212> TYPE: DNA
<213> ORGANISM: Mus musculus

<400> SEQUENCE: 258
atgacctatg atttgacaga c                                               21

<210> SEQ ID NO 259
<211> LENGTH: 21
<212> TYPE: DNA
<213> ORGANISM: Homo sapiens

<400> SEQUENCE: 259
atgacctatg aattgacaga c                                               21

<210> SEQ ID NO 260
<211> LENGTH: 22
<212> TYPE: RNA
<213> ORGANISM: Homo sapiens

<400> SEQUENCE: 260
uucccuuugu cauccuaugc cu                                              22

<210> SEQ ID NO 261
<211> LENGTH: 22
<212> TYPE: DNA
<213> ORGANISM: Mus musculus
```

```
<400> SEQUENCE: 261 ttcccttgt catcctatgc ct                                                 22

<210> SEQ ID NO 262
<211> LENGTH: 22
<212> TYPE: DNA
<213> ORGANISM: Homo sapiens

<400> SEQUENCE: 262 ttcccttgt catcctatgc ct                                                 22

<210> SEQ ID NO 263
<211> LENGTH: 22
<212> TYPE: RNA
<213> ORGANISM: Homo sapiens

<400> SEQUENCE: 263
caucuuacug ggcagcauug ga                                                22

<210> SEQ ID NO 264
<211> LENGTH: 22
<212> TYPE: DNA
<213> ORGANISM: Mus musculus

<400> SEQUENCE: 264
catcttactg ggcagcattg ga                                                22

<210> SEQ ID NO 265
<211> LENGTH: 22
<212> TYPE: DNA
<213> ORGANISM: Homo sapiens

<400> SEQUENCE: 265
catcttactg ggcagcattg ga                                                22

<210> SEQ ID NO 266
<211> LENGTH: 22
<212> TYPE: RNA
<213> ORGANISM: Homo sapiens

<400> SEQUENCE: 266
cauugcacuu gucucggucu ga                                                22

<210> SEQ ID NO 267
<211> LENGTH: 22
<212> TYPE: DNA
<213> ORGANISM: Mus musculus

<400> SEQUENCE: 267
cattgcactt gtctcggtct ga                                                22

<210> SEQ ID NO 268
<211> LENGTH: 22
<212> TYPE: DNA
<213> ORGANISM: Homo sapiens

<400> SEQUENCE: 268
cattgcactt gtctcggtct ga                                                22

<210> SEQ ID NO 269
<211> LENGTH: 22
<212> TYPE: RNA
<213> ORGANISM: Homo sapiens
```

```
<400> SEQUENCE: 269
uccagcauca gugauuuugu ug                                              22

<210> SEQ ID NO 270
<211> LENGTH: 22
<212> TYPE: DNA
<213> ORGANISM: Mus musculus

<400> SEQUENCE: 270
tccagcatca gtgattttgt tg                                              22

<210> SEQ ID NO 271
<211> LENGTH: 22
<212> TYPE: DNA
<213> ORGANISM: Homo sapiens

<400> SEQUENCE: 271
tccagcatca gtgattttgt tg                                              22

<210> SEQ ID NO 272
<211> LENGTH: 22
<212> TYPE: RNA
<213> ORGANISM: Homo sapiens

<400> SEQUENCE: 272
uagguaguuu ccuguuguug gg                                              22

<210> SEQ ID NO 273
<211> LENGTH: 22
<212> TYPE: DNA
<213> ORGANISM: Mus musculus

<400> SEQUENCE: 273
taggtagttt cctgttgttg gg                                              22

<210> SEQ ID NO 274
<211> LENGTH: 22
<212> TYPE: DNA
<213> ORGANISM: Homo sapiens

<400> SEQUENCE: 274
taggtagttt cctgttgttg gg                                              22
```